US012760103B2

(12) United States Patent
Chen et al.

(10) Patent No.: US 12,760,103 B2
(45) **Date of Patent: *Oct. 13, 2026**

(54) VARIANT IgG FC POLYPEPTIDES AND USES THEREOF

(71) Applicant: Seismic Therapeutic, Inc., Watertown, MA (US)

(72) Inventors: Yen-Lin Chen, Cambridge, MA (US); Ryan Peckner, Berkeley, CA (US); Nathan Higginson-Scott, Hingham, MA (US); Daniela Cipolletta, Belmont, MA (US); Yanfeng Zhou, Boxborough, MA (US); Kevin Lewis Otipoby, Ashland, MA (US); Jyothsna Visweswaraiah, Arlington, MA (US)

(73) Assignee: Seismic Therapeutic, Inc., Watertown, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 18/614,199

(22) Filed: Mar. 22, 2024

(65) Prior Publication Data

US 2025/0074984 A1 Mar. 6, 2025

Related U.S. Application Data

(63) Continuation of application No. 18/494,454, filed on Oct. 25, 2023, now Pat. No. 12,030,945.

(60) Provisional application No. 63/517,493, filed on Aug. 3, 2023, provisional application No. 63/493,356, filed on Mar. 31, 2023, provisional application No. 63/380,853, filed on Oct. 25, 2022, provisional application No. 63/380,842, filed on Oct. 25, 2022.

(51) Int. Cl.
*C07K 16/28* (2006.01)

(52) U.S. Cl.
CPC ...... *C07K 16/2818* (2013.01); *C07K 16/2803* (2013.01); *C07K 2317/52* (2013.01); *C07K 2317/71* (2013.01); *C07K 2317/72* (2013.01); *C07K 2317/75* (2013.01)

(58) Field of Classification Search
None
See application file for complete search history.

(56) References Cited

U.S. PATENT DOCUMENTS 7,317,091 B2 1/2008 Lazar et al.
7,355,008 B2 4/2008 Stavenhagen et al.
7,425,619 B2 9/2008 Koenig et al.
7,425,620 B2 9/2008 Koenig et al.
7,521,542 B2 4/2009 Johnson et al.
7,632,497 B2 12/2009 Stavenhagen
7,655,229 B2 2/2010 Chan et al.
7,662,925 B2 2/2010 Lazar et al.
7,662,926 B2 2/2010 Chan et al.
7,700,100 B2 4/2010 Johnson et al.
7,786,270 B2 8/2010 Johnson et al.
7,897,729 B2 3/2011 Arnason et al.
7,960,512 B2 6/2011 Stavenhagen et al.
8,003,774 B2 8/2011 Stavenhagen et al.
8,044,180 B2 10/2011 Koenig et al.
8,084,582 B2 12/2011 Dahiyat et al.
8,093,357 B2 1/2012 Lazar et al.
8,124,358 B2 2/2012 Jung et al.
8,124,731 B2 2/2012 Lazar et al.
8,133,982 B2 3/2012 Johnson et al.
8,187,593 B2 5/2012 Koenig et al.
8,193,318 B2 6/2012 Koenig et al.
8,216,574 B2 7/2012 Stavenhagen et al.
8,216,579 B2 7/2012 Johnson et al.
8,217,147 B2 7/2012 Stavenhagen et al.
8,323,653 B2 12/2012 Damschroder et al.
8,435,517 B2 5/2013 Desjarlais et al.
8,445,645 B2 5/2013 Stavenhagen et al.
8,461,304 B2 6/2013 Cicortas Gunnarsson et al.
8,530,627 B2 9/2013 Koenig et al.
8,618,251 B1 12/2013 Ravetch et al.
8,652,466 B2 2/2014 Stavenhagen et al.
8,734,791 B2 5/2014 Lazar et al.
8,735,547 B2 5/2014 Lazar et al.
8,753,628 B2 6/2014 Lazar et al.
8,753,629 B2 6/2014 Lazar et al.
8,778,339 B2 7/2014 Tuaillon et al.
8,784,808 B2 7/2014 Johnson et al.
8,785,599 B2 7/2014 Johnson et al.
8,802,089 B2 8/2014 Van Den Brink et al.
(Continued)

FOREIGN PATENT DOCUMENTS

EP 1534335 A2 6/2005
EP 1587540 A2 10/2005
(Continued)

OTHER PUBLICATIONS

Curnock Adam P. et al., "Cell-targeted PD-1 agonists that mimic PD-LI are potent T cell inhibitors", JCI insight, vol. 6, No. 20, E152468, Oct. 22, 2021 (Oct. 22, 2021), XP093021891, DOI: 10.1172/jci.insight.152468, p. 20.
Kehry Marilyn: "Discovery of a PD-1 Checkpoint Agonist Antibody for Autoimmune/Inflammatory Disease", AnaptysBio, Mar. 2, 2020 (Mar. 2, 2020), pp. 1-16, XP093004746, p. 16.
Labrijn, A.F., et al., Species-specific determinants in the IgG CH3 domain enable Fab-arm exchange by affecting the noncovalent CH3—CH3 interaction strength, J Immunol., 187(6):3238-46 (2011).
Liu Rena et al: "Fe-Engineering for Modulated Effector Functions-Improving Antibodies for Cancer Treatment", Antibodies, vol. 9, No. 4, Dec. 17, 2020 (Dec. 17, 2020), p. 64, XP055918764, CH ISSN: 2073-4468, DOI: 10.3390/antib9040064, p. 34.
Mimoto, F., et al., Engineered antibody Fc variant with selectively enhanced FcγRIIb binding over both FcγRIIa(R131) and FcγRIIa(H131), Protein Eng Des Sel, 26(10): 589-598 (2013).
(Continued)

*Primary Examiner* — Nora M Rooney
(74) *Attorney, Agent, or Firm* — Goodwin Procter LLP

(57) ABSTRACT

Embodiments provided herein, provide for variant IgG Fc polypeptides, dimeric molecules, pharmaceutical compositions, and methods that can be used to target at cells to modulate the activity of the same to treat disorders, such as autoimmune disorders or cancers.

30 Claims, 10 Drawing Sheets

Specification includes a Sequence Listing.

(56) References Cited

U.S. PATENT DOCUMENTS

| | | | |
|---|---|---|---|
| 8,802,093 | B2 | 8/2014 | Johnson et al. |
| 8,802,823 | B2 | 8/2014 | Lazar et al. |
| 8,853,363 | B2 | 10/2014 | Huber et al. |
| 8,883,992 | B2 | 11/2014 | Damschroder et al. |
| 8,937,158 | B2 | 1/2015 | Lazar et al. |
| 8,946,387 | B2 | 2/2015 | Koenig et al. |
| 8,951,517 | B2 | 2/2015 | Stavenhagen et al. |
| 8,968,730 | B2 | 3/2015 | Koenig et al. |
| 8,986,698 | B2 | 3/2015 | Arnason et al. |
| 9,028,815 | B2 | 5/2015 | Stavenhagen et al. |
| 9,051,373 | B2 | 6/2015 | Lazar et al. |
| 9,062,117 | B2 | 6/2015 | Desjarlais et al. |
| 9,096,877 | B2 | 8/2015 | Johnson et al. |
| 9,127,063 | B2 | 9/2015 | Arnason et al. |
| 9,221,916 | B2 | 12/2015 | Desjarlais et al. |
| 9,234,038 | B2 | 1/2016 | Jung et al. |
| 9,243,069 | B2 | 1/2016 | Johnson et al. |
| 9,260,523 | B2 | 2/2016 | Chu et al. |
| 9,266,966 | B2 | 2/2016 | Desjarlais et al. |
| 9,284,375 | B2 | 3/2016 | Johnson et al. |
| 9,296,816 | B2 | 3/2016 | Johnson et al. |
| 9,328,170 | B2 | 5/2016 | Zha |
| 9,394,366 | B2 | 7/2016 | Chu et al. |
| 9,493,578 | B2 | 11/2016 | Lazar et al. |
| 9,540,451 | B2 | 1/2017 | Desjarlais et al. |
| 9,617,348 | B2 | 4/2017 | Desjarlais et al. |
| 9,657,101 | B2 | 5/2017 | Ravetch et al. |
| 9,657,106 | B2 | 5/2017 | Lazar et al. |
| 9,663,578 | B2 | 5/2017 | Van Den Brink et al. |
| 9,663,582 | B2 | 5/2017 | Lazar et al. |
| 9,708,408 | B2 | 7/2017 | Stavenhagen et al. |
| 9,737,599 | B2 | 8/2017 | Tuaillon et al. |
| 9,738,722 | B2 | 8/2017 | Moore et al. |
| 9,889,197 | B2 | 2/2018 | Johnson et al. |
| 9,890,218 | B2 | 2/2018 | Mimoto et al. |
| 9,896,505 | B2 | 2/2018 | Damschroder et al. |
| 9,902,773 | B2 | 2/2018 | Chu et al. |
| 9,914,778 | B2 | 3/2018 | Chu et al. |
| 9,926,362 | B2 | 3/2018 | Strome et al. |
| 9,963,510 | B2 | 5/2018 | Johnson et al. |
| 10,028,998 | B2 | 7/2018 | Buckel et al. |
| 10,093,739 | B2 | 10/2018 | Johnson et al. |
| 10,100,116 | B2 | 10/2018 | Johnson et al. |
| 10,113,001 | B2 | 10/2018 | Lazar et al. |
| 10,131,713 | B2 | 11/2018 | Johnson et al. |
| 10,208,105 | B2 | 2/2019 | Strome et al. |
| 10,253,100 | B2 | 4/2019 | Igawa et al. |
| 10,344,092 | B2 | 7/2019 | Johnson et al. |
| 10,407,499 | B2 | 9/2019 | Sondermann et al. |
| 10,526,408 | B2 | 1/2020 | Georgiou et al. |
| 10,584,176 | B2 | 3/2020 | Lazar et al. |
| 10,618,965 | B2 | 4/2020 | Igawa et al. |
| 10,711,069 | B2 | 7/2020 | Stavenhagen et al. |
| 10,730,946 | B2 | 8/2020 | Carle et al. |
| 10,766,960 | B2 | 9/2020 | Igawa et al. |
| 10,851,154 | B2 | 12/2020 | Strome et al. |
| 10,894,835 | B2 | 1/2021 | Ravetch et al. |
| 10,919,953 | B2 | 2/2021 | Katada et al. |
| 10,941,191 | B2 | 3/2021 | Strome et al. |
| 11,098,105 | B2 | 8/2021 | Escobar-Cabrera |
| 11,098,125 | B2 | 8/2021 | Johnson et al. |
| 11,142,563 | B2 | 10/2021 | Igawa et al. |
| 11,149,094 | B2 | 10/2021 | Chiu et al. |
| 11,236,168 | B2 | 2/2022 | Igawa et al. |
| 11,254,747 | B2 | 2/2022 | Johnson et al. |
| 11,254,748 | B2 | 2/2022 | Johnson et al. |
| 11,267,868 | B2 | 3/2022 | Mimoto et al. |
| 11,365,256 | B2 | 6/2022 | Zack et al. |
| 11,384,149 | B2 | 7/2022 | Johnson et al. |
| 11,434,295 | B2 | 9/2022 | Chu et al. |
| 11,447,552 | B2 | 9/2022 | Chu et al. |
| 11,566,080 | B2 | 1/2023 | Desjarlais et al. |
| 12,030,945 | B2 * | 7/2024 | Chen .................. C07K 16/2818 |
| 2003/0228634 | A1 | 12/2003 | Simard et al. |
| 2009/0215991 | A1 | 8/2009 | Lazar et al. |
| 2013/0131319 | A1 | 5/2013 | Igawa et al. |
| 2014/0093496 | A1 | 4/2014 | Mimoto et al. |
| 2014/0335089 | A1 | 11/2014 | Igawa et al. |
| 2015/0203577 | A1 | 7/2015 | Igawa et al. |
| 2016/0046693 | A1 | 2/2016 | Igawa et al. |
| 2016/0122435 | A1 | 5/2016 | Chu et al. |
| 2016/0244526 | A1 | 8/2016 | Igawa et al. |
| 2017/0002066 | A1 | 1/2017 | Igawa et al. |
| 2017/0002080 | A1 | 1/2017 | Igawa et al. |
| 2017/0226206 | A1 | 8/2017 | Igawa et al. |
| 2017/0247463 | A1 | 8/2017 | Ravetch et al. |
| 2018/0030111 | A1 | 2/2018 | Monnet et al. |
| 2018/0155451 | A1 | 6/2018 | Mimoto et al. |
| 2019/0062420 | A1 | 2/2019 | Chiu et al. |
| 2019/0092859 | A1 | 3/2019 | Johnson et al. |
| 2019/0112393 | A1 | 4/2019 | Igawa et al. |
| 2019/0127467 | A1 | 5/2019 | Shah et al. |
| 2019/0233499 | A1 | 8/2019 | Hatayama et al. |
| 2019/0233525 | A1 | 8/2019 | Igawa et al. |
| 2019/0309085 | A1 | 10/2019 | Monnet |
| 2020/0024369 | A1 | 1/2020 | Vilen |
| 2020/0055941 | A1 | 2/2020 | Bürger et al. |
| 2020/0131265 | A1 | 4/2020 | Koenig et al. |
| 2020/0199241 | A1 | 6/2020 | Igawa et al. |
| 2020/0362036 | A1 | 11/2020 | Frendéus et al. |
| 2020/0392245 | A1 | 12/2020 | Stavenhagen et al. |
| 2021/0009689 | A1 | 1/2021 | Chu et al. |
| 2021/0009690 | A1 | 1/2021 | Chu et al. |
| 2021/0061906 | A1 | 3/2021 | Damschroder et al. |
| 2021/0139600 | A1 | 5/2021 | Lazar et al. |
| 2021/0155699 | A1 | 5/2021 | Labrijn et al. |
| 2021/0205451 | A1 | 7/2021 | van Dijk et al. |
| 2021/0261648 | A1 | 8/2021 | Katada et al. |
| 2021/0395363 | A1 | 12/2021 | Chu et al. |
| 2022/0177574 | A1 | 6/2022 | Johnson et al. |
| 2022/0242934 | A1 | 8/2022 | Igawa et al. |
| 2022/0259309 | A1 | 8/2022 | Frendéus et al. |
| 2022/0275082 | A1 | 9/2022 | Johnson et al. |
| 2022/0275089 | A1 | 9/2022 | Xia et al. |
| 2022/0372144 | A1 | 11/2022 | Johnson et al. |
| 2022/0389055 | A1 | 12/2022 | Davis et al. |
| 2022/0389098 | A1 | 12/2022 | Zack et al. |
| 2022/0389118 | A1 | 12/2022 | Igawa et al. |
| 2022/0403043 | A1 | 12/2022 | Dahan et al. |
| 2022/0411483 | A1 | 12/2022 | Mimoto et al. |
| 2023/0053681 | A1 | 2/2023 | Vilen |
| 2023/0058982 | A1 | 2/2023 | Katada et al. |
| 2023/0063965 | A1 | 3/2023 | Dahan et al. |
| 2023/0220042 | A1 | 7/2023 | Li et al. |
| 2024/0010742 | A1 | 1/2024 | Georgiou et al. |

FOREIGN PATENT DOCUMENTS

| | | | |
|---|---|---|---|
| EP | 1709073 | A2 | 10/2006 |
| EP | 1919503 | A2 | 5/2008 |
| EP | 1919950 | A1 | 5/2008 |
| EP | 2021029 | A2 | 2/2009 |
| EP | 2029173 | A2 | 3/2009 |
| EP | 2066349 | A2 | 6/2009 |
| EP | 2158221 | A2 | 3/2010 |
| EP | 2176298 | A1 | 4/2010 |
| EP | 2185589 | A2 | 5/2010 |
| EP | 2234641 | A2 | 10/2010 |
| EP | 2247304 | A2 | 11/2010 |
| EP | 2268296 | A1 | 1/2011 |
| EP | 2331578 | A1 | 6/2011 |
| EP | 2364996 | A1 | 9/2011 |
| EP | 2376109 | A1 | 10/2011 |
| EP | 2471813 | A1 | 7/2012 |
| EP | 2486141 | A1 | 8/2012 |
| EP | 2552955 | A2 | 2/2013 |
| EP | 2573114 | A1 | 3/2013 |
| EP | 2641913 | A2 | 9/2013 |
| EP | 2679681 | A1 | 1/2014 |
| EP | 2698431 | A1 | 2/2014 |
| EP | 2703415 | A1 | 3/2014 |
| EP | 2728002 | A1 | 5/2014 |
| EP | 2760890 | A2 | 8/2014 |
| EP | 2762166 | A1 | 8/2014 |

(56) References Cited

FOREIGN PATENT DOCUMENTS

| | | | |
|---|---|---|---|
| EP | 2786762 | A2 | 10/2014 |
| EP | 2796469 | A2 | 10/2014 |
| EP | 2818183 | A1 | 12/2014 |
| EP | 2853545 | A1 | 4/2015 |
| EP | 2862875 | A1 | 4/2015 |
| EP | 2889376 | A1 | 7/2015 |
| EP | 2889377 | A1 | 7/2015 |
| EP | 2914624 | A1 | 9/2015 |
| EP | 2940043 | A1 | 11/2015 |
| EP | 2940135 | A1 | 11/2015 |
| EP | 2982689 | A1 | 2/2016 |
| EP | 3030264 | A1 | 6/2016 |
| EP | 3033357 | A1 | 6/2016 |
| EP | 3180358 | A1 | 6/2017 |
| EP | 3181581 | A1 | 6/2017 |
| EP | 3190128 | A1 | 7/2017 |
| EP | 3292145 | A1 | 3/2018 |
| EP | 3342782 | A1 | 7/2018 |
| EP | 3392273 | A1 | 10/2018 |
| EP | 3423489 | A1 | 1/2019 |
| EP | 3424951 | A1 | 1/2019 |
| EP | 3431993 | A1 | 1/2019 |
| EP | 3468997 | A1 | 4/2019 |
| EP | 3481865 | A1 | 5/2019 |
| EP | 3482769 | A1 | 5/2019 |
| EP | 3517609 | A1 | 7/2019 |
| EP | 3549956 | A2 | 10/2019 |
| EP | 3581588 | A1 | 12/2019 |
| EP | 3597747 | A1 | 1/2020 |
| EP | 3604330 | A1 | 2/2020 |
| EP | 3606952 | A1 | 2/2020 |
| EP | 3672611 | A1 | 7/2020 |
| EP | 3680251 | A1 | 7/2020 |
| EP | 3702368 | A1 | 9/2020 |
| EP | 3721900 | A1 | 10/2020 |
| EP | 3737698 | A2 | 11/2020 |
| EP | 3738980 | A1 | 11/2020 |
| EP | 3783017 | A1 | 2/2021 |
| EP | 3825325 | A2 | 5/2021 |
| WO | WO-2010029434 | A1 | 3/2010 |
| WO | WO-2011110621 | A1 | 9/2011 |
| WO | WO-2016177984 | A1 | 11/2016 |
| WO | WO-2017058859 | A1 | 4/2017 |
| WO | WO-2017151176 | A1 | 9/2017 |
| WO | WO-2017214452 | A1 | 12/2017 |
| WO | WO-2018007453 | A1 | 1/2018 |
| WO | WO-2018185284 | A1 | 10/2018 |
| WO | WO-2018226580 | A2 | 12/2018 |
| WO | WO-2019040808 | A1 | 2/2019 |
| WO | WO-2019138005 | A2 | 7/2019 |
| WO | WO-2019168745 | A1 | 9/2019 |
| WO | WO-2020247648 | A2 | 12/2020 |
| WO | WO-2021009358 | A1 | 1/2021 |
| WO | WO-2021110110 | A1 | 6/2021 |
| WO | WO-2021232162 | A1 | 11/2021 |
| WO | WO-2022044248 | A1 | 3/2022 |
| WO | WO-2022045276 | A1 | 3/2022 |
| WO | WO-2022133543 | A1 | 6/2022 |
| WO | WO-2022180342 | A1 | 9/2022 |
| WO | WO-2022239820 | A1 | 11/2022 |
| WO | WO-2023089377 | A2 | 5/2023 |
| WO | WO-2024040206 | A2 | 2/2024 |
| WO | WO-2024196694 | A2 | 9/2024 |
| WO | WO-2025030000 | A1 | 2/2025 |
| WO | WO-2025030003 | A2 | 2/2025 |
| WO | WO-2025030009 | A1 | 2/2025 |

OTHER PUBLICATIONS

PCT/US2022/078537 International Search Report and Written Opinion mailed Feb. 1, 2023, 15 pages.

PCT/US2023/077719 International Search Report and Written Opinion mailed Mar. 15, 2024, 17 pages.

PCT/US2023/077768 International Preliminary Report on Patentability mailed May 8, 2025.

PCT/US2023/077768 International Search Report and Written Opinion mailed Mar. 14, 2024, 20 pages.

* cited by examiner

SEQUENCE LISTING

```
Sequence total quantity: 116
SEQ ID NO: 1            moltype = AA  length = 330
FEATURE                 Location/Qualifiers
source                  1..330
                        mol_type = protein
                        organism = synthetic construct
SEQUENCE: 1
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
FSVFLFPPKP KDTLMISRTP EVTCVVVDVK HEDPEVKFNW YVDGVEVHNA KTKPREEQYN  180
STYRVVSVLT VLHQDWLNGK EYKCKVSNKA MPEPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 2            moltype = AA  length = 330
FEATURE                 Location/Qualifiers
source                  1..330
                        mol_type = protein
                        organism = synthetic construct
SEQUENCE: 2
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
FSVFLFPPKP KDTLMISRTP EVTCVVVDVK HEDPEVKFNW YVDGVEVHNA KTKPREEQYN  180
STYRVVSVLT VLHQDWLNGK EYKCKVSNKD MPEPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 3            moltype = AA  length = 330
FEATURE                 Location/Qualifiers
source                  1..330
                        mol_type = protein
                        organism = synthetic construct
SEQUENCE: 3
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGH  120
FSVFLFPPKP KDTLMISRTP EVTCVVVDVK HEDPEVKFNW YVDGVEVHNA KTKPREEQYN  180
STYRVVSVLT VLHQDWLNGK EYKCKVSNKD MPEPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 4            moltype = AA  length = 330
FEATURE                 Location/Qualifiers
source                  1..330
                        mol_type = protein
                        organism = synthetic construct
SEQUENCE: 4
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGM  120
FSVFLFPPKP KDTLMISRTP EVTCVVVDVK HEDPEVKFNW YVDGVEVHNA KTKPREEQYN  180
STYRVVSVLT VLHQDWLNGK EYKCKVSNKD MPEPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 5            moltype = AA  length = 330
FEATURE                 Location/Qualifiers
source                  1..330
                        mol_type = protein
                        organism = synthetic construct
SEQUENCE: 5
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 6            moltype = AA  length = 330
FEATURE                 Location/Qualifiers
source                  1..330
                        mol_type = protein
                        organism = synthetic construct
SEQUENCE: 6
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELGQG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330
```

```
SEQ ID NO: 7            moltype = AA  length = 330
FEATURE                 Location/Qualifiers
source                  1..330
                        mol_type = protein
                        organism = synthetic construct
SEQUENCE: 7
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEPGQG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 8            moltype = AA  length = 330
FEATURE                 Location/Qualifiers
source                  1..330
                        mol_type = protein
                        organism = synthetic construct
SEQUENCE: 8
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELGQG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA WRAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 9            moltype = AA  length = 330
FEATURE                 Location/Qualifiers
source                  1..330
                        mol_type = protein
                        organism = synthetic construct
SEQUENCE: 9
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELGQR  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA WRAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 10           moltype = AA  length = 330
FEATURE                 Location/Qualifiers
source                  1..330
                        mol_type = protein
                        organism = synthetic construct
SEQUENCE: 10
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELGQG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LDAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 11           moltype = AA  length = 330
FEATURE                 Location/Qualifiers
source                  1..330
                        mol_type = protein
                        organism = synthetic construct
SEQUENCE: 11
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPLKLGA  120
PSVFLFPPKP KDTLMISRTP EVTCVVVDVS PENPEVKFNW YVDGVEVHNA KTKPREEQYN  180
STYRVVSVLT VLHQDWLNGK EYKCKVSTST IPGQIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 12           moltype = AA  length = 330
FEATURE                 Location/Qualifiers
source                  1..330
                        mol_type = protein
                        organism = synthetic construct
SEQUENCE: 12
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPMGGGA  120
PSVFLFPPKP KDTLMISRTP EVTCVVVDVS PEDPEVEFNW YVDGVEVHNA KTKPREEQYN  180
STYRVVSVLT VLHQDWLNGK EYKCKVSTPS QPADIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330
```

```
SEQ ID NO: 13          moltype = AA  length = 330
FEATURE                Location/Qualifiers
source                 1..330
                       mol_type = protein
                       organism = synthetic construct
SEQUENCE: 13
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPITPGA  120
PSVFLFPPKP KDTLMISRTP EVTCVVVDVS PEAPEVEFNW YVDGVEVHNA KTKPREEQYN  180
STYRVVSVLT VLHQDWLNGK EYKCKVSTAG LGSNIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 14          moltype = AA  length = 330
FEATURE                Location/Qualifiers
source                 1..330
                       mol_type = protein
                       organism = synthetic construct
SEQUENCE: 14
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPRTPAL  120
PSVFLFPPKP KDTLMISRTP EVTCVVVDVS PEDPEVEFNW YVDGVEVHNA KTKPREEQYN  180
STYRVVSVLT VLHQDWLNGK EYKCKVSNGE IREHIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 15          moltype = AA  length = 330
FEATURE                Location/Qualifiers
source                 1..330
                       mol_type = protein
                       organism = synthetic construct
SEQUENCE: 15
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGL  120
PSVFLFPPKP KDTLMISRTP EVTCVVVDVS HEDPEVKFNW YVDGVEVHNA KTKPREEQYN  180
QTYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 16          moltype = AA  length = 330
FEATURE                Location/Qualifiers
source                 1..330
                       mol_type = protein
                       organism = synthetic construct
SEQUENCE: 16
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGL  120
PSVFLFPPKP KDTLMISRTP EVTCVVVDVS HEDPEVKFNW YVDGVEVHNA KTKPREEQYN  180
QRYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 17          moltype = AA  length = 330
FEATURE                Location/Qualifiers
source                 1..330
                       mol_type = protein
                       organism = synthetic construct
SEQUENCE: 17
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLPL  120
PSVFLFPPKP KDTLMISRTP EVTCVVVDVS HEDPEVKFNW YVDGVEVHNA KTKPREEQYN  180
QTYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 18          moltype = AA  length = 330
FEATURE                Location/Qualifiers
source                 1..330
                       mol_type = protein
                       organism = synthetic construct
SEQUENCE: 18
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGL  120
PSVFLFPPKP KDTLMISRTP EVTCVVVDVS HEDPEVKFNW YVDGVEVHNA KTKPREEQYN  180
QTYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 19          moltype = AA  length = 330
```

```
FEATURE                 Location/Qualifiers
source                  1..330
                        mol_type = protein
                        organism = synthetic construct
SEQUENCE: 19
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEMLPL  120
PSVFLFPPKP KDTLMISRTP EVTCVVVDVS HEDPEVKFNW YVDGVEVHNA KTKPREEQYN  180
QTYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 20           moltype = AA  length = 330
FEATURE                 Location/Qualifiers
source                  1..330
                        mol_type = protein
                        organism = synthetic construct
SEQUENCE: 20
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEMLPL  120
PSVFLFPPKP KDTLMISRTP EVTCVVVDVS HEDPEVKFNW YVDGVEVHNA KTKPREEQYN  180
QRYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 21           moltype = AA  length = 330
FEATURE                 Location/Qualifiers
source                  1..330
                        mol_type = protein
                        organism = synthetic construct
SEQUENCE: 21
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEMLPL  120
PSVFLFPPKP KDTLMISRTP EVTCVVVDVS HEDPEVKFNW YVDGVEVHNA KTKPREEQYN  180
QTYRVVSVLT VLHQDWLNGK EYKCKVSDKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 22           moltype = AA  length = 330
FEATURE                 Location/Qualifiers
source                  1..330
                        mol_type = protein
                        organism = synthetic construct
SEQUENCE: 22
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVWDVS HEDPEVKFNW YVDGVEVHNA KTKPREEQYN  180
STYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 23           moltype = AA  length = 330
FEATURE                 Location/Qualifiers
source                  1..330
                        mol_type = protein
                        organism = synthetic construct
SEQUENCE: 23
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVWDVS HEDPEVKFNW YVDGVEVHNA KTKPREEQYN  180
STYRVVSVLT VLHQDWLNGK EYKCKVSDKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 24           moltype = AA  length = 330
FEATURE                 Location/Qualifiers
source                  1..330
                        mol_type = protein
                        organism = synthetic construct
SEQUENCE: 24
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVWDHS HEDPEVKFNW YVDGVEVHNA KTKPREEQYN  180
STYRVVSVLT VLHQDWLNGK EYKCKVSDKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 25           moltype = AA  length = 330
FEATURE                 Location/Qualifiers
```

```
source                  1..330
                        mol_type = protein
                        organism = synthetic construct
SEQUENCE: 25
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 26           moltype = AA  length = 330
FEATURE                 Location/Qualifiers
source                  1..330
                        mol_type = protein
                        organism = synthetic construct
SEQUENCE: 26
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDAS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 27           moltype = AA  length = 330
FEATURE                 Location/Qualifiers
source                  1..330
                        mol_type = protein
                        organism = synthetic construct
SEQUENCE: 27
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 28           moltype = AA  length = 330
FEATURE                 Location/Qualifiers
source                  1..330
                        mol_type = protein
                        organism = synthetic construct
SEQUENCE: 28
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS NYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 29           moltype = AA  length = 330
FEATURE                 Location/Qualifiers
source                  1..330
                        mol_type = protein
                        organism = synthetic construct
SEQUENCE: 29
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS QYEPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 30           moltype = AA  length = 330
FEATURE                 Location/Qualifiers
source                  1..330
                        mol_type = protein
                        organism = synthetic construct
SEQUENCE: 30
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDAS QYEPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 31           moltype = AA  length = 330
FEATURE                 Location/Qualifiers
source                  1..330
```

```
                      mol_type = protein
                      organism = synthetic construct
SEQUENCE: 31
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS NYEPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 32         moltype = AA  length = 330
FEATURE               Location/Qualifiers
source                1..330
                      mol_type = protein
                      organism = synthetic construct
SEQUENCE: 32
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVFVS QYEPEVKFNW YVDGVEVHNA KTKPREEQNN  180
STYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 33         moltype = AA  length = 330
FEATURE               Location/Qualifiers
source                1..330
                      mol_type = protein
                      organism = synthetic construct
SEQUENCE: 33
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPMKEGA  120
PSVFLFPPKP KDTLMISRTP EVTCVVVDVS PKSPEVEFNW YVDGVEVHNA KTKPREEQYN  180
STYRVVSVLT VLHQDWLNGK EYKCKVSTSA LAAEIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 34         moltype = AA  length = 330
FEATURE               Location/Qualifiers
source                1..330
                      mol_type = protein
                      organism = synthetic construct
SEQUENCE: 34
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPGPGS  120
PSVFLFPPKP KDTLMISRTP EVTCVVVDVS PADPEVHFNW YVDGVEVHNA KTKPREEQYN  180
STYRVVSVLT VLHQDWLNGK EYKCKVSNNA LIGQIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 35         moltype = AA  length = 330
FEATURE               Location/Qualifiers
source                1..330
                      mol_type = protein
                      organism = synthetic construct
SEQUENCE: 35
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPVISGG  120
PSVFLFPPKP KDTLMISRTP EVTCVVVDVS PENPEVKFNW YVDGVEVHNA KTKPREEQYN  180
STYRVVSVLT VLHQDWLNGK EYKCKVSTKN HPQPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 36         moltype = AA  length = 330
FEATURE               Location/Qualifiers
source                1..330
                      mol_type = protein
                      organism = synthetic construct
SEQUENCE: 36
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPKLLGA  120
PSVFLFPPKP KDTLMISRTP EVTCVVVDVS PSDPEVHFNW YVDGVEVHNA KTKPREEQYN  180
STYRVVSVLT VLHQDWLNGK EYKCKVSNKN VNGVIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 37         moltype = AA  length = 330
FEATURE               Location/Qualifiers
source                1..330
                      mol_type = protein
```

```
                         organism = synthetic construct
SEQUENCE: 37
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 38            moltype = AA  length = 330
FEATURE                  Location/Qualifiers
source                   1..330
                         mol_type = protein
                         organism = synthetic construct
SEQUENCE: 38
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVWDHS HEDPEVKFNW YVDGVEVHNA KTKPREEQYN  180
STYRVVSVLT VLHQDWLNGK EYKCKVSNKD LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330

SEQ ID NO: 39            moltype = AA  length = 330
FEATURE                  Location/Qualifiers
source                   1..330
                         mol_type = protein
                         organism = synthetic construct
SEQUENCE: 39
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
ESVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 40            moltype = AA  length = 330
FEATURE                  Location/Qualifiers
source                   1..330
                         mol_type = protein
                         organism = synthetic construct
SEQUENCE: 40
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGE  120
ESVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 41            moltype = AA  length = 330
FEATURE                  Location/Qualifiers
source                   1..330
                         mol_type = protein
                         organism = synthetic construct
SEQUENCE: 41
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
ESVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 42            moltype = AA  length = 330
FEATURE                  Location/Qualifiers
source                   1..330
                         mol_type = protein
                         organism = synthetic construct
SEQUENCE: 42
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
NSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 43            moltype = AA  length = 330
FEATURE                  Location/Qualifiers
source                   1..330
                         mol_type = protein
                         organism = synthetic construct
```

SEQUENCE: 43
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGE 120
NSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 44 moltype = AA length = 330
FEATURE Location/Qualifiers
source 1..330
mol_type = protein
organism = synthetic construct
SEQUENCE: 44
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGD 120
NSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 45 moltype = AA length = 330
FEATURE Location/Qualifiers
source 1..330
mol_type = protein
organism = synthetic construct
SEQUENCE: 45
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGG 120
NSVFLFPPKP KDTLMISRTP EVTCVVVDVK HEDPEVKFNW YVDGVEVHNA KTKPREEQYN 180
STYRVVSVLT VLHQDWLNGK EYKCKVSNKA MPEPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 46 moltype = AA length = 330
FEATURE Location/Qualifiers
source 1..330
mol_type = protein
organism = synthetic construct
SEQUENCE: 46
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGG 120
FSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 47 moltype = AA length = 330
FEATURE Location/Qualifiers
source 1..330
mol_type = protein
organism = synthetic construct
SEQUENCE: 47
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGE 120
FSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 48 moltype = AA length = 330
FEATURE Location/Qualifiers
source 1..330
mol_type = protein
organism = synthetic construct
SEQUENCE: 48
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGD 120
FSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 49 moltype = AA length = 330
FEATURE Location/Qualifiers
source 1..330
mol_type = protein
organism = synthetic construct
SEQUENCE: 49

```
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
FSVFLFPPKP KDTLMISRTP EVTCVVVDVK HEDPEVKFNW YVDGVEVHNA KTKPREEQYN  180
STYRVVSVLT VLHQDWLNGK EYKCKVSNKA MPEPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 50          moltype = AA  length = 330
FEATURE                Location/Qualifiers
source                 1..330
                       mol_type = protein
                       organism = synthetic construct
SEQUENCE: 50
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
QSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 51          moltype = AA  length = 330
FEATURE                Location/Qualifiers
source                 1..330
                       mol_type = protein
                       organism = synthetic construct
SEQUENCE: 51
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGE  120
QSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 52          moltype = AA  length = 330
FEATURE                Location/Qualifiers
source                 1..330
                       mol_type = protein
                       organism = synthetic construct
SEQUENCE: 52
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
QSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 53          moltype = AA  length = 330
FEATURE                Location/Qualifiers
source                 1..330
                       mol_type = protein
                       organism = synthetic construct
SEQUENCE: 53
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
QSVFLFPPKP KDTLMISRTP EVTCVVVDVK HEDPEVKFNW YVDGVEVHNA KTKPREEQYN  180
STYRVVSVLT VLHQDWLNGK EYKCKVSNKA MPEPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 54          moltype = AA  length = 330
FEATURE                Location/Qualifiers
source                 1..330
                       mol_type = protein
                       organism = synthetic construct
SEQUENCE: 54
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
MSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 55          moltype = AA  length = 330
FEATURE                Location/Qualifiers
source                 1..330
                       mol_type = protein
                       organism = synthetic construct
SEQUENCE: 55
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKKVEP KSCDKTHTCP PCPAPELLGE  120
MSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 56          moltype = AA  length = 330
FEATURE                Location/Qualifiers
source                 1..330
                       mol_type = protein
                       organism = synthetic construct
SEQUENCE: 56
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
MSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 57          moltype = AA  length = 330
FEATURE                Location/Qualifiers
source                 1..330
                       mol_type = protein
                       organism = synthetic construct
SEQUENCE: 57
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
MSVFLFPPKP KDTLMISRTP EVTCVVVDVK HEDPEVKFNW YVDGVEVHNA KTKPREEQYN  180
STYRVVSVLT VLHQDWLNGK EYKCKVSNKA MPEPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 58          moltype = AA  length = 331
FEATURE                Location/Qualifiers
source                 1..331
                       mol_type = protein
                       organism = synthetic construct
SEQUENCE: 58
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEGLLG  120
GDSVFLFPPK PKDTLMISRT PEVTCVVVDV KHEDPEVKFN WYVDGVEVHN AKTKPREEQY  180
NSTYRVVSVL TVLHQDWLNG KEYKCKVSNK AMPEPIEKTI SKAKGQPREP QVYTLPPSRD  240
ELTKNQVSLT CLVKGFYPSD IAVEWESNGQ PENNYKTTPP VLDSDGSFFL YSKLTVDKSR  300
WQQGNVFSCS VMHEALHNHY TQKSLSLSPG K                                331

SEQ ID NO: 59          moltype = AA  length = 331
FEATURE                Location/Qualifiers
source                 1..331
                       mol_type = protein
                       organism = synthetic construct
SEQUENCE: 59
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEGLLG  120
GDSVFLFPPK PKDTLMISRT PEVTCVVVDV KHEDPEVKFN WYVDGVEVHN AKTKPREEQY  180
NSTYRVVSVL TVLHQDWLNG KEYKCKVSNK DMPEPIEKTI SKAKGQPREP QVYTLPPSRD  240
ELTKNQVSLT CLVKGFYPSD IAVEWESNGQ PENNYKTTPP VLDSDGSFFL YSKLTVDKSR  300
WQQGNVFSCS VMHEALHNHY TQKSLSLSPG K                                331

SEQ ID NO: 60          moltype = AA  length = 331
FEATURE                Location/Qualifiers
source                 1..331
                       mol_type = protein
                       organism = synthetic construct
SEQUENCE: 60
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEGLLG  120
HDSVFLFPPK PKDTLMISRT PEVTCVVVDV KHEDPEVKFN WYVDGVEVHN AKTKPREEQY  180
NSTYRVVSVL TVLHQDWLNG KEYKCKVSNK AMPEPIEKTI SKAKGQPREP QVYTLPPSRD  240
ELTKNQVSLT CLVKGFYPSD IAVEWESNGQ PENNYKTTPP VLDSDGSFFL YSKLTVDKSR  300
WQQGNVFSCS VMHEALHNHY TQKSLSLSPG K                                331

SEQ ID NO: 61          moltype = AA  length = 330
FEATURE                Location/Qualifiers
source                 1..330
                       mol_type = protein
                       organism = synthetic construct
SEQUENCE: 61
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
```

```
PSVFLFPPKP KDTLMISRTP EVTCVVVDVS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 62          moltype = AA  length = 330
FEATURE                Location/Qualifiers
source                 1..330
                       mol_type = protein
                       organism = synthetic construct
SEQUENCE: 62
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDAS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 63          moltype = AA  length = 330
FEATURE                Location/Qualifiers
source                 1..330
                       mol_type = protein
                       organism = synthetic construct
SEQUENCE: 63
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS QYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 64          moltype = AA  length = 330
FEATURE                Location/Qualifiers
source                 1..330
                       mol_type = protein
                       organism = synthetic construct
SEQUENCE: 64
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS NYDPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 65          moltype = AA  length = 330
FEATURE                Location/Qualifiers
source                 1..330
                       mol_type = protein
                       organism = synthetic construct
SEQUENCE: 65
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS QYEPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 66          moltype = AA  length = 330
FEATURE                Location/Qualifiers
source                 1..330
                       mol_type = protein
                       organism = synthetic construct
SEQUENCE: 66
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDAS QYEPEVKFNW YVDGVEVHNA KTKPREEQNN  180
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 67          moltype = AA  length = 330
FEATURE                Location/Qualifiers
source                 1..330
                       mol_type = protein
                       organism = synthetic construct
SEQUENCE: 67
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVDVS NYEPEVKFNW YVDGVEVHNA KTKPREEQNN  180
```

```
SFYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 68          moltype = AA  length = 330
FEATURE                Location/Qualifiers
source                 1..330
                       mol_type = protein
                       organism = synthetic construct
SEQUENCE: 68
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PEVFLFPPKP KDTLMISRTP EVTCVVVFVS QYEPEVKFNW YVDGVEVHNA KTKPREEQNN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 69          moltype = AA  length = 330
FEATURE                Location/Qualifiers
source                 1..330
                       mol_type = protein
                       organism = synthetic construct
SEQUENCE: 69
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LDAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 70          moltype = AA  length = 330
FEATURE                Location/Qualifiers
source                 1..330
                       mol_type = protein
                       organism = synthetic construct
SEQUENCE: 70
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKD LDAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 71          moltype = AA  length = 330
FEATURE                Location/Qualifiers
source                 1..330
                       mol_type = protein
                       organism = synthetic construct
SEQUENCE: 71
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSDKA LDAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 72          moltype = AA  length = 330
FEATURE                Location/Qualifiers
source                 1..330
                       mol_type = protein
                       organism = synthetic construct
SEQUENCE: 72
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSDKD LDAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 73          moltype = AA  length = 330
FEATURE                Location/Qualifiers
source                 1..330
                       mol_type = protein
                       organism = synthetic construct
SEQUENCE: 73
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LEAPIEKTIS KAKGQPREPQ VYTLPPSRDE  240
```

```
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 74          moltype = AA  length = 330
FEATURE                Location/Qualifiers
source                 1..330
                       mol_type = protein
                       organism = synthetic construct
SEQUENCE: 74
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 75          moltype = AA  length = 330
FEATURE                Location/Qualifiers
source                 1..330
                       mol_type = protein
                       organism = synthetic construct
SEQUENCE: 75
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 76          moltype = AA  length = 330
FEATURE                Location/Qualifiers
source                 1..330
                       mol_type = protein
                       organism = synthetic construct
SEQUENCE: 76
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 77          moltype = AA  length = 330
FEATURE                Location/Qualifiers
source                 1..330
                       mol_type = protein
                       organism = synthetic construct
SEQUENCE: 77
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PSVFLFPPKP KDTLMISRTP EVTCVVVDVS DEDGEVKFNW YVDGVEVHNA KTKPREEQYN  180
STYRVVSVLT VLHQDWLNGK EYKCKVSNKA LAAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 78          moltype = AA  length = 330
FEATURE                Location/Qualifiers
source                 1..330
                       mol_type = protein
                       organism = synthetic construct
SEQUENCE: 78
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
DSVFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 79          moltype = AA  length = 330
FEATURE                Location/Qualifiers
source                 1..330
                       mol_type = protein
                       organism = synthetic construct
SEQUENCE: 79
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELVGG  120
ESVFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
```

```
QQGNVFSCSV MHEALHNHYT QKSLSLSPGK                                    330

SEQ ID NO: 80           moltype = AA  length = 330
FEATURE                 Location/Qualifiers
source                  1..330
                        mol_type = protein
                        organism = synthetic construct
SEQUENCE: 80
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
SSVFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 81           moltype = AA  length = 330
FEATURE                 Location/Qualifiers
source                  1..330
                        mol_type = protein
                        organism = synthetic construct
SEQUENCE: 81
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PSVFLFPPKP KDTLMISRTP EVTCVVVDVS DEDGEVQFNW YVDGVEVHNA KTKPREEQFN  180
STYRVVSVLT VLHQDWLNGK EYKCKVSNKA LASSIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 82           moltype = AA  length = 330
FEATURE                 Location/Qualifiers
source                  1..330
                        mol_type = protein
                        organism = synthetic construct
SEQUENCE: 82
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
GSVFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 83           moltype = AA  length = 330
FEATURE                 Location/Qualifiers
source                  1..330
                        mol_type = protein
                        organism = synthetic construct
SEQUENCE: 83
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PDVFLFPPKP KDTLMISRTP EVTCVVVDVS DEDGEVQFNW YVDGVEVHNA KTKPREEQFN  180
STYRVVSVLT VLHQDWLNGK EYKCKVSNKA LASSIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                    330

SEQ ID NO: 84           moltype = AA  length = 330
FEATURE                 Location/Qualifiers
source                  1..330
                        mol_type = protein
                        organism = synthetic construct
SEQUENCE: 84
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
SGVFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 85           moltype = AA  length = 330
FEATURE                 Location/Qualifiers
source                  1..330
                        mol_type = protein
                        organism = synthetic construct
SEQUENCE: 85
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PSVFLFPPKP KDTLMISRTP EVTCVVVDVS QEDPEVQFNW YVDGVEVHNA KTKPREEQFN  180
STYRVVSVLT VLHQDWLNGK EYKCKVSNKA LPSSIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                    330
```

```
SEQ ID NO: 86           moltype = AA  length = 330
FEATURE                 Location/Qualifiers
source                  1..330
                        mol_type = protein
                        organism = synthetic construct
SEQUENCE: 86
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
GSAFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 87           moltype = AA  length = 333
FEATURE                 Location/Qualifiers
source                  1..333
                        mol_type = protein
                        organism = synthetic construct
SEQUENCE: 87
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEGEVL  120
VGGDSVFLFP PKPKDTLMIS RTPEVTCVVV DVSHDEPEVK FNWYVDGVEV HNAKTKPREE  180
QYNSTYRVVS VLTVLHQDWL NGKEYKCKVS NKALPRPIEK TISKAKGQPR EPQVYTLPPS  240
RDELTKNQVS LWCLVKGFYP SDIAVEWESN GQPENNYKTT PPVLDSDGSF FLYSKLTVDK  300
SRWQQGNVFS CSVMHEALHN HYTQKSLSLS PGK                              333

SEQ ID NO: 88           moltype = AA  length = 330
FEATURE                 Location/Qualifiers
source                  1..330
                        mol_type = protein
                        organism = synthetic construct
SEQUENCE: 88
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 89           moltype = AA  length = 326
FEATURE                 Location/Qualifiers
source                  1..326
                        mol_type = protein
                        organism = synthetic construct
SEQUENCE: 89
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                      326

SEQ ID NO: 90           moltype = AA  length = 377
FEATURE                 Location/Qualifiers
source                  1..377
                        mol_type = protein
                        organism = synthetic construct
SEQUENCE: 90
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                               377

SEQ ID NO: 91           moltype = AA  length = 327
FEATURE                 Location/Qualifiers
source                  1..327
                        mol_type = protein
                        organism = synthetic construct
SEQUENCE: 91
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327
```

```
SEQ ID NO: 92          moltype = AA  length = 23
FEATURE                Location/Qualifiers
source                 1..23
                       mol_type = protein
                       organism = synthetic construct
SEQUENCE: 92
EPKSCDKTHT CPPCPAPELL GGP                                            23

SEQ ID NO: 93          moltype = AA  length = 25
FEATURE                Location/Qualifiers
source                 1..25
                       mol_type = protein
                       organism = synthetic construct
SEQUENCE: 93
ELKTPLGDTT HTCPRCPAPE LLGGP                                          25

SEQ ID NO: 94          moltype = AA  length = 70
FEATURE                Location/Qualifiers
source                 1..70
                       mol_type = protein
                       organism = synthetic construct
SEQUENCE: 94
ELKTPLGDTT HTCPRCPEPK SCDTPPPCPR CPEPKSCDTP PPCPRCPEPK SCDTPPPCPR  60
CPAPELLGGP                                                           70

SEQ ID NO: 95          moltype = AA  length = 20
FEATURE                Location/Qualifiers
source                 1..20
                       mol_type = protein
                       organism = synthetic construct
SEQUENCE: 95
ESKYGPPCPS CPAPEFLGGP                                                20

SEQ ID NO: 96          moltype = AA  length = 113
FEATURE                Location/Qualifiers
source                 1..113
                       mol_type = protein
                       organism = synthetic construct
SEQUENCE: 96
PCPAPELLGG PSVFLFPPKP KDTLMISRTP EVTCVVVDVS HEDPEVKFNW YVDGVEVHNA  60
KTKPREEQYN STYRVVSVLT VLHQDWLNGK EYKCKVSNKA LPAPIEKTIS KAK         113

SEQ ID NO: 97          moltype = AA  length = 109
FEATURE                Location/Qualifiers
source                 1..109
                       mol_type = protein
                       organism = synthetic construct
SEQUENCE: 97
APPVAGPSVF LFPPKPKDTL MISRTPEVTC VVVDVSHEDP EVQFNWYVDG VEVHNAKTKP  60
REEQFNSTFR VVSVLTVVHQ DWLNGKEYKC KVSNKGLPAP IEKTISKTK              109

SEQ ID NO: 98          moltype = AA  length = 110
FEATURE                Location/Qualifiers
source                 1..110
                       mol_type = protein
                       organism = synthetic construct
SEQUENCE: 98
APELLGGPSV FLFPPKPKDT LMISRTPEVT CVVVDVSHED PEVQFKWYVD GVEVHNAKTK  60
PREEQYNSTF RVVSVLTVLH QDWLNGKEYK CKVSNKALPA PIEKTISKTK             110

SEQ ID NO: 99          moltype = AA  length = 110
FEATURE                Location/Qualifiers
source                 1..110
                       mol_type = protein
                       organism = synthetic construct
SEQUENCE: 99
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK             110

SEQ ID NO: 100         moltype = AA  length = 101
FEATURE                Location/Qualifiers
source                 1..101
                       mol_type = protein
                       organism = synthetic construct
SEQUENCE: 100
SVFLFPPKPK DTLMISRTPE VTCVVVDVSH EDPEVKFNWY VDGVEVHNAK TKPREEQYNS  60
TYRVVSVLTV LHQDWLNGKE YKCKVSNKAL PAPIEKTISK A                      101
```

```
SEQ ID NO: 101          moltype = AA  length = 101
FEATURE                Location/Qualifiers
source                 1..101
                       mol_type = protein
                       organism = synthetic construct
SEQUENCE: 101
SVFLFPPKPK DTLMISRTPE VTCVVVDVSQ EDPEVQFNWY VDGVEVHNAK TKPREEQFNS  60
TYRVVSVLTV LHQDWLNGKE YKCKVSNKGL PSSIEKTISK A                      101

SEQ ID NO: 102          moltype = AA  length = 329
FEATURE                Location/Qualifiers
source                 1..329
                       mol_type = protein
                       organism = synthetic construct
SEQUENCE: 102
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGE  120
ESVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 103          moltype = AA  length = 329
FEATURE                Location/Qualifiers
source                 1..329
                       mol_type = protein
                       organism = synthetic construct
SEQUENCE: 103
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGD  120
GSAFLFPPKP KDTLMISRTP EVTCVVVDVS HDEPEVKFNW YVDGVEVHNA KTKPREEQYN  180
STYRVVSVLT VLHQDWLNGK EYKCKVSNKA LPRPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 104          moltype = AA  length = 329
FEATURE                Location/Qualifiers
source                 1..329
                       mol_type = protein
                       organism = synthetic construct
SEQUENCE: 104
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PSVFLFPPKP KDTLMISRTP EVTCVVVDVS DEDGEVKFNW YVDGVEVHNA KTKPREEQYN  180
STYRVVSVLT VLHQDWLNGK EYKCKVSNKA LAAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 105          moltype = AA  length = 5
FEATURE                Location/Qualifiers
source                 1..5
                       mol_type = protein
                       organism = synthetic construct
SEQUENCE: 105
GGGGS                                                              5

SEQ ID NO: 106          moltype = AA  length = 10
FEATURE                Location/Qualifiers
source                 1..10
                       mol_type = protein
                       organism = synthetic construct
SEQUENCE: 106
GGGGSGGGGS                                                         10

SEQ ID NO: 107          moltype = AA  length = 15
FEATURE                Location/Qualifiers
source                 1..15
                       mol_type = protein
                       organism = synthetic construct
SEQUENCE: 107
GGGGSGGGGS GGGGS                                                   15

SEQ ID NO: 108          moltype = AA  length = 20
FEATURE                Location/Qualifiers
source                 1..20
                       mol_type = protein
                       organism = synthetic construct
SEQUENCE: 108
GGGGSGGGGS GGGGSGGGGS                                              20
```

-continued

```
SEQ ID NO: 109          moltype = AA  length = 8
FEATURE                 Location/Qualifiers
source                  1..8
                        mol_type = protein
                        organism = synthetic construct
SEQUENCE: 109
GGGGGGGG                                                                8

SEQ ID NO: 110          moltype = AA  length = 6
FEATURE                 Location/Qualifiers
source                  1..6
                        mol_type = protein
                        organism = synthetic construct
SEQUENCE: 110
GGGGGG                                                                  6

SEQ ID NO: 111          moltype = AA  length = 15
FEATURE                 Location/Qualifiers
source                  1..15
                        mol_type = protein
                        organism = synthetic construct
SEQUENCE: 111
EAAAKEAAAK EAAAK                                                        15

SEQ ID NO: 112          moltype = AA  length = 4
FEATURE                 Location/Qualifiers
source                  1..4
                        mol_type = protein
                        organism = synthetic construct
SEQUENCE: 112
EAAK                                                                    4

SEQ ID NO: 113          moltype = AA  length = 8
FEATURE                 Location/Qualifiers
source                  1..8
                        mol_type = protein
                        organism = synthetic construct
SEQUENCE: 113
EAAKEAAK                                                                8

SEQ ID NO: 114          moltype = AA  length = 12
FEATURE                 Location/Qualifiers
source                  1..12
                        mol_type = protein
                        organism = synthetic construct
SEQUENCE: 114
EAAKEAAKEA AK                                                           12

SEQ ID NO: 115          moltype = AA  length = 46
FEATURE                 Location/Qualifiers
source                  1..46
                        mol_type = protein
                        organism = synthetic construct
SEQUENCE: 115
AEAAAKEAAA KEAAAKEAAA KALEAEAAAK EAAAKEAAAK EAAAKA                      46

SEQ ID NO: 116          moltype = AA  length = 12
FEATURE                 Location/Qualifiers
source                  1..12
                        mol_type = protein
                        organism = synthetic construct
SEQUENCE: 116
AEAAAKEAAA KA                                                           12
```

VARIANT IgG FC POLYPEPTIDES AND USES THEREOF

CROSS-REFERENCE TO RELATED APPLICATIONS

This application is a continuation of U.S. Non-Provisional application Ser. No. 18/494,454, filed Oct. 25, 2023, now U.S. Pat. No. 12,030,945, issued Jul. 9, 2024, which claims priority to U.S. Provisional Application No. 63/380,842, filed Oct. 25, 2022, U.S. Provisional Application No. 63/380,853, filed Oct. 25, 2022, U.S. Provisional Application No. 63/493,356, filed Mar. 31, 2023, and U.S. Provisional Application No. 63/517,493, filed Aug. 3, 2023, each of which is hereby incorporated by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Oct. 25, 2023, is named "SES-005WO_SEQ.XML" and is 132,581 bytes in size.

FIELD

The embodiments provided herein relate to compositions targeting cells to regulate an immune response.

BACKGROUND

FcγRIIβ is the only FcγR expressed on B cells (Smith, K. G. C., and Clatworthy, M. R., Nat Rev Immunol. 2010 May; 10 (5): 328-343). Interaction of the antibody Fc region with FcγRIIβ has been reported to suppress the primary immune response of B cells (Smith, K. G. C., and Clatworthy, M. R., Nat Rev Immunol. 2010 May; 10 (5): 328-343). Furthermore, it is reported that when FcγRIIβ on B cells and a B cell receptor (BCR) are cross-linked via an immune complex in blood, B cell activation is suppressed, and antibody production by B cells is suppressed IgG1, mainly used as a commercially available therapeutic antibody, is known to bind not only to FcγRIIβ, but also strongly to activating FcγR. It may be possible to develop therapeutic antibodies having greater immunosuppressive properties compared with those of IgG1, by utilizing an Fc region with enhanced FcγRIIβ binding, or improved FcγRIIβ-binding selectivity compared with activating FcγR. Accordingly, an antibody having an Fc with improved FcγRIIβ-binding activity is suggested to be promising as a therapeutic agent for inflammatory diseases such as autoimmune diseases. The embodiments provided for herein fulfill these needs as well as others.

SUMMARY

In some embodiments, a variant IgG Fc polypeptide that selectively binds to FcγRIIβ over FcγRIIα, wherein the variant IgG Fc polypeptide comprises a mutation selected from a mutation associated with any of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90, is provided.

In some embodiments, a polypeptide comprising a variant IgG Fc polypeptide that selectively binds to FcγRIIβ over FcγRIIα, wherein the variant IgG Fc polypeptide comprises an amino acid sequence that is at least 80, 85, 86, 87, 88, 89, 90, 91, 92, 93, 94, 95, 96, 97, 98, or 99% identical to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; and an inhibitory receptor effector domain, is provided.

In some embodiments, a polypeptide comprising a variant IgG Fc polypeptide that selectively binds to FcγRIIβ over FcγRIIα, wherein the variant IgG Fc polypeptide comprises an amino acid sequence that is at least 80, 85, 86, 87, 88, 89, 90, 91, 92, 93, 94, 95, 96, 97, 98, or 99% identical to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO:

73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; an inhibitory receptor effector domain; and a FcγRII binding effector domain, is provided.

In some embodiments, a method of treating an autoimmune disorder in a subject is provided, wherein the method comprises administering a variant IgG Fc polypeptide, such as those provided herein, a polypeptide, such as those provided herein, or a pharmaceutical composition comprising the same, to the subject.

In some embodiments, a method of treating a cancer in a subject is provided, wherein the method comprises administering a variant IgG Fc polypeptide, such as those provided herein, a polypeptide, such as those provided herein, or a pharmaceutical composition comprising the same, to the subject.

In some embodiments, a method of modulating the interaction of cells of at least two distinct types is provided, wherein the method comprises administering a variant IgG Fc polypeptide, such as those provided herein, a polypeptide, such as those provided herein, or a pharmaceutical composition comprising the same, to the subject.

In some embodiments, a method of inhibiting an activated immune cell that is in contact with a B cell, an antigen presenting cell (APC), or a myeloid cell is provided, wherein the method comprises administering a variant IgG Fc polypeptide, such as those provided herein, a polypeptide, such as those provided herein, or a pharmaceutical composition comprising the same, to the subject.

In some embodiments, a method of activating or enhancing the behavior of an activated immune cell that is in contact with a B cell, an antigen presenting cell (APC), or a myeloid cell is provided, wherein the method comprises administering a variant IgG Fc polypeptide, such as those provided herein, a polypeptide, such as those provided herein, or a pharmaceutical composition comprising the same, to the subject.

DETAILED DESCRIPTION

Figure 1A:
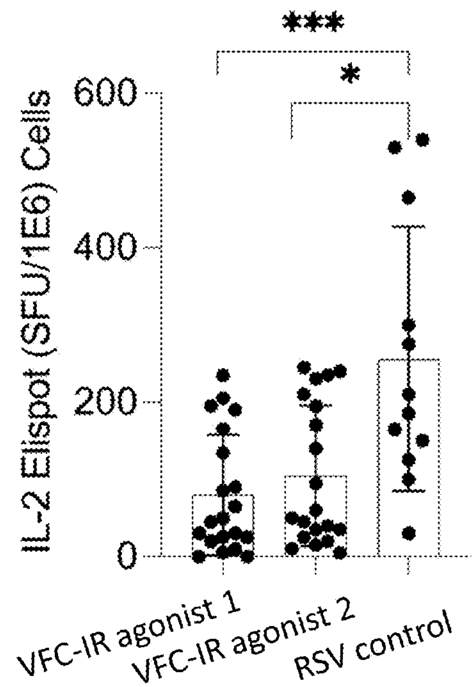
FIG. 1A-1C are bar graphs showing IL-2 (A), IFNg (B), and TNFa (C) production levels following treatment with VFC-IR agonists or control molecules.

This application incorporates by reference U.S. Provisional Application No. 63/380,842, filed Oct. 25, 2022, U.S. Provisional Application No. 63/380,853, filed Oct. 25, 2022, U.S. Provisional Application No. 63/493,356, filed Mar. 31, 2023, and U.S. Provisional Application No. 63/517,493, filed Aug. 3, 2023, each of which is hereby incorporated by reference in its entirety.

As used herein and in the appended claims, the singular forms “a”, “an” and “the” include plural reference unless the context clearly dictates otherwise.

As used herein, the term “about” means that the numerical value is approximate and small variations would not significantly affect the practice of the disclosed embodiments. Where a numerical limitation is used, unless indicated otherwise by the context, “about” means the numerical value can vary by ±5% and remain within the scope of the disclosed embodiments. Thus, about 100 means 95 to 105.

As used herein, the term “animal” includes, but is not limited to, humans and non-human vertebrates such as wild, domestic, and farm animals. As used herein, the term “mammal” means a rodent (i.e., a mouse, a rat, or a guinea pig), a monkey, a cat, a dog, a cow, a horse, a pig, or a human. In some embodiments, the mammal is a human.

As used herein, the term “contacting” means bringing together of two elements in an in vitro system or an in vivo system. For example, “contacting” a therapeutic compound with an individual or patient or cell includes the administration of the compound to an individual or patient, such as a human, as well as, for example, introducing a compound into a sample containing a cellular or purified preparation containing target.

As used herein, the terms “comprising” (and any form of comprising, such as “comprise”, “comprises”, and “comprised”), “having” (and any form of having, such as “have” and “has”), “including” (and any form of including, such as “includes” and “include”), or “containing” (and any form of containing, such as “contains” and “contain”), are inclusive or open-ended and do not exclude additional, unrecited elements or method steps. Any composition or method that recites the term “comprising” should also be understood to also describe such compositions as consisting, consisting of, or consisting essentially of the recited components or elements.

As used herein, the term “fused” or “linked” when used in reference to a protein or molecule having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another.

As used herein, the term “individual,” “subject,” or “patient,” used interchangeably, means any animal, including mammals, such as mice, rats, other rodents, rabbits, dogs, cats, swine, cattle, sheep, horses, or primates, such as humans.

As used herein, the term “inhibit” refers to a result, symptom, or activity being reduced as compared to the activity or result in the absence of the compound that is inhibiting the result, symptom, or activity. In some embodiments, the result, symptom, or activity, is inhibited by about, or, at least, 10%, 20%, 30%, 40%, 50%, 60%, 70%, 80%, 90%, 95%, or 99%. A result, symptom, or activity can also be inhibited if it is completely eliminated or extinguished.

As used herein, the phrase “in need thereof” means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, or condition is prevalent.

As used herein, the phrase “integer from X to Y” means any integer that includes the endpoints. For example, the phrase “integer from 1 to 5” means 1, 2, 3, 4, or 5.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

In some embodiments, the pharmaceutical compositions can be ophthalmically acceptable or suitable for ophthalmic administration.

In some embodiments, the term "therapeutic molecule" can be used interchangeably with "therapeutic compound," "molecule," or "therapeutic," and refers to any polypeptide, or protein described herein.

"Specific binding" or "specifically binds to" or is "specific for" a particular antigen, target, or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen, target, or an epitope can be exhibited, for example, by an antibody having a $K_D$ for an antigen or epitope of at least about $10^{-4M}$, at least about $10^{-5M}$, at least about $10^{-6\ M}$, at least about $10^{-7M}$, at least about $10^{-8M}$, at least about $10^{-9M}$ alternatively at least about $10^{-10\ M}$, at least about $10^{-11M}$, at least about $10_{-12M}$, or greater, where $K_D$ refers to a dissociation rate of a particular antibody-target interaction. Typically, an antibody that specifically binds an antigen or target will have a $K_D$ that is, or at least, 2-, 4-, 5-, 10-, 20-, 50-, 100-, 500-, 1000-, 5,000-, 10,000-, or more times greater for a control molecule relative to the antigen or epitope.

In some embodiments, specific binding for a particular antigen, target, or an epitope can be exhibited, for example, by an antibody having a $K_A$ or $K_a$ for a target, antigen, or epitope of at least 2-, 4-, 5-, 20-, 50-, 100-, 500-, 1000-, 5,000-, 10,000- or more times greater for the target, antigen, or epitope relative to a control, where $K_A$ or $K_a$ refers to an association rate of a particular antibody-antigen interaction.

As provided herein, the compounds and compositions provided for herein can be used in methods of treatment as provided herein. As used herein, the terms "treat," "treated," or "treating" mean both therapeutic treatment and prophylactic measures wherein the object is to slow down (lessen) an undesired physiological condition, disorder or disease, or obtain beneficial or desired clinical results. For purposes of these embodiments, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival, as applicable for a specific disease, as compared to expected survival if not receiving treatment. Thus, "treatment of an autoimmune condition" or "treating autoimmunity" means an activity that alleviates or ameliorates any of the primary phenomena or secondary symptoms associated with the autoimmune condition other condition described herein when the terms "treat," "treated," or "treating" are used in conjunction with such condition.

As used herein, terms "variant," "molecule," "therapeutic," "therapeutic compound," "compound," "polypeptide," or "protein" can be used interchangeably and relate to the variants, molecules, therapeutics, therapeutic compounds, compounds, polypeptides, and proteins disclosed herein.

Variant Fc Molecules

As used herein, "isotype" refers to the immunoglobulin class (e.g., IgG1, IgG2, IgG3, IgG4, IgM, IgA1, IgA2, IgD, and IgE antibody) that is encoded by the heavy chain constant domain genes. The full-length amino acid sequence of each wild type human IgG constant region (including all domains, i.e., CH1 domain, hinge, CH2 domain, and CH3 domain) is cataloged in the UniProt database available on-line, e.g., as P01857 (IgG1), P01859 (IgG2), P01860 (IgG3), and P01861 (IgG4), or different allotypes thereof (SEQ ID NOs: 1, 2, 3, and 4, respectively). As used herein, a domain of a heavy chain constant region, e.g., the hinge, is of an "IgG1 isotype," "IgG2 isotype," "IgG3 isotype," or "IgG4 isotype," if the domain comprises the amino acid sequence of the corresponding domain of the respective isotype, or a variant thereof (that has a higher homology to the corresponding domain of the respective isotype than it does to that of the other isotypes).

As used herein, "variant Fc polypeptide" and "variant IgG Fc polypeptide" refer to the same Fc polypeptide comprising at least one mutation relative to the wild-type isotype amino acid sequence, and thus, the terms "variant Fc polypeptide" and "variant IgG Fc polypeptide" can be used interchangeably.

"Allotype" refers to naturally occurring variants within a specific isotype group, which variants differ in a few amino acids (see, e.g., Jefferies et al. (2009) mAbs 1:1). Molecules described herein may be of any allotype.

A "wild-type" protein or portion thereof is a version of the protein as it is found in nature. An amino acid sequence of a wild-type protein, e.g., a heavy chain constant region, is the amino acid sequence of the protein as it occurs in nature. Due to allotypic differences, there can be more than one amino acid sequence for a wild-type protein. For example, there are several allotypes of naturally occurring human IGg1 heavy chain constant regions (e.g., Jeffries et al. (2009) mAbs 1:1).

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the antibodies described herein are of the human IgG1 or IgG2 subtype. Immunoglobulins, e.g., human IgG1, exist in several allotypes, which differ from each other in at most a few amino acids.

In some embodiments, the IgG proteins (hinge region underlined) are as provided in Table 1.

TABLE 1

| Isotype | Sequence |
|---|---|
| IgG1 | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSCDKTHTCPPCPAPELLGGPSVFLFPPK |

TABLE 1-continued

| Isotype | Sequence |
|---|---|
| | PKDTLMISRTPEVTCVVVDVSHEDPEVKFNWYVDGVEVHNAKT<br>KPREEQYNSTYRVVSVLTVLHQDWLNGKEYKCKVSNKALPAPI<br>EKTISKAKGQPREPQVYTLPPSRDELTKNQVSLTCLVKGFYPS<br>DIAVEWESNGQPENNYKTTPPVLDSDGSFFLYSKLTVDKSRWQ<br>QGNVFSCSVMHEALHNHYTQKSLSLSPGK<br>(SEQ ID NO: 88) |
| IgG2 | ASTKGPSVFPLAPCSRSTSESTAALGCLVKDYFPEPVTVSWNS<br>GALTSGVHTFPAVLQSSGLYSLSSVVTVPSSNFGTQTYTCNVD<br>HKPSNTKVDKTVERKCCVECPPCPAPPVAGPSVFLFPPKPKDT<br>LMISRTPEVTCVVVDVSHEDPEVQFNWYVDGVEVHNAKTKPRE<br>EQFNSTFRVVSVLTVVHQDWLNGKEYKCKVSNKGLPAPIEKTI<br>SKTKGQPREPQVYTLPPSREEMTKNQVSLTCLVKGFYPSDISV<br>EWESNGQPENNYKTTPPMLDSDGSFFLYSKLTVDKSRWQQGNV<br>FSCSVMHEALHNHYTQKSLSLSPGK (SEQ ID NO: 89) |
| IgG3 | ASTKGPSVFPLAPCSRSTSGGTAALGCLVKDYFPEPVTVSWNS<br>GALTSGVHTFPAVLQSSGLYSLSSVVTVPSSSLGTQTYTCNVN<br>HKPSNTKVDKRVELKTPLGDTTHTCPRCPEPKSCDTPPPCPRC<br>PEPKSCDTPPPCPRCPEPKSCDTPPPCPRCPAPELLGGPSVFL<br>FPPKPKDTLMISRTPEVTCVVVDVSHEDPEVQFKWYVDGVEVH<br>NAKTKPREEQYNSTFRVVSVLTVLHQDWLNGKEYKCKVSNKAL<br>PAPIEKTISKTKGQPREPQVYTLPPSREEMTKNQVSLTCLVKG<br>FYPSDIAVEWESSGQPENNYNTTPPMLDSDGSFFLYSKLTVDK<br>SRWQQGNIFSCSVMHEALHNRFTQKSLSLSPGK<br>(SEQ ID NO: 90) |
| IgG4 | ASTKGPSVFPLAPCSRSTSESTAALGCLVKDYFPEPVTVSWNS<br>GALTSGVHTFPAVLQSSGLYSLSSVVTVPSSSLGTKTYTCNVD<br>HKPSNTKVDKRVESKYGPPCPSCPAPEFLGGPSVFLFPPKPKD<br>TLMISRTPEVTCVVVDVSQEDPEVQFNWYVDGVEVHNAKTKPR<br>EEQFNSTYRVVSVLTVLHQDWLNGKEYKCKVSNKGLPSSIEKT<br>ISKAKGQPREPQVYTLPPSQEEMTKNQVSLTCLVKGFYPSDIA<br>VEWESNGQPENNYKTTPPVLDSDGSFFLYSRLTVDKSRWQEGN<br>VFSCSVMHEALHNHYTQKSLSLSLGK (SEQ ID NO: 91) |

An “Fc region” (fragment crystallizable region) or “Fc domain” or “Fc” refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region of an antibody of isotype IgG comprises the heavy chain constant region of the antibody excluding the first constant region immunoglobulin domain (CH1). In IgG, IgA and IgD antibody isotypes, the Fc region comprises CH2 and CH3 constant domains in each of the antibody’s two heavy chains; IgM and IgE Fc regions comprise three heavy chain constant domains (CH domains 2-4) in each polypeptide chain. For IgG, the Fc region comprises immunoglobulin domains consisting of the hinge, CH2 and CH3. For purposes herein, the Fc region is defined as starting at amino acid 216 and ending at amino acid 447, wherein the numbering is according to the EU index as in Kabat. Kabat et al. (1991) Sequences of Proteins of Immunological Interest, National Institutes of Health, Bethesda, MD, and according to FIGS. 3*c*-3*f* of U.S. Pat. App. Pub. No. 2008/0248028, which can be referred to as EU numbering. In some embodiments, the Fc region comprises the hinge region. The Fc may be a native (or naturally-occurring or wild-type) Fc, including any allotypic variant, or a variant Fc (e.g., a non-naturally occurring Fc), comprising, e.g., 1, 2, 3, 4, 5, 1-5, 1-10 or 5-10 or more amino acid mutations, e.g., substitutions, additions or deletions. For example, a variant Fc may comprise an amino acid sequence that is at least 75%, 80%, 85%, 90%, 95%, 96%, 97%, 98% or 99% identical to a wild-type Fc. Modified or mutated Fcs may have enhanced or reduced effector function and/or half-life. Fc may refer to this region in isolation or in the context of an Fc-comprising protein polypeptide such as a “binding protein comprising an Fc region,” also referred to as an “Fc fusion protein” (e.g., an antibody or immunoadhesin). In some embodiments, modified or variant Fc molecules have enhanced binding to FcγRIIb.

A “hinge”, “hinge domain” or “hinge region” or “antibody hinge region” refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. The term “hinge” includes wild-type hinges, as well as variants thereof (e.g., non-naturally-occurring hinges or modified hinges). For example, the term “IgG1 hinge” includes wild-type IgG1 hinge, as shown below, and variants having 1, 2, 3, 4, 5, 1-3, 1-5, 3-5 and/or at most 5, 4, 3, 2, or 1 mutations, e.g., substitutions, deletions or additions. In some embodiments, the hinge regions are as provided in Table 2.

TABLE 2

| Isotype | Hinge Sequence |
|---|---|
| IgG1 | EPKSCDKTHTCPPCPAPELLGGP (SEQ ID NO: 92) |
| IgG2 | ELKTPLGDTTHTCPRCPAPELLGGP (SEQ ID NO: 93) |
| IgG3 | ELKTPLGDTTHTCPRCPEPKSCDTPPPCPRCPEPKSCDTPPPC<br>PRCPEPKSCDTPPPCPRCPAPELLGGP (SEQ ID NO: 94) |
| IgG4 | ESKYGPPCPSCPAPEFLGGP (SEQ ID NO: 95) |

The term “CH1 domain” refers to the heavy chain constant region linking the variable domain to the hinge in a heavy chain constant domain. As used herein, a CH1 domain includes wild type CH1 domains, as well as variants thereof (e.g., non-naturally-occurring CH1 domains or modified CH1 domains). As used herein, CH1 domain includes amino acid residues 1-98 of IgG1; 1-98 of IgG2; 1-98 of IgG3; and 1-98 of IgG4. For example, the term “CH1 domain” includes wild-type CH1 domains and variants thereof having 1, 2, 3, 4, 5, 1-3, 1-5, 3-5 and/or at most 5, 4, 3, 2, or 1 mutations, e.g., substitutions, deletions or additions.

The term “CH2 domain” refers to the heavy chain constant region linking the hinge to the CH3 domain in a heavy chain constant domain. As used herein, a CH2 domain includes wild-type CH2 domains, as well as variants thereof (e.g., non-naturally-occurring CH2 domains or modified CH2 domains). As used herein, CH2 domain includes amino acid residues 111-223 of IgG1; 111-219 of IgG2; 161-270 of IgG3; and 111-220 of IgG4. For example, the term “CH2 domain” includes wild-type CH2 domains and variants thereof having 1, 2, 3, 4, 5, 1-3, 1-5, 3-5 and/or at most 5, 4, 3, 2, or 1 mutations, e.g., substitutions, deletions or additions.

The term “CH3 domain” refers to the heavy chain constant region that is C-terminal to the CH2 domain in a heavy chain constant domain. As used herein, a CH3 domain includes wild-type CH3 domains, as well as variants thereof (e.g., non-naturally-occurring CH3 domains or modified CH3 domains). As used herein, CH3 domain includes amino acid residues 224-330 of IgG1; 220-326 of IgG2; 271-376 of IgG3; and 226-322 of IgG4. For example, the term “CH3 domain” includes wild-type CH3 domains and variants thereof having 1, 2, 3, 4, 5, 1-3, 1-5, 3-5 and/or at most 5, 4, 3, 2, or 1 mutations, e.g., substitutions, deletions or additions.

In some embodiments, the hinge/CH2 domain has an amino acid sequence such as those provided in Table 3 below.

TABLE 3

| Isotype | Hinge/CH2 Sequence |
|---|---|
| IgG1 | PCPAPELLGGPSVFLFPPKPKDTLMISRTPEVTCVVVDVSHED PEVKFNWYVDGVEVHNAKTKPREEQYNSTYRVVSVLTVLHQDW LNGKEYKCKVSNKALPAPIEKTISKAK (SEQ ID NO: 96) |
| IgG2 | APPVAGPSVFLFPPKPKDTLMISRTPEVTCVVVDVSHEDPEVQ FNWYVDGVEVHNAKTKPREEQFNSTFRVVSVLTVVHQDWLNGK EYKCKVSNKGLPAPIEKTISKTK (SEQ ID NO: 97) |
| IgG3 | APELLGGPSVFLFPPKPKDTLMISRTPEVTCVVVDVSHEDPEV QFKWYVDGVEVHNAKTKPREEQYNSTFRVVSVLTVLHQDWLNG KEYKCKVSNKALPAPIEKTISKTK (SEQ ID NO: 98) |
| IgG4 | APEFLGGPSVFLFPPKPKDTLMISRTPEVTCVVVDVSQEDPEV QFNWYVDGVEVHNAKTKPREEQFNSTYRVVSVLTVLHQDWLNG KEYKCKVSNKGLPSSIEKTISKAK (SEQ ID NO: 99) |

Without being bound to a particular theory, mutation, or isotype swapping, of the entire hinge region or CH2 region, or certain portions of a hinge region or CH2 region in an IgG1 results in the modified IgG1 having enhanced or altered properties relative to the IgG1 with a wild-type IgG1 constant region. For example, IgG1 can have residues 111-223 replaced with residues 111-220 of IgG4. Other non-limiting examples include IgG1 having at least 50%, at least 60%, at least 70%, at least 75%, at least 80%, at least 85%, at least 90%, at least 95%, or 100% residues 111-223 replaced with at least 50%, at least 60%, at least 70%, at least 75%, at least 80%, at least 85%, at least 90%, at least 95%, or 100% residues 111-220 of IgG4.

In some embodiments, a variant Fc molecule is a hybrid Fc molecule that comprises sequences from at least two IgG isotypes. For example, a variant Fc molecule may comprise the CH2 or CH3 region from one or more other isotypes. For example, a variant Fc can be an IgG1/IgG4 Fc molecule.

In some embodiments, a variant Fc comprises a CH2 region swapped from another IgG isotype. Examples of CH2 regions include, but are not limited to:

(IgG1 CH2, SEQ ID NO: 100)
SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

A;
or (IgG4 CH2, SEQ ID NO: 101)
SVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISK

A.

Provided herein are variant Fc molecules comprising variant Fc domains. Exemplary variant Fc molecules comprising variant Fc domains include an IgG1 hinge, a CH1 domain, a CH2 domain and a CH3 domain, wherein at least one amino acid residue is mutated, wherein the mutation is a substitution, an insertion, or a deletion. In some embodiments, the insertion can be 1-5 residues. In some embodiments, a variant Fc molecule comprises an IgG1 hinge and IgG4 CH2 domain. In some embodiments, a variant Fc molecule comprises a mutated IgG1 hinge and IgG4 CH2 domain. A variant Fc molecule may have effector function similar to that of wild-type IgG, or may be engineered to have enhanced effector function relative to that of the wild-type IgG. In some embodiments, a variant Fc molecule may have FcγRIIβ binding affinity similar to that of wild-type IgG. In some embodiments, a variant Fc molecule may have FcγRIIβ binding affinity that is enhanced to that of wild-type IgG. A variant Fc molecule may comprise a wild-type CH1, hinge, CH2 and/or CH3 domain, or a variant thereof, e.g., a CH1, hinge, CH2 and/or CH3 domain having one or more amino acid substitutions, deletions or additions relative to the corresponding wild-type domain, and/or having an amino acid sequence that is at least 70%, at least 75&, at least 80%, at least 85%, at least 90%, at least 91%, at least 92%, at least 93%, at least 94%, at least 95%, at least 96%, at least 97%, at least 98%, or at least 99% identical, or more, to the corresponding wild-type sequence.

In some embodiments, a variant Fc molecule comprises a mutation that confers selective binding to FcγRIIβ over FcγRIIα. As used herein, in reference to FcγRIIβ, the term "selective binding" means that the Fc domain binds preferentially to FcγRIIβ over FcγRIIα, that is with a higher affinity to FcγRIIβ over FcγRIIα. Examples of such mutations are provided for in, for example, U.S. Pat. Nos. 7,662,926, 7,655,229, US 2009/0087428, U.S. Pat. No. 10,919,952, US 2007/0253948, and US 2006/0073142, each of which is hereby incorporated by reference in its entirety, including the specific mutations that are descried that affect FcγRIIβ binding. In some embodiments, the mutation is as described in Shields et al., J. Biol. Chem. 2001, 276:6591-6604, which is hereby incorporated by reference in its entirety.

In some embodiments, the Fc mutation is as described in U.S. Pat. No. 10,618,965; EP Serial No. 2679681; EP Serial No. 3604330, US 2014/0093496, US 2015/0203577, U.S. Pat. No. 9,540,451, EP Serial No. 2331578; EP Serial No. 3190128; U.S. Pat. No. 9,902,773; EP. Serial No. 3342782, U.S. Publication No. 2020/0332024; EP Serial No. 2796469; EP Serial No. 2331578; EP Serial No. 3190128; U.S. Pat. No. 9,902,773, EP Serial No. 2331578; EP Serial No. 3190128, U.S. Pat. Nos. 9,493,578, 9,394,366, 9,914,778, EP Serial No. 2940043, U.S. Pat. No. 9,890,218, EP Serial No. 2940135; U.S. Pat. Nos. 10,766,960, 10,919,953, EP 3721900, EP2889377, US 2016/0039912, EP 2982689, or EP 3783017, each of which is hereby incorporated by reference in its entirety, including the specific mutations that are descried that affect the FcγRIIb or FcγRIIa binding.

In some embodiments, the Fc polypeptide comprises a mutation, mutations, or a mutation set that increases selectivity for FcγRIIb. In some embodiments, the Fc polypeptide comprises a mutation, mutations, or a mutation set that increases affinity for FcγRIIb. In some embodiments, the Fc polypeptide comprises a mutation, mutations, or a mutation set that increases selectivity and affinity for FcγRIIb. In some embodiments, the Fc polypeptide comprises a mutation, mutations, or a mutation set that increases selectivity for FcγRIIb over FcγRIIa. In some embodiments, the Fc polypeptide comprises a mutation, mutations, or a mutation set that increases affinity for FcγRIIb over FcγRIIa. In some embodiments, the Fc polypeptide comprises a mutation, mutations, or a mutation set that increases selectivity and affinity for FcγRIIb over FcγRIIa. In some embodiments, the mutation, mutations, or the mutation set is such as those described herein.

In some embodiments, a variant Fc domain comprises a mutation that corresponds to a mutation at position 226, 227, 228, 229, 230, 231, 232, 233, 234, 235, 236, 237, 238, or any combination thereof, according to SEQ ID NO: 88, wherein the mutation is an insertion, a deletion, or a substitution. In some embodiments, a variant Fc domain comprises a mutation that corresponds to a mutation at position 226 according to SEQ ID NO: 88. In some embodiments, a variant Fc domain comprises a mutation that corresponds to a mutation at position 227 according to SEQ ID NO: 88. In some embodiments, a variant Fc domain comprises a mutation that corresponds to a mutation at position 228 according to SEQ ID NO: 88. In some embodiments, a variant Fc domain comprises a mutation that corresponds to a mutation at position 229 according to SEQ ID NO: 88. In some embodiments, a variant Fc domain comprises a mutation that corresponds to a mutation at position 230 according to SEQ ID NO: 88. In some embodiments, a variant Fc domain comprises a mutation that corresponds to a mutation at position 231 according to SEQ ID NO: 88. In some embodiments, a variant Fc domain comprises a mutation that corresponds to a mutation at position 232 according to SEQ ID NO: 88. In some embodiments, a variant Fc domain comprises a mutation that corresponds to a mutation at position 233 according to SEQ ID NO: 88. In some embodiments, a variant Fc domain comprises a mutation that corresponds to a mutation at position 234 according to SEQ ID NO: 88. In some embodiments, a variant Fc domain comprises a mutation that corresponds to a mutation at position 235 according to SEQ ID NO: 88. In some embodiments, a variant Fc domain comprises a mutation that corresponds to a mutation at position 236 according to SEQ ID NO: 88. In some embodiments, a variant Fc domain comprises a mutation that corresponds to a mutation at position 237 according to SEQ ID NO: 88. In some embodiments, a variant Fc domain comprises a mutation that corresponds to a mutation at position 238 according to SEQ ID NO: 88. In some embodiments, a variant Fc domain comprises a mutation that corresponds to a mutation at position 228, 234, 235, or any combination thereof, according to SEQ ID NO: 88, and wherein the mutation is an insertion, a deletion, or a substitution. In some embodiments, a variant Fc domain comprises a mutation that corresponds to a mutation at position 228 and 234 according to SEQ ID NO: 88. In some embodiments, a variant Fc domain comprises a mutation that corresponds to a mutation at position 228 and 235 according to SEQ ID NO: 88. In some embodiments, a variant Fc domain comprises a mutation that corresponds to a mutation at position 234 and 235 according to SEQ ID NO: 88.

In some embodiments, a variant Fc domain comprises a mutation that corresponds to a mutation at position 226, 227, 228, 229, 230, 231, 232, 233, 234, 235, 236, 237, 238, 268, 274, 276, 296, 300, 309, 327, 330, 331, 339, or any combination thereof, according to SEQ ID NO: 88, wherein the mutation is an insertion, a deletion, or a substitution. In some embodiments, a variant Fc domain comprises a mutation that corresponds to a mutation at position 228, 234, 235, 268, 274, 276, 296, 300, 309, 327, 330, 331, 339, or any combination thereof, according to SEQ ID NO: 88, wherein the mutation is an insertion, a deletion, or a substitution. In some embodiments, a variant Fc domain comprises a mutation that corresponds to a mutation at position 228, 234, 235, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 228, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 228, 234, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 228, 235, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 235, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 234, 235, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 234, 268, 274, 296, 327, 330, 331, or any combination thereof, according to SEQ ID NO: 88, wherein the mutation is an insertion, a deletion, or a substitution. In some embodiments, a variant Fc domain comprises a mutation that corresponds to a mutation at position 237, 238, or any combination thereof, according to SEQ ID NO: 88, wherein the mutation is an insertion, a deletion, or a substitution.

In some embodiments, a variant Fc domain comprises a mutation that corresponds to a mutation at position C226, P227, P228, C229, P230, A231, P232, E233, L234, L235, G236, G237, P238, or any combination thereof, according to SEQ ID NO: 88, wherein the mutation is an insertion, a deletion, or a substitution. In some embodiments, a variant Fc domain comprises a mutation that corresponds to a mutation at position C226 according to SEQ ID NO: 88. In some embodiments, a variant Fc domain comprises a mutation that corresponds to a mutation at position P227 according to SEQ ID NO: 88. In some embodiments, a variant Fc domain comprises a mutation that corresponds to a mutation at position P228 according to SEQ ID NO: 88. In some embodiments, a variant Fc domain comprises a mutation that corresponds to a mutation at position C229 according to SEQ ID NO: 88. In some embodiments, a variant Fc domain comprises a mutation that corresponds to a mutation at position P230 according to SEQ ID NO: 88. In some embodiments, a variant Fc domain comprises a mutation that corresponds to a mutation at position A231 according to SEQ ID NO: 88. In some embodiments, a variant Fc domain comprises a mutation that corresponds to a mutation at position P232 according to SEQ ID NO: 88. In some embodiments, a variant Fc domain comprises a mutation that corresponds to a mutation at position E233 according to SEQ ID NO: 88. In some embodiments, a variant Fc domain comprises a mutation that corresponds to a mutation at position L234 according to SEQ ID NO: 88. In some embodiments, a variant Fc domain comprises a mutation that corresponds to a mutation at position L235 according to SEQ ID NO: 88. In some embodiments, a variant Fc domain comprises a mutation that corresponds to a mutation at position G236 according to SEQ ID NO: 88. In some embodiments, a variant Fc domain comprises a mutation that corresponds to a mutation at position G237 according to SEQ ID NO: 88. In some embodiments, a variant Fc domain comprises a mutation that corresponds to a mutation at position P238 according to SEQ ID NO: 88. In some embodiments, a variant Fc domain comprises a mutation that corresponds to a mutation at position P228, L234, L235, or any combination thereof, according to SEQ ID NO: 88, and wherein the mutation is an insertion, a deletion, or a substitution. In some embodiments, a variant Fc domain comprises a mutation that corresponds to a mutation at position P228 and L234 according to SEQ ID NO: 88. In some embodiments, a variant Fc domain comprises a mutation that corresponds to a mutation at position P228 and L235 according to SEQ ID NO: 88. In some embodiments, a variant Fc domain comprises a mutation that corresponds to a mutation at position L234 and L235 according to SEQ ID NO: 88. In some embodiments, a variant Fc domain comprises a mutation that corresponds to a mutation at position G237 and P238 according to SEQ ID NO: 88.

In some embodiments, a variant Fc domain comprises a mutation that corresponds to a mutation at position C226, P227, P228, C229, P230, A231, P232, E233, L234, L235, G236, G237, P238, H268, K274, N276, Y296, Y300, L309, A327, A330, P331, A339, or any combination thereof, according to SEQ ID NO: 88, wherein the mutation is an insertion, a deletion, or a substitution. In some embodiments, a variant Fc domain comprises a mutation that corresponds to a mutation at position P228, L234, L235, H268, K274, N276, Y296, Y300, L309, A327, A330, P331, A339, or any combination thereof, according to SEQ ID NO: 88, wherein the mutation is an insertion, a deletion, or a substitution. In some embodiments, a variant Fc domain comprises a mutation that corresponds to a mutation at position P228, L234, L235, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, L234, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, L235, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position L235, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position L234, L235, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position L234, H268, K274, Y296, A327, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, L234, L235, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, L234, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position P228, L235, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position L235, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position L234, L235, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position L234, H268, K274, Y296, A330, P331, or any combination thereof, according to SEQ ID NO: 88, wherein the mutation is an insertion, a deletion, or a substitution. In some embodiments, a variant Fc domain comprises a mutation that corresponds to a mutation at position G237, P238, or any combination thereof, according to SEQ ID NO: 88, wherein the mutation is an insertion, a deletion, or a substitution.

In some embodiments, a variant Fc domain comprises a mutation that corresponds to a mutation of S228P, L234F, L235E, H268Q, K274Q, N276K, Y296F, Y300F, L309V, A327G, A330S, P331S, A339T, or any combination thereof, according to SEQ ID NO: 88. In some embodiments, a variant Fc domain comprises a mutation that corresponds to a mutation of S228P, L234F, L235E, H268Q, K274Q, Y296F, A327G, A330S, P331S, or any combination thereof, according to SEQ ID NO: 88. In some embodiments, a variant Fc domain comprises a mutation that corresponds to a mutation at position S228P according to SEQ ID NO: 88. In some embodiments, a variant Fc domain comprises a mutation that corresponds to a mutation at position L234F according to SEQ ID NO: 88. In some embodiments, a variant Fc domain comprises a mutation that corresponds to a mutation at position L235E according to SEQ ID NO: 88. In some embodiments, a variant Fc domain comprises a mutation that corresponds to a mutation at position S228P and L234F according to SEQ ID NO: 88. In some embodiments, a variant Fc domain comprises a mutation that corresponds to a mutation at position S228P and L235E according to SEQ ID NO: 88. In some embodiments, a variant Fc domain comprises a mutation that corresponds to a mutation at position L234F and L235E according to SEQ ID NO: 88. In some embodiments, a variant Fc domain comprises a mutation that corresponds to a mutation of S228P, H268Q, K274Q, Y296F, A327G, A330S, P331S, or any combination thereof, according to SEQ ID NO: 88. In some embodiments, a variant Fc domain comprises a mutation that corresponds to a mutation of S228P, L234F, H268Q, K274Q, Y296F, A327G, A330S, P331S, or any combination thereof, according to SEQ ID NO: 88. In some embodiments, a variant Fc domain comprises a mutation that corresponds to a mutation of S228P, L235E, H268Q, K274Q, Y296F, A327G, A330S, P331S, or any combination thereof, according to SEQ ID NO: 88. In some embodiments, a variant Fc domain comprises a mutation that corresponds to a mutation of L235E, H268Q, K274Q, Y296F, A327G, A330S, P331S, or any combination thereof, according to SEQ ID NO: 88. In some embodiments, a variant Fc domain comprises a mutation that corresponds to a mutation of L234F, L235E, H268Q, K274Q, Y296F, A327G, A330S, P331S, or any combination thereof, according to SEQ ID NO: 88. In some embodiments, a variant Fc domain comprises a mutation that corresponds to a mutation of L234F, H268Q, K274Q, Y296F, A327G, A330S, P331S, or any combination thereof, according to SEQ ID NO: 88. In some embodiments, a variant Fc domain comprises a mutation that corresponds to a mutation of S228P, L234F, L235E, H268Q, K274Q, Y296F, A330S, P331S, or any combination thereof, according to SEQ ID NO: 88. In some embodiments, a variant Fc domain comprises a mutation that corresponds to a mutation of S228P, H268Q, K274Q, Y296F, A330S, P331S, or any combination thereof, according to SEQ ID NO: 88. In some embodiments, a variant Fc domain comprises a mutation that corresponds to a mutation of S228P, L234F, H268Q, K274Q, Y296F, A330S, P331S, or any combination thereof, according to SEQ ID NO: 88. In some embodiments, a variant Fc domain comprises a mutation that corresponds to a mutation of S228P, L235E, H268Q, K274Q, Y296F, A330S, P331S, or any combination thereof, according to SEQ ID NO: 88. In some embodiments, a variant Fc domain comprises a mutation that corresponds to a mutation of L235E, H268Q, K274Q, Y296F, A330S, P331S, or any combination thereof, according to SEQ ID NO: 88. In some embodiments, a variant Fc domain comprises a mutation that corresponds to a mutation of L234F, L235E, H268Q, K274Q, Y296F, A330S, P331S, or any combination thereof, according to SEQ ID NO: 88. In some embodiments, a variant Fc domain comprises a mutation that corresponds to a mutation of L234F, H268Q, K274Q, Y296F, A330S, P331S, or any combination thereof, according to SEQ ID NO: 88.

In some embodiments, a variant IgG2 Fc domain comprises a mutation that corresponds to a mutation at position 226, 227, 228, 229, 230, 231, 232, 233, 234, 235, 236, 237, 238, or any combination thereof, according to SEQ ID NO: 89, and wherein the mutation is an insertion, a deletion, or a substitution. In some embodiments, a variant IgG2 Fc domain comprises a mutation that corresponds to a mutation at position 226 according to SEQ ID NO: 89. In some embodiments, a variant IgG2 Fc domain comprises a mutation that corresponds to a mutation at position 227 according to SEQ ID NO: 89. In some embodiments, a variant IgG2 Fc domain comprises a mutation that corresponds to a mutation at position 228 according to SEQ ID NO: 89. In some embodiments, a variant IgG2 Fc domain comprises a mutation that corresponds to a mutation at position 229 according to SEQ ID NO: 89. In some embodiments, a variant IgG2 Fc domain comprises a mutation that corresponds to a mutation at position 230 according to SEQ ID NO: 89. In some embodiments, a variant IgG2 Fc domain comprises a mutation that corresponds to a mutation at position 231 according to SEQ ID NO: 89. In some embodiments, a variant IgG2 Fc domain comprises a mutation that corresponds to a mutation at position 232 according to SEQ ID NO: 89. In some embodiments, a variant IgG2 Fc domain comprises a mutation that corresponds to a mutation at position 233 according to SEQ ID NO: 89. In some embodiments, a variant IgG2 Fc domain comprises a mutation that corresponds to a mutation at position 234 according to SEQ ID NO: 89. In some embodiments, a v IgG2 Fc domain comprises a mutation that corresponds to a mutation at position 235 according to SEQ ID NO: 89. In some embodiments, a variant IgG2 Fc domain comprises a mutation that corresponds to a mutation at position 236 according to SEQ ID NO: 89. In some embodiments, a variant IgG2 Fc domain comprises a mutation that corresponds to a mutation at position 237 according to SEQ ID NO: 89. In some embodiments, a variant IgG2 Fc domain comprises a mutation that corresponds to a mutation at position 238 according to SEQ ID NO: 89. In some embodiments, a variant IgG2 Fc domain comprises a mutation that corresponds to a mutation at position 228, 234, 235, or any combination thereof, according to SEQ ID NO: 89, and wherein the mutation is an insertion, a deletion, or a substitution. In some embodiments, a variant IgG2 Fc domain comprises a mutation that corresponds to a mutation at position 228 and 234 according to SEQ ID NO: 89. In some embodiments, a variant IgG2 Fc domain comprises a mutation that corresponds to a mutation at position 228 and 235 according to SEQ ID NO: 89. In some embodiments, a variant IgG2 Fc domain comprises a mutation that corresponds to a mutation at position 234 and 235 according to SEQ ID NO: 89.

In some embodiments, a variant IgG3 Fc domain comprises a mutation that corresponds to a mutation at position 226, 227, 228, 229, 230, 231, 232, 233, 234, 235, 236, 237, 238, 268, 274, 276, 296, 300, 309, 327, 330, 331, 339, or any combination thereof, according to SEQ ID NO: 90, and wherein the mutation is an insertion, a deletion, or a substitution. In some embodiments, a variant IgG3 Fc domain comprises a mutation that corresponds to a mutation at position 226 according to SEQ ID NO: 90. In some embodiments, a variant IgG3 Fc domain comprises a mutation that corresponds to a mutation at position 227 according to SEQ ID NO: 90. In some embodiments, a variant IgG3 Fc domain comprises a mutation that corresponds to a mutation at position 228 according to SEQ ID NO: 90. In some embodiments, a variant IgG3 Fc domain comprises a mutation that corresponds to a mutation at position 229 according to SEQ ID NO: 90. In some embodiments, a variant IgG3 Fc domain comprises a mutation that corresponds to a mutation at position 230 according to SEQ ID NO: 90. In some embodiments, a variant IgG3 Fc domain comprises a mutation that corresponds to a mutation at position 231 according to SEQ ID NO: 90. In some embodiments, a variant IgG3 Fc domain comprises a mutation that corresponds to a mutation at position 232 according to SEQ ID NO: 90. In some embodiments, a variant IgG3 Fc domain comprises a mutation that corresponds to a mutation at position 233 according to SEQ ID NO: 90. In some embodiments, a variant IgG3 Fc domain comprises a mutation that corresponds to a mutation at position 234 according to SEQ ID NO: 90. In some embodiments, a variant IgG3 Fc domain comprises a mutation that corresponds to a mutation at position 235 according to SEQ ID NO: 90. In some embodiments, a variant IgG3 Fc domain comprises a mutation that corresponds to a mutation at position 236 according to SEQ ID NO: 90. In some embodiments, a variant IgG3 Fc domain comprises a mutation that corresponds to a mutation at position 237 according to SEQ ID NO: 90. In some embodiments, a variant IgG3 Fc domain comprises a mutation that corresponds to a mutation at position 238 according to SEQ ID NO: 90. In some embodiments, a variant IgG3 Fc domain comprises a mutation that corresponds to a mutation at position 228, 234, 235, or any combination thereof, according to SEQ ID NO: 90, and wherein the mutation is an insertion, a deletion, or a substitution. In some embodiments, a variant IgG3 Fc domain comprises a mutation that corresponds to a mutation at position 228 and 234 according to SEQ ID NO: 90. In some embodiments, a variant IgG3 Fc domain comprises a mutation that corresponds to a mutation at position 228 and 235 according to SEQ ID NO: 90. In some embodiments, a variant IgG3 Fc domain comprises a mutation that corresponds to a mutation at position 234 and 235 according to SEQ ID NO: 90.

In some embodiments, a variant Fc domain comprises a mutation that corresponds to a mutation at position 226, 227, 228, 229, 230, 231, 232, 233, 234, 235, 236, 237, 238, 268, 274, 276, 296, 300, 309, 327, 330, 331, 339, or any combination thereof, according to SEQ ID NO: 91, wherein the mutation is an insertion, a deletion, or a substitution. In some embodiments, a variant Fc domain comprises a mutation that corresponds to a mutation at position 226 according to SEQ ID NO: 91. In some embodiments, a variant Fc domain comprises a mutation that corresponds to a mutation at position 227 according to SEQ ID NO: 91. In some embodiments, a variant Fc domain comprises a mutation that corresponds to a mutation at position 228 according to SEQ ID NO: 91. In some embodiments, a variant Fc domain comprises a mutation that corresponds to a mutation at position 229 according to SEQ ID NO: 91. In some embodiments, a variant Fc domain comprises a mutation that corresponds to a mutation at position 230 according to SEQ ID NO: 91. In some embodiments, a variant Fc domain comprises a mutation that corresponds to a mutation at position 231 according to SEQ ID NO: 91. In some embodiments, a variant Fc domain comprises a mutation that corresponds to a mutation at position 232 according to SEQ ID NO: 91. In some embodiments, a variant Fc domain comprises a mutation that corresponds to a mutation at position 233 according to SEQ ID NO: 91. In some embodiments, a variant Fc domain comprises a mutation that corresponds to a mutation at position 234 according to SEQ ID NO: 91. In some embodiments, a variant Fc domain comprises a mutation that corresponds to a mutation at position 235 according to SEQ ID NO: 91. In some embodiments, a variant Fc domain comprises a mutation that corresponds to a mutation at position 236 according to SEQ ID NO: 91. In some embodiments, a variant Fc domain comprises a mutation that corresponds to a mutation at position 237 according to SEQ ID NO: 91. In some embodiments, a variant Fc domain comprises a mutation that corresponds to a mutation at position 238 according to SEQ ID NO: 91. In some embodiments, a variant Fc domain comprises a mutation that corresponds to a mutation at position 228, 234, 235, or any combination thereof, according to SEQ ID NO: 91, and wherein the mutation is an insertion, a deletion, or a substitution. In some embodiments, a variant Fc domain comprises a mutation that corresponds to a mutation at position 228 and 234 according to SEQ ID NO: 91. In some embodiments, a variant Fc domain comprises a mutation that corresponds to a mutation at position 228 and 235 according to SEQ ID NO: 91. In some embodiments, a variant Fc domain comprises a mutation that corresponds to a mutation at position 234 and 235 according to SEQ ID NO: 91. In some embodiments, a variant Fc domain comprises a mutation that corresponds to a mutation at position 237 and 238 according to SEQ ID NO: 91.

In some embodiments, a variant Fc domain comprises a mutation that corresponds to a mutation at position 226, 227, 228, 229, 230, 231, 232, 233, 234, 235, 236, 237, 238, 268, 274, 276, 296, 300, 309, 327, 330, 331, 339, or any combination thereof, according to SEQ ID NO: 91, wherein the mutation is an insertion, a deletion, or a substitution. In some embodiments, a variant Fc domain comprises a mutation that corresponds to a mutation at position 228, 234, 235, 268, 274, 276, 296, 300, 309, 327, 330, 331, 339, or any combination thereof, according to SEQ ID NO: 91, wherein the mutation is an insertion, a deletion, or a substitution. In some embodiments, a variant Fc domain comprises a mutation that corresponds to a mutation at position 228, 234, 235, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 228, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 228, 234, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 228, 235, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 235, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 234, 235, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 234, 268, 274, 296, 327, 330, 331, or any combination thereof, according to SEQ ID NO: 91, wherein the mutation is an insertion, a deletion, or a substitution. In some embodiments, a variant Fc domain comprises a mutation that corresponds to a mutation at position 237, 238, or any combination thereof, according to SEQ ID NO: 91, wherein the mutation is an insertion, a deletion, or a substitution.

In some embodiments, a variant Fc domain comprises a mutation that corresponds to a mutation at position C226, P227, S228, C229, P230, A231, P232, E233, F234, L235, G236, G237, P238, or any combination thereof, according to SEQ ID NO: 91, wherein the mutation is an insertion, a deletion, or a substitution. In some embodiments, a variant Fc domain comprises a mutation that corresponds to a mutation at position C226 according to SEQ ID NO: 91. In some embodiments, a variant Fc domain comprises a mutation that corresponds to a mutation at position P227 according to SEQ ID NO: 91. In some embodiments, a variant Fc domain comprises a mutation that corresponds to a mutation at position S228 according to SEQ ID NO: 91. In some embodiments, a variant Fc domain comprises a mutation that corresponds to a mutation at position C229 according to SEQ ID NO: 91. In some embodiments, a variant Fc domain comprises a mutation that corresponds to a mutation at position P230 according to SEQ ID NO: 91. In some embodiments, a variant Fc domain comprises a mutation that corresponds to a mutation at position A231 according to SEQ ID NO: 91. In some embodiments, a variant Fc domain comprises a mutation that corresponds to a mutation at position P232 according to SEQ ID NO: 91. In some embodiments, a variant Fc domain comprises a mutation that corresponds to a mutation at position E233 according to SEQ ID NO: 91. In some embodiments, a variant Fc domain comprises a mutation that corresponds to a mutation at position F234 according to SEQ ID NO: 91. In some embodiments, a variant Fc domain comprises a mutation that corresponds to a mutation at position L235 according to SEQ ID NO: 91. In some embodiments, a variant Fc domain comprises a mutation that corresponds to a mutation at position G236 according to SEQ ID NO: 91. In some embodiments, a variant Fc domain comprises a mutation that corresponds to a mutation at position G237 according to SEQ ID NO: 91. In some embodiments, a variant Fc domain comprises a mutation that corresponds to a mutation at position P238 according to SEQ ID NO: 91. In some embodiments, a variant Fc domain comprises a mutation that corresponds to a mutation at position S228, F234, L235, or any combination thereof, according to SEQ ID NO: 91, and wherein the mutation is an insertion, a deletion, or a substitution. In some embodiments, a variant Fc domain comprises a mutation that corresponds to a mutation at position S228 and F234 according to SEQ ID NO: 91. In some embodiments, a variant Fc domain comprises a mutation that corresponds to a mutation at position S228 and L235 according to SEQ ID NO: 91. In some embodiments, a variant Fc domain comprises a mutation that corresponds to a mutation at position F234 and L235 according to SEQ ID NO: 91. In some embodiments, a variant Fc domain comprises a mutation that corresponds to a mutation at position G237 and P238 according to SEQ ID NO: 91.

In some embodiments, a variant Fc domain comprises a mutation that corresponds to a mutation at position C226, P227, S228, C229, P230, A231, P232, E233, F234, L235, G236, G237, P238, Q268, Q274, N276, F296, Y300, L309, G327, S330, S331, A339, or any combination thereof, according to SEQ ID NO: 91, wherein the mutation is an insertion, a deletion, or a substitution. In some embodiments, a variant Fc domain comprises a mutation that corresponds to a mutation at position S228, F234, L235, Q268, Q274, N276, F296, Y300, L309, G327, S330, S331, A339, or any combination thereof, according to SEQ ID NO: 91, wherein the mutation is an insertion, a deletion, or a substitution. In some embodiments, a variant Fc domain comprises a mutation that corresponds to a mutation at position S228, F234, L235, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, F234, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, L235, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position L235, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position F234, L235, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position F234, Q268, Q274, F296, G327, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, F234, L235, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, F234, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position S228, L235, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position L235, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position F234, L235, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position F234, Q268, Q274, F296, S330, S331, or any combination thereof, according to SEQ ID NO: 91, wherein the mutation is an insertion, a deletion, or a substitution. In some embodiments, a variant Fc domain comprises a mutation that corresponds to a mutation at position G237, P238, or any combination thereof, according to SEQ ID NO: 91, wherein the mutation is an insertion, a deletion, or a substitution.

In some embodiments, a variant Fc domain comprises a mutation that corresponds to a mutation of S228P, F234L, L235E, Q268H, Q274K, N276K, F296Y, Y300F, L309V, G327A, S330A, S331P, A339T, or any combination thereof, according to SEQ ID NO: 91. In some embodiments, a variant Fc domain comprises a mutation that corresponds to a mutation of S228P, F234L, L235E, Q268H, Q274K, F296Y, G327A, S330A, S331P, or any combination thereof, according to SEQ ID NO: 91. In some embodiments, a variant Fc domain comprises a mutation that corresponds to a mutation at position S228P according to SEQ ID NO: 91. In some embodiments, a variant Fc domain comprises a mutation that corresponds to a mutation at position F234L according to SEQ ID NO: 91. In some embodiments, a variant Fc domain comprises a mutation that corresponds to a mutation at position L235E according to SEQ ID NO: 91. In some embodiments, a variant Fc domain comprises a mutation that corresponds to a mutation at position S228P and F234L according to SEQ ID NO: 91. In some embodiments, a variant Fc domain comprises a mutation that corresponds to a mutation at position S228P and L235E according to SEQ ID NO: 91. In some embodiments, a variant Fc domain comprises a mutation that corresponds to a mutation at position F234L and L235E according to SEQ ID NO: 91. In some embodiments, a variant Fc domain comprises a mutation that corresponds to a mutation of S228P, Q268H, Q274K, F296Y, G327A, S330A, S331P, or any combination thereof, according to SEQ ID NO: 91. In some embodiments, a variant Fc domain comprises a mutation that corresponds to a mutation of S228P, F234L, Q268H, Q274K, F296Y, G327A, S330A, S331P, or any combination thereof, according to SEQ ID NO: 91. In some embodiments, a variant Fc domain comprises a mutation that corresponds to a mutation of S228P, L235E, Q268H, Q274K, F296Y, G327A, S330A, S331P, or any combination thereof, according to SEQ ID NO: 91. In some embodiments, a variant Fc domain comprises a mutation that corresponds to a mutation of L235E, Q268H, Q274K, F296Y, G327A, S330A, S331P, or any combination thereof, according to SEQ ID NO: 91. In some embodiments, a variant Fc domain comprises a mutation that corresponds to a mutation of F234L, L235E, Q268H, Q274K, F296Y, G327A, S330A, S331P, or any combination thereof, according to SEQ ID NO: 91. In some embodiments, a variant Fc domain comprises a mutation that corresponds to a mutation of F234L, Q268H, Q274K, F296Y, G327A, S330A, S331P, or any combination thereof, according to SEQ ID NO: 91. In some embodiments, a variant Fc domain comprises a mutation that corresponds to a mutation of S228P, F234L, L235E, Q268H, Q274K, F296Y, S330A, S331P, or any combination thereof, according to SEQ ID NO: 91. In some embodiments, a variant Fc domain comprises a mutation that corresponds to a mutation of S228P, Q268H, Q274K, F296Y, S330A, S331P, or any combination thereof, according to SEQ ID NO: 91. In some embodiments, a variant Fc domain comprises a mutation that corresponds to a mutation of S228P, F234L, Q268H, Q274K, F296Y, S330A, S331P, or any combination thereof, according to SEQ ID NO: 91. In some embodiments, a variant Fc domain comprises a mutation that corresponds to a mutation of S228P, L235E, Q268H, Q274K, F296Y, S330A, S331P, or any combination thereof, according to SEQ ID NO: 91. In some embodiments, a variant Fc domain comprises a mutation that corresponds to a mutation of L235E, Q268H, Q274K, F296Y, S330A, S331P, or any combination thereof, according to SEQ ID NO: 91. In some embodiments, a variant Fc domain comprises a mutation that corresponds to a mutation of F234L, L235E, Q268H, Q274K, F296Y, S330A, S331P, or any combination thereof, according to SEQ ID NO: 91. In some embodiments, a variant Fc domain comprises a mutation that corresponds to a mutation of F234L, Q268H, Q274K, F296Y, S330A, S331P, or any combination thereof, according to SEQ ID NO: 91.

In some embodiments, a variant Fc polypeptide is a chimeric IgG Fc polypeptide. In some embodiments, the chimeric IgG Fc polypeptide is a chimeric IgG1/IgG2 polypeptide, a chimeric IgG1/IgG3 polypeptide, a chimeric IgG1/IgG4 polypeptide, a chimeric IgG2/IgG3 polypeptide, a chimeric IgG2/IgG4 polypeptide, or a chimeric IgG3/IgG4 polypeptide.

In some embodiments, the variant Fc polypeptide comprises a mutation in the CH2 region and/or hinge region. In some embodiments, the mutation is a substitution, an insertion, or a deletion. In some embodiments, the substation of the variant Fc polypeptide replaces the CH2 region of the IgG isotype with a CH2 region of a different IgG isotype. In some embodiments, the variant Fc polypeptide comprises a CH2 domain amino acid sequence having at least 50%, at least 85%, at least 90%, at least 94%, at least 95%, or at least 99% identity to SEQ ID NO: 96, SEQ ID NO: 97, SEQ ID NO: 98, SEQ ID NO: 99, SEQ ID NO: 100, or SEQ ID NO: 101. In some embodiments, the variant Fc polypeptide comprises a CH2 domain amino acid sequence having at least 50%, at least 85%, at least 90%, at least 94%, at least 95%, or at least 99% identity to SEQ ID NO: 96. In some embodiments, the variant Fc polypeptide comprises a CH2 domain amino acid sequence having at least 50%, at least 85%, at least 90%, at least 94%, at least 95%, or at least 99% identity to SEQ ID NO: 97. In some embodiments, the variant Fc polypeptide comprises a CH2 domain amino acid sequence having at least 50%, at least 85%, at least 90%, at least 94%, at least 95%, or at least 99% identity to SEQ ID NO: 98. In some embodiments, the variant Fc polypeptide comprises a CH2 domain amino acid sequence having at least 50%, at least 85%, at least 90%, at least 94%, at least 95%, or at least 99% identity to SEQ ID NO: 99. In some embodiments, the variant Fc polypeptide comprises a CH2 domain amino acid sequence having at least 50%, at least 85%, at least 90%, at least 94%, at least 95%, or at least 99% identity to SEQ ID NO: 100. In some embodiments, the variant Fc polypeptide comprises a CH2 domain amino acid sequence having at least 50%, at least 85%, at least 90%, at least 94%, at least 95%, or at least 99% identity to SEQ ID NO: 101.

In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, or SEQ ID NO: 101; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 97; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 98; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 99; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 100; and a mutation at position 228, 234, 235, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 101; and a mutation at position 228, 234, 235, or any combination thereof, as compared to SEQ ID NO: 88, and wherein the Fc polypeptide selectively binds to FcγRIIβ over FcγRIIα.

In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO; 14, SEQ ID NO: 98, SEQ ID NO: 99, SEQ ID NO: 100, or SEQ ID NO: 101; and a mutation at position 228, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, or SEQ ID NO: 101; and a mutation at position 234, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, or SEQ ID NO: 101; and a mutation at position 235, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, or SEQ ID NO: 101; and a mutation at position 228 and 234, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation at position 228 and 235, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation at position 234 and 235, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation at position 228, 234, and 235, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of S228P, L234F, L235E, or any combination thereof, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of S228P, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of L234F, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of L235E, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO:

96, SEQ ID NO: 97, SEQ ID NO: 98, SEQ ID NO: 99, SEQ ID NO: 100, OR SEQ ID NO: 101; and a mutation of S228P and L234F, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of S228P and L235E, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of L234F and L235E, as compared to SEQ ID NO: 88, and wherein the Fc polypeptide selectively binds to FcγRIIβ over FcγRIIα. In some embodiments, a variant Fc polypeptide comprises a sequence having at least 50%, at least 60%, at least 70%, at least 80%, at least 85%, at least 90%, at least 95%, or at least 99% identity to SEQ ID NO: 88, provided that the variant Fc polypeptide comprises a CH2 region comprising a sequence of SEQ ID NO: 96, SEQ ID NO: 97, SEQ ID NO: 98, SEQ ID NO: 99, SEQ ID NO: 100, OR SEQ ID NO: 101; and a mutation of S228P, L234F, and L235E, as compared to SEQ ID NO: 88, and wherein the Fc polypeptide selectively binds to FcγRIIβ over FcγRIIα.

In some embodiments, a variant IgG Fc polypeptide comprises one or more mutations that confers selective binding to FcγRIIβ over FcγRIIα. In some embodiments, a variant IgG Fc polypeptide comprises one or more mutations that enhance selective binding to FcγRIIβ over FcγRIIα. In some embodiments, a variant IgG Fc polypeptide comprises one or more mutations selected from mutations associated with any one of VFC-1 through VFC-90, as provided in Table 4. In some embodiments, a variant IgG Fc polypeptide comprises one or more mutations selected from mutations associated with any one of VFC-1 through VFC-87, as provided in Table 4, and does not comprise the C-terminal lysine (K).

| ID | Variant Fc Sequence |
|---|---|
| VFC-1 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGFSVFLFPPKPKDTLMISRTPEVTCVVVDVKHEDPEVKFNWYVDGVEVHNAKTKPREE<br>QYNSTYRVVSVLTVLHQDWLNGKEYKCKVSNKAMPEPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 1) |
| VFC-2 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGFSVFLFPPKPKDTLMISRTPEVTCVVVDVKHEDPEVKFNWYVDGVEVHNAKTKPREE<br>QYNSTYRVVSVLTVLHQDWLNGKEYKCKVSNKDMPEPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 2) |
| VFC-3 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GHFSVFLFPPKPKDTLMISRTPEVTCVVVDVKHEDPEVKFNWYVDGVEVHNAKTKPREE<br>QYNSTYRVVSVLTVLHQDWLNGKEYKCKVSNKDMPEPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 3) |
| VFC-4 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GMFSVFLFPPKPKDTLMISRTPEVTCVVVDVKHEDPEVKFNWYVDGVEVHNAKTKPREE<br>QYNSTYRVVSVLTVLHQDWLNGKEYKCKVSNKDMPEPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 4) |
| VFC-5 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 5) |
| VFC-6 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELG<br>QGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALRAPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 6) |
| VFC-7 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEPG<br>QGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALRAPIEKTISKAKGQPREPQVYTLPP<br>SRDELTKNQVSLWCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 7) |

-continued

| ID | Variant Fc Sequence |
|---|---|
| VFC-8 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELG QGPSVFLFPPKPKDTLMISRTPEVTCVVVDVSHEDPEVKFNWYVDGVEVHNAKTKPREE QYNSTYRVVSVLTVLHQDWLNGKEYKCKVSNKAWRAPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 8) |
| VFC-9 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELG QRPSVFLFPPKPKDTLMISRTPEVTCVVVDVSHEDPEVKFNWYVDGVEVHNAKTKPREE QYNSTYRVVSVLTVLHQDWLNGKEYKCKVSNKAWRAPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 9) |
| VFC-10 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELG QGPSVFLFPPKPKDTLMISRTPEVTCVVVDVSHEDPEVKFNWYVDGVEVHNAKTKPREE QYNSTYRVVSVLTVLHQDWLNGKEYKCKVSNKALDAPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 10) |
| VFC-11 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPLKL GAPSVFLFPPKPKDTLMISRTPEVTCVVVDVSPENPEVKFNWYVDGVEVHNAKTKPREE QYNSTYRVVSVLTVLHQDWLNGKEYKCKVSTSTIPGQIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 11) |
| VFC-12 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPMGG GAPSVFLFPPKPKDTLMISRTPEVTCVVVDVSPEDPEVEFNWYVDGVEVHNAKTKPREE QYNSTYRVVSVLTVLHQDWLNGKEYKCKVSTPSQPADIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 12) |
| VFC-13 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPITP GAPSVFLFPPKPKDTLMISRTPEVTCVVVDVSPEAPEVEFNWYVDGVEVHNAKTKPREE QYNSTYRVVSVLTVLHQDWLNGKEYKCKVSTAGLGSNIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 13) |
| VFC-14 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPRTP ALPSVFLFPPKPKDTLMISRTPEVTCVVVDVSPEDPEVEFNWYVDGVEVHNAKTKPREE QYNSTYRVVSVLTVLHQDWLNGKEYKCKVSNGEIREHIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 14) |
| VFC-15 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GLPSVFLFPPKPKDTLMISRTPEVTCVVVDVSHEDPEVKFNWYVDGVEVHNAKTKPREE QYNQTYRVVSVLTVLHQDWLNGKEYKCKVSNKDLPAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 15) |
| VFC-16 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GLPSVFLFPPKPKDTLMISRTPEVTCVVVDVSHEDPEVKFNWYVDGVEVHNAKTKPREE QYNQRYRVVSVLTVLHQDWLNGKEYKCKVSNKDLPAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 16) |
| VFC-17 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL PLPSVFLFPPKPKDTLMISRTPEVTCVVVDVSHEDPEVKFNWYVDGVEVHNAKTKPREE QYNQTYRVVSVLTVLHQDWLNGKEYKCKVSNKDLPAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 17) |
| VFC-18 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GLPSVFLFPPKPKDTLMISRTPEVTCVVVDVSHEDPEVKFNWYVDGVEVHNAKTKPREE QYNQTYRVVSVLTVLHQDWLNGKEYKCKVSDKDLPAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 18) |

-continued

| ID | Variant Fc Sequence |
|---|---|
| VFC-19 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEML<br>PLPSVFLFPPKPKDTLMISRTPEVTCVVVDVSHEDPEVKFNWYVDGVEVHNAKTKPREE<br>QYNQTYRVVSVLTVLHQDWLNGKEYKCKVSNKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 19) |
| VFC-20 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEML<br>PLPSVFLFPPKPKDTLMISRTPEVTCVVVDVSHEDPEVKFNWYVDGVEVHNAKTKPREE<br>QYNQRYRVVSVLTVLHQDWLNGKEYKCKVSNKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 20) |
| VFC-21 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEML<br>PLPSVFLFPPKPKDTLMISRTPEVTCVVVDVSHEDPEVKFNWYVDGVEVHNAKTKPREE<br>QYNQTYRVVSVLTVLHQDWLNGKEYKCKVSDKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 21) |
| VFC-22 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVWDVSHEDPEVKFNWYVDGVEVHNAKTKPREE<br>QYNSTYRVVSVLTVLHQDWLNGKEYKCKVSNKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 22) |
| VFC-23 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVWDVSHEDPEVKFNWYVDGVEVHNAKTKPREE<br>QYNSTYRVVSVLTVLHQDWLNGKEYKCKVSDKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 23) |
| VFC-24 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVWDHSHEDPEVKFNWYVDGVEVHNAKTKPREE<br>QYNSTYRVVSVLTVLHQDWLNGKEYKCKVSDKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 24) |
| VFC-25 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 25) |
| VFC-26 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDASQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 26) |
| VFC-27 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 27) |
| VFC-28 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSNYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 28) |
| VFC-29 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSQYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 29) |

-continued

| ID | Variant Fc Sequence |
|---|---|
| VFC-30 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDASQYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 30) |
| VFC-31 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSNYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 31) |
| VFC-32 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVFVSQYEPEVKFNWYVDGVEVHNAKTKPREE<br>QNNSTYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 32) |
| VFC-33 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPMKE<br>GAPSVFLFPPKPKDTLMISRTPEVTCVVVDVSPKSPEVEFNWYVDGVEVHNAKTKPREE<br>QYNSTYRVVSVLTVLHQDWLNGKEYKCKVSTSALAAEIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 33) |
| VFC-34 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPPGP<br>GSPSVFLFPPKPKDTLMISRTPEVTCVVVDVSPADPEVHFNWYVDGVEVHNAKTKPREE<br>QYNSTYRVVSVLTVLHQDWLNGKEYKCKVSNNALIGQIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 34) |
| VFC-35 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPVIS<br>GGPSVFLFPPKPKDTLMISRTPEVTCVVVDVSPENPEVKFNWYVDGVEVHNAKTKPREE<br>QYNSTYRVVSVLTVLHQDWLNGKEYKCKVSTKNHPQPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 35) |
| VFC-36 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPKLL<br>GAPSVFLFPPKPKDTLMISRTPEVTCVVVDVSPSDPEVHFNWYVDGVEVHNAKTKPREE<br>QYNSTYRVVSVLTVLHQDWLNGKEYKCKVSNKNVNGVIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 36) |
| VFC-37 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 37) |
| VFC-38 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVWDHSHEDPEVKFNWYVDGVEVHNAKTKPREE<br>QYNSTYRVVSVLTVLHQDWLNGKEYKCKVSNKDLPAPIEKTISKAKGQPREPQVYTLPP<br>SRDELTKNQVSLSCAVKGFYPSDIAVEWESNGQPENNYKTTPPVLDSDGSFFLVSKLTV<br>DKSRWQQGNVFSCSVMHEALHNHYTQKSLSLSPGK (SEQ ID NO: 38) |
| VFC-39 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGESVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 39) |
| VFC-40 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GEESVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 40) |

-continued

| ID | Variant Fc Sequence |
|---|---|
| VFC-41 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GDESVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 41) |
| VFC-42 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGNSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 42) |
| VFC-43 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GENSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 43) |
| VFC-44 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GDNSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 44) |
| VFC-45 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGNSVFLFPPKPKDTLMISRTPEVTCVVVDVKHEDPEVKFNWYVDGVEVHNAKTKPREE<br>QYNSTYRVVSVLTVLHQDWLNGKEYKCKVSNKAMPEPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 45) |
| VFC-46 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGFSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 46) |
| VFC-47 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GEFSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 47) |
| VFC-48 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GDFSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 48) |
| VFC-49 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGFSVFLFPPKPKDTLMISRTPEVTCVVVDVKHEDPEVKFNWYVDGVEVHNAKTKPREE<br>QYNSTYRVVSVLTVLHQDWLNGKEYKCKVSNKAMPEPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 49) |
| VFC-50 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGQSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 50) |
| VFC-51 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GEQSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 51) |

-continued

| ID | Variant Fc Sequence |
|---|---|
| VFC-52 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GDQSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 52) |
| VFC-53 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGQSVFLFPPKPKDTLMISRTPEVTCVVVDVKHEDPEVKFNWYVDGVEVHNAKTKPREE<br>QYNSTYRVVSVLTVLHQDWLNGKEYKCKVSNKAMPEPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 53) |
| VFC-54 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGMSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 54) |
| VFC-55 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GEMSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 55) |
| VFC-56 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GDMSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 56) |
| VFC-57 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGMSVFLFPPKPKDTLMISRTPEVTCVVVDVKHEDPEVKFNWYVDGVEVHNAKTKPREE<br>QYNSTYRVVSVLTVLHQDWLNGKEYKCKVSNKAMPEPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 57) |
| VFC-58 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEGL<br>LGGDSVFLFPPKPKDTLMISRTPEVTCVVVDVKHEDPEVKFNWYVDGVEVHNAKTKPRE<br>EQYNSTYRVVSVLTVLHQDWLNGKEYKCKVSNKAMPEPIEKTISKAKGQPREPQVYTLP<br>PSRDELTKNQVSLTCLVKGFYPSDIAVEWESNGQPENNYKTTPPVLDSDGSFFLYSKLT<br>VDKSRWQQGNVFSCSVMHEALHNHYTQKSLSLSPGK (SEQ ID NO: 58) |
| VFC-59 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEGL<br>LGGDSVFLFPPKPKDTLMISRTPEVTCVVVDVKHEDPEVKFNWYVDGVEVHNAKTKPRE<br>EQYNSTYRVVSVLTVLHQDWLNGKEYKCKVSNKDMPEPIEKTISKAKGQPREPQVYTLP<br>PSRDELTKNQVSLTCLVKGFYPSDIAVEWESNGQPENNYKTTPPVLDSDGSFFLYSKLT<br>VDKSRWQQGNVFSCSVMHEALHNHYTQKSLSLSPGK (SEQ ID NO: 59) |
| VFC-60 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEGL<br>LGHDSVFLFPPKPKDTLMISRTPEVTCVVVDVKHEDPEVKFNWYVDGVEVHNAKTKPRE<br>EQYNSTYRVVSVLTVLHQDWLNGKEYKCKVSNKAMPEPIEKTISKAKGQPREPQVYTLP<br>PSRDELTKNQVSLTCLVKGFYPSDIAVEWESNGQPENNYKTTPPVLDSDGSFFLYSKLT<br>VDKSRWQQGNVFSCSVMHEALHNHYTQKSLSLSPGK (SEQ ID NO: 60) |
| VFC-61 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 61) |
| VFC-62 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDASQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 62) |

-continued

| ID | Variant Fc Sequence |
|---|---|
| VFC-63 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSQYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 63) |
| VFC-64 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSNYDPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 64) |
| VFC-65 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSQYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 65) |
| VFC-66 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDASQYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 66) |
| VFC-67 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVDVSNYEPEVKFNWYVDGVEVHNAKTKPREE<br>QNNSFYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 67) |
| VFC-68 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPEVFLFPPKPKDTLMISRTPEVTCVVVFVSQYEPEVKFNWYVDGVEVHNAKTKPREE<br>QNNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 68) |
| VFC-69 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALDAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 69) |
| VFC-70 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKDLDAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 70) |
| VFC-71 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSDKALDAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 71) |
| VFC-72 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSDKDLDAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 72) |
| VFC-73 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALEAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 73) |

-continued

| ID | Variant Fc Sequence |
|---|---|
| VFC-74 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALRAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPGK (SEQ ID NO: 74) |
| VFC-75 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 75) |
| VFC-76 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 76) |
| VFC-77 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEFE GGPSVFLFPPKPKDTLMISRTPEVTCVVVDVSDEDGEVKFNWYVDGVEVHNAKTKPREE QYNSTYRVVSVLTVLHQDWLNGKEYKCKVSNKALAAPIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 77) |
| VFC-78 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGDSVFLFPPKPKDTLMISRTPEVTCVVVDVSHEDPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 78) |
| VFC-79 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELV GGESVFLFPPKPKDTLMISRTPEVTCVVVDVSHEDPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 79) |
| VFC-80 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGSSVFLFPPKPKDTLMISRTPEVTCVVVDVSHEDPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 80) |
| VFC-81 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEFE GGPSVFLFPPKPKDTLMISRTPEVTCVVVDVSDEDGEVQFNWYVDGVEVHNAKTKPREE QFNSTYRVVSVLTVLHQDWLNGKEYKCKVSNKALASSIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 81) |
| VFC-82 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GDGSVFLFPPKPKDTLMISRTPEVTCVVVDVSHEDPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 82) |
| VFC-83 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEFE GGPDVFLFPPKPKDTLMISRTPEVTCVVVDVSDEDGEVQFNWYVDGVEVHNAKTKPREE QFNSTYRVVSVLTVLHQDWLNGKEYKCKVSNKALASSIEKTISKAKGQPREPQVYTLPP SRDELTKNQVSLSCAVKGFYPSDIAVEWESNGQPENNYKTTPPVLDSDGSFFLVSKLTV DKSRWQQGNVFSCSVMHEALHNHYTQKSLSLSPGK (SEQ ID NO: 83) |
| VFC-84 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GDSGVFLFPPKPKDTLMISRTPEVTCVVVDVSHEDPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 84) |

-continued

| ID | Variant Fc Sequence |
|---|---|
| VFC-85 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEFE GGPSVFLFPPKPKDTLMISRTPEVTCVVVDVSQEDPEVQFNWYVDGVEVHNAKTKPREE QFNSTYRVVSVLTVLHQDWLNGKEYKCKVSNKALPSSIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 85) |
| VFC-86 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GDGSAFLFPPKPKDTLMISRTPEVTCVVVDVSHDEPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 86) |
| VFC-87 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEGE VLVGGDSVFLFPPKPKDTLMISRTPEVTCVVVDVSHDEPEVKFNWYVDGVEVHNAKTKP REEQYNSTYRVVSVLTVLHQDWLNGKEYKCKVSNKALPRPIEKTISKAKGQPREPQVYT LPPSRDELTKNQVSLWCLVKGFYPSDIAVEWESNGQPENNYKTTPPVLDSDGSFFLYSK LTVDKSRWQQGNVFSCSVMHEALHNHYTQKSLSLSPGK (SEQ ID NO: 87) |
| VFC-88 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GEESVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 102) |
| VFC-89 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GDGSAFLFPPKPKDTLMISRTPEVTCVVVDVSHDEPEVKFNWYVDGVEVHNAKTKPREE QYNSTYRVVSVLTVLHQDWLNGKEYKCKVSNKALPRPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 103) |
| VFC-90 | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPEFE GGPSVFLFPPKPKDTLMISRTPEVTCVVVDVSDEDGEVKFNWYVDGVEVHNAKTKPREE QYNSTYRVVSVLTVLHQDWLNGKEYKCKVSNKALAAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 104) |

In some embodiments, a variant IgG Fc polypeptide comprises one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, VFC-90, or any combination thereof. In some embodiments, a variant IgG Fc polypeptide comprising one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, VFC-90, or any combination thereof, has increased binding affinity to FcγRIIβ over FcγRIIα, as compared to that of wild-type IgG.

In some embodiments, a variant IgG Fc polypeptide comprises one or more mutations selected from mutations associated with VFC-1. In some embodiments, a variant IgG Fc polypeptide comprises one or more mutations selected from mutations associated with VFC-2. In some embodiments, a variant IgG Fc polypeptide comprises one or more mutations selected from mutations associated with VFC-3. In some embodiments, a variant IgG Fc polypeptide comprises one or more mutations selected from mutations associated with VFC-4. In some embodiments, a variant IgG Fc polypeptide comprises one or more mutations selected from mutations associated with VFC-5. In some embodiments, a variant IgG Fc polypeptide comprises one or more mutations selected from mutations associated with VFC-6. In some embodiments, a variant IgG Fc polypeptide comprises one or more mutations selected from mutations associated with VFC-7. In some embodiments, a variant IgG Fc polypeptide comprises one or more mutations selected from mutations associated with VFC-8. In some embodiments, a variant IgG Fc polypeptide comprises one or more mutations selected from mutations associated with VFC-8. In some embodiments, a variant IgG Fc polypeptide comprises one or more mutations selected from mutations associated with VFC-9. In some embodiments, a variant IgG Fc polypeptide comprises one or more mutations selected from mutations associated with VFC-10. In some embodiments, a variant IgG Fc polypeptide comprises one or more mutations selected from mutations associated with VFC-11. In some embodiments, a variant IgG Fc polypeptide comprises one or more mutations selected from mutations associated with VFC-12. In some embodiments, a variant IgG Fc polypeptide comprises one or more mutations selected from mutations associated with VFC-13. In some embodiments, a variant IgG Fc polypeptide comprises one or more mutations selected from mutations associated with VFC-14. In some embodiments, a variant IgG Fc polypeptide comprises one or more mutations selected from mutations associated with VFC-15. In some embodiments, a variant IgG Fc polypeptide comprises one or more mutations selected from mutations associated with VFC-16. In some embodiments, a variant IgG Fc polypeptide comprises one or more mutations selected from mutations associated with VFC-27. In some embodiments, a variant IgG Fc polypeptide comprises one or more mutations selected from mutations associated with VFC-28. In some embodiments, a variant IgG Fc polypeptide comprises one or more mutations selected from mutations associated with VFC-29. In some embodiments, a variant IgG Fc polypeptide comprises one or more mutations selected from mutations associated with VFC-30. In some embodiments, a variant IgG Fc polypeptide comprises one or more mutations selected from mutations associated with VFC-31. In some embodiments, a variant IgG Fc polypeptide comprises one or more mutations selected from mutations associated with VFC-32. In some embodiments, a variant IgG Fc polypeptide comprises one or more mutations selected from mutations associated with VFC-33. In some embodiments, a variant IgG Fc polypeptide comprises one or more mutations selected from mutations associated with VFC-34. In some embodiments, a variant IgG Fc polypeptide comprises one or more mutations selected from mutations associated with VFC-35. In some embodiments, a variant IgG Fc polypeptide comprises one or more mutations selected from mutations associated with VFC-36. In some embodiments, a variant IgG Fc polypeptide comprises one or more mutations selected from mutations associated with VFC-37. In some embodiments, a variant IgG Fc polypeptide comprises one or more mutations selected from mutations associated with VFC-38. In some embodiments, a variant IgG Fc polypeptide comprises one or more mutations selected from mutations associated with VFC-39. In some embodiments, a variant IgG Fc polypeptide comprises one or more mutations selected from mutations associated with VFC-40. In some embodiments, a variant IgG Fc polypeptide comprises one or more mutations selected from mutations associated with VFC-41. In some embodiments, a variant IgG Fc polypeptide comprises one or more mutations selected from mutations associated with VFC-42. In some embodiments, a variant IgG Fc polypeptide comprises one or more mutations selected from mutations associated with VFC-43. In some embodiments, a variant IgG Fc polypeptide comprises one or more mutations selected from mutations associated with VFC-44. In some embodiments, a variant IgG Fc polypeptide comprises one or more mutations selected from mutations associated with VFC-45. In some embodiments, a variant IgG Fc polypeptide comprises one or more mutations selected from mutations associated with VFC-46. In some embodiments, a variant IgG Fc polypeptide comprises one or more mutations selected from mutations associated with VFC-47. In some embodiments, a variant IgG Fc polypeptide comprises one or more mutations selected from mutations associated with VFC-48. In some embodiments, a variant IgG Fc polypeptide comprises one or more mutations selected from mutations associated with VFC-49. In some embodiments, a variant IgG Fc polypeptide comprises one or more mutations selected from mutations associated with VFC-50. In some embodiments, a variant IgG Fc polypeptide comprises one or more mutations selected from mutations associated with VFC-51. In some embodiments, a variant IgG Fc polypeptide comprises one or more mutations selected from mutations associated with VFC-52. In some embodiments, a variant IgG Fc polypeptide comprises one or more mutations selected from mutations associated with VFC-53. In some embodiments, a variant IgG Fc polypeptide comprises one or more mutations selected from mutations associated with VFC-54. In some embodiments, a variant IgG Fc polypeptide comprises one or more mutations selected from mutations associated with VFC-55. In some embodiments, a variant IgG Fc polypeptide comprises one or more mutations selected from mutations associated with VFC-56. In some embodiments, a variant IgG Fc polypeptide comprises one or more mutations selected from mutations associated with VFC-57. In some embodiments, a variant IgG Fc polypeptide comprises one or more mutations selected from mutations associated with VFC-58. In some embodiments, a variant IgG Fc polypeptide comprises one or more mutations selected from mutations associated with VFC-59. In some embodiments, a variant IgG Fc polypeptide comprises one or more mutations selected from mutations associated with VFC-60. In some embodiments, a variant IgG Fc polypeptide comprises one or more mutations selected from mutations associated with VFC-61. In some embodiments, a variant IgG Fc polypeptide comprises one or more mutations selected from mutations associated with VFC-62. In some embodiments, a variant IgG Fc polypeptide comprises one or more mutations selected from mutations associated with VFC-63. In some embodiments, a variant IgG Fc polypeptide comprises one or more mutations selected from mutations associated with VFC-64. In some embodiments, a variant IgG Fc polypeptide comprises one or more mutations selected from mutations associated with VFC-65. In some embodiments, a variant IgG Fc polypeptide comprises one or more mutations selected from mutations associated with VFC-66. In some embodiments, a variant IgG Fc polypeptide comprises one or more mutations selected from mutations associated with VFC-67. In some embodiments, a variant IgG Fc polypeptide comprises one or more mutations selected from mutations associated with VFC-68. In some embodiments, a variant IgG Fc polypeptide comprises one or more mutations selected from mutations associated with VFC-69. In some embodiments, a variant IgG Fc polypeptide comprises one or more mutations selected from mutations associated with VFC-70. In some embodiments, a variant IgG Fc polypeptide comprises one or more mutations selected from mutations associated with VFC-71. In some embodiments, a variant IgG Fc polypeptide comprises one or more mutations selected from mutations associated with VFC-72. In some embodiments, a variant IgG Fc polypeptide comprises one or more mutations selected from mutations associated with VFC-73. In some embodiments, a variant IgG Fc polypeptide comprises one or more mutations selected from mutations associated with VFC-74. In some embodiments, a variant IgG Fc polypeptide comprises one or more mutations selected from mutations associated with VFC-75. In some embodiments, a variant IgG Fc polypeptide comprises one or more mutations selected from mutations associated with VFC-76. In some embodiments, a variant IgG Fc polypeptide comprises one or more mutations selected from mutations associated with VFC-77. In some embodiments, a variant IgG Fc polypeptide comprises one or more mutations selected from mutations associated with VFC-78. In some embodiments, a variant IgG Fc polypeptide comprises one or more mutations selected from mutations associated with VFC-79. In some embodiments, a variant IgG Fc polypeptide comprises one or more mutations selected from mutations associated with VFC-80. In some embodiments, a variant IgG Fc polypeptide comprises one or more mutations selected from mutations associated with VFC-81. In some embodiments, a variant IgG Fc polypeptide comprises one or more mutations selected from mutations associated with VFC-82. In some embodiments, a variant IgG Fc polypeptide comprises one or more mutations selected from mutations associated with VFC-83. In some embodiments, a variant IgG Fc polypeptide comprises one or more mutations selected from mutations associated with VFC-84. In some embodiments, a variant IgG Fc polypeptide comprises one or more mutations selected from mutations associated with VFC-85. In some embodiments, a variant IgG Fc polypeptide comprises one or more mutations selected from mutations associated with VFC-86. In some embodiments, a variant IgG Fc polypeptide comprises one or more mutations selected from mutations associated with VFC-87. In some embodiments, a variant IgG Fc polypeptide comprises one or more mutations selected from mutations associated with VFC-88. In some embodiments, a variant IgG Fc polypeptide comprises one or more mutations selected from mutations associated with VFC-89. In some embodiments, a variant IgG Fc polypeptide comprises one or more mutations selected from mutations associated with VFC-90.

In some embodiments, the mutation is a substitutions, an insertion, or a deletion. In some embodiments, the insertion can be 1-5 residues, or more.

In some embodiments, a variant IgG Fc polypeptide comprises a mutation selected from a mutation at one or more of the positions (according to EU numbering) selected from 233, 234, 235, 237, 238, 239, 240, 268, 269, 270, 271, 329, 330, and any combination thereof, as compared to SEQ ID NO: 88. In some embodiments, a variant IgG Fc polypeptide comprises a mutation at position 233, as compared to SEQ ID NO: 88. In some embodiments, a variant IgG Fc polypeptide comprises a mutation at position 234, as compared to SEQ ID NO: 88. In some embodiments, a variant IgG Fc polypeptide comprises a mutation at position 235, as compared to SEQ ID NO: 88. In some embodiments, a variant IgG Fc polypeptide comprises a mutation at position 237, as compared to SEQ ID NO: 88. In some embodiments, a variant IgG Fc polypeptide comprises a mutation at position 238, as compared to SEQ ID NO: 88. In some embodiments, a variant IgG Fc polypeptide comprises a mutation at position 239, as compared to SEQ ID NO: 88. In some embodiments, a variant IgG Fc polypeptide comprises a mutation at position 240, as compared to SEQ ID NO: 88. In some embodiments, a variant IgG Fc polypeptide comprises a mutation at position 268, as compared to SEQ ID NO: 88. In some embodiments, a variant IgG Fc polypeptide comprises a mutation at position 269, as compared to SEQ ID NO: 88. In some embodiments, a variant IgG Fc polypeptide comprises a mutation at position 270, as compared to SEQ ID NO: 88. In some embodiments, a variant IgG Fc polypeptide comprises a mutation at position 271, as compared to SEQ ID NO: 88. In some embodiments, a variant IgG Fc polypeptide comprises a mutation at position 329, as compared to SEQ ID NO: 88. In some embodiments, a variant IgG Fc polypeptide comprises a mutation at position 330, as compared to SEQ ID NO: 88.

In some embodiments, a variant IgG Fc polypeptide comprises a mutation at any one or more of the positions selected from 238, 269, 270, or 330, as compared to SEQ ID NO: 88. In some embodiments, a variant IgG Fc polypeptide comprises a set of mutations at positions 238, 269, 270, and 330, as compared to SEQ ID NO: 88. In some embodiments, a variant IgG Fc polypeptide comprises a mutation at any one or more of the positions selected from 237, 238, 269, 270, or 330, as compared to SEQ ID NO: 88. In some embodiments, a variant IgG Fc polypeptide comprises a set of mutations at positions 237, 238, 269, 270, and 330, as compared to SEQ ID NO: 88. In some embodiments, a variant IgG Fc polypeptide comprises a mutation at any one or more of the positions selected from 237, 238, 239, 269, 270, or 330, as compared to SEQ ID NO: 88. In some embodiments, a variant IgG Fc polypeptide comprises a set of mutations at positions 237, 238, 239, 269, 270, and 330, as compared to SEQ ID NO: 88. In some embodiments, a variant IgG Fc polypeptide comprises a mutation at any one or more of the positions selected from 237, 238, 240, 269, 270, or 330, as compared to SEQ ID NO: 88. In some embodiments, a variant IgG Fc polypeptide comprises a set of mutations at positions 237, 238, 240, 269, 270, and 330, as compared to SEQ ID NO: 88. In some embodiments, a variant IgG Fc polypeptide comprises a mutation at any one or more of the positions selected from 235, 238, 269, 270, or 330, as compared to SEQ ID NO: 88. In some embodiments, a variant IgG Fc polypeptide comprises a set of mutations at positions 235, 238, 269, 270, and 330, as compared to SEQ ID NO: 88. In some embodiments, a variant IgG Fc polypeptide comprises a mutation at any one or more of the positions selected from 233, 235, 238, 269, 270, or 330, as compared to SEQ ID NO: 88. In some embodiments, a variant IgG Fc polypeptide comprises a set of mutations at positions 233, 235, 238, 269, 270, and 330, as compared to SEQ ID NO: 88. In some embodiments, a variant IgG Fc polypeptide comprises a mutation at any one or more of the positions selected from 235, 238, 269, 270, or 330, and an insertion between positions 233 and 234, as compared to SEQ ID NO: 88. In some embodiments, a variant IgG Fc polypeptide comprises a set of mutations at positions 235, 238, 269, 270, and 330, and an insertion between positions 233 and 234, as compared to SEQ ID NO: 88. In some embodiments, a variant IgG Fc polypeptide comprises a mutation at any one or more of the positions selected from 234, 235, 268, 271, or 329, as compared to SEQ ID NO: 88. In some embodiments, a variant IgG Fc polypeptide comprises a set of mutations at positions 234, 235, 268, 271, and 329, as compared to SEQ ID NO: 88. In some embodiments, a variant IgG Fc polypeptide comprises a mutation at any one or more of the positions selected from 234, 235, 239, 268, 271, or 329, as compared to SEQ ID NO: 88. In some embodiments, a variant IgG Fc polypeptide comprises a set of mutations at positions 234, 235, 239, 268, 271, and 329, as compared to SEQ ID NO: 88. In some embodiments, a variant IgG Fc polypeptide comprises a mutation at any one or more of the positions selected from 234 or 235, as compared to SEQ ID NO: 88. In some embodiments, a variant IgG Fc polypeptide comprises a set of mutations at positions 234 and 235, as compared to SEQ ID NO: 88. In some embodiments, a variant IgG Fc polypeptide comprises a set of mutations at positions 237 and 238, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88, provided that the variant IgG Fc polypeptide comprises one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90. Non-limiting examples include variant IgG Fc polypeptides comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88, provided that the variant IgG Fc polypeptide comprises one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90, wherein variant IgG Fc polypeptides comprises one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90, and one or more mutations in the amino acid sequence that is not the one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, VFC-90, or any combination thereof. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-1. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-2. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-3. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-4. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-5. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-6. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-7. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-8. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-9. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-10. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-11. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-12. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-13. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-14. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-15. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-16. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-17. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-18. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-19. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-20. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-21. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-22. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-23. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-24. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-25. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-26. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-27. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-28. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-29. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-30. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-31. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-32. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-33. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-34. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-35. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-36. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-37. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-38. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-39. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-40. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-41. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-42. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-43. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-44. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-45. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-46. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-47. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-48. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-49. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-50. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-51. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-52. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-53. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-54. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-55. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-56. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-57. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-58. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-59. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-60. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-61. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-62. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-63. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-64. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-65. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-66. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-67. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-68. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-69. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-70. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-71. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-72. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-73. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-74. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-75. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-76. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-77. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-78. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-79. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-80. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-81. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-82. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-83. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-84. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-85. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-86. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-87. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-89. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more mutations selected from mutations associated with VFC-90.

Non-limiting examples of variant IgG Fc polypeptides comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88, provided that the variant IgG Fc polypeptide comprises a mutation selected from a mutation at one or more of the positions selected from 233, 234, 235, 237, 238, 239, 240, 268, 269, 270, 271, 329, 330, and any combination thereof, as compared to SEQ ID NO: 88, include variant IgG Fc polypeptides comprising a mutation selected from a mutation at one or more of the positions selected from 233, 234, 235, 237, 238, 239, 240, 268, 269, 270, 271, 329, 330, and any combination thereof, as compared to SEQ ID NO: 88 and one or more mutations in the amino acid sequence that is not the mutation selected from the mutation at one or more of the positions selected from 233, 234, 235, 237, 238, 239, 240, 268, 269, 270, 271, 329, 330, and any combination thereof, as compared to SEQ ID NO: 14.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation selected from a mutation at one or more of the positions selected from 233, 234, 235, 237, 238, 239, 240, 268, 269, 270, 271, 329, 330, and any combination thereof, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 233, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 235, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 237, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 238, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 239, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 240, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 268, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 269, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 270, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 271, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 238, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 238, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 237, 238, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 237, 238, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 237, 238, 239, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 237, 238, 239, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 237, 238, 240, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 237, 238, 240, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 235, 238, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 235, 238, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 233, 235, 238, 269, 270, or 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 233, 235, 238, 269, 270, and 330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 235, 238, 269, 270, or 330, and an insertion between positions 233 and 234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 235, 238, 269, 270, and 330, and an insertion between positions 233 and 234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 234, 235, 268, 271, or 329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 234, 235, 268, 271, and 329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 234, 235, 239, 268, 271, or 329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions 234, 235, 239, 268, 271, and 329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 234 or 235, as compared to SEQ ID NO: 88. In some embodiments, a variant IgG Fc polypeptide comprises a set of mutations at positions 234 and 235, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from 237 or 237, as compared to SEQ ID NO: 88. In some embodiments, a variant IgG Fc polypeptide comprises a set of mutations at positions 237 and 238, as compared to SEQ ID NO: 88.

In some embodiments, a variant IgG Fc polypeptide comprises a mutation selected from a mutation at one or more of the positions selected from 233, L234, L235, G237, P238, S239, V240, H268, E269, D270, P271, P329, A330, and any combination thereof, as compared to SEQ ID NO: 14. In some embodiments, a variant IgG Fc polypeptide comprises a mutation at position 233, as compared to SEQ ID NO: 88. In some embodiments, a variant IgG Fc polypeptide comprises a mutation at position L234, as compared to SEQ ID NO: 88. In some embodiments, a variant IgG Fc polypeptide comprises a mutation at position L235, as compared to SEQ ID NO: 88. In some embodiments, a variant IgG Fc polypeptide comprises a mutation at position G237, as compared to SEQ ID NO: 88. In some embodiments, a variant IgG Fc polypeptide comprises a mutation at position P238, as compared to SEQ ID NO: 88. In some embodiments, a variant IgG Fc polypeptide comprises a mutation at position S239, as compared to SEQ ID NO: 88. In some embodiments, a variant IgG Fc polypeptide comprises a mutation at position V240, as compared to SEQ ID NO: 88. In some embodiments, a variant IgG Fc polypeptide comprises a mutation at position H268, as compared to SEQ ID NO: 88. In some embodiments, a variant IgG Fc polypeptide comprises a mutation at position E269, as compared to SEQ ID NO: 88. In some embodiments, a variant IgG Fc polypeptide comprises a mutation at position D270, as compared to SEQ ID NO: 88. In some embodiments, a variant IgG Fc polypeptide comprises a mutation at position P271, as compared to SEQ ID NO: 88. In some embodiments, a variant IgG Fc polypeptide comprises a mutation at position P329, as compared to SEQ ID NO: 88. In some embodiments, a variant IgG Fc polypeptide comprises a mutation at position A330, as compared to SEQ ID NO: 88.

In some embodiments, a variant IgG Fc polypeptide comprises a mutation at any one or more of the positions selected from P238, E269, D270, or A330, as compared to SEQ ID NO: 88. In some embodiments, a variant IgG Fc polypeptide comprises a set of mutations at positions P238, E269, D270, and A330, as compared to SEQ ID NO: 88. In some embodiments, a variant IgG Fc polypeptide comprises a mutation at any one or more of the positions selected from G237, P238, E269, D270, or A330, as compared to SEQ ID NO: 88. In some embodiments, a variant IgG Fc polypeptide comprises a set of mutations at positions G237, P238, E269, D270, and A330, as compared to SEQ ID NO: 88. In some embodiments, a variant IgG Fc polypeptide comprises a mutation at any one or more of the positions selected from G237, P238, S239, E269, D270, or A330, as compared to SEQ ID NO: 88. In some embodiments, a variant IgG Fc polypeptide comprises a set of mutations at positions G237, P238, S239, E269, D270, and A330, as compared to SEQ ID NO: 88. In some embodiments, a variant IgG Fc polypeptide comprises a mutation at any one or more of the positions selected from G237, P238, V240, E269, D270, or A330, as compared to SEQ ID NO: 88. In some embodiments, a variant IgG Fc polypeptide comprises a set of mutations at positions G237, P238, V240, E269, D270, and A330, as compared to SEQ ID NO: 88. In some embodiments, a variant IgG Fc polypeptide comprises a mutation at any one or more of the positions selected from L235, P238, E269, D270, or A330, as compared to SEQ ID NO: 88. In some embodiments, a variant IgG Fc polypeptide comprises a set of mutations at positions L235, P238, E269, D270, and A330, as compared to SEQ ID NO: 88. In some embodiments, a variant IgG Fc polypeptide comprises a mutation at any one or more of the positions selected from E233, L235, P238, E269, D270, or A330, as compared to SEQ ID NO: 88. In some embodiments, a variant IgG Fc polypeptide comprises a set of mutations at positions E233, L235, P238, E269, D270, and A330, as compared to SEQ ID NO: 88. In some embodiments, a variant IgG Fc polypeptide comprises a mutation at any one or more of the positions selected from L235, P238, E269, D270, or A330, and an insertion between positions E233 and L234, as compared to SEQ ID NO: 88. In some embodiments, a variant IgG Fc polypeptide comprises a set of mutations at positions L235, P238, E269, D270, and A330, and an insertion between positions 233 and L234, as compared to SEQ ID NO: 88. In some embodiments, a variant IgG Fc polypeptide comprises a mutation at any one or more of the positions selected from L234, L235, H268, P271, or P329, as compared to SEQ ID NO: 88. In some embodiments, a variant IgG Fc polypeptide comprises a set of mutations at positions L234, L235, H268, P271, and P329, as compared to SEQ ID NO: 88. In some embodiments, a variant IgG Fc polypeptide comprises a mutation at any one or more of the positions selected from L234, L235, S239, H268, P271, or P329, as compared to SEQ ID NO: 88. In some embodiments, a variant IgG Fc polypeptide comprises a set of mutations at positions L234, L235, S239, H268, P271, and P329, as compared to SEQ ID NO: 88. In some embodiments, a variant IgG Fc polypeptide comprises a mutation at any one or more of the positions selected from L234 or L235, as compared to SEQ ID NO: 88. In some embodiments, a variant IgG Fc polypeptide comprises a set of mutations at positions L234 and L235, as compared to SEQ ID NO: 88. In some embodiments, a variant IgG Fc polypeptide comprises a set of mutations at positions G237 and P238, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation selected from a mutation at one or more of the positions selected from E233, L234, L235, G237, P238, S239, V240, H268, E269, D270, P271, P329, A330, and any combination thereof, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position E233, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position L234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position L235, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position G237, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position P238, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position S239, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position V240, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position H268, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position E269, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position D270, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position P271, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position P329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at position A330, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from P238, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions P238, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from G237, P238, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions G237, P238, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from G237, P238, S239, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions G237, P238, S239, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from G237, P238, V240, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions G237, P238, V240, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from L235, P238, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions L235, P238, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from E233, L235, P238, E269, D270, or A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions E233, L235, P238, E269, D270, and A330, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from L235, P238, E269, D270, or A330, and an insertion between positions E233 and L234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions L235, P238, E269, D270, and A330, and an insertion between positions E233 and L234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from L234, L235, H268, P271, or P329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions L234, L235, H268, P271, and P329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from L234, L235, S239, H268, P271, or P329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a set of mutations at positions L234, L235, S239, H268, P271, and P329, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from L234 or L235, as compared to SEQ ID NO: 88. In some embodiments, a variant IgG Fc polypeptide comprises a set of mutations at positions L234 and L235, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation at any one or more of the positions selected from G237 or P238, as compared to SEQ ID NO: 88. In some embodiments, a variant IgG Fc polypeptide comprises a set of mutations at positions G237 and P238, as compared to SEQ ID NO: 88.

In some embodiments, a variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88. In some embodiments, a variant IgG Fc polypeptide comprises a mutation of L234F as compared to SEQ ID NO: 88. In some embodiments, a variant IgG Fc polypeptide comprises a mutation of L235E, as compared to SEQ ID NO: 88. In some embodiments, a variant IgG Fc polypeptide comprises a mutation of L235V, as compared to SEQ ID NO: 88. In some embodiments, a variant IgG Fc polypeptide comprises a mutation of G237D, as compared to SEQ ID NO: 88. In some embodiments, a variant IgG Fc polypeptide comprises a mutation of G237E, as compared to SEQ ID NO: 88. In some embodiments, a variant IgG Fc polypeptide comprises a mutation of P238D, as compared to SEQ ID NO: 88. In some embodiments, a variant IgG Fc polypeptide comprises a mutation of P238G, as compared to SEQ ID NO: 88. In some embodiments, a variant IgG Fc polypeptide comprises a mutation of P238E, as compared to SEQ ID NO: 88. In some embodiments, a variant IgG Fc polypeptide comprises a mutation of S239G, as compared to SEQ ID NO: 88. In some embodiments, a variant IgG Fc polypeptide comprises a mutation of S239D, as compared to SEQ ID NO: 88. In some embodiments, a variant IgG Fc polypeptide comprises a mutation of V240A, as compared to SEQ ID NO: 88. In some embodiments, a variant IgG Fc polypeptide comprises a mutation of H268D, as compared to SEQ ID NO: 88. In some embodiments, a variant IgG Fc polypeptide comprises a mutation of E269D, as compared to SEQ ID NO: 88. In some embodiments, a variant IgG Fc polypeptide comprises a mutation of D270E, as compared to SEQ ID NO: 88. In some embodiments, a variant IgG Fc polypeptide comprises a mutation of P271G, as compared to SEQ ID NO: 88. In some embodiments, a variant IgG Fc polypeptide comprises a mutation of P329A, as compared to SEQ ID NO: 88. In some embodiments, a variant IgG Fc polypeptide comprises a mutation of A330R, as compared to SEQ ID NO: 88. In some embodiments, a variant IgG Fc polypeptide comprises an insertion of an amino acid sequence GEV between positions 233 and 234, as compared to SEQ ID NO: 88.

In some embodiments, a variant IgG Fc polypeptide comprises a mutation set selected from:

- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;

- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of G237D, P238G, V240A, E269D, D270E, A330R, L234F, L235E, P329A, H268D, and P271G, as compared to SEQ ID NO: 88;
- a mutation set of P238D, E269D, D270E, A330R, L234F, L235E, S239D, P329A, H268D, and P271G as compared to SEQ ID NO: 88;
- a mutation set of L234F and L235E, as compared to SEQ ID NO: 88;
- a mutation set of G237E and P238E, as compared to SEQ ID NO: 88; or
- any combination thereof.

In some embodiments, a variant IgG Fc polypeptide comprises a mutation set of P238D, E269D, D270E, and A330R, as compared to SEQ ID NO: 88. In some embodiments, a variant IgG Fc polypeptide comprises a mutation set of G237D, P238G, E269D, D270E, and A330R, as compared to SEQ ID NO: 88. In some embodiments, a variant IgG Fc polypeptide comprises a mutation set of G237D, P238S, S239G, E269D, D270E, and A330R, as compared to SEQ ID NO: 88. In some embodiments, a variant IgG Fc polypeptide comprises a mutation set of G237D, P238G, V240A, E269D, D270E, and A330R, as compared to SEQ ID NO: 88. In some embodiments, a variant IgG Fc polypeptide comprises a mutation set of L235V, P238E, E269D, D270E, and A330R, as compared to SEQ ID NO: 88. In some embodiments, a variant IgG Fc polypeptide comprises a mutation set of L235V, P238D, E269D, D270E, and A330R, and an insertion of an amino acid sequence GEV between positions 233 and 234, as compared to SEQ ID NO: 88. In some embodiments, a variant IgG Fc polypeptide comprises a mutation set of P238S, E269D, D270E, and A330R, as compared to SEQ ID NO: 88. In some embodiments, a variant IgG Fc polypeptide comprises a mutation set of L234F, L235E, P329A, H268D, and P271G, as compared to SEQ ID NO: 88. In some embodiments, a variant IgG Fc polypeptide comprises a mutation set of L234F, L235E, S239D, P329A, H268D, and P271G, as compared to SEQ ID NO: 88. In some embodiments, a variant IgG Fc polypeptide comprises a mutation set of L234F and L235E, as compared to SEQ ID NO: 88. In some embodiments, a variant IgG Fc polypeptide comprises a mutation set of G237E and P238E, as compared to SEQ ID NO: 88. In some embodiments, a variant IgG Fc polypeptide comprises a mutation set of G237D, P238G, V240A, E269D, D270E, A330R, L234F, L235E, P329A, H268D, and P271G, as compared to SEQ ID NO: 88. In some embodiments, a variant IgG Fc polypeptide comprises a mutation set of P238D, E269D, D270E, A330R, L234F, L235E, S239D, P329A, H268D, and P271G, as compared to SEQ ID NO: 88.

In some embodiments, a variant IgG Fc polypeptide comprises a variant sequence of SEQ ID NO: 88, wherein the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88. In some embodiments, a variant IgG Fc polypeptide comprises a variant sequence of SEQ ID NO: 88, wherein the variant IgG Fc polypeptide comprises a mutation of L234F as compared to SEQ ID NO: 88. In some embodiments, a variant IgG Fc polypeptide comprises a variant sequence of SEQ ID NO: 88, wherein the variant IgG Fc polypeptide comprises a mutation of L235E, as compared to SEQ ID NO: 88. In some embodiments, a variant IgG Fc polypeptide comprises a variant sequence of SEQ ID NO: 88, wherein the variant IgG Fc polypeptide comprises a variant sequence of SEQ ID NO: 88, wherein the variant IgG Fc polypeptide comprises a mutation of L235V, as compared to SEQ ID NO: 88. In some embodiments, a variant IgG Fc polypeptide comprises a variant sequence of SEQ ID NO: 88, wherein the variant IgG Fc polypeptide comprises a mutation of G237D, as compared to SEQ ID NO: 88. In some embodiments, a variant IgG Fc polypeptide comprises a variant sequence of SEQ ID NO: 88, wherein the variant IgG Fc polypeptide comprises a mutation of G237E, as compared to SEQ ID NO: 88. In some embodiments, a variant IgG Fc polypeptide comprises a variant sequence of SEQ ID NO: 88, wherein the variant IgG Fc polypeptide comprises a mutation of P238D, as compared to SEQ ID NO: 88. In some embodiments, a variant IgG Fc polypeptide comprises a variant sequence of SEQ ID NO: 88, wherein the variant IgG Fc polypeptide comprises a mutation of P238G, as compared to SEQ ID NO: 88. In some embodiments, a variant IgG Fc polypeptide comprises a variant sequence of SEQ ID NO: 88, wherein the variant IgG Fc polypeptide comprises a mutation of P238E, as compared to SEQ ID NO: 88. In some embodiments, a variant IgG Fc polypeptide comprises a variant sequence of SEQ ID NO: 88, wherein the variant IgG Fc polypeptide comprises a mutation of S239G, as compared to SEQ ID NO: 88. In some embodiments, a variant IgG Fc polypeptide comprises a variant sequence of SEQ ID NO: 88, wherein the variant IgG Fc polypeptide comprises a mutation of S239D, as compared to SEQ ID NO: 88. In some embodiments, a variant IgG Fc polypeptide comprises a variant sequence of SEQ ID NO: 88, wherein the variant IgG Fc polypeptide comprises a mutation of V240A, as compared to SEQ ID NO: 88. In some embodiments, a variant IgG Fc polypeptide comprises a variant sequence of SEQ ID NO: 88, wherein the variant IgG Fc polypeptide comprises a mutation of H268D, as compared to SEQ ID NO: 88. In some embodiments, a variant IgG Fc polypeptide comprises a variant sequence of SEQ ID NO: 88, wherein the variant IgG Fc polypeptide comprises a mutation of E269D, as compared to SEQ ID NO: 88. In some embodiments, a variant IgG Fc polypeptide comprises a variant sequence of SEQ ID NO: 88, wherein the variant IgG Fc polypeptide comprises a mutation of D270E, as compared to SEQ ID NO: 88. In some embodiments, a variant IgG Fc polypeptide comprises a variant sequence of SEQ ID NO: 88, wherein the variant IgG Fc polypeptide comprises a mutation of P271G, as compared to SEQ ID NO: 88. In some embodiments, a variant IgG Fc polypeptide comprises a variant sequence of SEQ ID NO: 88, wherein the variant IgG Fc polypeptide comprises a mutation of P329A, as compared to SEQ ID NO: 88. In some embodiments, a variant IgG Fc polypeptide comprises a variant sequence of SEQ ID NO: 88, wherein the variant IgG Fc polypeptide comprises a mutation of A330R, as compared to SEQ ID NO: 88. In some embodiments, a variant IgG Fc polypeptide comprises a variant sequence of SEQ ID NO: 88, wherein the variant IgG Fc polypeptide comprises an insertion of an amino acid sequence GEV between positions 233 and 234, as compared to SEQ ID NO: 88.

In some embodiments, a variant IgG Fc polypeptide comprises a variant sequence of SEQ ID NO: 88, wherein the variant IgG Fc polypeptide comprises a mutation set selected from:

- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of G237D, P238G, V240A, E269D, D270E, A330R, L234F, L235E, P329A, H268D, and P271G, as compared to SEQ ID NO: 14; or
- a mutation set of P238D, E269D, D270E, A330R, L234F, L235E, S239D, P329A, H268D, and P271G as compared to SEQ ID NO: 14;
- a mutation set of L234F and L235E, as compared to SEQ ID NO: 88;
- a mutation set of G237E and P238E, as compared to SEQ ID NO: 88; or
- any combination thereof.

In some embodiments, a variant IgG Fc polypeptide comprises a variant sequence of SEQ ID NO: 88, wherein the variant IgG Fc polypeptide comprises a mutation set of P238D, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of G237D, P238G, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of G237D, P238S, S239G, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of G237D, P238G, V240A, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of L235V, P238E, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of L235V, P238D, E269D, D270E, and A330R, and an insertion of an amino acid sequence GEV between positions 233 and 234, as compared to SEQ ID NO: 88. In some embodiments, a variant IgG Fc polypeptide comprises a variant sequence of SEQ ID NO: 88, wherein the variant IgG Fc polypeptide comprises a mutation set of P238S, E269D, D270E, and A330R, as compared to SEQ ID NO: 88. In some embodiments, a variant IgG Fc polypeptide comprises a variant sequence of SEQ ID NO: 88, wherein the variant IgG Fc polypeptide comprises a mutation set of L234F, L235E, P329A, H268D, and P271G, as compared to SEQ ID NO: 88. In some embodiments, a variant IgG Fc polypeptide comprises a variant sequence of SEQ ID NO: 88, wherein the variant IgG Fc polypeptide comprises a mutation set of L234F, L235E, S239D, P329A, H268D, and P271G, as compared to SEQ ID NO: 88. In some embodiments, a variant IgG Fc polypeptide comprises a variant sequence of SEQ ID NO: 88, wherein the variant IgG Fc polypeptide comprises a mutation set of L234F and L235E, as compared to SEQ ID NO: 88. In some embodiments, a variant IgG Fc polypeptide comprises a variant sequence of SEQ ID NO: 88, wherein the variant IgG Fc polypeptide comprises a mutation set of G237E and P238E, as compared to SEQ ID NO: 88. In some embodiments, a variant IgG Fc polypeptide comprises a variant sequence of SEQ ID NO: 88, wherein the variant IgG Fc polypeptide comprises a mutation set of G237D, P238G, V240A, E269D, D270E, A330R, L234F, L235E, P329A, H268D, and P271G, as compared to SEQ ID NO: 88. In some embodiments, a variant IgG Fc polypeptide comprises a variant sequence of SEQ ID NO: 88, wherein the variant IgG Fc polypeptide comprises a mutation set of G237D, P238G, V240A, E269D, D270E, A330R, L234F, L235E, P329A, H268D, and P271G, as compared to SEQ ID NO: 88. In some embodiments, a variant IgG Fc polypeptide comprises a variant sequence of SEQ ID NO: 88, wherein the variant IgG Fc polypeptide comprises a mutation set of P238D, E269D, D270E, A330R, L234F, L235E, S239D, P329A, H268D, and P271G, as compared to SEQ ID NO: 88. In some embodiments, a variant IgG Fc polypeptide comprises a variant sequence of SEQ ID NO: 88, wherein the variant IgG Fc polypeptide comprises a mutation set of P238D, E269D, D270E, A330R, L234F, L235E, S239D, P329A, H268D, and P271G, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

Non-limiting examples of variant IgG Fc polypeptides comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88, provided that the variant IgG Fc polypeptide comprises a mutation selected from a mutation at one or more of the positions selected from L234F, L235E, L235V, G237D, G237E, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88, include variant IgG Fc polypeptides comprising a mutation selected from a mutation at one or more of the positions selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88, and one or more mutations in the amino acid sequence that is not the mutation selected from the mutation at one or more of the positions selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of L234F as compared to SEQ ID NO: 88. In some embodiments, a variant IgG Fc polypeptide comprises a mutation of L234F, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of L235E as compared to SEQ ID NO: 88. In some embodiments, a variant IgG Fc polypeptide comprises a mutation of L235E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of G237D, as compared to SEQ ID NO: 88. In some embodiments, a variant IgG Fc polypeptide comprises a mutation of G237D, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of G237E, as compared to SEQ ID NO: 88. In some embodiments, a variant IgG Fc polypeptide comprises a mutation of G237E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of P238D, as compared to SEQ ID NO: 88. In some embodiments, a variant IgG Fc polypeptide comprises a mutation of P238D, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of P238G, as compared to SEQ ID NO: 88. In some embodiments, a variant IgG Fc polypeptide comprises a mutation of P238G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of P238E, as compared to SEQ ID NO: 88. In some embodiments, a variant IgG Fc polypeptide comprises a mutation of P238E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of S239G, as compared to SEQ ID NO: 88. In some embodiments, a variant IgG Fc polypeptide comprises a mutation of S239G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of S239D, as compared to SEQ ID NO: 88. In some embodiments, a variant IgG Fc polypeptide comprises a mutation of S239D, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of V240A, as compared to SEQ ID NO: 88. In some embodiments, a variant IgG Fc polypeptide comprises a mutation of V240A, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of H268D, as compared to SEQ ID NO: 88. In some embodiments, a variant IgG Fc polypeptide comprises a mutation of H268D, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of E269D, as compared to SEQ ID NO: 88. In some embodiments, a variant IgG Fc polypeptide comprises a mutation of E269D, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of D270E, as compared to SEQ ID NO: 88. In some embodiments, a variant IgG Fc polypeptide comprises a mutation of D270E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of P271G, as compared to SEQ ID NO: 88. In some embodiments, a variant IgG Fc polypeptide comprises a mutation of P271G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of P329A, as compared to SEQ ID NO: 88. In some embodiments, a variant IgG Fc polypeptide comprises a mutation of P329A, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation of A330R, as compared to SEQ ID NO: 88. In some embodiments, a variant IgG Fc polypeptide comprises a mutation of A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises an insertion of an amino acid sequence GEV between positions 233 and 234, as compared to SEQ ID NO: 88. In some embodiments, a variant IgG Fc polypeptide comprises an insertion of an amino acid sequence GEV between positions 233 and 234, as compared to SEQ ID NO: 88.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set selected from:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of G237D, P238G, V240A, E269D, D270E, A330R, L234F, L235E, P329A, H268D, and P271G, as compared to SEQ ID NO: 14;

a mutation set of P238D, E269D, D270E, A330R, L234F, L235E, S239D, P329A,

H268D, and P271G as compared to SEQ ID NO: 14;

a mutation set of L234F and L235E, as compared to SEQ ID NO: 88;

a mutation set of G237E and P238E, as compared to SEQ ID NO: 88; or any combination thereof.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of P238D, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238G, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238S, S239G, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238G, V240A, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L235V, P238E, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L235V, P238D, E269D, D270E, and A330R, and an insertion of an amino acid sequence GEV between positions 233 and 234, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of P238S, E269D, D270E, and A330R, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F, L235E, P329A, H268D, and P271G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F, L235E, S239D, P329A, H268D, and P271G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F and L235E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237E and P238E, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238G, V240A, E269D, D270E, A330R, L234F, L235E, P329A, H268D, and P271G, as compared to SEQ ID NO: 88. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of P238D, E269D, D270E, A330R, L234F, L235E, S239D, P329A, H268D, and P271G, as compared to SEQ ID NO: 88.

In some embodiments, a variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 14, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

Non-limiting examples include variant IgG Fc polypeptides comprising one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, wherein the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88, and at least, about, or exactly 1-10, 1-20, 1, 2, 3, 4, 5, 6, 7, 8, 9, 10, 11, 12, 13, 14, 15, 16, 17, 18, 19 or 20 mutations that is/are not the mutation(s) selected from the one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

In some embodiments, a variant IgG Fc polypeptide comprises a mutation of L234F as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of L235E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of L235V, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of G237D, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of G237E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of P238D, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of P238G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of P238E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of S239G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of S239D, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of V240A, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of H268D, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 14. In some embodiments, a variant IgG Fc polypeptide comprises a mutation of E269D, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of D270E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of P329A, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation of A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises an insertion of an amino acid sequence GEV between positions 233 and 234, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a variant IgG Fc polypeptide comprises a mutation set selected from:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of G237D, P238G, V240A, E269D, D270E, A330R, L234F, L235E, P329A, H268D, and P271G, as compared to SEQ ID NO: 14;

a mutation set of P238D, E269D, D270E, A330R, L234F, L235E, S239D, P329A,

H268D, and P271G as compared to SEQ ID NO: 14;

a mutation set of L234F and L235E, as compared to SEQ ID NO: 88;

a mutation set of G237E and P238E, as compared to SEQ ID NO: 88; or any combination thereof, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a variant IgG Fc polypeptide comprises a mutation set of P238D, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of G237D, P238G, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of G237D, P238S, S239G, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of G237D, P238G, V240A, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of L235V, P238E, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of L235V, P238D, E269D, D270E, and A330R, and an insertion of an amino acid sequence GEV between positions 233 and 234, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of P238S, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of L234F, L235E, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of L234F, L235E, S239D, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of L234F and L235E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of G237E and P238E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of G237D, P238G, V240A, E269D, D270E, A330R, L234F, L235E, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a variant IgG Fc polypeptide comprises a mutation set of P238D, E269D, D270E, A330R, L234F, L235E, S239D, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a variant IgG Fc polypeptide comprises a mutation in the CH2 region and/or hinge region. In some embodiments, the mutation is a substitution, an insertion, or a deletion. In some embodiments, the substation comprises swapping of CH2 region to CH2 region of another IgG isotype. In some embodiments, the variant Fc molecule comprises a CH2 domain sequence having at least 50%, at least 85%, at least 90%, at least 94%, at least 95%, or at least 99% identity to SEQ ID NO: 96-101. In some embodiments, the variant Fc molecule comprises a CH2 domain sequence having at least 50%, at least 85%, at least 90%, at least 94%, at least 95%, or at least 99% identity to SEQ ID NO: 96. In some embodiments, the variant Fc molecule comprises a CH2 domain sequence having at least 50%, at least 85%, at least 90%, at least 94%, at least 95%, or at least 99% identity to SEQ ID NO: 97. In some embodiments, the variant Fc molecule comprises a CH2 domain sequence having at least 50%, at least 85%, at least 90%, at least 94%, at least 95%, or at least 99% identity to SEQ ID NO: 98. In some embodiments, the variant Fc molecule comprises a CH2 domain sequence having at least 50%, at least 85%, at least 90%, at least 94%, at least 95%, or at least 99% identity to SEQ ID NO: 99. In some embodiments, the variant Fc molecule comprises a CH2 domain sequence having at least 50%, at least 85%, at least 90%, at least 94%, at least 95%, or at least 99% identity to SEQ ID NO: 100. In some embodiments, the variant Fc molecule comprises a CH2 domain sequence having at least 50%, at least 85%, at least 90%, at least 94%, at least 95%, or at least 99% identity to SEQ ID NO: 101.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set selected from:

- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of L234F and L235E, as compared to SEQ ID NO: 88;
- a mutation set of G237E and P238E, as compared to SEQ ID NO: 88; or
- any combination thereof, wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of P238D, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238G, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238S, S239G, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237D, P238G, V240A, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L235V, P238E, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L235V, P238D, E269D, D270E, and A330R, and an insertion of an amino acid sequence GEV between positions 233 and 234, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of P238S, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F, L235E, P329A, H268D, and P271G, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F, L235E, S239D, P329A, H268D, and P271G, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of L234F and L235E, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the variant IgG Fc polypeptide comprises a mutation set of G237E and P238E, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises a mutation set selected from:

- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of L234F and L235E, as compared to SEQ ID NO: 88;
- a mutation set of G237E and P238E, as compared to SEQ ID NO: 88; or
- any combination thereof, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises a mutation set of P238D, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of G237D, P238G, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of G237D, P238S, S239G, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of G237D, P238G, V240A, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of L235V, P238E, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of L235V, P238D, E269D, D270E, and A330R, and an insertion of an amino acid sequence GEV between positions 233 and 234, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of P238S, E269D, D270E, and A330R, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of L234F, L235E, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of L234F, L235E, S239D, P329A, H268D, and P271G, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of L234F and L235E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a mutation set of G237E and P238E, as compared to SEQ ID NO: 88, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises a variant sequence of SEQ ID NO: 88, wherein the variant IgG Fc polypeptide comprises a mutation set selected from:

- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of L234F and L235E, as compared to SEQ ID NO: 88;
- a mutation set of G237E and P238E, as compared to SEQ ID NO: 88; or
- any combination thereof, wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises a variant sequence of SEQ ID NO: 88, wherein the variant IgG Fc polypeptide comprises a mutation set of P238D, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of G237D, P238G, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of G237D, P238S, S239G, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of G237D, P238G, V240A, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of L235V, P238E, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of L235V, P238D, E269D, D270E, and A330R, and an insertion of an amino acid sequence GEV between positions 233 and 234, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of P238S, E269D, D270E, and A330R, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of L234F, L235E, P329A, H268D, and P271G, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of L234F, L235E, S239D, P329A, H268D, and P271G, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of L234F and L235E, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101. In some embodiments, a variant IgG Fc polypeptide comprises a variant sequence of SEQ ID NO: 88, wherein the variant IgG Fc polypeptide comprises a mutation set of G237E and P238E, as compared to SEQ ID NO: 88, and wherein the variant IgG Fc polypeptide further comprises a CH2 region comprising an amino acid sequence that is at least 50, 60, 70, 75, 80, 85, 86, 87, 88, 89, 90, 91, 92, 93, 94, 95, 96, 97, 98, or 99% identical to SEQ ID NO: 96-101.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence selected from any one of those provide in Table 4. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

In some embodiments, a variant IgG Fc polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO:

36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, has increased binding affinity to FcγRIIβ over FcγRIIα, as compared to that of wild-type IgG. In some embodiments, a variant IgG Fc polypeptide comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, has increased binding affinity to FcγRIIβ over FcγRIIα, as compared to that of wild-type IgG.

In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 1. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 2. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 3. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 4. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 5. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 6. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 7. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 8. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 9. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 10. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 11. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 12. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 13. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 14. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 15. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 16. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 17. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 18. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 19. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 20. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 21. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 22. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 23. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 24. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 25. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 26. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 27. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 28. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 29. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 30. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 31. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 32. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 33. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 34. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 35. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 36. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 37. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 38. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 39. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 40. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 41. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 42. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 43. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 44. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 45. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 46. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 47. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 48. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 49. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 50. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 51. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 52. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 53. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 54. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 55. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 56. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 57. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 58. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 59. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 60. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 61. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 62. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 63. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 64. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 65. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 66. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 67. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 68. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 69. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 70. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 71. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 72. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 73. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 74. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 75. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 76. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 77. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 78. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 79. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 80. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 81. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 82. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 83. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 84. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 85. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 86. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 87. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 102. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 103. In some embodiments, a variant IgG Fc polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 104.

In some embodiments, a variant IgG Fc polypeptide comprises an amino acid sequence selected from any one of those provide in Table 4. In some embodiments, a variant IgG Fc polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104. In some embodiments, a variant IgG Fc polypeptide comprises an amino acid sequence of SEQ ID NO: 2. In some embodiments, a variant IgG Fc polypeptide comprises an amino acid sequence of SEQ ID NO: 3. In some embodiments, a variant IgG Fc polypeptide comprises an amino acid sequence of SEQ ID NO: 4. In some embodiments, a variant IgG Fc polypeptide comprises an amino acid sequence of SEQ ID NO: 5. In some embodiments, a variant IgG Fc polypeptide comprises an amino acid sequence of SEQ ID NO: 6. In some embodiments, a variant IgG Fc polypeptide comprises an amino acid sequence of SEQ ID NO: 7. In some embodiments, a variant IgG Fc polypeptide comprises an amino acid sequence of SEQ ID NO: 8. In some embodiments, a variant IgG Fc polypeptide comprises an amino acid sequence of SEQ ID NO: 9. In some embodiments, a variant IgG Fc polypeptide comprises an amino acid sequence of SEQ ID NO: 10. In some embodiments, a variant IgG Fc polypeptide comprises an amino acid sequence of SEQ ID NO: 11. In some embodiments, a variant IgG Fc polypeptide comprises an amino acid sequence of SEQ ID NO: 12. In some embodiments, a variant IgG Fc polypeptide comprises an amino acid sequence of SEQ ID NO: 13. In some embodiments, a variant IgG Fc polypeptide comprises an amino acid sequence of SEQ ID NO: 14. In some embodiments, a variant IgG Fc polypeptide comprises an amino acid sequence of SEQ ID NO: 15. In some embodiments, a variant IgG Fc polypeptide comprises an amino acid sequence of SEQ ID NO: 16. In some embodiments, a variant IgG Fc polypeptide comprises an amino acid sequence of SEQ ID NO: 17. In some embodiments, a variant IgG Fc polypeptide comprises an amino acid sequence of SEQ ID NO: 18. In some embodiments, a variant IgG Fc polypeptide comprises an amino acid sequence of SEQ ID NO: 19. In some embodiments, a variant IgG Fc polypeptide comprises an amino acid sequence of SEQ ID NO: 20. In some embodiments, a variant IgG Fc polypeptide comprises an amino acid sequence of SEQ ID NO: 21. In some embodiments, a variant IgG Fc polypeptide comprises an amino acid sequence of SEQ ID NO: 22. In some embodiments, a variant IgG Fc polypeptide comprises an amino acid sequence of SEQ ID NO: 23. In some embodiments, a variant IgG Fc polypeptide comprises an amino acid sequence of SEQ ID NO: 24. In some embodiments, a variant IgG Fc polypeptide comprises an amino acid sequence of SEQ ID NO: 25. In some embodiments, a variant IgG Fc polypeptide comprises an amino acid sequence of SEQ ID NO: 26. In some embodiments, a variant IgG Fc polypeptide comprises an amino acid sequence of SEQ ID NO: 27. In some embodiments, a variant IgG Fc polypeptide comprises an amino acid sequence of SEQ ID NO: 28. In some embodiments, a variant IgG Fc polypeptide comprises an amino acid sequence of SEQ ID NO: 29. In some embodiments, a variant IgG Fc polypeptide comprises an amino acid sequence of SEQ ID NO: 30. In some embodiments, a variant IgG Fc polypeptide comprises an amino acid sequence of SEQ ID NO: 31. In some embodiments, a variant IgG Fc polypeptide comprises an amino acid sequence of SEQ ID NO: 32. In some embodiments, a variant IgG Fc polypeptide comprises an amino acid sequence of SEQ ID NO: 33. In some embodiments, a variant IgG Fc polypeptide comprises an amino acid sequence of SEQ ID NO: 34. In some embodiments, a variant IgG Fc polypeptide comprises an amino acid sequence of SEQ ID NO: 35. In some embodiments, a variant IgG Fc polypeptide comprises an amino acid sequence of SEQ ID NO: 36. In some embodiments, a variant IgG Fc polypeptide comprises an amino acid sequence of SEQ ID NO: 37. In some embodiments, a variant IgG Fc polypeptide comprises an amino acid sequence of SEQ ID NO: 38. In some embodiments, a variant IgG Fc polypeptide comprises an amino acid sequence of SEQ ID NO: 39. In some embodiments, a variant IgG Fc polypeptide comprises an amino acid sequence of SEQ ID NO: 40. In some embodiments, a variant IgG Fc polypeptide comprises an amino acid sequence of SEQ ID NO: 41. In some embodiments, a variant IgG Fc polypeptide comprises an amino acid sequence of SEQ ID NO: 42. In some embodiments, a variant IgG Fc polypeptide comprises an amino acid sequence of SEQ ID NO: 43. In some embodiments, a variant IgG Fc polypeptide comprises an amino acid sequence of SEQ ID NO: 44. In some embodiments, a variant IgG Fc polypeptide comprises an amino acid sequence of SEQ ID NO: 45. In some embodiments, a variant IgG Fc polypeptide comprises an amino acid sequence of SEQ ID NO: 46. In some embodiments, a variant IgG Fc polypeptide comprises an amino acid sequence of SEQ ID NO: 47. In some embodiments, a variant IgG Fc polypeptide comprises an amino acid sequence of SEQ ID NO: 48. In some embodiments, a variant IgG Fc polypeptide comprises an amino acid sequence of SEQ ID NO: 49. In some embodiments, a variant IgG Fc polypeptide comprises an amino acid sequence of SEQ ID NO: In some embodiments, a variant IgG Fc polypeptide comprises an amino acid sequence of SEQ ID NO: 50. In some embodiments, a variant IgG Fc polypeptide comprises an amino acid sequence of SEQ ID NO: 51. In some embodiments, a variant IgG Fc polypeptide comprises an amino acid sequence of SEQ ID NO: 52. In some embodiments, a variant IgG Fc polypeptide comprises an amino acid sequence of SEQ ID NO: 53. In some embodiments, a variant IgG Fc polypeptide comprises an amino acid sequence of SEQ ID NO: 54. In some embodiments, a variant IgG Fc polypeptide comprises an amino acid sequence of SEQ ID NO: 55. In some embodiments, a variant IgG Fc polypeptide comprises an amino acid sequence of SEQ ID NO: 56. In some embodiments, a variant IgG Fc polypeptide comprises an amino acid sequence of SEQ ID NO: 57. In some embodiments, a variant IgG Fc polypeptide comprises an amino acid sequence of SEQ ID NO: 58. In some embodiments, a variant IgG Fc polypeptide comprises an amino acid sequence of SEQ ID NO: 59. In some embodiments, a variant IgG Fc polypeptide comprises an amino acid sequence of SEQ ID NO: 60. In some embodiments, a variant IgG Fc polypeptide comprises an amino acid sequence of SEQ ID NO: 61. In some embodiments, a variant IgG Fc polypeptide comprises an amino acid sequence of SEQ ID NO: 62. In some embodiments, a variant IgG Fc polypeptide comprises an amino acid sequence of SEQ ID NO: 63. In some embodiments, a variant IgG Fc polypeptide comprises an amino acid sequence of SEQ ID NO: 64. In some embodiments, a variant IgG Fc polypeptide comprises an amino acid sequence of SEQ ID NO: 65. In some embodiments, a variant IgG Fc polypeptide comprises an amino acid sequence of SEQ ID NO: 66. In some embodiments, a variant IgG Fc polypeptide comprises an amino acid sequence of SEQ ID NO: 67. In some embodiments, a variant IgG Fc polypeptide comprises an amino acid sequence of SEQ ID NO: 68. In some embodiments, a variant IgG Fc polypeptide comprises an amino acid sequence of SEQ ID NO: 69. In some embodiments, a variant IgG Fc polypeptide comprises an amino acid sequence of SEQ ID NO: 70. In some embodiments, a variant IgG Fc polypeptide comprises an amino acid sequence of SEQ ID NO: 71. In some embodiments, a variant IgG Fc polypeptide comprises an amino acid sequence of SEQ ID NO: 72. In some embodiments, a variant IgG Fc polypeptide comprises an amino acid sequence of SEQ ID NO: 73. In some embodiments, a variant IgG Fc polypeptide comprises an amino acid sequence of SEQ ID NO: 74. In some embodiments, a variant IgG Fc polypeptide comprises an amino acid sequence of SEQ ID NO: 75. In some embodiments, a variant IgG Fc polypeptide comprises an amino acid sequence of SEQ ID NO: 76. In some embodiments, a variant IgG Fc polypeptide comprises an amino acid sequence of SEQ ID NO: 77. In some embodiments, a variant IgG Fc polypeptide comprises an amino acid sequence of SEQ ID NO: 78. In some embodiments, a variant IgG Fc polypeptide comprises an amino acid sequence of SEQ ID NO: 79. In some embodiments, a variant IgG Fc polypeptide comprises an amino acid sequence of SEQ ID NO: 80. In some embodiments, a variant IgG Fc polypeptide comprises an amino acid sequence of SEQ ID NO: 81. In some embodiments, a variant IgG Fc polypeptide comprises an amino acid sequence of SEQ ID NO: 82. In some embodiments, a variant IgG Fc polypeptide comprises an amino acid sequence of SEQ ID NO: 83. In some embodiments, a variant IgG Fc polypeptide comprises an amino acid sequence of SEQ ID NO: 84. In some embodiments, a variant IgG Fc polypeptide comprises an amino acid sequence of SEQ ID NO: 85. In some embodiments, a variant IgG Fc polypeptide comprises an amino acid sequence of SEQ ID NO: 86. In some embodiments, a variant IgG Fc polypeptide comprises an amino acid sequence of SEQ ID NO: 87. In some embodiments, a variant IgG Fc polypeptide comprises an amino acid sequence of SEQ ID NO: 102. In some embodiments, a variant IgG Fc polypeptide comprises an amino acid sequence of SEQ ID NO: 103. In some embodiments, a variant IgG Fc polypeptide comprises an amino acid sequence of SEQ ID NO: 104.

In some embodiments, the variant IgG Fc polypeptide provided herein in Table 4 have mutations that enhance or confer selective binding to FcγRIIβ over FcγRIIα. In some embodiments, the mutations that enhance or confer selective binding to FcγRIIβ over FcγRIIa are such as any one of those associated with VFC-1 through VFC-90.

Dimeric Variant Fc Molecules

In some embodiments, two (or more) linkers associate, either covalently or non-covalently, e.g., to form a hetero or homo-dimeric therapeutic compound. In some embodiments, the linker can comprise an Fc region and two Fc regions associate with one another. In some embodiments of a therapeutic compound comprising two linker regions, the linker regions can self-associate, e.g., as two identical Fc regions. In some embodiments of a therapeutic compound comprising two linker regions, the linker regions are not capable of, or not capable of substantial, self-association, e.g., the two Fc regions can be members of a knob and hole pair. In some embodiments, the polypeptide comprises a first polypeptide and a second polypeptide. In some embodiments, the first polypeptide comprises a knob mutation, and the second polypeptide comprises a hole mutation. In some embodiments, the first polypeptide comprises a hole mutation, and the second polypeptide comprises a knob mutation. In some embodiments, the knob mutation is such as those provided herein. In some embodiments, the hole mutation is such as those provided herein. In some embodiments, the knob mutation is such as those provided in any one of SEQ ID NO: 75, 78, 79, 80, 82, 84, 85, 86, or 87. In some embodiments, the hole mutation is such as those provided in any one of SEQ ID NO: 76, 77, 81, or 83.

In some embodiments, a polypeptide can associate with another polypeptide. In some embodiments, the polypeptide associated with another polypeptide forms a dimer molecule.

In some embodiments, the dimer is a homodimer molecule. In some embodiments, the dimer is a heterodimer molecule.

As used herein, the term "non-covalently conjugated" can mean that a polypeptide is tethered to another polypeptide through a linker. In some embodiments, the linker is a peptide linker. Non-limiting examples of peptide linkers that can be used are known in the art and are provide for herein.

As discussed herein the different domains, molecules, or polypeptide can be linked together with a linker domain or region. Any linker region described herein can be used as a linker. Linkers can be for example, glycine/serine linkers. In some embodiments, the linker can comprise one or more repeats of GGGGS (SEQ ID NO: 105). In some embodiments, the linker comprises 1, 2, 3, 4, or 5 repeats. In some embodiments, the linker comprises GGGGSGGGGS (SEQ ID NO: 106). In some embodiments, the linker comprises GGGGSGGGGSGGGGS (SEQ ID NO: 107). In some embodiments, the linker comprises: GGGGS (SEQ ID NO: 105), $(GGGGS)_3$ (SEQ ID NO: 107), $(GGGGS)^n$ (n=1, 2, 3, 4) (SEQ ID NO: 105, SEQ ID NO: 106, SEQ ID NO: 107, SEQ ID NO: 108)), $(Gly)_8$ (SEQ ID NO: 109). $(Gly)^6$ (SEQ ID NO: 110). $(EAAAK)_3$ (SEQ ID NO: 111), $(EAAK)_n$ (n=1-3) (SEQ ID NO: 112, SEQ ID NO: 113, SEQ ID NO: 114)), $A(EAAAK)_4ALEA(EAAAK)4A$ (SEQ ID NO: 115), or AEAAAKEAAAKA (SEQ ID NO: 116). These linkers can be used in any of the compounds or compositions provided herein.

These peptide linkers are non-limiting examples and other peptide linkers can also be used.

In some embodiments, the polypeptide forms a dimer. In some embodiments, the dimer is a homodimer. In some embodiments, the dimer is a heterodimer.

Non-limiting exemplary configurations of therapeutic compounds comprise the following (e.g., in N-terminus to C-terminus order):

R1-Linker Region A-R2

R3-Linker Region B-R4, wherein,

R1, R2, R3, and R4, each independently comprises an effector binding/modulating moiety, e.g., anti-PD1 antibody, anti-LAG3 antibody, anti-CTLA4 antibody, anti-FcγRIIb antibody; or is absent;

Linker Region A and Linker Region B comprise moieties that can associate with one another, e.g., Linker A and Linker Region B, each comprises an Fc polypeptide provided that an effector binding/modulating moiety and a specific targeting moiety are present. Furthermore, Linker A and Linker Region B, each comprise an Fc polypeptide that is selective for FcγRIIb. In some embodiments, the Fc polypeptide that is selective for FcγRIIb has increased selectivity for FcγRIIb. In some embodiments, the Fc polypeptide that is selective for FcγRIIb has increased affinity for FcγRIIb. In some embodiments, the Fc polypeptide that is selective for FcγRIIb has increased selectivity and affinity for FcγRIIb. In some embodiments, the Fc polypeptide that is selective for FcγRIIb has increased selectivity for FcγRIIb over FcγRIIa. In some embodiments, the Fc polypeptide that is selective for FcγRIIb has increased affinity for FcγRIIb over FcγRIIa. In some embodiments, the Fc polypeptide that is selective for FcγRIIb has increased selectivity and affinity for FcγRIIb over FcγRIIa. In some embodiments, Linker Region A and Linker Region B are both absent.

In some embodiments, the dimer comprises the formula of:

R1-Linker Region A-R2

R3-Linker Region B-R4, wherein,

R1, R2, R3, and R4, each independently comprises an effector binding/modulating moiety, e.g., anti-PD1 antibody, anti-LAG3 antibody, anti-CTLA4 antibody, anti-FcγRIIb antibody; or is absent; and Linker Region A and Linker Region B, each independently comprises an Fc polypeptide provided that the effector binding/modulating moieties are present, and wherein the Fc polypeptide selectively binds to FcγRIIb.

In some embodiments:

R1 comprises an effector binding/modulating moiety, e.g., anti-PD-1 antibody, or an antigen-binding fragment thereof, anti-LAG3 antibody, anti-CTLA4 antibody, or anti-FcγRIIb antibody, or is absent;

R2 comprises an effector binding/modulating moiety, e.g., anti-PD-1 antibody, or an antigen-binding fragment thereof, anti-LAG3 antibody, anti-CTLA4 antibody, or anti-FcγRIIb antibody;

R3 comprises an effector binding/modulating moiety, e.g., anti-PD-1 antibody, or an antigen-binding fragment thereof, anti-LAG3 antibody, anti-CTLA4 antibody, or anti-FcγRIIb antibody, or is absent;

R4 comprises an effector binding/modulating moiety, e.g., anti-PD-1 antibody, or an antigen-binding fragment thereof, anti-LAG3 antibody, anti-CTLA4 antibody, or anti-FcγRIIb antibody; and Linker Region A and Linker Region B comprise moieties that can associate with one another, e.g., Linker A and Linker Region B, each comprises an Fc polypeptide, provided that one of R1 or R3 is present and one of R2 or R4 is present. Furthermore, Linker A and Linker Region B, each comprise an Fc polypeptide that is selective for FcγRIIb. In some embodiments, the Fc polypeptide that is selective for FcγRIIb has increased selectivity for FcγRIIb. In some embodiments, the Fc polypeptide that is selective for FcγRIIb has increased affinity for FcγRIIb. In some embodiments, the Fc polypeptide that is selective for FcγRIIb has increased selectivity and affinity for FcγRIIb. In some embodiments, the Fc polypeptide that is selective for FcγRIIb has increased selectivity for FcγRIIb over FcγRIIα. In some embodiments, the Fc polypeptide that is selective for FcγRIIb has increased affinity for FcγRIIb over FcγRIIα. In some embodiments, the Fc polypeptide that is selective for FcγRIIb has increased selectivity and affinity for FcγRIIb over FcγRIIα.

In some embodiments, Linker Region A is such a those provided herein, e.g., VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90. In some embodiments, Linker Region B is such a those provided herein, e.g., VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90. In some embodiments, Linker Region A comprises the amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104. In some embodiments, Linker Region B comprises the amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104. In some embodiments, Linker Region A comprises the amino acid sequence of any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104. In some embodiments, Linker Region B comprises the amino acid sequence of any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

In some embodiments, a dimer molecule comprises a first polypeptide and a second polypeptide. In some embodiments, a dimer molecule comprises a first polypeptide and a second polypeptide, wherein the first polypeptide and the second polypeptide comprise different amino acid sequence. In some embodiments, a dimer molecule comprises a first polypeptide and a second polypeptide, wherein the first polypeptide and the second polypeptide comprise identical amino acid sequence. In some embodiments, the dimer molecule is a homodimer molecule. In some embodiments, the dimer molecule is a heterodimer molecule. In some embodiments, the dimer molecule comprises a pair of a first polypeptide and a second polypeptide, and wherein the first polypeptide and the second polypeptide comprise different amino acid sequences. In some embodiments, the dimer molecule comprises a pair of a first polypeptide and a second polypeptide, and wherein the first polypeptide and the second polypeptide comprise identical amino acid sequences. In some embodiments, the dimer molecule is a variant IgG Fc polypeptide comprising a first polypeptide and a second polypeptide. In some embodiments, the first polypeptide is a first variant IgG Fc polypeptide. In some embodiments, the second polypeptide is a second variant IgG Fc polypeptide. In some embodiments, the first variant IgG Fc polypeptide and the second variant IgG Fc polypeptide are the same. In some embodiments, the first variant IgG Fc polypeptide and the second variant IgG Fc polypeptide are not the same. In some embodiments, the first variant IgG Fc polypeptide and the second variant IgG Fc polypeptide are identical. In some embodiments, the first variant IgG Fc polypeptide and the second variant IgG Fc polypeptide are different. In some embodiments, the first polypeptide is such a those provided herein, e.g., VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90. In some embodiments, the second polypeptide is such a those provided herein, e.g., VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90.

In some embodiments, the first polypeptide is such a those provided herein, e.g., VFC-1, VFC-4, VFC-5, VFC-6, VFC-8, VFC-10, VFC-11, VFC-12, or VFC-13. In some embodiments, the second polypeptide is such a those provided herein, e.g., VFC-2, VFC-3, VFC-7, or VFC-9.

In some embodiments, a first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one sequence of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90. In some embodiments, a second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one sequence of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90.

In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one sequence of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one sequence of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, or VFC-90.

In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 1. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 2; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 2. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 3; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 3. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 4; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 4. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 5; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 5. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 6; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 6. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 7; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 7. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 8; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 8. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 9; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 9. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 10; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 10. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 11; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 11. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 12; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 12. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 13; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 13. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 14; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 14. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 15; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 15. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 16; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 16. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 17; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 17. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 18; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 18. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 19; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 19. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 20; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 20. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 21; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 21. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 22; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 22. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 23; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 23. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 24; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 24. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 25; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 25. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 26; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 26. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 27; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 27. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 28; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 28. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 29; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 29. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 30; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 30. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 31; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 31. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 32; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 32. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 33; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 33. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 34; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 34. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 35; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 35. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 36; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 36. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 37; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 37. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 38; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 38. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 39; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 39. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 40; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 40. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 41; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 41. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 42; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 42. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 43; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 43. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 44; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 44. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 45; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 45. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 46; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 46. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 47; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 47. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 48; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 48. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 49; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 49. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 50; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 50. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 51; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 51. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 52; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 52. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 53; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 53. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 54; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 54. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 55; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 55. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 56; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 56. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 57; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 57. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 58; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 58. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 59; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 59. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 60; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 60. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 61; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 61. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 62; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 62. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 63; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 63. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 64; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 64. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 65; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 65. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 66; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 66. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 67; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 67. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 68; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 68. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 69; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 69. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 70; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 70. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 71; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 71. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 72; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 72. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 73; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 73. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 74; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 74. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 75; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 75. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 76; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 76. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 77; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 77. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 78; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 78. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 79; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 79. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 80; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 80. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 81; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 81. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 82; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 82. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 83; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 83. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 84; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 84. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 85; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 85. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 86; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 86. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 87; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 87. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 102; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 102. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 103; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 103. In some embodiments, a dimer molecule comprises a first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 104; and a second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NO: 104.

In some embodiments, a dimer molecule comprises a first polypeptide comprising an amino acid sequence of SEQ ID NO: 1; and a second polypeptide comprising an amino acid sequence of SEQ ID NO: 1. In some embodiments, a dimer molecule comprises a first polypeptide comprising an amino acid sequence of SEQ ID NO: 2; and a second polypeptide comprising an amino acid sequence of SEQ ID NO: 2. In some embodiments, a dimer molecule comprises a first polypeptide comprising an amino acid sequence of SEQ ID NO: 3; and a second polypeptide comprising an amino acid sequence of SEQ ID NO: 3. In some embodiments, a dimer molecule comprises a first polypeptide comprising an amino acid sequence of SEQ ID NO: 4; and a second polypeptide comprising an amino acid sequence of SEQ ID NO: 4. In some embodiments, a dimer molecule comprises a first polypeptide comprising an amino acid sequence of SEQ ID NO: 5; and a second polypeptide comprising an amino acid sequence of SEQ ID NO: 5. In some embodiments, a dimer molecule comprises a first polypeptide comprising an amino acid sequence of SEQ ID NO: 6; and a second polypeptide comprising an amino acid sequence of SEQ ID NO: 6. In some embodiments, a dimer molecule comprises a first polypeptide comprising an amino acid sequence of SEQ ID NO: 7; and a second polypeptide comprising an amino acid sequence of SEQ ID NO: 7. In some embodiments, a dimer molecule comprises a first polypeptide comprising an amino acid sequence of SEQ ID NO: 8; and a second polypeptide comprising an amino acid sequence of SEQ ID NO: 8. In some embodiments, a dimer molecule comprises a first polypeptide comprising an amino acid sequence of SEQ ID NO: 9; and a second polypeptide comprising an amino acid sequence of SEQ ID NO: 9. In some embodiments, a dimer molecule comprises a first polypeptide comprising an amino acid sequence of SEQ ID NO: 10; and a second polypeptide comprising an amino acid sequence of SEQ ID NO: 10. In some embodiments, a dimer molecule comprises a first polypeptide comprising an amino acid sequence of SEQ ID NO: 11; and a second polypeptide comprising an amino acid sequence of SEQ ID NO: 11. In some embodiments, a dimer molecule comprises a first polypeptide comprising an amino acid sequence of SEQ ID NO: 12; and a second polypeptide comprising an amino acid sequence of SEQ ID NO: 12. In some embodiments, a dimer molecule comprises a first polypeptide comprising an amino acid sequence of SEQ ID NO: 13; and a second polypeptide comprising an amino acid sequence of SEQ ID NO: 13. In some embodiments, a dimer molecule comprises a first polypeptide comprising an amino acid sequence of SEQ ID NO: 14; and a second polypeptide comprising an amino acid sequence of SEQ ID NO: 14. In some embodiments, a dimer molecule comprises a first polypeptide comprising an amino acid sequence of SEQ ID NO: 15; and a second polypeptide comprising an amino acid sequence of SEQ ID NO: 15. In some embodiments, a dimer molecule comprises a first polypeptide comprising an amino acid sequence of SEQ ID NO: 16; and a second polypeptide comprising an amino acid sequence of SEQ ID NO: 16. In some embodiments, a dimer molecule comprises a first polypeptide comprising an amino acid sequence of SEQ ID NO: 17; and a second polypeptide comprising an amino acid sequence of SEQ ID NO: 17. In some embodiments, a dimer molecule comprises a first polypeptide comprising an amino acid sequence of SEQ ID NO: 18; and a second polypeptide comprising an amino acid sequence of SEQ ID NO: 18. In some embodiments, a dimer molecule comprises a first polypeptide comprising an amino acid sequence of SEQ ID NO: 19; and a second polypeptide comprising an amino acid sequence of SEQ ID NO: 19. In some embodiments, a dimer molecule comprises a first polypeptide comprising an amino acid sequence of SEQ ID NO: 20; and a second polypeptide comprising an amino acid sequence of SEQ ID NO: 20. In some embodiments, a dimer molecule comprises a first polypeptide comprising an amino acid sequence of SEQ ID NO: 21; and a second polypeptide comprising an amino acid sequence of SEQ ID NO: 21. In some embodiments, a dimer molecule comprises a first polypeptide comprising an amino acid sequence of SEQ ID NO: 22; and a second polypeptide comprising an amino acid sequence of SEQ ID NO: 22. In some embodiments, a dimer molecule comprises a first polypeptide comprising an amino acid sequence of SEQ ID NO: 23; and a second polypeptide comprising an amino acid sequence of SEQ ID NO: 23. In some embodiments, a dimer molecule comprises a first polypeptide comprising an amino acid sequence of SEQ ID NO: 24; and a second polypeptide comprising an amino acid sequence of SEQ ID NO: 24. In some embodiments, a dimer molecule comprises a first polypeptide comprising an amino acid sequence of SEQ ID NO: 25; and a second polypeptide comprising an amino acid sequence of SEQ ID NO: 25. In some embodiments, a dimer molecule comprises a first polypeptide comprising an amino acid sequence of SEQ ID NO: 26; and a second polypeptide comprising an amino acid sequence of SEQ ID NO: 26. In some embodiments, a dimer molecule comprises a first polypeptide comprising an amino acid sequence of SEQ ID NO: 27; and a second polypeptide comprising an amino acid sequence of SEQ ID NO: 27. In some embodiments, a dimer molecule comprises a first polypeptide comprising an amino acid sequence of SEQ ID NO: 28; and a second polypeptide comprising an amino acid sequence of SEQ ID NO: 28. In some embodiments, a dimer molecule comprises a first polypeptide comprising an amino acid sequence of SEQ ID NO: 29; and a second polypeptide comprising an amino acid sequence of SEQ ID NO: 29. In some embodiments, a dimer molecule comprises a first polypeptide comprising an amino acid sequence of SEQ ID NO: 30; and a second polypeptide comprising an amino acid sequence of SEQ ID NO: 30. In some embodiments, a dimer molecule comprises a first polypeptide comprising an amino acid sequence of SEQ ID NO: 31; and a second polypeptide comprising an amino acid sequence of SEQ ID NO: 31. In some embodiments, a dimer molecule comprises a first polypeptide comprising an amino acid sequence of SEQ ID NO: 32; and a second polypeptide comprising an amino acid sequence of SEQ ID NO: 32. In some embodiments, a dimer molecule comprises a first polypeptide comprising an amino acid sequence of SEQ ID NO: 33; and a second polypeptide comprising an amino acid sequence of SEQ ID NO: 33. In some embodiments, a dimer molecule comprises a first polypeptide comprising an amino acid sequence of SEQ ID NO: 34; and a second polypeptide comprising an amino acid sequence of SEQ ID NO: 34. In some embodiments, a dimer molecule comprises a first polypeptide comprising an amino acid sequence of SEQ ID NO: 35; and a second polypeptide comprising an amino acid sequence of SEQ ID NO: 35. In some embodiments, a dimer molecule comprises a first polypeptide comprising an amino acid sequence of SEQ ID NO: 36; and a second polypeptide comprising an amino acid sequence of SEQ ID NO: 36. In some embodiments, a dimer molecule comprises a first polypeptide comprising an amino acid sequence of SEQ ID NO: 37; and a second polypeptide comprising an amino acid sequence of SEQ ID NO: 37. In some embodiments, a dimer molecule comprises a first polypeptide comprising an amino acid sequence of SEQ ID NO: 38; and a second polypeptide comprising an amino acid sequence of SEQ ID NO: 38. In some embodiments, a dimer molecule comprises a first polypeptide comprising an amino acid sequence of SEQ ID NO: 39; and a second polypeptide comprising an amino acid sequence of SEQ ID NO: 39. In some embodiments, a dimer molecule comprises a first polypeptide comprising an amino acid sequence of SEQ ID NO: 40; and a second polypeptide comprising an amino acid sequence of SEQ ID NO: 40. In some embodiments, a dimer molecule comprises a first polypeptide comprising an amino acid sequence of SEQ ID NO: 41; and a second polypeptide comprising an amino acid sequence of SEQ ID NO: 41. In some embodiments, a dimer molecule comprises a first polypeptide comprising an amino acid sequence of SEQ ID NO: 42; and a second polypeptide comprising an amino acid sequence of SEQ ID NO: 42. In some embodiments, a dimer molecule comprises a first polypeptide comprising an amino acid sequence of SEQ ID NO: 43; and a second polypeptide comprising an amino acid sequence of SEQ ID NO: 43. In some embodiments, a dimer molecule comprises a first polypeptide comprising an amino acid sequence of SEQ ID NO: 44; and a second polypeptide comprising an amino acid sequence of SEQ ID NO: 44. In some embodiments, a dimer molecule comprises a first polypeptide comprising an amino acid sequence of SEQ ID NO: 45; and a second polypeptide comprising an amino acid sequence of SEQ ID NO: 45. In some embodiments, a dimer molecule comprises a first polypeptide comprising an amino acid sequence of SEQ ID NO: 46; and a second polypeptide comprising an amino acid sequence of SEQ ID NO: 46. In some embodiments, a dimer molecule comprises a first polypeptide comprising an amino acid sequence of SEQ ID NO: 47; and a second polypeptide comprising an amino acid sequence of SEQ ID NO: 47. In some embodiments, a dimer molecule comprises a first polypeptide comprising an amino acid sequence of SEQ ID NO: 48; and a second polypeptide comprising an amino acid sequence of SEQ ID NO: 48. In some embodiments, a dimer molecule comprises a first polypeptide comprising an amino acid sequence of SEQ ID NO: 49; and a second polypeptide comprising an amino acid sequence of SEQ ID NO: 49. In some embodiments, a dimer molecule comprises a first polypeptide comprising an amino acid sequence of SEQ ID NO: 50; and a second polypeptide comprising an amino acid sequence of SEQ ID NO: 50. In some embodiments, a dimer molecule comprises a first polypeptide comprising an amino acid sequence of SEQ ID NO: 51; and a second polypeptide comprising an amino acid sequence of SEQ ID NO: 51. In some embodiments, a dimer molecule comprises a first polypeptide comprising an amino acid sequence of SEQ ID NO: 52; and a second polypeptide comprising an amino acid sequence of SEQ ID NO: 52. In some embodiments, a dimer molecule comprises a first polypeptide comprising an amino acid sequence of SEQ ID NO: 53; and a second polypeptide comprising an amino acid sequence of SEQ ID NO: 53. In some embodiments, a dimer molecule comprises a first polypeptide comprising an amino acid sequence of SEQ ID NO: 54; and a second polypeptide comprising an amino acid sequence of SEQ ID NO: 54. In some embodiments, a dimer molecule comprises a first polypeptide comprising an amino acid sequence of SEQ ID NO: 55; and a second polypeptide comprising an amino acid sequence of SEQ ID NO: 55. In some embodiments, a dimer molecule comprises a first polypeptide comprising an amino acid sequence of SEQ ID NO: 56; and a second polypeptide comprising an amino acid sequence of SEQ ID NO: 56. In some embodiments, a dimer molecule comprises a first polypeptide comprising an amino acid sequence of SEQ ID NO: 57; and a second polypeptide comprising an amino acid sequence of SEQ ID NO: 57. In some embodiments, a dimer molecule comprises a first polypeptide comprising an amino acid sequence of SEQ ID NO: 58; and a second polypeptide comprising an amino acid sequence of SEQ ID NO: 58. In some embodiments, a dimer molecule comprises a first polypeptide comprising an amino acid sequence of SEQ ID NO: 59; and a second polypeptide comprising an amino acid sequence of SEQ ID NO: 59. In some embodiments, a dimer molecule comprises a first polypeptide comprising an amino acid sequence of SEQ ID NO: 60; and a second polypeptide comprising an amino acid sequence of SEQ ID NO: 60. In some embodiments, a dimer molecule comprises a first polypeptide comprising an amino acid sequence of SEQ ID NO: 61; and a second polypeptide comprising an amino acid sequence of SEQ ID NO: 61. In some embodiments, a dimer molecule comprises a first polypeptide comprising an amino acid sequence of SEQ ID NO: 62; and a second polypeptide comprising an amino acid sequence of SEQ ID NO: 62. In some embodiments, a dimer molecule comprises a first polypeptide comprising an amino acid sequence of SEQ ID NO: 63; and a second polypeptide comprising an amino acid sequence of SEQ ID NO: 63. In some embodiments, a dimer molecule comprises a first polypeptide comprising an amino acid sequence of SEQ ID NO: 64; and a second polypeptide comprising an amino acid sequence of SEQ ID NO: 64. In some embodiments, a dimer molecule comprises a first polypeptide comprising an amino acid sequence of SEQ ID NO: 65; and a second polypeptide comprising an amino acid sequence of SEQ ID NO: 65 In some embodiments, a dimer molecule comprises a first polypeptide comprising an amino acid sequence of SEQ ID NO: 66; and a second polypeptide comprising an amino acid sequence of SEQ ID NO: 66. In some embodiments, a dimer molecule comprises a first polypeptide comprising an amino acid sequence of SEQ ID NO: 67; and a second polypeptide comprising an amino acid sequence of SEQ ID NO: 67. In some embodiments, a dimer molecule comprises a first polypeptide comprising an amino acid sequence of SEQ ID NO: 68; and a second polypeptide comprising an amino acid sequence of SEQ ID NO: 68. In some embodiments, a dimer molecule comprises a first polypeptide comprising an amino acid sequence of SEQ ID NO: 69; and a second polypeptide comprising an amino acid sequence of SEQ ID NO: 69. In some embodiments, a dimer molecule comprises a first polypeptide comprising an amino acid sequence of SEQ ID NO: 70; and a second polypeptide comprising an amino acid sequence of SEQ ID NO: 70. In some embodiments, a dimer molecule comprises a first polypeptide comprising an amino acid sequence of SEQ ID NO: 71; and a second polypeptide comprising an amino acid sequence of SEQ ID NO: 71. In some embodiments, a dimer molecule comprises a first polypeptide comprising an amino acid sequence of SEQ ID NO: 72; and a second polypeptide comprising an amino acid sequence of SEQ ID NO: 72. In some embodiments, a dimer molecule comprises a first polypeptide comprising an amino acid sequence of SEQ ID NO: 73; and a second polypeptide comprising an amino acid sequence of SEQ ID NO: 73. In some embodiments, a dimer molecule comprises a first polypeptide comprising an amino acid sequence of SEQ ID NO: 74; and a second polypeptide comprising an amino acid sequence of SEQ ID NO: 74. In some embodiments, a dimer molecule comprises a first polypeptide comprising an amino acid sequence of SEQ ID NO: 75; and a second polypeptide comprising an amino acid sequence of SEQ ID NO: 75. In some embodiments, a dimer molecule comprises a first polypeptide comprising an amino acid sequence of SEQ ID NO: 76; and a second polypeptide comprising an amino acid sequence of SEQ ID NO: 76. In some embodiments, a dimer molecule comprises a first polypeptide comprising an amino acid sequence of SEQ ID NO: 77; and a second polypeptide comprising an amino acid sequence of SEQ ID NO: 77. In some embodiments, a dimer molecule comprises a first polypeptide comprising an amino acid sequence of SEQ ID NO: 78; and a second polypeptide comprising an amino acid sequence of SEQ ID NO: 78. In some embodiments, a dimer molecule comprises a first polypeptide comprising an amino acid sequence of SEQ ID NO: 79; and a second polypeptide comprising an amino acid sequence of SEQ ID NO: 79. In some embodiments, a dimer molecule comprises a first polypeptide comprising an amino acid sequence of SEQ ID NO: 80; and a second polypeptide comprising an amino acid sequence of SEQ ID NO: 80. In some embodiments, a dimer molecule comprises a first polypeptide comprising an amino acid sequence of SEQ ID NO: 81; and a second polypeptide comprising an amino acid sequence of SEQ ID NO: 81. In some embodiments, a dimer molecule comprises a first polypeptide comprising an amino acid sequence of SEQ ID NO: 82; and a second polypeptide comprising an amino acid sequence of SEQ ID NO: 82. In some embodiments, a dimer molecule comprises a first polypeptide comprising an amino acid sequence of SEQ ID NO: 83; and a second polypeptide comprising an amino acid sequence of SEQ ID NO: 83. In some embodiments, a dimer molecule comprises a first polypeptide comprising an amino acid sequence of SEQ ID NO: 84; and a second polypeptide comprising an amino acid sequence of SEQ ID NO: 84. In some embodiments, a dimer molecule comprises a first polypeptide comprising an amino acid sequence of SEQ ID NO: 85; and a second polypeptide comprising an amino acid sequence of SEQ ID NO: 85. In some embodiments, a dimer molecule comprises a first polypeptide comprising an amino acid sequence of SEQ ID NO: 86; and a second polypeptide comprising an amino acid sequence of SEQ ID NO: 86. In some embodiments, a dimer molecule comprises a first polypeptide comprising an amino acid sequence of SEQ ID NO: 87; and a second polypeptide comprising an amino acid sequence of SEQ ID NO: 87. In some embodiments, a dimer molecule comprises a first polypeptide comprising an amino acid sequence of SEQ ID NO: 102; and a second polypeptide comprising an amino acid sequence of SEQ ID NO: 102. In some embodiments, a dimer molecule comprises a first polypeptide comprising an amino acid sequence of SEQ ID NO: 103; and a second polypeptide comprising an amino acid sequence of SEQ ID NO: 103. In some embodiments, a dimer molecule comprises a first polypeptide comprising an amino acid sequence of SEQ ID NO: 104; and a second polypeptide comprising an amino acid sequence of SEQ ID NO: 104.

In some embodiments, the first polypeptide comprises an amino acid sequence that is at least 80, 85, 86, 87, 88, 89, 90, 91, 92, 93, 94, 95, 96, 97, 98, or 99% identical to a polypeptide comprising an amino acid sequence as provided in Table 5; and the second polypeptide comprises an amino acid sequence that is at least 80, 85, 86, 87, 88, 89, 90, 91, 92, 93, 94, 95, 96, 97, 98, or 99% identical to a polypeptide comprising an amino acid sequence as provided in Table 5. In some embodiments, the dimer molecule comprises the first Fc polypeptide comprising an amino acid sequence that is at least 80, 85, 86, 87, 88, 89, 90, 91, 92, 93, 94, 95, 96, 97, 98, or 99% identical to a polypeptide comprising an amino acid sequence as provided in Table 5; and the second Fc polypeptide comprising comprises an amino acid sequence that is at least 80, 85, 86, 87, 88, 89, 90, 91, 92, 93, 94, 95, 96, 97, 98, or 99% identical to a polypeptide comprising an amino acid sequence as provided in Table 5. In some embodiments, the dimer molecule comprises an amino acid sequence that is at least 80, 85, 86, 87, 88, 89, 90, 91, 92, 93, 94, 95, 96, 97, 98, or 99% identical to the amino acid sequence of AB-1 through AB-174, as provided in Table 5. In some embodiments, the Fc dimer consists of an amino acid sequence of AB-1 through AB-174, as provided in Table 5.

In some embodiments, the first polypeptide comprises an amino acid sequence as provided in Table 5; and the second polypeptide comprises an amino acid sequence as provided in Table 5. In some embodiments, the dimer molecule comprises the first Fc polypeptide comprising an amino acid sequence as provided in Table 5; and the second Fc polypeptide comprising an amino acid sequence as provided in Table 5. In some embodiments, the dimer molecule comprises the first Fc polypeptide comprising an amino acid sequence as provided in Table 5; and the second Fc polypeptide comprising an amino acid sequence as provided in Table 5, wherein the first Fc polypeptide amino acid sequence and the second Fc polypeptide amino acid sequence do not comprise the C-terminal lysine (K). In some embodiments, the dimer molecule comprises an amino acid sequence of AB-1 through AB-174, as provided in Table 5. In some embodiments, the Fc dimer consists of an amino acid sequence of AB-1 through AB-174, as provided in Table 5.

TABLE 5

| ID | First Variant IgG Fc Polypeptide Sequence | Second Variant IgG Fc Polypeptide Sequence |
|---|---|---|
| AB-1 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKAMPEPIEKTISKAKGQPREPQVY | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW |

TABLE 5-continued

| ID | First Variant IgG Fc Polypeptide Sequence | Second Variant IgG Fc Polypeptide Sequence |
|---|---|---|
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 37) |
| | TQKSLSLSPGK (SEQ ID NO: 1) | |
| AB-2 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPSVFLFPPKPKD |
| | LLGGFSVFLFPPKPKDTLMISRTPEVTCV | TLMISRTPEVTCVVVDVSQYDPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAMPEPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 25) |
| | TQKSLSLSPGK (SEQ ID NO: 1) | |
| AB-3 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPSVFLFPPKPKD |
| | LLGGFSVFLFPPKPKDTLMISRTPEVTCV | TLMISRTPEVTCVVVDASQYDPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAMPEPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 26) |
| | TQKSLSLSPGK (SEQ ID NO: 1) | |
| AB-4 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPEVFLFPPKPKD |
| | LLGGFSVFLFPPKPKDTLMISRTPEVTCV | TLMISRTPEVTCVVVDVSQYDPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAMPEPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 27) |
| | TQKSLSLSPGK (SEQ ID NO: 1) | |
| AB-5 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPSVFLFPPKPKD |
| | LLGGFSVFLFPPKPKDTLMISRTPEVTCV | TLMISRTPEVTCVVVDVSNYDPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAMPEPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 28) |
| | TQKSLSLSPGK (SEQ ID NO: 1) | |
| AB-6 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPEVFLFPPKPKD |
| | LLGGFSVFLFPPKPKDTLMISRTPEVTCV | TLMISRTPEVTCVVVDVSQYEPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAMPEPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 29) |
| | TQKSLSLSPGK (SEQ ID NO: 1) | |
| AB-7 | ASTKGPSVFPLAPSSKSTSGGTAALGCLV | ASTKGPSVFPLAPSSKSTSGGTAALGCLVKDYF |
| | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGGPEVFLFPPKPKD |
| | LLGGFSVFLFPPKPKDTLMISRTPEVTCV | TLMISRTPEVTCVVVDASQYEPEVKFNWYVDGV |
| | VVDVKHEDPEVKFNWYVDGVEVHNAKTKP | EVHNAKTKPREEQNNSFYRVVSVLTVLHQDWLN |
| | REEQYNSTYRVVSVLTVLHQDWLNGKEYK | GKEYKCKVSNKALPAPIEKTISKAKGQPREPQV |

TABLE 5-continued

| ID | First Variant IgG Fc Polypeptide Sequence | Second Variant IgG Fc Polypeptide Sequence |
|---|---|---|
| | CKVSNKAMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 1) | YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 30) |
| AB-8 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKAMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 1) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSNYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 31) |
| AB-9 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKAMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 1) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVFVSQYEPEVKFNWYVDGV<br>EVHNAKTKPREEQNNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 32) |
| AB-10 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-11 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 25) |
| AB-12 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDASQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 26) |
| AB-13 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYDPEVKFNWYVDGV<br>EVHNAKTKPREEQNNSFYRVVSVLTVLHQDWLN |

TABLE 5-continued

| ID | First Variant IgG Fc Polypeptide Sequence | Second Variant IgG Fc Polypeptide Sequence |
|---|---|---|
| | REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 27) |
| AB-14 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGOPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSNYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 28) |
| AB-15 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 29) |
| AB-16 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDASQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 30) |
| AB-17 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSNYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 31) |
| AB-18 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 2) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVFVSQYEPEVKFNWYVDGV<br>EVHNAKTKPREEQNNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 32) |
| AB-19 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV |

TABLE 5-continued

| ID | First Variant IgG Fc Polypeptide Sequence | Second Variant IgG Fc Polypeptide Sequence |
|---|---|---|
| | VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TKSLSLSPGK (SEQ ID NO: 3) | EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-20 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 25) |
| AB-21 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDASQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 26) |
| AB-22 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 27) |
| AB-23 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSNYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 28) |
| AB-24 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 29) |
| AB-25 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD |

TABLE 5-continued

| ID | First Variant IgG Fc Polypeptide Sequence | Second Variant IgG Fc Polypeptide Sequence |
|---|---|---|
| | LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | TLMISRTPEVTCVVVDASQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 30) |
| AB-26 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSNYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 31) |
| AB-27 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGHFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 3) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVFVSQYEPEVKFNWYVDGV<br>EVHNAKTKPREEQNNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 32) |
| AB-28 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-29 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 25) |
| AB-30 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDASQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 26) |
| AB-31 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE |

TABLE 5-continued

| ID | First Variant IgG Fc Polypeptide Sequence | Second Variant IgG Fc Polypeptide Sequence |
|---|---|---|
| | KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | PKSCDKTHTCPPCPAPELLGGPEVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 27) |
| AB-32 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSNYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 28) |
| AB-33 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 29) |
| AB-34 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDASQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 30) |
| AB-35 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSNYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 31) |
| AB-36 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGMFSVFLFPPKPKDTLMISRTPEVTCV<br>VVDVKHEDPEVKFNWYVDGVEVHNAKTKP<br>REEQYNSTYRVVSVLTVLHQDWLNGKEYK<br>CKVSNKDMPEPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 4) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVFVSQYEPEVKFNWYVDGV<br>EVHNAKTKPREEQNNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 32) |
| AB-37 | ASTKGPSVFPLAPSSKSTSGGTAALGCLV<br>KDYFPEPVTVSWNSGALTSGVHTFPAVLQ | ASTKGPSVFPLAPSSKSTSGGTAALGCLVKDYF<br>PEPVTVSWNSGALTSGVHTFPAVLQSSGLYSLS |

TABLE 5-continued

| ID | First Variant IgG Fc Polypeptide Sequence | Second Variant IgG Fc Polypeptide Sequence |
|---|---|---|
| | SSGLYSLSSVVTVPSSSLGTQTYICNVNH<br>KPSNTKVDKKVEPKSCDKTHTCPPCPAPE<br>LLGGESVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 39) | SVVTVPSSSLGTQTYICNVNHKPSNTKVDKKVE<br>PKSCDKTHTCPPCPAPELLGGESVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 39) |
| AB-38 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGEESVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGOPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 40) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGEESVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 40) |
| AB-39 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDESVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 41) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGDESVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 41) |
| AB-40 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGNSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 42) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGNSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 42) |
| AB-41 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGENSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 43) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGENSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 43) |
| AB-42 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDNSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 44) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGDNSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 44) |

TABLE 5-continued

| ID | First Variant IgG Fc Polypeptide Sequence | Second Variant IgG Fc Polypeptide Sequence |
|---|---|---|
| AB-43 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGNSVFLFPPKPKDTLMISRTPEVTCV VVDVKHEDPEVKFNWYVDGVEVHNAKTKP REEQYNSTYRVVSVLTVLHQDWLNGKEYK CKVSNKAMPEPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 45) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGNSVFLFPPKPKD TLMISRTPEVTCVVVDVKHEDPEVKFNWYVDGV EVHNAKTKPREEQYNSTYRVVSVLTVLHQDWLN GKEYKCKVSNKAMPEPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 45) |
| AB-44 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGFSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 46) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGFSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 46) |
| AB-45 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGEFSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 47) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGEFSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 47) |
| AB-46 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGDFSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 48) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGDFSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 48) |
| AB-47 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGFSVFLFPPKPKDTLMISRTPEVTCV VVDVKHEDPEVKFNWYVDGVEVHNAKTKP REEQYNSTYRVVSVLTVLHQDWLNGKEYK CKVSNKAMPEPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 49) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGFSVFLFPPKPKD TLMISRTPEVTCVVVDVKHEDPEVKFNWYVDGV EVHNAKTKPREEQYNSTYRVVSVLTVLHQDWLN GKEYKCKVSNKAMPEPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 49) |
| AB-48 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGQSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 50) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGQSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 50) |

TABLE 5-continued

| ID | First Variant IgG Fc Polypeptide Sequence | Second Variant IgG Fc Polypeptide Sequence |
|---|---|---|
| AB-49 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGEQSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 51) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGEQSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 51) |
| AB-50 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGDQSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 52) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGDQSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 52) |
| AB-51 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGQSVFLFPPKPKDTLMISRTPEVTCV VVDVKHEDPEVKFNWYVDGVEVHNAKTKP REEQYNSTYRVVSVLTVLHQDWLNGKEYK CKVSNKAMPEPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 53) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGQSVFLFPPKPKD TLMISRTPEVTCVVVDVKHEDPEVKFNWYVDGV EVHNAKTKPREEQYNSTYRVVSVLTVLHQDWLN GKEYKCKVSNKAMPEPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 53) |
| AB-52 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGMSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 54) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGMSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 54) |
| AB-53 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGEMSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 55) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGEMSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 55) |
| AB-54 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGDMSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLTCLVKGFYPSDIA VEWESNGQPENNYKTTPPVLDSDGSFFLY SKLTVDKSRWQQGNVFSCSVMHEALHNHY TQKSLSLSPGK (SEQ ID NO: 56) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGDMSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK (SEQ ID NO: 56) |

TABLE 5-continued

| ID | First Variant IgG Fc Polypeptide Sequence | Second Variant IgG Fc Polypeptide Sequence |
|---|---|---|
| AB-55 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGMSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 57) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGMSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 57) |
| AB-56 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGGDSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 58) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGGDSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 58) |
| AB-56 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGGDSVFLFPPKPKDTLMISRTPEVTCVVVDVKHEDPEVKFNWYVDGVEVHNAKTKPREEQYNSTYRVVSVLTVLHQDWLNGKEYKCKVSNKDMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 59) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGGDSVFLFPPKPKDTLMISRTPEVTCVVVDVKHEDPEVKFNWYVDGVEVHNAKTKPREEQYNSTYRVVSVLTVLHQDWLNGKEYKCKVSNKDMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 59) |
| AB-57 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGHDSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 60) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEGLLGHDSVFLFPPKPKDTLMISRTPEVTCVVVDVKHEDPEVKFNWYVDGVEVHNAKTKPREEQYNSTYRVVSVLTVLHQDWLNGKEYKCKVSNKAMPEPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 60) |
| AB-58 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSQYDPEVKFNWYVDGVEVHNAKTKPREEQNNSFYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 61) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSQYDPEVKFNWYVDGVEVHNAKTKPREEQNNSFYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 61) |
| AB-59 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDASQYDPEVKFNWYVDGVEVHNAKTKPREEQNNSFYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 62) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDASQYDPEVKFNWYVDGVEVHNAKTKPREEQNNSFYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 62) |

TABLE 5-continued

| ID | First Variant IgG Fc Polypeptide Sequence | Second Variant IgG Fc Polypeptide Sequence |
|---|---|---|
| AB-60 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPEVFLFPPKPKDTLMISRTPEVTCV<br>VVDVSQYDPEVKFNWYVDGVEVHNAKTKP<br>REEQNNSFYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 63) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 63) |
| AB-61 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSNYDPEVKFNWYVDGVEVHNAKTKP<br>REEQNNSFYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 64) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSNYDPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 64) |
| AB-62 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPEVFLFPPKPKDTLMISRTPEVTCV<br>VVDVSQYEPEVKFNWYVDGVEVHNAKTKP<br>REEQNNSFYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 65) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 65) |
| AB-63 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPEVFLFPPKPKDTLMISRTPEVTCV<br>VVDASQYEPEVKFNWYVDGVEVHNAKTKP<br>REEQNNSFYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 66) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDASQYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 66) |
| AB-64 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPEVFLFPPKPKDTLMISRTPEVTCV<br>VVDVSNYEPEVKFNWYVDGVEVHNAKTKP<br>REEQNNSFYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 67) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVDVSNYEPEVKFNWYVDGV<br>EVHNAKTKPREEQNNSFYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 67) |
| AB-65 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPEVFLFPPKPKDTLMISRTPEVTCV<br>VVFVSQYEPEVKFNWYVDGVEVHNAKTKP<br>REEQNNSTYRVVSVLTVLHQDWLNGKEYK<br>CKVSNKALPAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 68) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVVFVSQYEPEVKFNWYVDGV<br>EVHNAKTKPREEQNNSTYRVVSVLTVLHQDWLN<br>GKEYKCKVSNKALPAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 68) |

TABLE 5-continued

| ID | First Variant IgG Fc Polypeptide Sequence | Second Variant IgG Fc Polypeptide Sequence |
|---|---|---|
| AB-66 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 5) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGLPSVFLFPPKPKDTLMISRTPEVTCVVVDVSHEDPEVKFNWYVDGVEVHNAKTKPREEQYNQTYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 15) |
| AB-67 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 5) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGLPSVFLFPPKPKDTLMISRTPEVTCVVVDVSHEDPEVKFNWYVDGVEVHNAKTKPREEQYNQRYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 16) |
| AB-68 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 5) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLPLPSVFLFPPKPKDTLMISRTPEVTCVVVDVSHEDPEVKFNWYVDGVEVHNAKTKPREEQYNQTYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 17) |
| AB-69 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 5) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGLPSVFLFPPKPKDTLMISRTPEVTCVVVDVSHEDPEVKFNWYVDGVEVHNAKTKPREEQYNQTYRVVSVLTVLHQDWLNGKEYKCKVSDKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 18) |
| AB-70 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 5) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEMLPLPSVFLFPPKPKDTLMISRTPEVTCVVVDVSHEDPEVKFNWYVDGVEVHNAKTKPREEQYNQTYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 19) |
| AB-71 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKP | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEMLPLPSVFLFPPKPKDTLMISRTPEVTCVVVDVSHEDPEVKFNWYVDGVEVHNAKTKPREEQYNQRYRVVSVLTVLHQDWLN |

TABLE 5-continued

| ID | First Variant IgG Fc Polypeptide Sequence | Second Variant IgG Fc Polypeptide Sequence |
|---|---|---|
| | REEQYNSTYRVVSVLTVLHQDWLNGKEYK CKVSNKALPAPIEKTISKAKGQPREPQVY TLPPSRDELTKNQVSLWCLVKGFYPSDIA VEWESNGOPENNYKTTPPVLDSDGSFFLY SKLTVDKSRWQQGNVFSCSVMHEALHNHY TQKSLSLSPGK (SEQ ID NO: 5) | GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 20) |
| AB-72 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGPSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 5) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEMLPLPSVFLFPPKPKD TLMISRTPEVTCVVVDVSHEDPEVKFNWYVDGV EVHNAKTKPREEQYNQTYRVVSVLTVLHQDWLN GKEYKCKVSDKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 21) |
| AB-73 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 37) |
| AB-74 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGLPSVFLFPPKPKD TLMISRTPEVTCVVVDVSHEDPEVKFNWYVDGV EVHNAKTKPREEQYNQTYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 15) |
| AB-75 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGLPSVFLFPPKPKD TLMISRTPEVTCVVVDVSHEDPEVKFNWYVDGV EVHNAKTKPREEQYNQRYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 16) |
| AB-76 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLPLPSVFLFPPKPKD TLMISRTPEVTCVVVDVSHEDPEVKFNWYVDGV EVHNAKTKPREEQYNQTYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 17) |
| AB-77 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGLPSVFLFPPKPKD TLMISRTPEVTCVVVDVSHEDPEVKFNWYVDGV |

TABLE 5-continued

| ID | First Variant IgG Fc Polypeptide Sequence | Second Variant IgG Fc Polypeptide Sequence |
|---|---|---|
| | VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | EVHNAKTKPREEQYNQTYRVVSVLTVLHQDWLN GKEYKCKVSDKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 18) |
| AB-78 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEMLPLPSVFLFPPKPKD TLMISRTPEVTCVVVDVSHEDPEVKFNWYVDGV EVHNAKTKPREEQYNQTYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 19) |
| AB-79 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEMLPLPSVFLFPPKPKD TLMISRTPEVTCVVVDVSHEDPEVKFNWYVDGV EVHNAKTKPREEQYNQRYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 20) |
| AB-80 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 6) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEMLPLPSVFLFPPKPKD TLMISRTPEVTCVVVDVSHEDPEVKFNWYVDGV EVHNAKTKPREEQYNQTYRVVSVLTVLHQDWLN GKEYKCKVSDKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 21) |
| AB-81 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE PGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 7) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 37) |
| AB-82 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE PGQGPSVFLFPPKPKDTLMISRTPEVTCV VVDVSHEDPEVKFNWYVDGVEVHNAKTKP REEQYNSTYRVVSVLTVLHQDWLNGKEYK CKVSNKALRAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 7) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGLPSVFLFPPKPKD TLMISRTPEVTCVVVDVSHEDPEVKFNWYVDGV EVHNAKTKPREEQYNQTYRVVSVLTVLHQDWLN GKEYKCKVSNKDLPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 15) |
| AB-83 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGLPSVFLFPPKPKD |

TABLE 5-continued

| ID | First Variant IgG Fc Polypeptide Sequence | Second Variant IgG Fc Polypeptide Sequence |
|---|---|---|
| | PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | TLMISRTPEVTCVVVDVSHEDPEVKFNWYVDGV<br>EVHNAKTKPREEQYNQRYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 16) |
| AB-84 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLPLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 17) |
| AB-85 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 18) |
| AB-86 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 19) |
| AB-87 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQRYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 20) |
| AB-88 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>PGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 7) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 21) |
| AB-89 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE |

TABLE 5-continued

| ID | First Variant IgG Fc Polypeptide Sequence | Second Variant IgG Fc Polypeptide Sequence |
|---|---|---|
| | KPSNTKVDKKVEPKSCDKTHTCPPCPAPE | PKSCDKTHTCPPCPAPELLGGPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNSTYRVVSVLTVLHQDWLN |
| | REEQYNSTYRVVSVLTVLHQDWLNGKEYK | GKEYKCKVSNKALPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 37) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 90 | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGLPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNQTYRVVSVLTVLHQDWLN |
| | REEQYNSTYRVVSVLTVLHQDWLNGKEYK | GKEYKCKVSNKDLPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 15) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 91 | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGLPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNQRYRVVSVLTVLHQDWLN |
| | REEQYNSTYRVVSVLTVLHQDWLNGKEYK | GKEYKCKVSNKDLPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 16) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 92 | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLPLPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNQTYRVVSVLTVLHQDWLN |
| | REEQYNSTYRVVSVLTVLHQDWLNGKEYK | GKEYKCKVSNKDLPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 17) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 93 | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPELLGLPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNQTYRVVSVLTVLHQDWLN |
| | REEQYNSTYRVVSVLTVLHQDWLNGKEYK | GKEYKCKVSDKDLPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 18) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 94 | KDYFPEPVTVSWNSGALTSGVHTFPAVLQ | PEPVTVSWNSGALTSGVHTFPAVLQSSGLYSLS |
| | SSGLYSLSSVVTVPSSSLGTQTYICNVNH | SVVTVPSSSLGTQTYICNVNHKPSNTKVDKKVE |
| | KPSNTKVDKKVEPKSCDKTHTCPPCPAPE | PKSCDKTHTCPPCPAPEMLPLPSVFLFPPKPKD |
| | LGQGPSVFLFPPKPKDTLMISRTPEVTCV | TLMISRTPEVTCVVVDVSHEDPEVKFNWYVDGV |
| | VVDVSHEDPEVKFNWYVDGVEVHNAKTKP | EVHNAKTKPREEQYNQTYRVVSVLTVLHQDWLN |
| | REEQYNSTYRVVSVLTVLHQDWLNGKEYK | GKEYKCKVSNKDLPAPIEKTISKAKGQPREPQV |
| | CKVSNKAWRAPIEKTISKAKGQPREPQVY | YTLPPSRDELTKNQVSLSCAVKGFYPSDIAVEW |
| | TLPPSRDELTKNQVSLWCLVKGFYPSDIA | ESNGQPENNYKTTPPVLDSDGSFFLVSKLTVDK |
| | VEWESNGQPENNYKTTPPVLDSDGSFFLY | SRWQQGNVFSCSVMHEALHNHYTQKSLSLSPGK |
| | SKLTVDKSRWQQGNVFSCSVMHEALHNHY | (SEQ ID NO: 19) |
| | TQKSLSLSPGK (SEQ ID NO: 8) | |
| AB- | ASTKGPSVFPLAPSSKSTSGGTAALGCLV | ASTKGPSVFPLAPSSKSTSGGTAALGCLVKDYF |
| 95 | KDYFPEPVTVSWNSGALTSGVHTFPAVLQ | PEPVTVSWNSGALTSGVHTFPAVLQSSGLYSLS |

TABLE 5-continued

| ID | First Variant IgG Fc Polypeptide Sequence | Second Variant IgG Fc Polypeptide Sequence |
|---|---|---|
| | SSGLYSLSSVVTVPSSSLGTQTYICNVNHKPSNTKVDKKVEPKSCDKTHTCPPCPAPELGQGPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 8) | SVVTVPSSSLGTQTYICNVNHKPSNTKVDKKVEPKSCDKTHTCPPCPAPEMLPLPSVFLFPPKPKDTLMISRTPEVTCVVVDVSHEDPEVKFNWYVDGVEVHNAKTKPREEQYNQRYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 20) |
| AB-96 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELGQGPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 8) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEMLPLPSVFLFPPKPKDTLMISRTPEVTCVVVDVSHEDPEVKFNWYVDGVEVHNAKTKPREEQYNQTYRVVSVLTVLHQDWLNGKEYKCKVSDKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 21) |
| AB-97 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELGQRPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 37) |
| AB-98 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELGQRPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGLPSVFLFPPKPKDTLMISRTPEVTCVVVDVSHEDPEVKFNWYVDGVEVHNAKTKPREEQYNQTYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 15) |
| AB-99 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELGQRPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGLPSVFLFPPKPKDTLMISRTPEVTCVVVDVSHEDPEVKFNWYVDGVEVHNAKTKPREEQYNQRYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 16) |
| AB-100 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELGQRPSVFLFPPKPKDTLMISRTPEVTCVVVDVSHEDPEVKFNWYVDGVEVHNAKTKPREEQYNSTYRVVSVLTVLHQDWLNGKEYKCKVSNKAWRAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLPLPSVFLFPPKPKDTLMISRTPEVTCVVVDVSHEDPEVKFNWYVDGVEVHNAKTKPREEQYNQTYRVVSVLTVLHQDWLNGKEYKCKVSNKDLPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 17) |

TABLE 5-continued

| ID | First Variant IgG Fc Polypeptide Sequence | Second Variant IgG Fc Polypeptide Sequence |
|---|---|---|
| AB-101 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQRPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKAWRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 9) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 18) |
| AB-102 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQRPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKAWRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 9) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 19) |
| AB-103 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQRPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKAWRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 9) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQRYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 20) |
| AB-104 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQRPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKAWRAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 9) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEMLPLPSVFLFPPKPKD<br>TLMISRTPEVTCVVVDVSHEDPEVKFNWYVDGV<br>EVHNAKTKPREEQYNQTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 21) |
| AB-105 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDVSHEDPEVKFNWYVDGV<br>EVHNAKTKPREEQYNSTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 22) |
| AB-106 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDHSHEDPEVKFNWYVDGV<br>EVHNAKTKPREEQYNSTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 38) |

TABLE 5-continued

| ID | First Variant IgG Fc Polypeptide Sequence | Second Variant IgG Fc Polypeptide Sequence |
|---|---|---|
| AB-107 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDVSHEDPEVKFNWYVDGV<br>EVHNAKTKPREEQYNSTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 23) |
| AB-108 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDHSHEDPEVKFNWYVDGV<br>EVHNAKTKPREEQYNSTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 24) |
| AB-109 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALDAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 10) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-110 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALDAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 10) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDVSHEDPEVKFNWYVDGV<br>EVHNAKTKPREEQYNSTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 22) |
| AB-111 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALDAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 10) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDHSHEDPEVKFNWYVDGV<br>EVHNAKTKPREEQYNSTYRVVSVLTVLHQDWLN<br>GKEYKCKVSNKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 38) |
| AB-112 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQGPSVFLFPPKPKDTLMISRTPEVTCV<br>VVDVSHEDPEVKFNWYVDGVEVHNAKTKP<br>REEQYNSTYRVVSVLTVLHQDWINGKEYK | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDVSHEDPEVKFNWYVDGV<br>EVHNAKTKPREEQYNSTYRVVSVLTVLHQDWLN<br>GKEYKCKVSDKDLPAPIEKTISKAKGQPREPQV |

TABLE 5-continued

| ID | First Variant IgG Fc Polypeptide Sequence | Second Variant IgG Fc Polypeptide Sequence |
|---|---|---|
| | CKVSNKALDAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 10) | YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 23) |
| AB-113 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LGQGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALDAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 10) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPEVFLFPPKPKD<br>TLMISRTPEVTCVVWDHSHEDPEVKFNWYVDGV<br>EVHNAKTKPREEQYNSTYRVVSVLTVLHQDWLN<br>GKEYKCKVSDKDLPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 24) |
| AB-114 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALDAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 69) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALDAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 69) |
| AB-115 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKDLDAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 70) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKDLDAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 70) |
| AB-116 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSDKALDAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 71) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSDKALDAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 71) |
| AB-117 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSDKDLDAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 72) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSDKDLDAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 72) |
| AB-118 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN |

TABLE 5-continued

| ID | First Variant IgG Fc Polypeptide Sequence | Second Variant IgG Fc Polypeptide Sequence |
|---|---|---|
| | REEQYNSTYRVVSVLTVLHQDWLNGKEYK<br>CKVSNKALEAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 73) | GKEYKCKVSNKALEAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 73) |
| AB-119 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALRAPIEKTISKAKGQPREPQVY<br>TLPPSRDELTKNQVSLTCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 74) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALRAPIEKTISKAKGQPREPQV<br>YTLPPSRDELTKNQVSLTCLVKGFYPSDIAVEW<br>ESNGQPENNYKTTPPVLDSDGSFFLYSKLTVDK<br>SRWQQGNVFSCSVMHEALHNHYTQKSLSLSPGK<br>(SEQ ID NO: 74) |
| AB-120 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPMKEGAPSVFLFPPKPKD<br>TLMISRTPEVTCVVVDVSPKSPEVEFNWYVDGV<br>EVHNAKTKPREEQYNSTYRVVSVLTVLHQDWLN<br>GKEYKCKVSTSALAAEIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 33) |
| AB-121 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPPGPGSPSVFLFPPKPKD<br>TLMISRTPEVTCVVVDVSPADPEVHENWYVDGV<br>EVHNAKTKPREEQYNSTYRVVSVLTVLHQDWLN<br>GKEYKCKVSNNALIGQIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 34) |
| AB-122 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPVISGGPSVFLFPPKPKD<br>TLMISRTPEVTCVVVDVSPENPEVKFNWYVDGV<br>EVHNAKTKPREEQYNSTYRVVSVLTVLHQDWLN<br>GKEYKCKVSTKNHPQPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 35) |
| AB-123 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGPSVFLFPPKPKDTLMISRTPEVTCV<br>VVDVSHEDPEVKFNWYVDGVEVHNAKTKP<br>REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 5) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPKLLGAPSVFLFPPKPKD<br>TLMISRTPEVTCVVVDVSPSDPEVHFNWYVDGV<br>EVHNAKTKPREEQYNSTYRVVSVLTVLHQDWLN<br>GKEYKCKVSNKNVNGVIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 36) |
| AB-124 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPL<br>KLGAPSVFLFPPKPKDTLMISRTPEVTCV | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV |

TABLE 5-continued

| ID | First Variant IgG Fc Polypeptide Sequence | Second Variant IgG Fc Polypeptide Sequence |
|---|---|---|
| | VVDVSPENPEVKFNWYVDGVEVHNAKTKP<br>REEQYNSTYRVVSVLTVLHQDWLNGKEYK<br>CKVSTSTIPGQIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 11) | EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-125 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPL<br>KLGAPSVFLFPPKPKDTLMISRTPEVTCV<br>VVDVSPENPEVKFNWYVDGVEVHNAKTKP<br>REEQYNSTYRVVSVLTVLHQDWLNGKEYK<br>CKVSTSTIPGQIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 11) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPMKEGAPSVFLFPPKPKD<br>TLMISRTPEVTCVVVDVSPKSPEVEFNWYVDGV<br>EVHNAKTKPREEQYNSTYRVVSVLTVLHQDWLN<br>GKEYKCKVSTSALAAEIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 33) |
| AB-126 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPL<br>KLGAPSVFLFPPKPKDTLMISRTPEVTCV<br>VVDVSPENPEVKFNWYVDGVEVHNAKTKP<br>REEQYNSTYRVVSVLTVLHQDWLNGKEYK<br>CKVSTSTIPGQIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 11) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPPGPGSPSVFLFPPKPKD<br>TLMISRTPEVTCVVVDVSPADPEVHENWYVDGV<br>EVHNAKTKPREEQYNSTYRVVSVLTVLHQDWLN<br>GKEYKCKVSNNALIGQIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 34) |
| AB-127 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPL<br>KLGAPSVFLFPPKPKDTLMISRTPEVTCV<br>VVDVSPENPEVKFNWYVDGVEVHNAKTKP<br>REEQYNSTYRVVSVLTVLHQDWLNGKEYK<br>CKVSTSTIPGQIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 11) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPVISGGPSVFLFPPKPKD<br>TLMISRTPEVTCVVVDVSPENPEVKFNWYVDGV<br>EVHNAKTKPREEQYNSTYRVVSVLTVLHQDWLN<br>GKEYKCKVSTKNHPQPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 35) |
| AB-128 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPL<br>KLGAPSVFLFPPKPKDTLMISRTPEVTCV<br>VVDVSPENPEVKFNWYVDGVEVHNAKTKP<br>REEQYNSTYRVVSVLTVLHQDWLNGKEYK<br>CKVSTSTIPGQIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 11) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPKLLGAPSVFLFPPKPKD<br>TLMISRTPEVTCVVVDVSPSDPEVHFNWYVDGV<br>EVHNAKTKPREEQYNSTYRVVSVLTVLHQDWLN<br>GKEYKCKVSNKNVNGVIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 36) |
| AB-129 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPM<br>GGGAPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSTPSQPADIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 12) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-130 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPM | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPMKEGAPSVFLFPPKPKD |

TABLE 5-continued

| ID | First Variant IgG Fc Polypeptide Sequence | Second Variant IgG Fc Polypeptide Sequence |
|---|---|---|
| | GGGAPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSTPSQPADIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 12) | TLMISRTPEVTCVVVDVSPKSPEVEFNWYVDGV<br>EVHNAKTKPREEQYNSTYRVVSVLTVLHQDWLN<br>GKEYKCKVSTSALAAEIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 33) |
| AB-131 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPM<br>GGGAPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSTPSQPADIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 12) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPPGPGSPSVFLFPPKPKD<br>TLMISRTPEVTCVVVDVSPADPEVHENWYVDGV<br>EVHNAKTKPREEQYNSTYRVVSVLTVLHQDWLN<br>GKEYKCKVSNNALIGQIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 34) |
| AB-132 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPM<br>GGGAPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSTPSQPADIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 12) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPVISGGPSVFLFPPKPKD<br>TLMISRTPEVTCVVVDVSPENPEVKFNWYVDGV<br>EVHNAKTKPREEQYNSTYRVVSVLTVLHQDWLN<br>GKEYKCKVSTKNHPQPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 35) |
| AB-133 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPM<br>GGGAPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSTPSQPADIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 12) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPKLLGAPSVFLFPPKPKD<br>TLMISRTPEVTCVVVDVSPSDPEVHFNWYVDGV<br>EVHNAKTKPREEQYNSTYRVVSVLTVLHQDWLN<br>GKEYKCKVSNKNVNGVIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 36) |
| AB-134 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPI<br>TPGAPSVFLFPPKPKDTLMISRTPEVTCV<br>VVDVSPEAPEVEFNWYVDGVEVHNAKTKP<br>REEQYNSTYRVVSVLTVLHQDWINGKEYK<br>CKVSTAGLGSNIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 13) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-135 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPI<br>TPGAPSVFLFPPKPKDTLMISRTPEVTCV<br>VVDVSPEAPEVEFNWYVDGVEVHNAKTKP<br>REEQYNSTYRVVSVLTVLHQDWLNGKEYK<br>CKVSTAGLGSNIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 13) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPMKEGAPSVFLFPPKPKD<br>TLMISRTPEVTCVVVDVSPKSPEVEFNWYVDGV<br>EVHNAKTKPREEQYNSTYRVVSVLTVLHQDWLN<br>GKEYKCKVSTSALAAEIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 33) |
| AB-136 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE |

TABLE 5-continued

| ID | First Variant IgG Fc Polypeptide Sequence | Second Variant IgG Fc Polypeptide Sequence |
|---|---|---|
| | KPSNTKVDKKVEPKSCDKTHTCPPCPAPI<br>TPGAPSVFLFPPKPKDTLMISRTPEVTCV<br>VVDVSPEAPEVEFNWYVDGVEVHNAKTKP<br>REEQYNSTYRVVSVLTVLHQDWLNGKEYK<br>CKVSTAGLGSNIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 13) | PKSCDKTHTCPPCPAPPGPGSPSVFLFPPKPKD<br>TLMISRTPEVTCVVVDVSPADPEVHFNWYVDGV<br>EVHNAKTKPREEQYNSTYRVVSVLTVLHQDWLN<br>GKEYKCKVSNNALIGQIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 34) |
| AB-137 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPI<br>TPGAPSVFLFPPKPKDTLMISRTPEVTCV<br>VVDVSPEAPEVEFNWYVDGVEVHNAKTKP<br>REEQYNSTYRVVSVLTVLHQDWLNGKEYK<br>CKVSTAGLGSNIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 13) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPVISGGPSVFLFPPKPKD<br>TLMISRTPEVTCVVVDVSPENPEVKFNWYVDGV<br>EVHNAKTKPREEQYNSTYRVVSVLTVLHQDWLN<br>GKEYKCKVSTKNHPQPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 35) |
| AB-138 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPI<br>TPGAPSVFLFPPKPKDTLMISRTPEVTCV<br>VVDVSPEAPEVEFNWYVDGVEVHNAKTKP<br>REEQYNSTYRVVSVLTVLHQDWLNGKEYK<br>CKVSTAGLGSNIEKTISKAKGQPREPQVY<br>TLPPSRDELTKNQVSLWCLVKGFYPSDIA<br>VEWESNGOPENNYKTTPPVLDSDGSFFLY<br>SKLTVDKSRWQQGNVFSCSVMHEALHNHY<br>TQKSLSLSPGK (SEQ ID NO: 13) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPKLLGAPSVFLFPPKPKD<br>TLMISRTPEVTCVVVDVSPSDPEVHENWYVDGV<br>EVHNAKTKPREEQYNSTYRVVSVLTVLHQDWLN<br>GKEYKCKVSNKNVNGVIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 36) |
| AB-139 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPR<br>TPALPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSNGEIREHIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 14) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 37) |
| AB-140 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPR<br>TPALPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSNGEIREHIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 14) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPMKEGAPSVFLFPPKPKD<br>TLMISRTPEVTCVVVDVSPKSPEVEFNWYVDGV<br>EVHNAKTKPREEQYNSTYRVVSVLTVLHQDWLN<br>GKEYKCKVSTSALAAEIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 33) |
| AB-141 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPR<br>TPALPSVFLFPPKPKDTLMISRTPEVTCV<br>VVDVSPEDPEVEFNWYVDGVEVHNAKTKP<br>REEQYNSTYRVVSVLTVLHQDWLNGKEYK<br>CKVSNGEIREHIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 14) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPPGPGSPSVFLFPPKPKD<br>TLMISRTPEVTCVVVDVSPADPEVHENWYVDGV<br>EVHNAKTKPREEQYNSTYRVVSVLTVLHQDWLN<br>GKEYKCKVSNNALIGQIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 34) |
| AB-142 | ASTKGPSVFPLAPSSKSTSGGTAALGCLV<br>KDYFPEPVTVSWNSGALTSGVHTFPAVLQ | ASTKGPSVFPLAPSSKSTSGGTAALGCLVKDYF<br>PEPVTVSWNSGALTSGVHTFPAVLQSSGLYSLS |

TABLE 5-continued

| ID | First Variant IgG Fc Polypeptide Sequence | Second Variant IgG Fc Polypeptide Sequence |
|---|---|---|
| | SSGLYSLSSVVTVPSSSLGTQTYICNVNHKPSNTKVDKKVEPKSCDKTHTCPPCPAPRTPALPSVFLFPPKPKDTLMISRTPEVTCVVVDVSPEDPEVEFNWYVDGVEVHNAKTKPREEQYNSTYRVVSVLTVLHQDWLNGKEYKCKVSNGEIREHIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 14) | SVVTVPSSSLGTQTYICNVNHKPSNTKVDKKVEPKSCDKTHTCPPCPAPVISGGPSVFLFPPKPKDTLMISRTPEVTCVVVDVSPENPEVKFNWYVDGVEVHNAKTKPREEQYNSTYRVVSVLTVLHQDWLNGKEYKCKVSTKNHPQPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 35) |
| AB-143 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPRTPALPSVFLFPPKPKDTLMISRTPEVTCVVVDVSPEDPEVEFNWYVDGVEVHNAKTKPREEQYNSTYRVVSVLTVLHQDWLNGKEYKCKVSNGEIREHIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 14) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPKLLGAPSVFLFPPKPKDTLMISRTPEVTCVVVDVSPSDPEVHENWYVDGVEVHNAKTKPREEQYNSTYRVVSVLTVLHQDWLNGKEYKCKVSNKNVNGVIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 36) |
| AB-144 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 75) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 76) |
| AB-145 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 75) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEFEGGPSVFLFPPKPKDTLMISRTPEVTCVVVDVSDEDGEVKFNWYVDGVEVHNAKTKPREEQYNSTYRVVSVLTVLHQDWLNGKEYKCKVSNKALAAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 77) |
| AB-146 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGDSVFLFPPKPKDTLMISRTPEVTCVVVDVSHDEPEVKFNWYVDGVEVHNAKTKPREEQYNSTYRVVSVLTVLHQDWLNGKEYKCKVSNKALPRPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 78) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGOPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 76) |
| AB-147 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGDSVFLFPPKPKDTLMISRTPEVTCVVVDVSHDEPEVKFNWYVDGVEVHNAKTKPREEQYNSTYRVVSVLTVLHQDWLNGKEYKCKVSNKALPRPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 78) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEFEGGPSVFLFPPKPKDTLMISRTPEVTCVVVDVSDEDGEVKFNWYVDGVEVHNAKTKPREEQYNSTYRVVSVLTVLHQDWLNGKEYKCKVSNKALAAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK (SEQ ID NO: 77) |

TABLE 5-continued

| ID | First Variant IgG Fc Polypeptide Sequence | Second Variant IgG Fc Polypeptide Sequence |
|---|---|---|
| AB-<br>148 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGSSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 80) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 76) |
| AB-<br>149 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGSSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 80) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVKFNWYVDGV<br>EVHNAKTKPREEQYNSTYRVVSVLTVLHQDWLN<br>GKEYKCKVSNKALAAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 77) |
| AB-<br>150 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDGSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 82) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 76) |
| AB-<br>151 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDGSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 82) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVKFNWYVDGV<br>EVHNAKTKPREEQYNSTYRVVSVLTVLHQDWLN<br>GKEYKCKVSNKALAAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 77) |
| AB-<br>152 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDSGVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 84) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPELLGGPSVFLFPPKPKD<br>TLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 76) |
| AB-<br>153 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDSGVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 84) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVKFNWYVDGV<br>EVHNAKTKPREEQYNSTYRVVSVLTVLHQDWLN<br>GKEYKCKVSNKALAAPIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 77) |

TABLE 5-continued

| ID | First Variant IgG Fc Polypeptide Sequence | Second Variant IgG Fc Polypeptide Sequence |
|---|---|---|
| AB-154 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGDGSAFLFPPKPKDTLMISRTPEVTCV VVDVSHDEPEVKFNWYVDGVEVHNAKTKP REEQYNSTYRVVSVLTVLHQDWLNGKEYK CKVSNKALPRPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 86) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 76) |
| AB-155 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGDGSAFLFPPKPKDTLMISRTPEVTCV VVDVSHDEPEVKFNWYVDGVEVHNAKTKP REEQYNSTYRVVSVLTVLHQDWLNGKEYK CKVSNKALPRPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 86) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVKFNWYVDGV EVHNAKTKPREEQYNSTYRVVSVLTVLHQDWLN GKEYKCKVSNKALAAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 77) |
| AB-156 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LVGGESVFLFPPKPKDTLMISRTPEVTCV VVDVSHDEPEVKFNWYVDGVEVHNAKTKP REEQYNSTYRVVSVLTVLHQDWLNGKEYK CKVSNKALPRPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 79) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 76) |
| AB-157 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LVGGESVFLFPPKPKDTLMISRTPEVTCV VVDVSHDEPEVKFNWYVDGVEVHNAKTKP REEQYNSTYRVVSVLTVLHQDWLNGKEYK CKVSNKALPRPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 79) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVKFNWYVDGV EVHNAKTKPREEQYNSTYRVVSVLTVLHQDWLN GKEYKCKVSNKALAAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 77) |
| AB-158 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE GEVLVGGDSVFLFPPKPKDTLMISRTPEV TCVVVDVSHDEPEVKFNWYVDGVEVHNAK TKPREEQYNSTYRVVSVLTVLHQDWLNGK EYKCKVSNKALPRPIEKTISKAKGQPREP QVYTLPPSRDELTKNQVSLWCLVKGFYPS DIAVEWESNGQPENNYKTTPPVLDSDGSF FLYSKLTVDKSRWQQGNVFSCSVMHEALH NHYTQKSLSLSPGK (SEQ ID NO: 87) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 76) |
| AB-159 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE GEVLVGGDSVFLFPPKPKDTLMISRTPEV TCVVVDVSHDEPEVKFNWYVDGVEVHNAK TKPREEQYNSTYRVVSVLTVLHQDWLNGK | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVKFNWYVDGV EVHNAKTKPREEQYNSTYRVVSVLTVLHQDWLN GKEYKCKVSNKALAAPIEKTISKAKGQPREPQV |

TABLE 5-continued

| ID | First Variant IgG Fc Polypeptide Sequence | Second Variant IgG Fc Polypeptide Sequence |
|---|---|---|
| | EYKCKVSNKALPRPIEKTISKAKGQPREP QVYTLPPSRDELTKNQVSLWCLVKGFYPS DIAVEWESNGQPENNYKTTPPVLDSDGSF FLYSKLTVDKSRWQQGNVFSCSVMHEALH NHYTQKSLSLSPGK (SEQ ID NO: 87) | YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 77) |
| AB-160 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE FEGGPSVFLFPPKPKDTLMISRTPEVTCV VVDVSQEDPEVQFNWYVDGVEVHNAKTKP REEQFNSTYRVVSVLTVLHQDWLNGKEYK CKVSNKALPSSIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 85) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 76) |
| AB-161 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE FEGGPSVFLFPPKPKDTLMISRTPEVTCV VVDVSQEDPEVQFNWYVDGVEVHNAKTKP REEQFNSTYRVVSVLTVLHQDWLNGKEYK CKVSNKALPSSIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 85) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVQFNWYVDGV EVHNAKTKPREEQFNSTYRVVSVLTVLHQDWLN GKEYKCKVSNKALASSIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 81) |
| AB-162 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE FEGGPSVFLFPPKPKDTLMISRTPEVTCV VVDVSQEDPEVQFNWYVDGVEVHNAKTKP REEQFNSTYRVVSVLTVLHQDWLNGKEYK CKVSNKALPSSIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 85) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPDVFLFPPKPKD TLMISRTPEVTCVVVDVSDEDGEVQFNWYVDGV EVHNAKTKPREEQFNSTYRVVSVLTVLHQDWLN GKEYKCKVSNKALASSIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 83) |
| AB-163 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE FEGGPSVFLFPPKPKDTLMISRTPEVTCV VVDVSQEDPEVQFNWYVDGVEVHNAKTKP REEQFNSTYRVVSVLTVLHQDWLNGKEYK CKVSNKALPSSIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 85) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVKFNWYVDGV EVHNAKTKPREEQYNSTYRVVSVLTVLHQDWLN GKEYKCKVSNKALAAPIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 77) |
| AB-164 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGPSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 75) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPSVFLFPPKPKD TLMISRTPEVTCVVVDVSDEDGEVQFNWYVDGV EVHNAKTKPREEQFNSTYRVVSVLTVLHQDWLN GKEYKCKVSNKALASSIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 81) |
| AB-165 | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGPSVFLFPPKPKDTLMISRTPEVTCV VVDVSHEDPEVKFNWYVDGVEVHNAKTKP | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEFEGGPDVFLFPPKPKD TLMISRTPEVTCVVVDVSDEDGEVQFNWYVDGV EVHNAKTKPREEQFNSTYRVVSVLTVLHQDWLN |

TABLE 5-continued

| ID | First Variant IgG Fc Polypeptide Sequence | Second Variant IgG Fc Polypeptide Sequence |
|---|---|---|
| | REEQYNSTYRVVSVLTVLHQDWLNGKEYK<br>CKVSNKALPAPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 75) | GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 83) |
| AB-166 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGDSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 78) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVQFNWYVDGV<br>EVHNAKTKPREEQFNSTYRVVSVLTVLHQDWLN<br>GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 81) |
| AB-167 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGDSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 78) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPDVFLFPPKPKD<br>TLMISRTPEVTCVVVDVSDEDGEVQFNWYVDGV<br>EVHNAKTKPREEQFNSTYRVVSVLTVLHQDWLN<br>GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 83) |
| AB-168 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGSSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 80) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVQFNWYVDGV<br>EVHNAKTKPREEQFNSTYRVVSVLTVLHQDWLN<br>GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 81) |
| AB-169 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGGSSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 80) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPDVFLFPPKPKD<br>TLMISRTPEVTCVVVDVSDEDGEVQFNWYVDGV<br>EVHNAKTKPREEQFNSTYRVVSVLTVLHQDWLN<br>GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 83) |
| AB-170 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDGSVFLFPPKPKDTLMISRTPEVTCV<br>VVDVSHDEPEVKFNWYVDGVEVHNAKTKP<br>REEQYNSTYRVVSVLTVLHQDWLNGKEYK<br>CKVSNKALPRPIEKTISKAKGQPREPQVY<br>TLPPSRDELTKNQVSLWCLVKGFYPSDIA<br>VEWESNGQPENNYKTTPPVLDSDGSFFLY<br>SKLTVDKSRWQQGNVFSCSVMHEALHNHY<br>TQKSLSLSPGK (SEQ ID NO: 82) | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPSVFLFPPKPKD<br>TLMISRTPEVTCVVVDVSDEDGEVQFNWYVDGV<br>EVHNAKTKPREEQFNSTYRVVSVLTVLHQDWLN<br>GKEYKCKVSNKALASSIEKTISKAKGQPREPQV<br>YTLPPSRDELTKNQVSLSCAVKGFYPSDIAVEW<br>ESNGQPENNYKTTPPVLDSDGSFFLVSKLTVDK<br>SRWQQGNVFSCSVMHEALHNHYTQKSLSLSPGK<br>(SEQ ID NO: 81) |
| AB-171 | ASTKGPSVFPLAPSSKSTSGGTAALGCLV<br>KDYFPEPVTVSWNSGALTSGVHTFPAVLQ<br>SSGLYSLSSVVTVPSSSLGTQTYICNVNH<br>KPSNTKVDKKVEPKSCDKTHTCPPCPAPE<br>LLGDGSVFLFPPKPKDTLMISRTPEVTCV | ASTKGPSVFPLAPSSKSTSGGTAALGCLVKDYF<br>PEPVTVSWNSGALTSGVHTFPAVLQSSGLYSLS<br>SVVTVPSSSLGTQTYICNVNHKPSNTKVDKKVE<br>PKSCDKTHTCPPCPAPEFEGGPDVFLFPPKPKD<br>TLMISRTPEVTCVVVDVSDEDGEVQFNWYVDGV |

TABLE 5-continued

| ID | First Variant IgG Fc Polypeptide Sequence | Second Variant IgG Fc Polypeptide Sequence |
|---|---|---|
| | VVDVSHDEPEVKFNWYVDGVEVHNAKTKP REEQYNSTYRVVSVLTVLHQDWLNGKEYK CKVSNKALPRPIEKTISKAKGQPREPQVY TLPPSRDELTKNQVSLWCLVKGFYPSDIA VEWESNGQPENNYKTTPPVLDSDGSFFLY SKLTVDKSRWQQGNVFSCSVMHEALHNHY TQKSLSLSPGK (SEQ ID NO: 82) | EVHNAKTKPREEQFNSTYRVVSVLTVLHQDWLN GKEYKCKVSNKALASSIEKTISKAKGQPREPQV YTLPPSRDELTKNQVSLSCAVKGFYPSDIAVEW ESNGQPENNYKTTPPVLDSDGSFFLVSKLTVDK SRWQQGNVFSCSVMHEALHNHYTQKSLSLSPGK (SEQ ID NO: 83) |
| AB-172 | (SEQ ID NO: 102) | (SEQ ID NO: 102) |
| AB-173 | (SEQ ID NO: 103) | (SEQ ID NO: 103) |
| AB-174 | (SEQ ID NO: 104) | (SEQ ID NO: 104) |

In some embodiments, a dimer molecule comprises:

a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises:
- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88; or
- a mutation set of L234F and L235E, as compared to SEQ ID NO: 88;
- a mutation set of G237E and P238E, as compared to SEQ ID NO: 88; or
- any combination thereof; and a second polypeptide comprises an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises:
- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88; or
- a mutation set of L234F and L235E, as compared to SEQ ID NO: 88;
- a mutation set of G237E and P238E, as compared to SEQ ID NO: 88; or
- any combination thereof.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237E and P238E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237E and P238E, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO:

88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238D, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238S, S239G, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of G237D, P238G, V240A, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238E, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of P238S, E269D, D270E, and A330R, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F, L235E, S239D, P329A, H268D, and P271G, as compared to SEQ ID NO: 88. In some embodiments, a dimer molecule comprises a first polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88; and a second polypeptide comprising an amino acid sequence that is at least 80, 85, 86, 87, 88, 89, 90, 91, 92, 93, 94, 95, 96, 97, 98, or 99% identical to a polypeptide comprising an amino acid sequence of SEQ ID NO: 88 provided that the polypeptide comprises a mutation set of L234F and L235E, as compared to SEQ ID NO: 88.

In some embodiments, a dimer molecule comprises:

a first polypeptide comprises a variant sequence of SEQ ID NO: 88, wherein the first polypeptide comprises:
- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of G237E and P238E, as compared to SEQ ID NO: 88; or
- a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprises a variant sequence of SEQ ID NO: 88, wherein the second polypeptide comprises:
- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of G237E and P238E, as compared to SEQ ID NO: 88; or a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of G237E and P238E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237E and P238E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided d that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and a second polypeptide comprising a variant sequence of SEQ ID NO: 88, provided that the polypeptide comprises a mutation set of L234F and L235E, as compared to SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

In some embodiments, a dimer molecule comprises:

a first polypeptide comprises a variant sequence of SEQ ID NO: 88, wherein the first polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88; or a mutation set of L234F and L235E, as compared to SEQ ID NO: 88;

a mutation set of G237E and P238E, as compared to SEQ ID NO: 88; or any combination thereof; and a second polypeptide comprises a variant sequence of SEQ ID NO: 88, wherein the second polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88; or a mutation set of L234F and L235E, as compared to SEQ ID NO: 88;

a mutation set of G237E and P238E, as compared to SEQ ID NO: 88; or any combination thereof.

In some embodiments, a dimer molecule comprises a first polypeptide comprising a variant sequence of SEQ ID NO: 88, provided that the polypeptide comprises a mutation set of G237E and P238E, as compared to SEQ ID NO: 88; and a second polypeptide comprising a variant sequence of SEQ ID NO: 88, provided that the polypeptide comprises a mutation set of G237E and P238E, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of P238D, E269D, D270E, and A330R, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of G237D, P238G, E269D, D270E, and A330R, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of G237D, P238S, S239G, E269D, D270E, and A330R, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L235V, P238E, E269D, D270E, and A330R, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided d that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of P238S, E269D, D270E, and A330R, as compared to SEQ ID NO: 88; and a second polypeptide comprising a variant sequence of SEQ ID NO: 88, provided that the polypeptide comprises a mutation set of L234F and L235E, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F, L235E, P329A, H268D, and P271G, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F, L235E, S239D, P329A, H268D, and P271G, as compared to SEQ ID 5 NO: 88; and a second polypeptide comprising a variant sequence of SEQ ID NO: 88, provided that the polypeptide comprises a mutation set of L234F and L235E, as compared to SEQ ID NO: 88.

In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of P238D, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of G237D, P238G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of G237D, P238S, S239G, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of G237D, P238G, V240A, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of L235V, P238E, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of L235V, P238D, E269D, D270E, and A330R, and an insertion of an amino acid sequence GEV between positions 233 and 234, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of P238S, E269D, D270E, and A330R, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of L234F, L235E, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of L234F, L235E, S239D, P329A, H268D, and P271G, as compared to SEQ ID NO: 88. In some embodiments, a dimer molecule comprises a first polypeptide comprising a variant sequence of SEQ ID NO: 88, provided that the polypeptide comprises a mutation set of L234F and L235E, as compared to SEQ ID NO: 88; and a second polypeptide comprising a variant sequence of SEQ ID NO: 88, provided that the polypeptide comprises a mutation set of L234F and L235E, as compared to SEQ ID NO: 88.

In some embodiments, the variant IgG Fc polypeptide, such as those provided herein, is conjugated or linked to an inhibitory receptor effector domain. In some embodiments, the variant IgG Fc polypeptide, such as those provided herein, is conjugated or linked to at least one inhibitory receptor effector domain. In some embodiments, the variant IgG Fc polypeptide, such as those provided herein, is conjugated or linked to 2 inhibitory receptor effector domains. In some embodiments, the dimer molecule, such as those provided herein, is conjugated or linked to an inhibitory receptor effector domain. In some embodiments, the variant IgG Fc polypeptide of any one of VFC-1, VFC-2, VFC-3, VFC-4, VFC-5, VFC-6, VFC-7, VFC-8, VFC-9, VFC-10, VFC-11, VFC-12, VFC-13, VFC-14, VFC-15, VFC-16, VFC-17, VFC-18, VFC-19, VFC-20, VFC-21, VFC-22, VFC-23, VFC-24, VFC-25, VFC-26, VFC-27, VFC-28, VFC-29, VFC-30, VFC-31, VFC-32, VFC-33, VFC-34, VFC-35, VFC-36, VFC-37, VFC-38, VFC-39, VFC-40, VFC-41, VFC-42, VFC-43, VFC-44, VFC-45, VFC-46, VFC-47, VFC-48, VFC-49, VFC-50, VFC-51, VFC-52, VFC-53, VFC-54, VFC-55, VFC-56, VFC-57, VFC-58, VFC-59, VFC-60, VFC-61, VFC-62, VFC-63, VFC-64, VFC-65, VFC-66, VFC-67, VFC-68, VFC-69, VFC-70, VFC-71, VFC-72, VFC-73, VFC-74, VFC-75, VFC-76, VFC-77, VFC-78, VFC-79, VFC-80, VFC-81, VFC-82, VFC-83, VFC-84, VFC-85, VFC-86, VFC-87, VFC-88, VFC-89, VFC-90, is conjugated or linked to an inhibitory receptor effector domain.

Non-limiting examples of Fc domains linked to inhibitory receptor effector domains can be found in U.S. Non-Provisional application Ser. No. 18/048,747, or PCT Application No. PCT/US2022/078537, each of which is hereby incorporated by reference in its entirety.

In some embodiments, a N-terminus of a variant IgG Fc polypeptide is conjugated to a C-terminus of a inhibitory receptor effector domain. In some embodiments, a N-terminus of a variant IgG Fc polypeptide is conjugated to a C-terminus of a inhibitory receptor effector domain via a linker. In some embodiments, a N-terminus of a variant IgG Fc polypeptide is directly conjugated to a C-terminus of a inhibitory receptor effector domain. In some embodiments, a C-terminus of a variant IgG Fc polypeptide is conjugated to a N-terminus of a inhibitory receptor effector domain. In some embodiments, a C-terminus of a variant IgG Fc polypeptide is conjugated to a N-terminus of a inhibitory receptor effector domain via a linker. In some embodiments, a C-terminus of a variant IgG Fc polypeptide is directly conjugated to a N-terminus of a inhibitory receptor effector domain. In some embodiments, when a inhibitory receptor effector domain is an antibody, a N-terminus of a variant IgG Fc polypeptide is conjugated to a C-terminus of a heavy chain of a antibody that forms a inhibitor receptor effector domain. In some embodiments, when a inhibitory receptor effector domain is an antibody, a N-terminus of a variant IgG Fc polypeptide is conjugated, via a linker, to a C-terminus of a heavy chain of a antibody that forms a inhibitor receptor effector domain. In some embodiments, when a inhibitory receptor effector domain is an antibody, a N-terminus of a variant IgG Fc polypeptide is directly conjugated to a C-terminus of a heavy chain of a antibody that forms a inhibitor receptor effector domain. In some embodiments, when a inhibitory receptor effector domain is an antibody, a C-terminus of a variant IgG Fc polypeptide is conjugated to a N-terminus of a heavy chain of a antibody that forms a inhibitor receptor effector domain. In some embodiments, when a inhibitory receptor effector domain is an antibody, a C-terminus of a variant IgG Fc polypeptide is conjugated, via a linker, to a N-terminus of a heavy chain of a antibody that forms a inhibitor receptor effector domain. In some embodiments, when a inhibitory receptor effector domain is an antibody, a C-terminus of a variant IgG Fc polypeptide is directly conjugated to a N-terminus of a heavy chain of a antibody that forms a inhibitor receptor effector domain.

In some embodiments, a N-terminus of a variant IgG Fc polypeptide is conjugated to a C-terminus of a antibody. In some embodiments, a N-terminus of a variant IgG Fc polypeptide is conjugated to a C-terminus of a antibody via a linker. In some embodiments, a N-terminus of a variant IgG Fc polypeptide is directly conjugated to a C-terminus of a antibody. In some embodiments, a C-terminus of a variant IgG Fc polypeptide is conjugated to a N-terminus of a antibody. In some embodiments, a C-terminus of a variant IgG Fc polypeptide is conjugated to a N-terminus of a antibody via a linker. In some embodiments, a C-terminus of a variant IgG Fc polypeptide is directly conjugated to a N-terminus of a antibody.

In some embodiments, a N-terminus of a variant IgG Fc polypeptide is conjugated to a C-terminus of a inhibitory receptor effector domain, and a C-terminus of a variant IgG Fc polypeptide is conjugated to a N-terminus of an antibody. In some embodiments, a C-terminus of a variant IgG Fc polypeptide is conjugated to a N-terminus of a inhibitory receptor effector domain, and a N-terminus of a variant IgG Fc polypeptide is conjugated to a C-terminus of an antibody. In some embodiments, a N-terminus of a variant IgG Fc polypeptide is conjugated to a C-terminus of a inhibitory receptor effector domain via a linker, and a C-terminus of a variant IgG Fc polypeptide is conjugated to a N-terminus of an antibody. In some embodiments, a C-terminus of a variant IgG Fc polypeptide is conjugated to a N-terminus of a inhibitory receptor effector domain, and a N-terminus of a variant IgG Fc polypeptide is conjugated to a C-terminus of an antibody via a linker. In some embodiments, a N-terminus of a variant IgG Fc polypeptide is directly conjugated to a C-terminus of a inhibitory receptor effector domain, and a C-terminus of a variant IgG Fc polypeptide is directly conjugated to a N-terminus of an antibody. In some embodiments, a C-terminus of a variant IgG Fc polypeptide is directly conjugated to a N-terminus of a inhibitory receptor effector domain, and a N-terminus of a variant IgG Fc polypeptide is directly conjugated to a C-terminus of an antibody.

In some embodiments, a N-terminus of a Fc polypeptide is conjugated to a C-terminus of a inhibitory receptor effector domain. In some embodiments, a N-terminus of a Fc polypeptide is conjugated to a C-terminus of a inhibitory receptor effector domain via a linker. In some embodiments, a N-terminus of a Fc polypeptide is directly conjugated to a C-terminus of a inhibitory receptor effector domain. In some embodiments, a C-terminus of a Fc polypeptide is conjugated to a N-terminus of a inhibitory receptor effector domain. In some embodiments, a C-terminus of a Fc polypeptide is conjugated to a N-terminus of a inhibitory receptor effector domain via a linker. In some embodiments, a C-terminus of a Fc polypeptide is directly conjugated to a N-terminus of a inhibitory receptor effector domain. In some embodiments, when a inhibitory receptor effector domain is an antibody, a N-terminus of a Fc polypeptide is conjugated to a C-terminus of a heavy chain of a antibody that forms a inhibitor receptor effector domain. In some embodiments, when a inhibitory receptor effector domain is an antibody, a N-terminus of a Fc polypeptide is conjugated, via a linker, to a C-terminus of a heavy chain of a antibody that forms a inhibitor receptor effector domain. In some embodiments, when a inhibitory receptor effector domain is an antibody, a N-terminus of a Fc polypeptide is directly conjugated to a C-terminus of a heavy chain of a antibody that forms a inhibitor receptor effector domain. In some embodiments, when a inhibitory receptor effector domain is an antibody, a C-terminus of a Fc polypeptide is conjugated to a N-terminus of a heavy chain of a antibody that forms a inhibitor receptor effector domain. In some embodiments, when a inhibitory receptor effector domain is an antibody, a C-terminus of a Fc polypeptide is conjugated, via a linker, to a N-terminus of a heavy chain of a antibody that forms a inhibitor receptor effector domain. In some embodiments, when a inhibitory receptor effector domain is an antibody, a C-terminus of a Fc polypeptide is directly conjugated to a N-terminus of a heavy chain of a antibody that forms a inhibitor receptor effector domain.

In some embodiments, a N-terminus of a Fc polypeptide is conjugated to a C-terminus of a antibody. In some embodiments, a N-terminus of a Fc polypeptide is conjugated to a C-terminus of a antibody via a linker. In some embodiments, a N-terminus of a Fc polypeptide is directly conjugated to a C-terminus of a antibody. In some embodiments, a C-terminus of a Fc polypeptide is conjugated to a N-terminus of a antibody. In some embodiments, a C-terminus of a Fc polypeptide is conjugated to a N-terminus of a antibody via a linker. In some embodiments, a C-terminus of a Fc polypeptide is directly conjugated to a N-terminus of a antibody.

In some embodiments, a N-terminus of a Fc polypeptide is conjugated to a C-terminus of a inhibitory receptor effector domain, and a C-terminus of a Fc polypeptide is conjugated to a N-terminus of an antibody. In some embodiments, a C-terminus of a Fc polypeptide is conjugated to a N-terminus of a inhibitory receptor effector domain, and a N-terminus of a Fc polypeptide is conjugated to a C-terminus of an antibody. In some embodiments, a N-terminus of a Fc polypeptide is conjugated to a C-terminus of a inhibitory receptor effector domain via a linker, and a C-terminus of a Fc polypeptide is conjugated to a N-terminus of an antibody. In some embodiments, a C-terminus of a Fc polypeptide is conjugated to a N-terminus of a inhibitory receptor effector domain, and a N-terminus of a Fc polypeptide is conjugated to a C-terminus of an antibody via a linker. In some embodiments, a N-terminus of a Fc polypeptide is directly conjugated to a C-terminus of a inhibitory receptor effector domain, and a C-terminus of a Fc polypeptide is directly conjugated to a N-terminus of an antibody. In some embodiments, a C-terminus of a Fc polypeptide is directly conjugated to a N-terminus of a inhibitory receptor effector domain, and a N-terminus of a Fc polypeptide is directly conjugated to a C-terminus of an antibody.

In some embodiments, a variant IgG Fc polypeptide is directly conjugated, such as without a linker sequence, to a inhibitory receptor effector domain. In some embodiments, a variant IgG Fc polypeptide is conjugated to a inhibitory receptor effector domain through a linker, such as a peptide linker. In some embodiments, the linker is as provided for herein.

In some embodiments, the inhibitory receptor effector domain binds and modulates the activity of inhibitory receptors encoded by the genes: LAG3, BTLA/CD272, CD200R1, CD200R1, CD22/Siglec2, CD300A, CD300LF/CD300F, CD33/Siglec3, CD5, CD72, CEACAM 1, CLEC12A, CLEC4A, CTLA4/CD152, FCGR2B/CD32B, KIRs, KLRB1/CD161, KLRC1, KLRG1, LAIR1, LILRB1, LILRB2, LILRB4, LILRB5, NCR2/NKp44, PDCD1, PECAM1/CD31, PILRA, PVR/CD155, SIGLEC11, SIGLEC5, SIGLEC7, SIGLEC8, SIGLEC9, SIRPA, TIGIT, VSTM1/SIRL1, MAFA, NKG2A, CMRF35H, CD66a, CD66d, CD33, SIGLEC6, ILT2, ILT3, ILT4, ILT5, LIR8, KIR2DL, KIR2DL1, KIR3DL, SIRPa, KIR2DL2/3, KIR2DL5, KIRDL1, KIRDL2, KIRDL3, TIM3, Tactile, IRp60, NKRP1, IAP, PIR-B, CD5, 2B4, GP49B, Ly49Q, MICL, CD160, FCRL4, KIR3DL1, KIR2DL2, LILRB3, DCIR, NKRP-ID, LY49, MAIR-I, CD79a, CD79b, CD19, CD21, CD40, TLR3, CD28, CCR5, or CCR1.

In some embodiments, the inhibitory receptor effector domain binds and modulates the activity of the inhibitory receptor encoded by BTLA/CD272. In some embodiments, the inhibitory receptor effector domain binds and modulates the activity of the inhibitory receptor encoded by CD200R1. In some embodiments, the inhibitory receptor effector domain binds and modulates the activity of the inhibitory receptor encoded by CD22/Siglec2. In some embodiments, the inhibitory receptor effector domain binds and modulates the activity of the inhibitory receptor encoded by CD300A. In some embodiments, the inhibitory receptor effector domain binds and modulates the activity of the inhibitory receptor encoded by CD300LF/CD300F. In some embodiments, the inhibitory receptor effector domain binds and modulates the activity of the inhibitory receptor encoded by CD33/Siglec3. In some embodiments, the inhibitory receptor effector domain binds and modulates the activity of the inhibitory receptor encoded by CD5. In some embodiments, the inhibitory receptor effector domain binds and modulates the activity of the inhibitory receptor encoded by CD72. In some embodiments, the inhibitory receptor effector domain binds and modulates the activity of the inhibitory receptor encoded by CEACAM 1. In some embodiments, the inhibitory receptor effector domain binds and modulates the activity of the inhibitory receptor encoded by CLEC12A. In some embodiments, the inhibitory receptor effector domain binds and modulates the activity of the inhibitory receptor encoded by CLEC4A. In some embodiments, the inhibitory receptor effector domain binds and modulates the activity of the inhibitory receptor encoded by CTLA4/CD152. In some embodiments, the inhibitory receptor effector domain binds and modulates the activity of the inhibitory receptor encoded by FCGR2B/CD32B. In some embodiments, the inhibitory receptor effector domain binds and modulates the activity of the inhibitory receptor encoded by KIRs. In some embodiments, the inhibitory receptor effector domain binds and modulates the activity of the inhibitory receptor encoded by KLRB1/CD161. In some embodiments, the inhibitory receptor effector domain binds and modulates the activity of the inhibitory receptor encoded by KLRC1. In some embodiments, the inhibitory receptor effector domain binds and modulates the activity of the inhibitory receptor encoded by KLRG1. In some embodiments, the inhibitory receptor effector domain binds and modulates the activity of the inhibitory receptor encoded by LAIR1. In some embodiments, the inhibitory receptor effector domain binds and modulates the activity of the inhibitory receptor encoded by LILRB1. In some embodiments, the inhibitory receptor effector domain binds and modulates the activity of the inhibitory receptor encoded by LILRB2. In some embodiments, the inhibitory receptor effector domain binds and modulates the activity of the inhibitory receptor encoded by LILRB4. In some embodiments, the inhibitory receptor effector domain binds and modulates the activity of the inhibitory receptor encoded by LILRB5. In some embodiments, the inhibitory receptor effector domain binds and modulates the activity of the inhibitory receptor encoded by NCR2/NKp44. In some embodiments, the inhibitory receptor effector domain binds and modulates the activity of the inhibitory receptor encoded by PDCD1. In some embodiments, the inhibitory receptor effector domain binds and modulates the activity of the inhibitory receptor encoded by PECAM1/CD31. In some embodiments, the inhibitory receptor effector domain binds and modulates the activity of the inhibitory receptor encoded by PILRA. In some embodiments, the inhibitory receptor effector domain binds and modulates the activity of the inhibitory receptor encoded by PVR/CD155. In some embodiments, the inhibitory receptor effector domain binds and modulates the activity of the inhibitory receptor encoded by SIGLEC11. In some embodiments, the inhibitory receptor effector domain binds and modulates the activity of the inhibitory receptor encoded by SIGLEC5. In some embodiments, the inhibitory receptor effector domain binds and modulates the activity of the inhibitory receptor encoded by SIGLEC7. In some embodiments, the inhibitory receptor effector domain binds and modulates the activity of the inhibitory receptor encoded by SIGLEC8. In some embodiments, the inhibitory receptor effector domain binds and modulates the activity of the inhibitory receptor encoded by SIGLEC9. In some embodiments, the inhibitory receptor effector domain binds and modulates the activity of the inhibitory receptor encoded by SIRPA. In some embodiments, the inhibitory receptor effector domain binds and modulates the activity of the inhibitory receptor encoded by TIGIT. In some embodiments, the inhibitory receptor effector domain binds and modulates the activity of the inhibitory receptor encoded by VSTM1/SIRL1. In some embodiments, the inhibitory receptor effector domain binds and modulates the activity of the inhibitory receptor encoded by MAFA. In some embodiments, the inhibitory receptor effector domain binds and modulates the activity of the inhibitory receptor encoded by NKG2A. In some embodiments, the inhibitory receptor effector domain binds and modulates the activity of the inhibitory receptor encoded by CMRF35H. In some embodiments, the inhibitory receptor effector domain binds and modulates the activity of the inhibitory receptor encoded by CD66a. In some embodiments, the inhibitory receptor effector domain binds and modulates the activity of the inhibitory receptor encoded by CD66d. In some embodiments, the inhibitory receptor effector domain binds and modulates the activity of the inhibitory receptor encoded by CD33. In some embodiments, the inhibitory receptor effector domain binds and modulates the activity of the inhibitory receptor encoded by SIGLEC6. In some embodiments, the inhibitory receptor effector domain binds and modulates the activity of the inhibitory receptor encoded by ILT2. In some embodiments, the inhibitory receptor effector domain binds and modulates the activity of the inhibitory receptor encoded by ILT3. In some embodiments, the inhibitory receptor effector domain binds and modulates the activity of the inhibitory receptor encoded by ILT4. In some embodiments, the inhibitory receptor effector domain binds and modulates the activity of the inhibitory receptor encoded by ILT5. In some embodiments, the inhibitory receptor effector domain binds and modulates the activity of the inhibitory receptor encoded by LIR8. In some embodiments, the inhibitory receptor effector domain binds and modulates the activity of the inhibitory receptor encoded by KIR2DL. In some embodiments, the inhibitory receptor effector domain binds and modulates the activity of the inhibitory receptor encoded by KIR3DL. In some embodiments, the inhibitory receptor effector domain binds and modulates the activity of the inhibitory receptor encoded by SIRPa. In some embodiments, the inhibitory receptor effector domain binds and modulates the activity of the inhibitory receptor encoded by KIR2DL2/3. In some embodiments, the inhibitory receptor effector domain binds and modulates the activity of the inhibitory receptor encoded by KIR2DL5. In some embodiments, the inhibitory receptor effector domain binds and modulates the activity of the inhibitory receptor encoded by KIRDL1. In some embodiments, the inhibitory receptor effector domain binds and modulates the activity of the inhibitory receptor encoded by KIRDL2. In some embodiments, the inhibitory receptor effector domain binds and modulates the activity of the inhibitory receptor encoded by KIRDL3. In some embodiments, the inhibitory receptor effector domain binds and modulates the activity of the inhibitory receptor encoded by TIM3. In some embodiments, the inhibitory receptor effector domain binds and modulates the activity of the inhibitory receptor encoded by Tactile. In some embodiments, the inhibitory receptor effector domain binds and modulates the activity of the inhibitory receptor encoded by IRp60. In some embodiments, the inhibitory receptor effector domain binds and modulates the activity of the inhibitory receptor encoded by NKRP1. In some embodiments, the inhibitory receptor effector domain binds and modulates the activity of the inhibitory receptor encoded by IAP. In some embodiments, the inhibitory receptor effector domain binds and modulates the activity of the inhibitory receptor encoded by PIR-B. In some embodiments, the inhibitory receptor effector domain binds and modulates the activity of the inhibitory receptor encoded by 2B4. In some embodiments, the inhibitory receptor effector domain binds and modulates the activity of the inhibitory receptor encoded by GP49B. In some embodiments, the inhibitory receptor effector domain binds and modulates the activity of the inhibitory receptor encoded by Ly49Q. In some embodiments, the inhibitory receptor effector domain binds and modulates the activity of the inhibitory receptor encoded by MICL. In some embodiments, the inhibitory receptor effector domain binds and modulates the activity of the inhibitory receptor encoded by LAG3. In some embodiments, the inhibitory receptor effector domain binds and modulates the activity of the inhibitory receptor encoded by CD160. In some embodiments, the inhibitory receptor effector domain binds and modulates the activity of the inhibitory receptor encoded by FCRL4. In some embodiments, the inhibitory receptor effector domain binds and modulates the activity of the inhibitory receptor encoded by KIR3DL1. In some embodiments, the inhibitory receptor effector domain binds and modulates the activity of the inhibitory receptor encoded by KIR2DL2. In some embodiments, the inhibitory receptor effector domain binds and modulates the activity of the inhibitory receptor encoded by LILRB3. In some embodiments, the inhibitory receptor effector domain binds and modulates the activity of the inhibitory receptor encoded by DCIR. In some embodiments, the inhibitory receptor effector domain binds and modulates the activity of the inhibitory receptor encoded by NKRP-1D. In some embodiments, the inhibitory receptor effector domain binds and modulates the activity of the inhibitory receptor encoded by LY49. In some embodiments, the inhibitory receptor effector domain binds and modulates the activity of the inhibitory receptor encoded by MAIR-I. In some embodiments, the inhibitory receptor effector domain binds and modulates the activity of the inhibitory receptor encoded by CD79a. In some embodiments, the inhibitory receptor effector domain binds and modulates the activity of the inhibitory receptor encoded by CD79b. In some embodiments, the inhibitory receptor effector domain binds and modulates the activity of the inhibitory receptor encoded by CD19. In some embodiments, the inhibitory receptor effector domain binds and modulates the activity of the inhibitory receptor encoded by CD21. In some embodiments, the inhibitory receptor effector domain binds and modulates the activity of the inhibitory receptor encoded by CD40. In some embodiments, the inhibitory receptor effector domain binds and modulates the activity of the inhibitory receptor encoded by TLR3. In some embodiments, the inhibitory receptor effector domain binds and modulates the activity of the inhibitory receptor encoded by CD28. In some embodiments, the inhibitory receptor effector domain binds and modulates the activity of the inhibitory receptor encoded by 5 CCR5. In some embodiments, the inhibitory receptor effector domain binds and modulates the activity of the inhibitory receptor encoded by CCR1.

In some embodiments, the variant IgG Fc polypeptide is also linked to the FcγRII binding effector domain. Non-limiting examples of Fc domains linked to FcγRII binding effector domains can be found in U.S. Non-Provisional application Ser. No. 18/048,747, or PCT Application No. PCT/US2022/078537, each of which is hereby incorporated by reference in its entirety. In some embodiments, the C-terminus of the variant IgG Fc polypeptide is linked to the N-terminus of the FcγRII binding effector domain. In some embodiments, the N-terminus of the variant IgG Fc polypeptide is linked to a C-terminus of the inhibitory receptor effector domain and the C-terminus of the variant IgG Fc polypeptide is linked to the N-terminus of the FcγRII binding effector domain. In some embodiments, the variant IgG Fc polypeptide is linked to the FcγRII binding effector domain directly, such as without a peptide linker. In some embodiments, the variant IgG Fc polypeptide is linked to the FcγRII binding effector domain through a peptide linker.

In some embodiments, the Fc domain is linked to an inhibitory receptor binding domain and an FcγRII binding effector domain, such as, but not limited to, those disclosed in U.S. Non-Provisional application Ser. No. 18/048,747, or PCT Application No. PCT/US2022/078537, each of which is hereby incorporated by reference in its entirety.

Examples of peptide linkers that can be used are known in the art and non-limiting examples are provide for herein.

As used herein, the term "FcγRII binding effector domain" refers to a polypeptide, such as an antibody, that binds to FcγRII receptor. Examples of such receptors include the FcγRIIa or FcγRIIb receptor. In some embodiments, the FcγRII binding effector domain is an antibody. In some embodiments, the FcγRII binding effector domain is a scFv antibody. In some embodiments, the N-terminus of the FcγRII binding effector domain is bound to the C-terminus of the Fc domain.

In some embodiments, the variant IgG Fc polypeptides provided herein can be conjugated to effector domains and/or antibodies. Antibody molecule, as that term is used herein, refers to a polypeptide, e.g., an immunoglobulin chain or fragment thereof, comprising at least one functional immunoglobulin variable domain sequence. An antibody molecule encompasses antibodies (e.g., full-length antibodies) and antibody fragments. In some embodiments, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')2 fragments, and single chain variable fragments (scFvs).

The term "antibody molecule" also encompasses whole or antigen binding fragments of domain, or single domain, antibodies, which can also be referred to as "sdAb" or "VHH." Domain antibodies comprise either $V_H$ or $V_L$ that can act as stand-alone, antibody fragments. Additionally, domain antibodies include heavy-chain-only antibodies (HCAbs). Domain antibodies also include a CH2 domain of an IgG as the base scaffold into which CDR loops are grafted. It can also be generally defined as a polypeptide or protein comprising an amino acid sequence that is comprised of four framework regions interrupted by three complementarity determining regions. This is represented as FR1-CDR1-FR2-CDR2-FR3-CDR3-FR4. sdAbs can be produced in camelids such as llamas, but can also be synthetically generated using techniques that are well known in the art. The numbering of the amino acid residues of a sdAb or polypeptide is according to the general numbering for VH domains given by Kabat et al. ("Sequence of proteins of immunological interest," US Public Health Services, NIH Bethesda, MD, Publication No. 91, which is hereby incorporated by reference). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113. Domain antibodies are also described in WO2004041862 and WO2016065323, each of which is hereby incorporated by reference. The domain antibodies can be a targeting moiety as described herein.

Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g, tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide. Effector, as that term is used herein, refers to an entity, e.g., a cell or molecule, e.g., a soluble or cell surface molecule, which mediates an immune response. In some embodiments, the effector is an antibody. In some embodiments, the effectors binding domains as provided for herein, refers to a polypeptide (e.g.) that has sufficient binding specificity that it can bind the effector with sufficient specificity that it can serve as an effector binding/modulating molecule. In some embodiments, it binds to effector with at least 10, 20, 30, 40, 50, 60, 70, 80, 90, or 95% of the affinity of the naturally occurring counter-ligand. In some embodiments, it has at least 60, 70, 80, 90, 95, 99, or 100% sequence identity, or substantial sequence identity, with a naturally occurring counter-ligand for the effector.

Elevated risk, as used herein, refers to the risk of a disorder in a subject, wherein the subject has one or more of a medical history of the disorder or a symptom of the disorder, a biomarker associated with the disorder or a symptom of the disorder, or a family history of the disorder or a symptom of the disorder.

In some embodiments, the inhibitory effector binding domain can be referred to as an inhibitory immune checkpoint molecule. This can refer to a polypeptide that can bind to the checkpoint molecule and agonize its cognate inhibitory activity. For example, the antibody can be an anti-PD-1 antibody that binds to PD-1 and agonizes its activity. In some embodiments, the antibody inhibits the inhibitory checkpoint activity, such that it antagonizes the inhibitory activity. For example, the antibody can be an anti-PD-1 antibody that binds to PD-1 and antagonizes its activity. The same can be done if the target is any of the inhibitory receptors, such as those provided for herein. In some embodiments, the inhibitory checkpoint receptor is LAG-3.

Inhibitory receptor agonism can be elicited either by engagement of the natural ligand of the inhibitory receptor or via antibody crosslinking and higher order clustering of the inhibitory receptors. Thus, immune homeostasis may be restored by agonizing multiple inhibitory receptors (IRs) with one antibody. Without wishing to be bound by a particular theory, agonism of IRs may modulate the network interactions of multiple pathologic immune cell types, thus restoring immune homeostasis in diseases of cell-mediated immunity. Agonizing inhibitory receptors with an antibody molecules can require IR superclustering on the surface of the cell, which is not efficiently induced by Fc-null antibodies. For example, Programmed cell death 1 (PD-1) is a negative costimulatory receptor essential for suppression of T cell activation both in in vitro and in vivo. Studies show that upon interacting with its ligand, PD-L1, PD-1 forms clusters with T cell receptors (TCRs) and transiently associates with the phosphatase SHP2 (Src homology 2 domain-containing tyrosine phosphatase. These inhibitory microclusters trigger the dephosphorylation of nearby TCR signaling molecules, resulting in suppression of T cell activation (Yokosuka T, Takamatsu M, Kobayashi-Imanishi W, Hashimoto-Tane A, Azuma M, Saito T. Programmed cell death 1 forms negative costimulatory microclusters that directly inhibit T cell receptor signaling by recruiting phosphatase SHP2. J Exp Med. 2012 Jun. 4; 209 (6): 1201-17. doi: 10.1084/jem.20112741. Epub 2012 May 28. PMID: 22641383; PMCID: PMC3371732). Thus, agonist antibody molecules may rely on simultaneous Fc (constant region) tethering on antigen presenting cells (APC), thereby allowing efficient IR superclustering and downstream signaling. Agonistic molecules targeting IRs and containing an IgG1 wild-type Fc bind both activating and inhibitory Fc receptors, thus triggering unwanted production of inflammatory cytokines by APCs as a result of binding the activating Fc receptors. However, selectively binding to FcgRIIb (the only inhibitory Fc receptor) prevents proinflammatory cytokine production and may also inhibit pathogenic B cell and APC activity.

Accordingly, in some embodiments, provided herein are variant Fc polypeptides comprising a mutation, or set of mutations, that increase selectivity for an FcGRIIb receptor. In some embodiments, provided herein are a dimer molecule comprising variant Fc polypeptides comprising a mutation, or set of mutations, that increase selectivity for an FcGRIIb receptor. In some embodiments, the dimer molecule comprising variant Fc polypeptides comprising a mutation, or set of mutations, that increase selectivity for FcgRIIb, binds to one FcGRIIb receptor. In some embodiments, the dimer molecule comprises a first variant Fc polypeptide comprising a mutation, or set of mutations, that increase selectivity for FcGRIIb, and a second variant Fc polypeptide comprising a mutation, or set of mutations, that increase selectivity for FcGRIIb. In some embodiments, the first variant Fc polypeptide and the second variant Fc polypeptide are the same, such that it is a homodimer in respect to the variant Fc polypeptide. In some embodiments, the first variant Fc polypeptide and the second variant Fc polypeptide are different, such that it is a heterodimer in respect to the variant Fc polypeptide. In some embodiments, the first variant Fc polypeptide comprising a mutation, or set of mutations, that increase selectivity for FcGRIIb, and the second variant Fc polypeptide comprising a mutation, or set of mutations, that increase selectivity for FcGRIIb, both bind to the same FcGRIIb receptor. In some embodiments, a mutation, or set of mutations, that increase selectivity for FcGRIIb may also affect binding of the antibody to the IR. In some embodiments, a mutation, or set of mutations, that increase selectivity for FcGRIIb may also increase binding of the antibody to the IR. In some embodiments, a mutation, or set of mutations, that increase selectivity for FcGRIIb may also decrease binding of the antibody to the IR. In some embodiments, the variant Fc polypeptide comprising a mutation, or set of mutations, that increase selectivity for FcGRIIb is conjugated or linked to an antibody. In some embodiments, the variant Fc polypeptide comprising a mutation, or set of mutations, that increase selectivity for FcGRIIb is conjugated or linked to an agonistic antibody. In some embodiments, the first variant Fc polypeptide comprising a mutation, or set of mutations, that increase selectivity for FcGRIIb is conjugated or linked to an antibody. In some embodiments, the first variant Fc polypeptide comprising a mutation, or set of mutations, that increase selectivity for FcGRIIb is conjugated or linked to an agonistic antibody. In some embodiments, the second variant Fc polypeptide comprising a mutation, or set of mutations, that increase selectivity for FcGRIIb is conjugated or linked to an antibody. In some embodiments, the second variant Fc polypeptide comprising a mutation, or set of mutations, that increase selectivity for FcGRIIb is conjugated or linked to an agonistic antibody. In some embodiments, the first variant Fc polypeptide and the second variant Fc polypeptide, each comprising a mutation, or set of mutations, that increase selectivity for FcGRIIb is each conjugated or linked to an antibody. In some embodiments, the first variant Fc polypeptide and the second variant Fc polypeptide, each comprising a mutation, or set of mutations, that increase selectivity for FcGRIIb is each conjugated or linked to an agonistic antibody. In some embodiments, the antibody binds to an IR. In some embodiments, the agonistic antibody binds to an IR. In some embodiments, a mutation, or set of mutations, that increase selectivity for FegRIIb may also affect binding of the antibody to the IR. In some embodiments, a mutation, or set of mutations, that increase selectivity for FcGRIIb may also increase binding of the antibody to the IR. In some embodiments, a mutation, or set of mutations, that increase selectivity for FcGRIIb may also decrease binding of the antibody to the IR. In some embodiments, a mutation, or set of mutations, that increase selectivity for FcGRIIb may affect clustering of PD-1. In some embodiments, a mutation, or set of mutations, that increase selectivity for FcGRIIb may increase clustering of PD-1. In some embodiments, a mutation, or set of mutations, that increase selectivity for FcGRIIb may decrease clustering of PD-1. In some embodiments, a mutation, or set of mutations, that increase selectivity for FcGRIIb may affect clustering of PD-1, wherein affecting clustering of PD-1 also affects agonism of PD-1. In some embodiments, a mutation, or set of mutations, that increase selectivity for FcGRIIb may increase clustering of PD-1, wherein increasing clustering of PD-1 also increases agonism of PD-1. In some embodiments, a mutation, or set of mutations, that increase selectivity for FcGRIIb may decrease clustering of PD-1, wherein decrease clustering of PD-1 also decrease agonism of PD-1.

The domains can have similarity to those as provided for herein or those that are incorporated by reference. Sequence identity, percentage identity, and related terms, as those terms are used herein, refer to the relatedness of two sequences, e.g., two nucleic acid sequences or two amino acid or polypeptide sequences. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., an amino acid sequence provided herein.

In the context of nucleotide sequence, such as those encoding for the domains, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., an amino acid sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence. For example, a Fc variant can have the amino acid sequence of a Fc domain but comprise a mutation that affects its binding to the FcγRIIa or FcγRIIb receptor.

Calculations of homology or sequence identity between sequences (the terms are used interchangeably herein) can be performed as follows.

To determine the percent identity of two amino acid sequences, or of two nucleic acid sequences, the amino acid sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the amino acid sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to for example any a nucleic acid sequence provided herein. BLAST protein searches can be performed with the XBLAST program, score=50, wordlength=3 to obtain amino acid sequences homologous to protein molecules provided herein. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. Sec http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present embodiments may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The molecules and polypeptides provided for herein can be used to treat autoimmune diseases. Thus, in some embodiments, embodiments are provided for methods of treating an autoimmune disease or disorder in a subject. In some embodiments, the methods comprise administering to the subject a compound as provided for herein. In some embodiments, the subject has or is at risk of having an autoimmune disorder. In some embodiments, the autoimmune disorder is Type 1 Diabetes, Multiple Sclerosis, Cardiomyositis, vitiligo, alopecia, inflammatory bowel disease (IBD, e.g. Crohn's disease or ulcerative colitis), Sjogren's syndrome, focal segmented glomerular sclerosis (FSGS), scleroderma/systemic sclerosis (SSc) or rheumatoid arthritis. In some embodiments, the treatment minimizes rejection of, minimizes immune effector cell mediated damage to, prolongs the survival of subject tissue undergoing, or a risk for, autoimmune attack, such as from a transplant.

Other examples of autoimmune disorders and diseases that can be treated with the molecules and polypeptides described herein include, but are not limited to, myocarditis, postmyocardial infarction syndrome, postpericardiotomy syndrome, subacute bacterial endocarditis, anti-glomerular basement membrane nephritis, interstitial cystitis, lupus nephritis, membranous glomerulonephropathy, chronic kidney disease (CKD), autoimmune hepatitis, primary biliary cirrhosis, primary sclerosing cholangitis, antisynthetase syndrome, alopecia areata, autoimmune angioedema, autoimmune progesterone dermatitis, overlap connective tissues disease syndromes, polymyalgia rheumatic, autoimmune urticaria, bullous pemphigoid, cicatricial pemphigoid, dermatitis herpetiformis, discoid lupus erythematosus, epidermolysis bullosa acquisita, erythema nodosum, anti-neutrophil cytoplasmic antibody associated vasculitis, Henoch-Schonlein purpura, Cogan's syndrome, Buerger's disease, Susan's disease, immune complex vasculitis, primary angiitis of the CNS, gestational pemphigoid, hidradenitis suppurativa, lichen planus, lichen sclerosus, linear iga disease (lad), morphea, pemphigus vulgaris, *Pityriasis lichenoides* et varioliformis acuta, mucha-habermann disease, psoriasis, systemic scleroderma, vitiligo, Addison's disease, autoimmune polyendocrine syndrome (APS) type 1, autoimmune polyendocrine syndrome (APS) type 2, juvenile idiopathic arthritis, idiopathic inflammatory myopathies, giant cell arteritis, juvenile dermatomyositis, autoimmune brain disease, autoimmune polyendocrine syndrome (APS) type 3, autoimmune pancreatitis (AIP), diabetes mellitus type 1, autoimmune thyroiditis, Ord's thyroiditis, Graves' disease, autoimmune oophoritis, endometriosis, autoimmune orchitis, Sjögren's syndrome, autoimmune enteropathy, Coeliac disease, Crohn's disease, microscopic colitis, ulcerative colitis, thrombocytopenia, adiposis, dolorosa, adult-onset Still's disease, ankylosing spondylitis, CREST syndrome, drug-induced lupus, enthesitis-related arthritis, cosinophilic fasciitis, Felty syndrome, IgG4-related disease, juvenile arthritis, lyme disease (chronic), mixed connective tissue disease (MCTD), palindromic rheumatism, Parry Romberg syndrome, Parsonage-Turner syndrome, psoriatic arthritis, IBD-associated arthritis, reactive arthritis, relapsing polychondritis, retroperitoneal fibrosis, rheumatic fever, rheumatoid arthritis, autoimmune complications of immune checkpoint inhibitors (IRAEs), sarcoidosis, neurosarcoidosis, Schnitzler syndrome, systemic lupus erythematosus (SLE), undifferentiated connective tissue disease (UCTD), dermatomyositis, IgG4 related disease, fibromyalgia, antiphospholipid syndrome, inclusion body myositis, myositis, myasthenia gravis, neuromyotonia, parancoplastic cerebellar degeneration, polymyositis, acute disseminated encephalomyelitis (ADEM), adult onset Still's disease, acute motor axonal neuropathy, anti-N-Methyl-D-Aspartate (anti-NMDA) receptor encephalitis, warm antibody hemolytic anemia (wAIHA), immune thrombocytopenia, immune thrombotic thrombocytopenia, thrombotic thrombocytopenia, pernicious anemia, aplastic anemia, Evan's syndrome, autoimmune neutropenia, acquired von Willibrand syndrome, recurring fetal loss, Rh mismatch, Balo concentric sclerosis, Bickerstaff's encephalitis, chronic inflammatory demyelinating polyneuropathy, Guillain-Barre syndrome, Hashimoto's encephalopathy, idiopathic inflammatory demyelinating diseases, Lambert-Eaton myasthenic syndrome, primary biliary sclerosis, glomerulonephritis, glomerular basement membrane disease, multiple sclerosis, Oshtoran syndrome, pediatric autoimmune neuropsychiatric disorder associated with *Streptococcus* (PANDAS), progressive inflammatory neuropathy, cutaneous lupus crythematosus, restless leg syndrome, pemphigus foliaceus including fogo selvage, transplantation, antibody-mediated rejection, alloantibody hypersensitization, xenoantibody mediated rejection, solid organ rejection, graft vs host disease acute and chronic, stiff person syndrome, Sydenham chorea, transverse myelitis, autoimmune retinopathy, autoimmune uveitis, uveitis, Cogan syndrome, Graves ophthalmopathy, amyotrophic lateral sclerosis (ALS), Parkinson's disease, autoimmune encephalitis, CNS vasculitis, chronic idiopathic demyelinating polyneuropathy (CIDP), keratitis, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, rheumatic heart disease, chronic rhinosinusitis with nasal polyps, allergic bronchoplmonary mycosis, hypersensitivity pneumonitis, rheumatoid arthritis-associated interstitial lung disease (RA-ILD), nonspecific interstitial pneumonia, allergic asthma, infectious disease/vaccination, antibody dependent enhancement (as with dengue virus infection), chronic meningitis, anti-myelin oligodendrocyte glycoprotein (MOG) disease, activated-DLBCL, anti-drug antibody, anti-gene therapy vector antibody (anti-AAV antibody), antibody to therapeutic biologic agents (cytokines, monoclonal antibodies, enzymes, coagulation factors), autoimmune inner car disease (AIED), Ménière's disease, Behcet's disease, cosinophilic granulomatosis with polyangiitis (EGPA), giant cell arteritis, polyglandular autoimmune endocrine syndromes, granulmatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumaticia, vasculitis, primary immune deficiency, and the like.

Other examples of potential autoimmune disorders and diseases, as well as autoimmune comorbidities that can be treated with the molecules and polypeptides described herein include, but are not limited to, Chronic fatigue syndrome, Complex regional pain syndrome, Eosinophilic esophagitis, Gastritis, Interstitial lung disease, POEMS syndrome, Raynaud's phenomenon, Primary immunodeficiency, Pyoderma gangrenosum, Agammaglobulinemia, Anyloidosis, Anyotrophic lateral sclerosis, Anti-tubular basement membrane nephritis, Atopic allergy, Atopic dermatitis, Autoimmune peripheral neuropathy, Blau syndrome, Castleman's disease, Chagas disease, Chronic obstructive pulmonary disease, Chronic recurrent multifocal osteomyelitis, Complement component 2 deficiency, Contact dermatitis, Cushing's syndrome, Cutaneous leukocytoclastic angiitis, Dego' deiase, Eczema, Eosinophilic gastroenteritis, Eosinophilic pneumonia, Erythroblastosis fetalsis, Fibrodysplasia ossificans progressive, Gastrointestinal pemphigoid, Hypogammaglobulinemia, Idiopathic giant-cell myocarditis, Idiopathic pulmonary fibrosis, IgA nephropathy, Immunoregulatory lipoproteins, IPEX syndrome, Ligenous conjunctivitis, Majeed syndrome, Narcolepsy, Rasmussen's encephalitis, Schizophrenia, Serum sickness, Spondyloathropathy, Sweet's syndrome, Takayasu's arteritis, and the like.

In some embodiments, the autoimmune disorder does not comprise pemphigus Vulgaris, pemphigus. In some embodiments, the autoimmune disorder does not comprise pemphigus foliaceus. In some embodiments, the autoimmune disorder does not comprise bullous pemphigoid. In some embodiments, the autoimmune disorder does not comprise Goodpasture's Disease. In some embodiments, the autoimmune disorder does not comprise psoriasis. In some embodiments, the autoimmune disorder does not comprise a skin disorder. In some embodiments, the disorder does not comprise a neoplastic disorder, e.g., cancer.

In some embodiments, the condition to be treated is a neoplastic disorder, such as a cancer. In contrast, to the molecule that is used to treat an autoimmune disorder the molecule is used to antagonize the inhibitor receptor to which the inhibitory receptor effector domain binds to. Additionally, the Fc domain comprises mutations that are not inhibitory. In some embodiments, the FcγRII binding effector domain binds preferentially to the FcγRII binding effector domain.

In some embodiments, the cancer is a solid or liquid tumor. In some embodiments, the liquid or solid tumor include, but are not limited to, hematopoietic cancer, lymphoid cancer, skin cancer, head and neck cancer, genitourinary cancer, blood cancer, lung cancer, breast cancer, brain cancer, esophageal cancer, colorectal cancer, pancreatic cancer, and any combination thereof.

In some embodiments, the polypeptide that is the compound comprises at the N-terminus an antibody comprised of F(ab')2 on an IgG1 Fc backbone fused with scFvs on the C-terminus of the IgG Fc backbone. In some embodiments, the IgG Fc backbone is a IgG1 Fc backbone. In some embodiments, the IgG1 backbone is replaced with a IgG4 backbone, IgG2 backbone, or other similar IgG backbone. The IgG backbones described in this paragraph can be used throughout this application where a Fc region is referred to as part of the therapeutic compound. The Fc backbone can be the Fc region as provided for herein and have a mutation as provided for herein.

Thus, in some embodiments, the antibody comprised of F(ab')2 on an IgG1 Fc backbone can be an anti-PD-1 antibody, an anti-LAG-3, an anti-CTLA4 antibody (or any other antibody that binds to an inhibitory receptor) on an IgG1 Fc. In some embodiments, the scFV segments fused to the C-terminus could be the FcγRII binding effector domain. In some embodiments, the polypeptide comprises two antibodies linked separately to two separate FcγRII binding effector domains. In some embodiments, the F(ab')2 bind to PD-1 or LAG-3. In some embodiments, one antibody binds to PD-1 and the other binds to LAG-3.

In some embodiments, the FcγRII binding effector domain as provided for herein, for any of the polypeptides provided for herein are selective for FcγRIIb over the FcγRIIα-R131 isoform or the FcγRIIα-H131 isoform. Without being bound to any particular theory, these FcγRIIb binding effector domain can be used to help down regulate an immune response.

In some embodiments, when the inhibitory receptor effector domain is a checkpoint agonist, the Fc domain comprises mutations that are FcγRIIb selective mutations and the FcγRII binding effector domains is a FcγRIIb-specific scFv antibody.

Pharmaceutical Compositions and Kits

In some embodiments, the present embodiments provide compositions, e.g., pharmaceutically acceptable compositions, which include a therapeutic compound described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, local, ophthalmic, topical, spinal or epidermal administration (e.g. by injection or infusion). As used herein, the term "carrier" means a diluent, adjuvant, or excipient with which a compound is administered. In some embodiments, pharmaceutical carriers can also be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. The carriers can be used in pharmaceutical compositions comprising the therapeutic compounds provided for herein.

The compositions and compounds of the embodiments provided for herein may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions. In some embodiments, the mode of administration is parenteral (e.g., intravenous, subcutaneous, intraperitoneal, intramuscular). In some embodiments, the therapeutic molecule is administered by intravenous infusion or injection. In another embodiment, the therapeutic molecule is administered by intramuscular or subcutaneous injection. In another embodiment, the therapeutic molecule is administered locally, e.g., by injection, or topical application, to a target site.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The compositions typically should be sterile and stable under the conditions of manufacture and storage. The composition can be formulated as a solution, microemulsion, dispersion, liposome, or other ordered structure suitable to high therapeutic molecule concentration. Sterile injectable solutions can be prepared by incorporating the active compound (i.e., therapeutic molecule) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. Sec, e.g., Sustained and Controlled Release Drug Delivery Systems, J. R. Robinson, ed., Marcel Dekker, Inc., New York, 1978.

In certain embodiments, a therapeutic compound can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a therapeutic compound is 0.1-30 mg/kg, more preferably 1-25 mg/kg. Dosages and therapeutic regimens of the therapeutic compound can be determined by a skilled artisan. In certain embodiments, the therapeutic compound is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the therapeutic compound is administered at a dose from about 10 to 20 mg/kg every other week. The therapeutic compound can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the infusion rate of about 110 to 130 mg/m2 achieves a level of about 3 mg/kg. In other embodiments, the therapeutic compound can be administered by intravenous infusion at a rate of less than 10 mg/min, e.g., less than or equal to 5 mg/min to reach a dose of about 1 to 100 mg/m2, e.g., about 5 to 50 mg/m2, about 7 to 25 mg/m2, or, about 10 mg/m2. In some embodiments, the therapeutic compound is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions may include a "therapeutically effective amount" or a "prophylactically effective amount" of a therapeutic molecule. A "therapeutically effective amount" refers to an amount effective, at dosages and for periods of time necessary, to achieve the desired therapeutic result. A therapeutically effective amount of a therapeutic molecule may vary according to factors such as the disease state, age, sex, and weight of the individual, and the ability of the therapeutic compound to elicit a desired response in the individual. A therapeutically effective amount is also one in which any toxic or detrimental effects of a therapeutic molecule t is outweighed by the therapeutically beneficial effects. A "therapeutically effective dosage" preferably inhibits a measurable parameter, e.g., immune attack at least about 20%, more preferably by at least about 40%, even more preferably by at least about 60%, and still more preferably by at least about 80% relative to untreated subjects. The ability of a compound to inhibit a measurable parameter, e.g., immune attack, can be evaluated in an animal model system predictive of efficacy in transplant rejection or autoimmune disorders. Alternatively, this property of a composition can be evaluated by examining the ability of the compound to inhibit, such inhibition in vitro by assays known to the skilled practitioner. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the embodiments is a kit comprising a therapeutic compound described herein. The kit can include one or more other elements including: instructions for use; other reagents, e.g., a label, a therapeutic agent, or an agent useful for chelating, or otherwise coupling, a therapeutic molecule to a label or other therapeutic agent, or a radioprotective composition; devices or other materials for preparing the a therapeutic molecule for administration; pharmaceutically acceptable carriers; and devices or other materials for administration to a subject.

ENUMERATED EMBODIMENTS

1. A variant IgG Fc polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

2. The variant IgG Fc polypeptide of embodiment 1, wherein the variant IgG Fc polypeptide comprises a mutation that enhances selective binding to FcγRIIβ over FcγRIIα.

3. The variant IgG Fc polypeptide of any one of embodiments 1-2, wherein the variant IgG Fc polypeptide comprises a mutation set selected from:
   - a mutation at positions 238, 269, 270, and 330, as compared to SEQ ID NO: 88;
   - a mutation at positions 237, 238, 269, 270, and 330, as compared to SEQ ID NO: 88;
   - a mutation at positions 237, 238, 239, 269, 270, and 330, as compared to SEQ ID NO: 88;
   - a mutation at positions 237, 238, 240, 269, 270, and 330, as compared to SEQ ID NO: 88;
   - a mutation at positions 235, 238, 269, 270, and 330, as compared to SEQ ID NO: 88;
   - a mutation at positions 235, 238, 269, 270, and 330, and an insertion of an amino acid sequence GEV between positions 233 and 234, as compared to SEQ ID NO: 88;
   - a mutation at positions 238, 269, 270, and 330, as compared to SEQ ID NO: 88;
   - a mutation at positions 234, 235, 329, 268, and 271, as compared to SEQ ID NO: 88;
   - a mutation at positions 234, 235, 239, 329, 268, and 271, as compared to SEQ ID NO: 88;
   - a mutation at positions 234 and 235, as compared to SEQ ID NO: 88;
   - a mutation at positions 237 and 238, as compared to SEQ ID NO: 88; or
   - any combination thereof.

4. The variant IgG Fc polypeptide of any one of embodiments 1-3, wherein the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

5. The variant IgG Fc polypeptide of embodiment 4, wherein the variant IgG Fc polypeptide comprises a mutation set selected from:
   - a mutation set of P238D, E269D, D270E, and A330R, as compared to SEQ ID NO: 88;
   - a mutation set of G237D, P238G, E269D, D270E, and A330R, as compared to SEQ ID NO: 88;
   - a mutation set of G237D, P238S, S239G, E269D, D270E, and A330R, as compared to SEQ ID NO: 88;
   - a mutation set of G237D, P238G, V240A, E269D, D270E, and A330R, as compared to SEQ ID NO: 88;
   - a mutation set of L235V, P238E, E269D, D270E, and A330R, as compared to SEQ ID NO: 88;
   - a mutation set of L235V, P238D, E269D, D270E, and A330R, and an insertion of an amino acid sequence GEV between positions 233 and 234, as compared to SEQ ID NO: 88;
   - a mutation set of P238S, E269D, D270E, and A330R, as compared to SEQ ID NO: 88;
   - a mutation set of L234F, L235E, P329A, H268D, and P271G, as compared to SEQ ID NO: 88;
   - a mutation set of L234F, L235E, S239D, P329A, H268D, and P271G, as compared to SEQ ID NO: 88;
   - a mutation set of L234F and L235E, as compared to SEQ ID NO: 88;
   - a mutation set of G237E and P238E, as compared to SEQ ID NO: 88; or
   - any combination thereof.

6. The variant IgG Fc polypeptide of any one of embodiments 1-5, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

7. The variant IgG Fc polypeptide of any one of embodiments 1-6, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

8. The variant IgG Fc polypeptide of embodiment 7, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

9. The variant IgG Fc polypeptide of embodiment 8, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

10. The variant IgG Fc polypeptide of any one of embodiments 1-9, wherein the variant IgG Fc polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

11. The variant IgG Fc polypeptide of any one of embodiments 1-10, wherein the variant IgG Fc polypeptide associates with another variant IgG Fc polypeptide to form a dimer molecule.

12. The variant IgG Fc polypeptide of embodiment 11, wherein the dimer molecule is a heterodimer molecule.

13. The variant IgG Fc polypeptide of any one of embodiments 11 or 12, wherein the heterodimer molecule comprises a pair of a first polypeptide and a second polypeptide, and wherein the first polypeptide and the second polypeptide comprise different amino acid sequences.

14. The variant IgG Fc polypeptide of embodiment 11, wherein the dimer molecule is a homodimer molecule.

15. The variant IgG Fc polypeptide of any one of embodiments 11 or 14, wherein the homodimer molecule comprises a first polypeptide and a second polypeptide, and wherein the first polypeptide and the second polypeptide comprise identical amino acid sequences.

16. The variant IgG Fc polypeptide of any one of embodiments 11-15, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

17. The variant IgG Fc polypeptide of any one of embodiments 11-15, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

18. The variant IgG Fc polypeptide of any one of embodiments 11-17, wherein the dimer molecule comprises:

- the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;
  - a mutation at positions 237, 238, 269, 270, and 330, as compared to SEQ ID NO: 88;
  - a mutation at positions 237, 238, 239, 269, 270, and 330, as compared to SEQ ID NO: 88;
  - a mutation at positions 237, 238, 240, 269, 270, and 330, as compared to SEQ ID NO: 88;
  - a mutation at positions 235, 238, 269, 270, and 330, as compared to SEQ ID NO: 88;
  - a mutation at positions 235, 238, 269, 270, and 330, and an insertion of an amino acid sequence GEV between positions 233 and 234, as compared to SEQ ID NO: 88;
  - a mutation at positions 238, 269, 270, and 330, as compared to SEQ ID NO: 88;
  - a mutation at positions 234, 235, 329, 268, and 271, as compared to SEQ ID NO: 88;
  - a mutation at positions 234, 235, 239, 329, 268, and 271, as compared to SEQ ID NO: 88;
  - a mutation at positions 234 and 235, as compared to SEQ ID NO: 88;
  - a mutation at positions 237 and 238, as compared to SEQ ID NO: 88; or
  - any combination thereof; and
- the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;
  - a mutation at positions 237, 238, 269, 270, and 330, as compared to SEQ ID NO: 88;
  - a mutation at positions 237, 238, 239, 269, 270, and 330, as compared to SEQ ID NO: 88;
  - a mutation at positions 237, 238, 240, 269, 270, and 330, as compared to SEQ ID NO: 88;

a mutation at positions 235, 238, 269, 270, and 330, as compared to SEQ ID NO: 88;

a mutation at positions 235, 238, 269, 270, and 330, and an insertion of an amino acid sequence GEV between positions 233 and 234, as compared to SEQ ID NO: 88;

a mutation at positions 238, 269, 270, and 330, as compared to SEQ ID NO: 88;

a mutation at positions 234, 235, 329, 268, and 271, as compared to SEQ ID NO: 88;

a mutation at positions 234, 235, 239, 329, 268, and 271, as compared to SEQ ID NO: 88;

a mutation at positions 234 and 235, as compared to SEQ ID NO: 88;

a mutation at positions 237 and 238, as compared to SEQ ID NO: 88; or any combination thereof.

19. The variant IgG Fc polypeptide of any one of embodiments 11-18, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

20. The variant IgG Fc polypeptide of any one of embodiments 11-18, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

21. The variant IgG Fc polypeptide of any one of embodiments 11-20, wherein the dimer molecule comprises:

the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof; and the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

22. The variant IgG Fc polypeptide of any one of embodiments 11-21, wherein the first polypeptide comprises a variant sequence of SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and the second polypeptide comprises a variant sequence of SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

23. The variant IgG Fc polypeptide of any one of embodiments 11-22, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

24. The variant IgG Fc polypeptide of any one of embodiments 11-22, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

25. The variant IgG Fc polypeptide of any one of embodiments 11-24, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

26. The variant IgG Fc polypeptide of any one of embodiments 11-24, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

27. The variant IgG Fc polypeptide of any one of embodiments 11-25, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

28. The variant IgG Fc polypeptide of any one of embodiments 11-26, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

29. The variant IgG Fc polypeptide of any of embodiments 11-28, wherein the first polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; and the second polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

30. The variant IgG Fc polypeptide of any of embodiments 14-29, wherein the first polypeptide comprises an amino acid sequence of SEQ ID NO: 1, and the second polypeptide comprises an amino acid sequence of SEQ ID NO: 1;

the first polypeptide comprises an amino acid sequence of SEQ ID NO: 2, and the second polypeptide comprises an amino acid sequence of SEQ ID NO: 2;

the first polypeptide comprises an amino acid sequence of SEQ ID NO: 3, and the second polypeptide comprises an amino acid sequence of SEQ ID NO: 3;

the first polypeptide comprises an amino acid sequence of SEQ ID NO: 4, and the second polypeptide comprises an amino acid sequence of SEQ ID NO: 4;

the first polypeptide comprises an amino acid sequence of SEQ ID NO: 5, and the second polypeptide comprises an amino acid sequence of SEQ ID NO: 5;

the first polypeptide comprises an amino acid sequence of SEQ ID NO: 6, and the second polypeptide comprises an amino acid sequence of SEQ ID NO: 6;

the first polypeptide comprises an amino acid sequence of SEQ ID NO: 7, and the second polypeptide comprises an amino acid sequence of SEQ ID NO: 7;

the first polypeptide comprises an amino acid sequence of SEQ ID NO: 8, and the second polypeptide comprises an amino acid sequence of SEQ ID NO: 8;

the first polypeptide comprises an amino acid sequence of SEQ ID NO: 9, and the second polypeptide comprises an amino acid sequence of SEQ ID NO: 9;

the first polypeptide comprises an amino acid sequence of SEQ ID NO: 10, and the second polypeptide comprises an amino acid sequence of SEQ ID NO: 10;

the first polypeptide comprises an amino acid sequence of SEQ ID NO: 11, and the second polypeptide comprises an amino acid sequence of SEQ ID NO: 11;

the first polypeptide comprises an amino acid sequence of SEQ ID NO: 12, and the second polypeptide comprises an amino acid sequence of SEQ ID NO: 12;

the first polypeptide comprises an amino acid sequence of SEQ ID NO: 13, and the second polypeptide comprises an amino acid sequence of SEQ ID NO: 13;

the first polypeptide comprises an amino acid sequence of SEQ ID NO: 14, and the second polypeptide comprises an amino acid sequence of SEQ ID NO: 14;

the first polypeptide comprises an amino acid sequence of SEQ ID NO: 15, and the second polypeptide comprises an amino acid sequence of SEQ ID NO: 15;

the first polypeptide comprises an amino acid sequence of SEQ ID NO: 16, and the second polypeptide comprises an amino acid sequence of SEQ ID NO: 16;

the first polypeptide comprises an amino acid sequence of SEQ ID NO: 17, and the second polypeptide comprises an amino acid sequence of SEQ ID NO: 17;

the first polypeptide comprises an amino acid sequence of SEQ ID NO: 18, and the second polypeptide comprises an amino acid sequence of SEQ ID NO: 18;

the first polypeptide comprises an amino acid sequence of SEQ ID NO: 19, and the second polypeptide comprises an amino acid sequence of SEQ ID NO: 19;

the first polypeptide comprises an amino acid sequence of SEQ ID NO: 20, and the second polypeptide comprises an amino acid sequence of SEQ ID NO: 20;

the first polypeptide comprises an amino acid sequence of SEQ ID NO: 21, and the second polypeptide comprises an amino acid sequence of SEQ ID NO: 21;

the first polypeptide comprises an amino acid sequence of SEQ ID NO: 22, and the second polypeptide comprises an amino acid sequence of SEQ ID NO: 22;

the first polypeptide comprises an amino acid sequence of SEQ ID NO: 23, and the second polypeptide comprises an amino acid sequence of SEQ ID NO: 23;

the first polypeptide comprises an amino acid sequence of SEQ ID NO: 24, and the second polypeptide comprises an amino acid sequence of SEQ ID NO: 24;

the first polypeptide comprises an amino acid sequence of SEQ ID NO: 25, and the second polypeptide comprises an amino acid sequence of SEQ ID NO: 25;

the first polypeptide comprises an amino acid sequence of SEQ ID NO: 26, and the second polypeptide comprises an amino acid sequence of SEQ ID NO: 26;

the first polypeptide comprises an amino acid sequence of SEQ ID NO: 27, and the second polypeptide comprises an amino acid sequence of SEQ ID NO: 27;

the first polypeptide comprises an amino acid sequence of SEQ ID NO: 28, and the second polypeptide comprises an amino acid sequence of SEQ ID NO: 28;

the first polypeptide comprises an amino acid sequence of SEQ ID NO: 29, and the second polypeptide comprises an amino acid sequence of SEQ ID NO: 29;

the first polypeptide comprises an amino acid sequence of SEQ ID NO: 30, and the second polypeptide comprises an amino acid sequence of SEQ ID NO: 30;

the first polypeptide comprises an amino acid sequence of SEQ ID NO: 31, and the second polypeptide comprises an amino acid sequence of SEQ ID NO: 31;

the first polypeptide comprises an amino acid sequence of SEQ ID NO: 32, and the second polypeptide comprises an amino acid sequence of SEQ ID NO: 32;

the first polypeptide comprises an amino acid sequence of SEQ ID NO: 33, and the second polypeptide comprises an amino acid sequence of SEQ ID NO: 33;

the first polypeptide comprises an amino acid sequence of SEQ ID NO: 34, and the second polypeptide comprises an amino acid sequence of SEQ ID NO: 34;

the first polypeptide comprises an amino acid sequence of SEQ ID NO: 35, and the second polypeptide comprises an amino acid sequence of SEQ ID NO: 35;

the first polypeptide comprises an amino acid sequence of SEQ ID NO: 36, and the second polypeptide comprises an amino acid sequence of SEQ ID NO: 36;

the first polypeptide comprises an amino acid sequence of SEQ ID NO: 37, and the second polypeptide comprises an amino acid sequence of SEQ ID NO: 37;

the first polypeptide comprises an amino acid sequence of SEQ ID NO: 38, and the second polypeptide comprises an amino acid sequence of SEQ ID NO: 38;

the first polypeptide comprises an amino acid sequence of SEQ ID NO: 39, and the second polypeptide comprises an amino acid sequence of SEQ ID NO: 39;

the first polypeptide comprises an amino acid sequence of SEQ ID NO: 40, and the second polypeptide comprises an amino acid sequence of SEQ ID NO: 40;

the first polypeptide comprises an amino acid sequence of SEQ ID NO: 41, and the second polypeptide comprises an amino acid sequence of SEQ ID NO: 41;

the first polypeptide comprises an amino acid sequence of SEQ ID NO: 42, and the second polypeptide comprises an amino acid sequence of SEQ ID NO: 42;

the first polypeptide comprises an amino acid sequence of SEQ ID NO: 43, and the second polypeptide comprises an amino acid sequence of SEQ ID NO: 43;

the first polypeptide comprises an amino acid sequence of SEQ ID NO: 44, and the second polypeptide comprises an amino acid sequence of SEQ ID NO: 44;

the first polypeptide comprises an amino acid sequence of SEQ ID NO: 45, and the second polypeptide comprises an amino acid sequence of SEQ ID NO: 45;

the first polypeptide comprises an amino acid sequence of SEQ ID NO: 46, and the second polypeptide comprises an amino acid sequence of SEQ ID NO: 46;

the first polypeptide comprises an amino acid sequence of SEQ ID NO: 47, and the second polypeptide comprises an amino acid sequence of SEQ ID NO: 47;

the first polypeptide comprises an amino acid sequence of SEQ ID NO: 48, and the second polypeptide comprises an amino acid sequence of SEQ ID NO: 48;

the first polypeptide comprises an amino acid sequence of SEQ ID NO: 49, and the second polypeptide comprises an amino acid sequence of SEQ ID NO: 49;

the first polypeptide comprises an amino acid sequence of SEQ ID NO: 50, and the second polypeptide comprises an amino acid sequence of SEQ ID NO: 50;

the first polypeptide comprises an amino acid sequence of SEQ ID NO: 51, and the second polypeptide comprises an amino acid sequence of SEQ ID NO: 51;

the first polypeptide comprises an amino acid sequence of SEQ ID NO: 52, and the second polypeptide comprises an amino acid sequence of SEQ ID NO: 52;

the first polypeptide comprises an amino acid sequence of SEQ ID NO: 53, and the second polypeptide comprises an amino acid sequence of SEQ ID NO: 53;

the first polypeptide comprises an amino acid sequence of SEQ ID NO: 54, and the second polypeptide comprises an amino acid sequence of SEQ ID NO: 54;

the first polypeptide comprises an amino acid sequence of SEQ ID NO: 55, and the second polypeptide comprises an amino acid sequence of SEQ ID NO: 55;

the first polypeptide comprises an amino acid sequence of SEQ ID NO: 56, and the second polypeptide comprises an amino acid sequence of SEQ ID NO: 56;

the first polypeptide comprises an amino acid sequence of SEQ ID NO: 57, and the second polypeptide comprises an amino acid sequence of SEQ ID NO: 57;

the first polypeptide comprises an amino acid sequence of SEQ ID NO: 58, and the second polypeptide comprises an amino acid sequence of SEQ ID NO: 58;

the first polypeptide comprises an amino acid sequence of SEQ ID NO: 59, and the second polypeptide comprises an amino acid sequence of SEQ ID NO: 59;

the first polypeptide comprises an amino acid sequence of SEQ ID NO: 60, and the second polypeptide comprises an amino acid sequence of SEQ ID NO: 60;

the first polypeptide comprises an amino acid sequence of SEQ ID NO: 61, and the second polypeptide comprises an amino acid sequence of SEQ ID NO: 61;

the first polypeptide comprises an amino acid sequence of SEQ ID NO: 62, and the second polypeptide comprises an amino acid sequence of SEQ ID NO: 62;

the first polypeptide comprises an amino acid sequence of SEQ ID NO: 63, and the second polypeptide comprises an amino acid sequence of SEQ ID NO: 63;

the first polypeptide comprises an amino acid sequence of SEQ ID NO: 64, and the second polypeptide comprises an amino acid sequence of SEQ ID NO: 64;

the first polypeptide comprises an amino acid sequence of SEQ ID NO: 65, and the second polypeptide comprises an amino acid sequence of SEQ ID NO: 65;

the first polypeptide comprises an amino acid sequence of SEQ ID NO: 66, and the second polypeptide comprises an amino acid sequence of SEQ ID NO: 66;

the first polypeptide comprises an amino acid sequence of SEQ ID NO: 67, and the second polypeptide comprises an amino acid sequence of SEQ ID NO: 67;

the first polypeptide comprises an amino acid sequence of SEQ ID NO: 68, and the second polypeptide comprises an amino acid sequence of SEQ ID NO: 68;

the first polypeptide comprises an amino acid sequence of SEQ ID NO: 69, and the second polypeptide comprises an amino acid sequence of SEQ ID NO: 69;

the first polypeptide comprises an amino acid sequence of SEQ ID NO: 70, and the second polypeptide comprises an amino acid sequence of SEQ ID NO: 70;

the first polypeptide comprises an amino acid sequence of SEQ ID NO: 71, and the second polypeptide comprises an amino acid sequence of SEQ ID NO: 71;

the first polypeptide comprises an amino acid sequence of SEQ ID NO: 72, and the second polypeptide comprises an amino acid sequence of SEQ ID NO: 72;

the first polypeptide comprises an amino acid sequence of SEQ ID NO: 73, and the second polypeptide comprises an amino acid sequence of SEQ ID NO: 73;
the first polypeptide comprises an amino acid sequence of SEQ ID NO: 74, and the second polypeptide comprises an amino acid sequence of SEQ ID NO: 74;
the first polypeptide comprises an amino acid sequence of SEQ ID NO: 75, and the second polypeptide comprises an amino acid sequence of SEQ ID NO: 75;
the first polypeptide comprises an amino acid sequence of SEQ ID NO: 76, and the second polypeptide comprises an amino acid sequence of SEQ ID NO: 76;
the first polypeptide comprises an amino acid sequence of SEQ ID NO: 77, and the second polypeptide comprises an amino acid sequence of SEQ ID NO: 77;
the first polypeptide comprises an amino acid sequence of SEQ ID NO: 78, and the second polypeptide comprises an amino acid sequence of SEQ ID NO: 78;
the first polypeptide comprises an amino acid sequence of SEQ ID NO: 79, and the second polypeptide comprises an amino acid sequence of SEQ ID NO: 79;
the first polypeptide comprises an amino acid sequence of SEQ ID NO: 80, and the second polypeptide comprises an amino acid sequence of SEQ ID NO: 80;
the first polypeptide comprises an amino acid sequence of SEQ ID NO: 81, and the second polypeptide comprises an amino acid sequence of SEQ ID NO: 81;
the first polypeptide comprises an amino acid sequence of SEQ ID NO: 82, and the second polypeptide comprises an amino acid sequence of SEQ ID NO: 82;
the first polypeptide comprises an amino acid sequence of SEQ ID NO: 83, and the second polypeptide comprises an amino acid sequence of SEQ ID NO: 83;
the first polypeptide comprises an amino acid sequence of SEQ ID NO: 84, and the second polypeptide comprises an amino acid sequence of SEQ ID NO: 84;
the first polypeptide comprises an amino acid sequence of SEQ ID NO: 85, and the second polypeptide comprises an amino acid sequence of SEQ ID NO: 85;
the first polypeptide comprises an amino acid sequence of SEQ ID NO: 86, and the second polypeptide comprises an amino acid sequence of SEQ ID NO: 86;
the first polypeptide comprises an amino acid sequence of SEQ ID NO: 87, and the second polypeptide comprises an amino acid sequence of SEQ ID NO: 87;
the first polypeptide comprises an amino acid sequence of SEQ ID NO: 102, and the second polypeptide comprises an amino acid sequence of SEQ ID NO: 102;
the first polypeptide comprises an amino acid sequence of SEQ ID NO: 103, and the second polypeptide comprises an amino acid sequence of SEQ ID NO: 103; or
the first polypeptide comprises an amino acid sequence of SEQ ID NO: 104, and the second polypeptide comprises an amino acid sequence of SEQ ID NO: 104.

31. A polypeptide comprising:
a variant IgG Fc polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88; and
an inhibitory receptor effector domain.

32. The polypeptide of embodiment 31, wherein the variant IgG Fc polypeptide comprises a mutation that enhances selective binding to FcγRIIβ over FcγRIIα.

33. The polypeptide of any one of embodiments 31-32, wherein the variant IgG Fc polypeptide comprises a mutation set selected from:
a mutation at positions 238, 269, 270, and 330, as compared to SEQ ID NO: 88;
a mutation at positions 237, 238, 269, 270, and 330, as compared to SEQ ID NO: 88;
a mutation at positions 237, 238, 239, 269, 270, and 330, as compared to SEQ ID NO: 88;
a mutation at positions 237, 238, 240, 269, 270, and 330, as compared to SEQ ID NO: 88;
a mutation at positions 235, 238, 269, 270, and 330, as compared to SEQ ID NO: 88;
a mutation at positions 235, 238, 269, 270, and 330, and an insertion of an amino acid sequence GEV between positions 233 and 234, as compared to SEQ ID NO: 88;
a mutation at positions 238, 269, 270, and 330, as compared to SEQ ID NO: 88;
a mutation at positions 234, 235, 329, 268, and 271, as compared to SEQ ID NO: 88;
a mutation at positions 234, 235, 239, 329, 268, and 271, as compared to SEQ ID NO: 88;
a mutation at positions 234 and 235, as compared to SEQ ID NO: 88;
a mutation at positions 237 and 238, as compared to SEQ ID NO: 88; or
any combination thereof.

34. The polypeptide of any one of embodiments 31-33, wherein the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

35. The polypeptide of embodiment 34, wherein the variant IgG Fc polypeptide comprises a mutation set selected from:
a mutation set of P238D, E269D, D270E, and A330R, as compared to SEQ ID NO: 88;
a mutation set of G237D, P238G, E269D, D270E, and A330R, as compared to SEQ ID NO: 88;
a mutation set of G237D, P238S, S239G, E269D, D270E, and A330R, as compared to SEQ ID NO: 88;
a mutation set of G237D, P238G, V240A, E269D, D270E, and A330R, as compared to SEQ ID NO: 88;
a mutation set of L235V, P238E, E269D, D270E, and A330R, as compared to SEQ ID NO: 88;
a mutation set of L235V, P238D, E269D, D270E, and A330R, and an insertion of an amino acid sequence GEV between positions 233 and 234, as compared to SEQ ID NO: 88;
a mutation set of P238S, E269D, D270E, and A330R, as compared to SEQ ID NO: 88;
a mutation set of L234F, L235E, P329A, H268D, and P271G, as compared to SEQ ID NO: 88;
a mutation set of L234F, L235E, S239D, P329A, H268D, and P271G, as compared to SEQ ID NO: 88;
a mutation set of L234F and L235E, as compared to SEQ ID NO: 88;
a mutation set of G237E and P238E, as compared to SEQ ID NO: 88; or
any combination thereof.

36 The polypeptide of any one of embodiments 31-35, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

37. The polypeptide of any one of embodiments 31-36, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

38. The polypeptide of embodiment 37, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

39. The polypeptide of embodiment 37, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

40. The polypeptide of any one of embodiments 31-39, wherein the variant IgG Fc polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

41. The polypeptide of any one of embodiments 31-40, wherein the variant IgG Fc polypeptide associates with another variant IgG Fc polypeptide to form a dimer molecule.

42. The polypeptide of embodiment 41, wherein the dimer molecule is a heterodimer molecule.

43. The polypeptide of any one of embodiments 41-42, wherein the heterodimer molecule comprises a pair of a first polypeptide and a second polypeptide, and wherein the first polypeptide and the second polypeptide comprise different amino acid sequences.

44. The polypeptide of embodiment 43, wherein the dimer molecule is a homodimer molecule.

45. The polypeptide of any one of embodiments 41 or 44, wherein the homodimer molecule comprises a pair of a first polypeptide and a second polypeptide, and wherein the first polypeptide and the second polypeptide comprise identical amino acid sequences.

46. The polypeptide of any one of embodiments 41-45, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

47. The polypeptide of any one of embodiments 41-45, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

48. The polypeptide of any one of embodiments 41-47, wherein the dimer molecule comprises:

- the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;
  - a mutation at positions 237, 238, 269, 270, and 330, as compared to SEQ ID NO: 88;
  - a mutation at positions 237, 238, 239, 269, 270, and 330, as compared to SEQ ID NO: 88;
  - a mutation at positions 237, 238, 240, 269, 270, and 330, as compared to SEQ ID NO: 88;
  - a mutation at positions 235, 238, 269, 270, and 330, as compared to SEQ ID NO: 88;
  - a mutation at positions 235, 238, 269, 270, and 330, and an insertion of an amino acid sequence GEV between positions 233 and 234, as compared to SEQ ID NO: 88;
  - a mutation at positions 238, 269, 270, and 330, as compared to SEQ ID NO: 88;
  - a mutation at positions 234, 235, 329, 268, and 271, as compared to SEQ ID NO: 88;
  - a mutation at positions 234, 235, 239, 329, 268, and 271, as compared to SEQ ID NO: 88;
  - a mutation at positions 234 and 235, as compared to SEQ ID NO: 88;
  - a mutation at positions 237 and 238, as compared to SEQ ID NO: 88; or
  - any combination thereof; and
- the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;
  - a mutation at positions 237, 238, 269, 270, and 330, as compared to SEQ ID NO: 88;
  - a mutation at positions 237, 238, 239, 269, 270, and 330, as compared to SEQ ID NO: 88;

a mutation at positions 237, 238, 240, 269, 270, and 330, as compared to SEQ ID NO: 88;

a mutation at positions 235, 238, 269, 270, and 330, as compared to SEQ ID NO: 88;

a mutation at positions 235, 238, 269, 270, and 330, and an insertion of an amino acid sequence GEV between positions 233 and 234, as compared to SEQ ID NO: 88;

a mutation at positions 238, 269, 270, and 330, as compared to SEQ ID NO: 88;

a mutation at positions 234, 235, 329, 268, and 271, as compared to SEQ ID NO: 88;

a mutation at positions 234, 235, 239, 329, 268, and 271, as compared to SEQ ID NO: 88;

a mutation at positions 234 and 235, as compared to SEQ ID NO: 88;

a mutation at positions 237 and 238, as compared to SEQ ID NO: 88; or any combination thereof.

49. The polypeptide of any one of embodiments 41-48, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

50. The polypeptide of any one of embodiments 41-48, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

51. The polypeptide of any one of embodiments 40-50, wherein the dimer molecule comprises:

the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof; and the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

52. The variant IgG Fc polypeptide of any one of embodiments 41-51, wherein the first polypeptide comprises a variant sequence of SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and the second polypeptide comprises a variant sequence of SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

53. The variant IgG Fc polypeptide of any one of embodiments 41-52, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

54. The variant IgG Fc polypeptide of any one of embodiments 41-52, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

55. The variant IgG Fc polypeptide of any one of embodiments 41-54, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

56. The variant IgG Fc polypeptide of any one of embodiments 41-55, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

57. The variant IgG Fc polypeptide of any one of embodiments 41-56, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

58. The variant IgG Fc polypeptide of any one of embodiments 41-56, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

59. The variant IgG Fc polypeptide of any of embodiments 41-58, wherein the first polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; and the second polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

60. The variant IgG Fc polypeptide of any of embodiments 44-59, wherein the first polypeptide comprises an amino acid sequence of SEQ ID NO: 1, and the second polypeptide comprises an amino acid sequence of SEQ ID NO: 1;

the first polypeptide comprises an amino acid sequence of SEQ ID NO: 2, and the second polypeptide comprises an amino acid sequence of SEQ ID NO: 2;

the first polypeptide comprises an amino acid sequence of SEQ ID NO: 3, and the second polypeptide comprises an amino acid sequence of SEQ ID NO: 3;

the first polypeptide comprises an amino acid sequence of SEQ ID NO: 4, and the second polypeptide comprises an amino acid sequence of SEQ ID NO: 4;

the first polypeptide comprises an amino acid sequence of SEQ ID NO: 5, and the second polypeptide comprises an amino acid sequence of SEQ ID NO: 5;

the first polypeptide comprises an amino acid sequence of SEQ ID NO: 6, and the second polypeptide comprises an amino acid sequence of SEQ ID NO: 6;

the first polypeptide comprises an amino acid sequence of SEQ ID NO: 7, and the second polypeptide comprises an amino acid sequence of SEQ ID NO: 7;

the first polypeptide comprises an amino acid sequence of SEQ ID NO: 8, and the second polypeptide comprises an amino acid sequence of SEQ ID NO: 8;

the first polypeptide comprises an amino acid sequence of SEQ ID NO: 9, and the second polypeptide comprises an amino acid sequence of SEQ ID NO: 9;

the first polypeptide comprises an amino acid sequence of SEQ ID NO: 10, and the second polypeptide comprises an amino acid sequence of SEQ ID NO: 10;

the first polypeptide comprises an amino acid sequence of SEQ ID NO: 11, and the second polypeptide comprises an amino acid sequence of SEQ ID NO: 11;

the first polypeptide comprises an amino acid sequence of SEQ ID NO: 12, and the second polypeptide comprises an amino acid sequence of SEQ ID NO: 12;

the first polypeptide comprises an amino acid sequence of SEQ ID NO: 13, and the second polypeptide comprises an amino acid sequence of SEQ ID NO: 13;

the first polypeptide comprises an amino acid sequence of SEQ ID NO: 14, and the second polypeptide comprises an amino acid sequence of SEQ ID NO: 14;

the first polypeptide comprises an amino acid sequence of SEQ ID NO: 15, and the second polypeptide comprises an amino acid sequence of SEQ ID NO: 15;

the first polypeptide comprises an amino acid sequence of SEQ ID NO: 16, and the second polypeptide comprises an amino acid sequence of SEQ ID NO: 16;

the first polypeptide comprises an amino acid sequence of SEQ ID NO: 17, and the second polypeptide comprises an amino acid sequence of SEQ ID NO: 17;

the first polypeptide comprises an amino acid sequence of SEQ ID NO: 18, and the second polypeptide comprises an amino acid sequence of SEQ ID NO: 18;

the first polypeptide comprises an amino acid sequence of SEQ ID NO: 19, and the second polypeptide comprises an amino acid sequence of SEQ ID NO: 19;

the first polypeptide comprises an amino acid sequence of SEQ ID NO: 20, and the second polypeptide comprises an amino acid sequence of SEQ ID NO: 20;

the first polypeptide comprises an amino acid sequence of SEQ ID NO: 21, and the second polypeptide comprises an amino acid sequence of SEQ ID NO: 21;

the first polypeptide comprises an amino acid sequence of SEQ ID NO: 22, and the second polypeptide comprises an amino acid sequence of SEQ ID NO: 22;

the first polypeptide comprises an amino acid sequence of SEQ ID NO: 23, and the second polypeptide comprises an amino acid sequence of SEQ ID NO: 23;

the first polypeptide comprises an amino acid sequence of SEQ ID NO: 24, and the second polypeptide comprises an amino acid sequence of SEQ ID NO: 24;

the first polypeptide comprises an amino acid sequence of SEQ ID NO: 25, and the second polypeptide comprises an amino acid sequence of SEQ ID NO: 25;

the first polypeptide comprises an amino acid sequence of SEQ ID NO: 26, and the second polypeptide comprises an amino acid sequence of SEQ ID NO: 26;

the first polypeptide comprises an amino acid sequence of SEQ ID NO: 27, and the second polypeptide comprises an amino acid sequence of SEQ ID NO: 27;

the first polypeptide comprises an amino acid sequence of SEQ ID NO: 28, and the second polypeptide comprises an amino acid sequence of SEQ ID NO: 28;

the first polypeptide comprises an amino acid sequence of SEQ ID NO: 29, and the second polypeptide comprises an amino acid sequence of SEQ ID NO: 29;

the first polypeptide comprises an amino acid sequence of SEQ ID NO: 30, and the second polypeptide comprises an amino acid sequence of SEQ ID NO: 30;

the first polypeptide comprises an amino acid sequence of SEQ ID NO: 31, and the second polypeptide comprises an amino acid sequence of SEQ ID NO: 31;

the first polypeptide comprises an amino acid sequence of SEQ ID NO: 32, and the second polypeptide comprises an amino acid sequence of SEQ ID NO: 32;

the first polypeptide comprises an amino acid sequence of SEQ ID NO: 33, and the second polypeptide comprises an amino acid sequence of SEQ ID NO: 33;

the first polypeptide comprises an amino acid sequence of SEQ ID NO: 34, and the second polypeptide comprises an amino acid sequence of SEQ ID NO: 34;

the first polypeptide comprises an amino acid sequence of SEQ ID NO: 35, and the second polypeptide comprises an amino acid sequence of SEQ ID NO: 35;

the first polypeptide comprises an amino acid sequence of SEQ ID NO: 36, and the second polypeptide comprises an amino acid sequence of SEQ ID NO: 36;

the first polypeptide comprises an amino acid sequence of SEQ ID NO: 37, and the second polypeptide comprises an amino acid sequence of SEQ ID NO: 37;

the first polypeptide comprises an amino acid sequence of SEQ ID NO: 38, and the second polypeptide comprises an amino acid sequence of SEQ ID NO: 38;

the first polypeptide comprises an amino acid sequence of SEQ ID NO: 39, and the second polypeptide comprises an amino acid sequence of SEQ ID NO: 39;

the first polypeptide comprises an amino acid sequence of SEQ ID NO: 40, and the second polypeptide comprises an amino acid sequence of SEQ ID NO: 40;

the first polypeptide comprises an amino acid sequence of SEQ ID NO: 41, and the second polypeptide comprises an amino acid sequence of SEQ ID NO: 41;

the first polypeptide comprises an amino acid sequence of SEQ ID NO: 42, and the second polypeptide comprises an amino acid sequence of SEQ ID NO: 42;

the first polypeptide comprises an amino acid sequence of SEQ ID NO: 43, and the second polypeptide comprises an amino acid sequence of SEQ ID NO: 43;

the first polypeptide comprises an amino acid sequence of SEQ ID NO: 44, and the second polypeptide comprises an amino acid sequence of SEQ ID NO: 44;

the first polypeptide comprises an amino acid sequence of SEQ ID NO: 45, and the second polypeptide comprises an amino acid sequence of SEQ ID NO: 45;

the first polypeptide comprises an amino acid sequence of SEQ ID NO: 46, and the second polypeptide comprises an amino acid sequence of SEQ ID NO: 46;

the first polypeptide comprises an amino acid sequence of SEQ ID NO: 47, and the second polypeptide comprises an amino acid sequence of SEQ ID NO: 47;

the first polypeptide comprises an amino acid sequence of SEQ ID NO: 48, and the second polypeptide comprises an amino acid sequence of SEQ ID NO: 48;

the first polypeptide comprises an amino acid sequence of SEQ ID NO: 49, and the second polypeptide comprises an amino acid sequence of SEQ ID NO: 49;

the first polypeptide comprises an amino acid sequence of SEQ ID NO: 50, and the second polypeptide comprises an amino acid sequence of SEQ ID NO: 50;

the first polypeptide comprises an amino acid sequence of SEQ ID NO: 51, and the second polypeptide comprises an amino acid sequence of SEQ ID NO: 51;

the first polypeptide comprises an amino acid sequence of SEQ ID NO: 52, and the second polypeptide comprises an amino acid sequence of SEQ ID NO: 52;

the first polypeptide comprises an amino acid sequence of SEQ ID NO: 53, and the second polypeptide comprises an amino acid sequence of SEQ ID NO: 53;

the first polypeptide comprises an amino acid sequence of SEQ ID NO: 54, and the second polypeptide comprises an amino acid sequence of SEQ ID NO: 54;

the first polypeptide comprises an amino acid sequence of SEQ ID NO: 55, and the second polypeptide comprises an amino acid sequence of SEQ ID NO: 55;

the first polypeptide comprises an amino acid sequence of SEQ ID NO: 56, and the second polypeptide comprises an amino acid sequence of SEQ ID NO: 56;

the first polypeptide comprises an amino acid sequence of SEQ ID NO: 57, and the second polypeptide comprises an amino acid sequence of SEQ ID NO: 57;

the first polypeptide comprises an amino acid sequence of SEQ ID NO: 58, and the second polypeptide comprises an amino acid sequence of SEQ ID NO: 58;

the first polypeptide comprises an amino acid sequence of SEQ ID NO: 59, and the second polypeptide comprises an amino acid sequence of SEQ ID NO: 59;

the first polypeptide comprises an amino acid sequence of SEQ ID NO: 60, and the second polypeptide comprises an amino acid sequence of SEQ ID NO: 60;

the first polypeptide comprises an amino acid sequence of SEQ ID NO: 61, and the second polypeptide comprises an amino acid sequence of SEQ ID NO: 61;

the first polypeptide comprises an amino acid sequence of SEQ ID NO: 62, and the second polypeptide comprises an amino acid sequence of SEQ ID NO: 62;

the first polypeptide comprises an amino acid sequence of SEQ ID NO: 63, and the second polypeptide comprises an amino acid sequence of SEQ ID NO: 63;

the first polypeptide comprises an amino acid sequence of SEQ ID NO: 64, and the second polypeptide comprises an amino acid sequence of SEQ ID NO: 64;

the first polypeptide comprises an amino acid sequence of SEQ ID NO: 65, and the second polypeptide comprises an amino acid sequence of SEQ ID NO: 65;

the first polypeptide comprises an amino acid sequence of SEQ ID NO: 66, and the second polypeptide comprises an amino acid sequence of SEQ ID NO: 66;

the first polypeptide comprises an amino acid sequence of SEQ ID NO: 67, and the second polypeptide comprises an amino acid sequence of SEQ ID NO: 67;

the first polypeptide comprises an amino acid sequence of SEQ ID NO: 68, and the second polypeptide comprises an amino acid sequence of SEQ ID NO: 68;

the first polypeptide comprises an amino acid sequence of SEQ ID NO: 69, and the second polypeptide comprises an amino acid sequence of SEQ ID NO: 69;

the first polypeptide comprises an amino acid sequence of SEQ ID NO: 70, and the second polypeptide comprises an amino acid sequence of SEQ ID NO: 70;

the first polypeptide comprises an amino acid sequence of SEQ ID NO: 71, and the second polypeptide comprises an amino acid sequence of SEQ ID NO: 71;

the first polypeptide comprises an amino acid sequence of SEQ ID NO: 72, and the second polypeptide comprises an amino acid sequence of SEQ ID NO: 72;

the first polypeptide comprises an amino acid sequence of SEQ ID NO: 73, and the second polypeptide comprises an amino acid sequence of SEQ ID NO: 73;

the first polypeptide comprises an amino acid sequence of SEQ ID NO: 74, and the second polypeptide comprises an amino acid sequence of SEQ ID NO: 74;

the first polypeptide comprises an amino acid sequence of SEQ ID NO: 75, and the second polypeptide comprises an amino acid sequence of SEQ ID NO: 75;

the first polypeptide comprises an amino acid sequence of SEQ ID NO: 76, and the second polypeptide comprises an amino acid sequence of SEQ ID NO: 76;

the first polypeptide comprises an amino acid sequence of SEQ ID NO: 77, and the second polypeptide comprises an amino acid sequence of SEQ ID NO: 77;

the first polypeptide comprises an amino acid sequence of SEQ ID NO: 78, and the second polypeptide comprises an amino acid sequence of SEQ ID NO: 78;

the first polypeptide comprises an amino acid sequence of SEQ ID NO: 79, and the second polypeptide comprises an amino acid sequence of SEQ ID NO: 79;

the first polypeptide comprises an amino acid sequence of SEQ ID NO: 80, and the second polypeptide comprises an amino acid sequence of SEQ ID NO: 80;

the first polypeptide comprises an amino acid sequence of SEQ ID NO: 81, and the second polypeptide comprises an amino acid sequence of SEQ ID NO: 81;

the first polypeptide comprises an amino acid sequence of SEQ ID NO: 82, and the second polypeptide comprises an amino acid sequence of SEQ ID NO: 82;

the first polypeptide comprises an amino acid sequence of SEQ ID NO: 83, and the second polypeptide comprises an amino acid sequence of SEQ ID NO: 83;

the first polypeptide comprises an amino acid sequence of SEQ ID NO: 84, and the second polypeptide comprises an amino acid sequence of SEQ ID NO: 84;

the first polypeptide comprises an amino acid sequence of SEQ ID NO: 85, and the second polypeptide comprises an amino acid sequence of SEQ ID NO: 85;

the first polypeptide comprises an amino acid sequence of SEQ ID NO: 86, and the second polypeptide comprises an amino acid sequence of SEQ ID NO: 86;

the first polypeptide comprises an amino acid sequence of SEQ ID NO: 87, and the second polypeptide comprises an amino acid sequence of SEQ ID NO: 87;

the first polypeptide comprises an amino acid sequence of SEQ ID NO: 102, and the second polypeptide comprises an amino acid sequence of SEQ ID NO: 102;

the first polypeptide comprises an amino acid sequence of SEQ ID NO: 103, and the second polypeptide comprises an amino acid sequence of SEQ ID NO: 103; or the first polypeptide comprises an amino acid sequence of SEQ ID NO: 104, and the second polypeptide comprises an amino acid sequence of SEQ ID NO: 104.

61. A polypeptide having at least 95% identity to an amino acid sequence comprising the amino acid sequence of SEQ ID NO: 88 provided that the polypeptide comprises:

a glutamic (E) residue at position 237 and a glutamic (E) residue at position 238, wherein the positions are according to EU numbering;

an aspartic acid (aspartate) residue at position 237, a glycine residue at position 238, an alanine residue at position 240, an aspartic acid residue at position 269, a glutamic acid residue at position 270, and an arginine residue at position 330, wherein the positions are according to EU numbering; or a phenylalanine residue at position 234, a glutamic acid residue at position 235, an aspartic acid residue at position 268, a glycine residue at position 271, and an alanine residue at position 329, wherein the positions are according to EU numbering.

62. A polypeptide having at least 95% identity to an amino acid sequence comprising the amino acid sequence of SEQ ID NO: 88 provided that the polypeptide comprises a glutamic acid (glutamate) residue at position 237 and a glutamic acid (glutamate) residue at position 238, wherein the positions are according to EU numbering.

63. A polypeptide having at least 95% identity to an amino acid sequence comprising the amino acid sequence of SEQ ID NO: 88 provided that the polypeptide comprises an aspartic acid (aspartate) residue at position 237, a glycine residue at position 238, an alanine residue at position 240, an aspartic acid residue at position 269, a glutamic acid residue at position 270, and an arginine residue at position 330, wherein the positions are according to EU numbering.

64. A polypeptide having at least 95% identity to an amino acid sequence comprising the amino acid sequence of SEQ ID NO: 88 provided that the polypeptide comprises a phenylalanine residue at position 234, a glutamic acid residue at position 235, an aspartic acid residue at position 268, a glycine residue at position 271, and an alanine residue at position 329, wherein the positions are according to EU numbering.

65. The polypeptide of embodiment 62, wherein the polypeptide has at least 95% identity to an amino acid sequence comprising the sequence of SEQ ID NO: 40.

66. The polypeptide of embodiment 62, wherein the polypeptide comprises the amino acid sequence of SEQ ID NO: 40.

67. The polypeptide of embodiment 62, wherein the polypeptide has at least 95% identity to an amino acid sequence comprising the sequence of SEQ ID NO: 102.

68. The polypeptide of embodiment 62, wherein the polypeptide comprises the amino acid sequence of SEQ ID NO: 102.

69. The polypeptide of embodiment 63, wherein the polypeptide has at least 95% identity to an amino acid sequence comprising the sequence of SEQ ID NO: 77.

70. The polypeptide of embodiment 63, wherein the polypeptide comprises the amino acid sequence of SEQ ID NO: 77.

71. The polypeptide of embodiment 63, wherein the polypeptide has at least 95% identity to an amino acid sequence comprising the sequence of SEQ ID NO: 103.

72. The polypeptide of embodiment 63, wherein the polypeptide comprises the amino acid sequence of SEQ ID NO: 103.

73. The polypeptide of embodiment 64, wherein the polypeptide has at least 95% identity to an amino acid sequence comprising the sequence of SEQ ID NO: 86.

74. The polypeptide of embodiment 64, wherein the polypeptide comprises the amino acid sequence of SEQ ID NO: 86.

75. The polypeptide of embodiment 64, wherein the polypeptide has at least 95% identity to an amino acid sequence comprising the sequence of SEQ ID NO: 104.

76. The polypeptide of embodiment 64, wherein the polypeptide comprises the amino acid sequence of SEQ ID NO: 104.

77. A composition comprising a homodimer comprising a first polypeptide and a second polypeptide, wherein the first polypeptide and the second polypeptide comprise a polypeptide according to any one of embodiments 62-76, wherein the first polypeptide and the second polypeptide are the same.

78. A composition comprising a heterodimer comprising a first polypeptide and a second polypeptide, wherein the first polypeptide and the second polypeptide each comprise, independently, a polypeptide according to any one of embodiments 62-76, wherein the first polypeptide and the second polypeptide are different.

79. The polypeptide of any one of embodiments 62-76 or the compositions of embodiments 76 or 77, wherein the polypeptide is linked to an inhibitory receptor effector domain.

80. The polypeptide of embodiment 79, wherein the inhibitory receptor effector domain is an antibody that binds to PD-1, LAG-3, or CTLA4.

81. The polypeptide of embodiment 80, wherein the antibody is an antibody that binds to PD-1.

82. The polypeptide of embodiment 81, wherein the antibody that binds to PD-1 is a PD-1 agonist.

83. The polypeptide of embodiment 79, wherein the polypeptide comprises at least one inhibitory receptor effector domains.

84. The polypeptide of embodiment 83, wherein the polypeptide comprises 2 inhibitory receptor effector domains.

85. The polypeptide of embodiment 84, wherein the 2 inhibitory receptor effector domains bind to the same inhibitory receptor.

86. The polypeptide of embodiment 84, wherein the 2 inhibitory receptor effector domains bind to different inhibitory receptors. 87. The polypeptide of any one of embodiments 31-60 or 83-86, wherein the inhibitory receptor effector domain is an antibody.

88. The polypeptide of embodiment 87, wherein the antibody is in the format of an scFv, Fab, Fab', or F(ab')2.

89. The polypeptide of any one of embodiments 31-60 or 83-88, wherein the inhibitory receptor effector domain binds to a receptor encoded by PD-1, LAG3, CTLA4/CD152, BTLA/CD272, CD200R1, CD200R1, CD22/Siglec2, CD300A, CD300LF/CD300F, CD33/Siglec3, CD5, CD72, CEACAM 1, CLEC12A, CLEC4A, FCGR2B/CD32B, KIRs, KLRB1/CD161, KLRC1, KLRG1, LAIR1, LILRB1, LILRB2, LILRB4, LILRB5, NCR2/NKp44, PDCD1, PECAM1/CD31, PILRA, PVR/CD155, SIGLEC11, SIGLEC5, SIGLEC7, SIGLEC8, SIGLEC9, SIRPA, TIGIT, VSTM1/SIRL1, MAFA, NKG2A, CMRF35H, CD66a, CD66d, CD33, SIGLEC6, ILT2,3,4,5, LIR8, KIR2DL, KIR3DL, SIRPa, KIR2DL2/3, KIR2DL5, KIRDL1, KIRDL2, KIRDL3, TIM3, Tactile, IRp60, NKRP1, IAP, PIR-B, CD5, 2B4, GP49B, Ly49Q, or MICL.

90. The polypeptide of embodiment 89, wherein the inhibitory receptor effector domain binds to PD-1, LAG-3, or CTLA4.

91. The polypeptide of any one of embodiments 31-60 or 83-90, wherein the inhibitory receptor effector domain is an agonist of the receptor to which it binds.

92. The polypeptide of any one of embodiments 31-60 or 83-90, wherein the inhibitory receptor effector domain is an antagonist of the receptor to which it binds.

93. A polypeptide comprising:
- a variant IgG Fc polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88;
- an inhibitory receptor effector domain; and
- a FcγRII binding effector domain.

94. The polypeptide of embodiment 93, wherein the variant IgG Fc polypeptide comprises a mutation that enhances selective binding to FcγRIIβ over FcγRIIα.

95. The polypeptide of any one of embodiments 93-94, wherein the variant IgG Fc polypeptide comprises a mutation set selected from:
- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

96. The polypeptide of any one of embodiments 93-95, wherein the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

97. The polypeptide of embodiment 96, wherein the variant IgG Fc polypeptide comprises a mutation set selected from:
- a mutation set of P238D, E269D, D270E, and A330R, as compared to SEQ ID NO: 88;
- a mutation set of G237D, P238G, E269D, D270E, and A330R, as compared to SEQ ID NO: 88;
- a mutation set of G237D, P238S, S239G, E269D, D270E, and A330R, as compared to SEQ ID NO: 88;
- a mutation set of G237D, P238G, V240A, E269D, D270E, and A330R, as compared to SEQ ID NO: 88;
- a mutation set of L235V, P238E, E269D, D270E, and A330R, as compared to SEQ ID NO: 88;
- a mutation set of L235V, P238D, E269D, D270E, and A330R, and an insertion of an amino acid sequence GEV between positions 233 and 234, as compared to SEQ ID NO: 88;
- a mutation set of P238S, E269D, D270E, and A330R, as compared to SEQ ID NO: 88;
- a mutation set of L234F, L235E, P329A, H268D, and P271G, as compared to SEQ ID NO: 88;
- a mutation set of L234F, L235E, S239D, P329A, H268D, and P271G, as compared to SEQ ID NO: 88;
- a mutation set of L234F and L235E, as compared to SEQ ID NO: 88;

a mutation set of G237E and P238E, as compared to SEQ ID NO: 88; or any combination thereof.

98. The polypeptide of any one of embodiments 93-97, wherein the variant IgG Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

99. The polypeptide of any one of embodiments 93-98, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

100. The polypeptide of any one of embodiments 93-99, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

101. The polypeptide of any one of embodiments 93-100, wherein the variant IgG Fc polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

102. The polypeptide of any one of embodiments 93-101, wherein the variant IgG Fc polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

103. The polypeptide of any one of embodiments 93-102, wherein the variant IgG Fc polypeptide associates with another variant IgG Fc polypeptide to form a dimer molecule.

104. The polypeptide of embodiment 103, wherein the dimer molecule is a heterodimer molecule.

105. The polypeptide of embodiment 104, wherein the heterodimer molecule comprises a pair of a first polypeptide and a second polypeptide, and wherein the first polypeptide and the second polypeptide comprise different amino acid sequences.

106. The polypeptide of embodiment 103, wherein the dimer molecule is a homodimer molecule.

107. The polypeptide of embodiment 106, wherein the homodimer molecule comprises a first polypeptide and a second polypeptide, and wherein the first polypeptide and the second polypeptide comprise identical amino acid sequences.

108. The polypeptide of any one of embodiments 103-107, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

109. The polypeptide of any one of embodiments 103-107, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

- a mutation at positions 238, 269, 270, and 330, as compared to SEQ ID NO: 88;
- a mutation at positions 237, 238, 269, 270, and 330, as compared to SEQ ID NO: 88;
- a mutation at positions 237, 238, 239, 269, 270, and 330, as compared to SEQ ID NO: 88;
- a mutation at positions 237, 238, 240, 269, 270, and 330, as compared to SEQ ID NO: 88;
- a mutation at positions 235, 238, 269, 270, and 330, as compared to SEQ ID NO: 88;
- a mutation at positions 235, 238, 269, 270, and 330, and an insertion of an amino acid sequence GEV between positions 233 and 234, as compared to SEQ ID NO: 88;
- a mutation at positions 238, 269, 270, and 330, as compared to SEQ ID NO: 88;
- a mutation at positions 234, 235, 329, 268, and 271, as compared to SEQ ID NO: 88;
- a mutation at positions 234, 235, 239, 329, 268, and 271, as compared to SEQ ID NO: 88;
- a mutation at positions 234 and 235, as compared to SEQ ID NO: 88;
- a mutation at positions 237 and 238, as compared to SEQ ID NO: 88; or
- any combination thereof.

110. The polypeptide of any one of embodiments 103-109, wherein the dimer molecule comprises:

- the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;
  - a mutation at positions 237, 238, 269, 270, and 330, as compared to SEQ ID NO: 88;
  - a mutation at positions 237, 238, 239, 269, 270, and 330, as compared to SEQ ID NO: 88;
  - a mutation at positions 237, 238, 240, 269, 270, and 330, as compared to SEQ ID NO: 88;
  - a mutation at positions 235, 238, 269, 270, and 330, as compared to SEQ ID NO: 88;
  - a mutation at positions 235, 238, 269, 270, and 330, and an insertion of an amino acid sequence GEV between positions 233 and 234, as compared to SEQ ID NO: 88;
  - a mutation at positions 238, 269, 270, and 330, as compared to SEQ ID NO: 88;
  - a mutation at positions 234, 235, 329, 268, and 271, as compared to SEQ ID NO: 88;
  - a mutation at positions 234, 235, 239, 329, 268, and 271, as compared to SEQ ID NO: 88;
  - a mutation at positions 234 and 235, as compared to SEQ ID NO: 88;
  - a mutation at positions 237 and 238, as compared to SEQ ID NO: 88; or
  - any combination thereof; and
- the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:
  - a mutation at positions 238, 269, 270, and 330, as compared to SEQ ID NO: 88;

a mutation at positions 237, 238, 269, 270, and 330, as compared to SEQ ID NO: 88;

a mutation at positions 237, 238, 239, 269, 270, and 330, as compared to SEQ ID NO: 88;

a mutation at positions 237, 238, 240, 269, 270, and 330, as compared to SEQ ID NO: 88;

a mutation at positions 235, 238, 269, 270, and 330, as compared to SEQ ID NO: 88;

a mutation at positions 235, 238, 269, 270, and 330, and an insertion of an amino acid sequence GEV between positions 233 and 234, as compared to SEQ ID NO: 88;

a mutation at positions 238, 269, 270, and 330, as compared to SEQ ID NO: 88;

a mutation at positions 234, 235, 329, 268, and 271, as compared to SEQ ID NO: 88;

a mutation at positions 234, 235, 239, 329, 268, and 271, as compared to SEQ ID NO: 88;

a mutation at positions 234 and 235, as compared to SEQ ID NO: 88;

a mutation at positions 237 and 238, as compared to SEQ ID NO: 88; or any combination thereof.

111. The polypeptide of any one of embodiments 103-110, wherein the dimer molecule comprises the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

112. The polypeptide of any one of embodiments 103-110, wherein the dimer molecule comprises the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof.

113. The polypeptide of any one of embodiments 103-112, wherein the dimer molecule comprises:

the first polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;

a mutation set of G237D, P238G, V240A, E269D, D270E, and A330R, as compared to SEQ ID NO: 88;

a mutation set of L235V, P238E, E269D, D270E, and A330R, as compared to SEQ ID NO: 88;

a mutation set of L235V, P238D, E269D, D270E, and A330R, and an insertion of an amino acid sequence GEV between positions 233 and 234, as compared to SEQ ID NO: 88;

a mutation set of P238S, E269D, D270E, and A330R, as compared to SEQ ID NO: 88;

a mutation set of L234F, L235E, P329A, H268D, and P271G, as compared to SEQ ID NO: 88;

a mutation set of L234F, L235E, S239D, P329A, H268D, and P271G, as compared to SEQ ID NO: 88;

a mutation set of L234F and L235E, as compared to SEQ ID NO: 88;

a mutation set of G237E and P238E, as compared to SEQ ID NO: 88; or any combination thereof; and the second polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 88, provided that the variant IgG Fc polypeptide comprises:

a mutation set of P238D, E269D, D270E, and A330R, as compared to SEQ ID NO: 88;

a mutation set of G237D, P238G, E269D, D270E, and A330R, as compared to SEQ ID NO: 88;

a mutation set of G237D, P238S, S239G, E269D, D270E, and A330R, as compared to SEQ ID NO: 88;
a mutation set of G237D, P238G, V240A, E269D, D270E, and A330R, as compared to SEQ ID NO: 88;
a mutation set of L235V, P238E, E269D, D270E, and A330R, as compared to SEQ ID NO: 88;
a mutation set of L235V, P238D, E269D, D270E, and A330R, and an insertion of an amino acid sequence GEV between positions 233 and 234, as compared to SEQ ID NO: 88;
a mutation set of P238S, E269D, D270E, and A330R, as compared to SEQ ID NO: 88;
a mutation set of L234F, L235E, P329A, H268D, and P271G, as compared to SEQ ID NO: 88;
a mutation set of L234F, L235E, S239D, P329A, H268D, and P271G, as compared to SEQ ID NO: 88;
a mutation set of L234F and L235E, as compared to SEQ ID NO: 88;
a mutation set of G237E and P238E, as compared to SEQ ID NO: 88; or
any combination thereof.

114. The polypeptide of any one of embodiments 103-113, wherein the first polypeptide comprises a variant sequence of SEQ ID NO: 88, wherein the first polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88; and the second polypeptide comprises a variant sequence of SEQ ID NO: 88, wherein the second polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 88.

115. The polypeptide of any one of embodiments 103-114, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

116. The polypeptide of any one of embodiments 103-114, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

117. The polypeptide of any one of embodiments 103-116, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

118. The polypeptide of any one of embodiments 103-116, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises a mutation, or a set of mutations at any one position, or any combination of positions selected from 233, 234, 235, 237, 238, 239, 240, 268, 269, 270, 271, 329, 330 as compared to SEQ ID NO: 88.

119. The polypeptide of any one of embodiments 103-118, wherein the first polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

120. The polypeptide of any one of embodiments 103-118, wherein the second polypeptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104, provided that the variant IgG Fc polypeptide comprises one or more of the mutations selected from L234F, L235E, L235V, G237D, G237E, P238D, P238G, P238E, P238S, S239G, S239D, V240A, H268D, E269D, D270E, P271G, P329A, A330R, an insertion of an amino acid sequence GEV between positions 233 and 234, and any combination thereof, as compared to SEQ ID NO: 88.

121. The polypeptide of any of embodiments 103-110, wherein the first polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104; and the second polypeptide comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 102, SEQ ID NO: 103, or SEQ ID NO: 104.

122. The polypeptide of any of embodiments 106-121, wherein the first polypeptide comprises an amino acid sequence of SEQ ID NO: 1, and the second polypeptide comprises an amino acid sequence of SEQ ID NO: 1;

the first polypeptide comprises an amino acid sequence of SEQ ID NO: 2, and the second polypeptide comprises an amino acid sequence of SEQ ID NO: 2;

the first polypeptide comprises an amino acid sequence of SEQ ID NO: 3, and the second polypeptide comprises an amino acid sequence of SEQ ID NO: 3;

the first polypeptide comprises an amino acid sequence of SEQ ID NO: 4, and the second polypeptide comprises an amino acid sequence of SEQ ID NO: 4;

the first polypeptide comprises an amino acid sequence of SEQ ID NO: 5, and the second polypeptide comprises an amino acid sequence of SEQ ID NO: 5;

the first polypeptide comprises an amino acid sequence of SEQ ID NO: 6, and the second polypeptide comprises an amino acid sequence of SEQ ID NO: 6;

the first polypeptide comprises an amino acid sequence of SEQ ID NO: 7, and the second polypeptide comprises an amino acid sequence of SEQ ID NO: 7;

the first polypeptide comprises an amino acid sequence of SEQ ID NO: 8, and the second polypeptide comprises an amino acid sequence of SEQ ID NO: 8;

the first polypeptide comprises an amino acid sequence of SEQ ID NO: 9, and the second polypeptide comprises an amino acid sequence of SEQ ID NO: 9;

the first polypeptide comprises an amino acid sequence of SEQ ID NO: 10, and the second polypeptide comprises an amino acid sequence of SEQ ID NO: 10;

the first polypeptide comprises an amino acid sequence of SEQ ID NO: 11, and the second polypeptide comprises an amino acid sequence of SEQ ID NO: 11;

the first polypeptide comprises an amino acid sequence of SEQ ID NO: 12, and the second polypeptide comprises an amino acid sequence of SEQ ID NO: 12;

the first polypeptide comprises an amino acid sequence of SEQ ID NO: 13, and the second polypeptide comprises an amino acid sequence of SEQ ID NO: 13;

the first polypeptide comprises an amino acid sequence of SEQ ID NO: 14, and the second polypeptide comprises an amino acid sequence of SEQ ID NO: 14;

the first polypeptide comprises an amino acid sequence of SEQ ID NO: 15, and the second polypeptide comprises an amino acid sequence of SEQ ID NO: 15;

the first polypeptide comprises an amino acid sequence of SEQ ID NO: 16, and the second polypeptide comprises an amino acid sequence of SEQ ID NO: 16;

the first polypeptide comprises an amino acid sequence of SEQ ID NO: 17, and the second polypeptide comprises an amino acid sequence of SEQ ID NO: 17;

the first polypeptide comprises an amino acid sequence of SEQ ID NO: 18, and the second polypeptide comprises an amino acid sequence of SEQ ID NO: 18;

the first polypeptide comprises an amino acid sequence of SEQ ID NO: 19, and the second polypeptide comprises an amino acid sequence of SEQ ID NO: 19;

the first polypeptide comprises an amino acid sequence of SEQ ID NO: 20, and the second polypeptide comprises an amino acid sequence of SEQ ID NO: 20;

the first polypeptide comprises an amino acid sequence of SEQ ID NO: 21, and the second polypeptide comprises an amino acid sequence of SEQ ID NO: 21;

the first polypeptide comprises an amino acid sequence of SEQ ID NO: 22, and the second polypeptide comprises an amino acid sequence of SEQ ID NO: 22;

the first polypeptide comprises an amino acid sequence of SEQ ID NO: 23, and the second polypeptide comprises an amino acid sequence of SEQ ID NO: 23;

the first polypeptide comprises an amino acid sequence of SEQ ID NO: 24, and the second polypeptide comprises an amino acid sequence of SEQ ID NO: 24;

the first polypeptide comprises an amino acid sequence of SEQ ID NO: 25, and the second polypeptide comprises an amino acid sequence of SEQ ID NO: 25;

the first polypeptide comprises an amino acid sequence of SEQ ID NO: 26, and the second polypeptide comprises an amino acid sequence of SEQ ID NO: 26;

the first polypeptide comprises an amino acid sequence of SEQ ID NO: 27, and the second polypeptide comprises an amino acid sequence of SEQ ID NO: 27;

the first polypeptide comprises an amino acid sequence of SEQ ID NO: 28, and the second polypeptide comprises an amino acid sequence of SEQ ID NO: 28;

the first polypeptide comprises an amino acid sequence of SEQ ID NO: 29, and the second polypeptide comprises an amino acid sequence of SEQ ID NO: 29;

the first polypeptide comprises an amino acid sequence of SEQ ID NO: 30, and the second polypeptide comprises an amino acid sequence of SEQ ID NO: 30;

the first polypeptide comprises an amino acid sequence of SEQ ID NO: 31, and the second polypeptide comprises an amino acid sequence of SEQ ID NO: 31;

the first polypeptide comprises an amino acid sequence of SEQ ID NO: 32, and the second polypeptide comprises an amino acid sequence of SEQ ID NO: 32;

the first polypeptide comprises an amino acid sequence of SEQ ID NO: 33, and the second polypeptide comprises an amino acid sequence of SEQ ID NO: 33;

the first polypeptide comprises an amino acid sequence of SEQ ID NO: 34, and the second polypeptide comprises an amino acid sequence of SEQ ID NO: 34;

the first polypeptide comprises an amino acid sequence of SEQ ID NO: 35, and the second polypeptide comprises an amino acid sequence of SEQ ID NO: 35;

the first polypeptide comprises an amino acid sequence of SEQ ID NO: 36, and the second polypeptide comprises an amino acid sequence of SEQ ID NO: 36;

the first polypeptide comprises an amino acid sequence of SEQ ID NO: 37, and the second polypeptide comprises an amino acid sequence of SEQ ID NO: 37;

the first polypeptide comprises an amino acid sequence of SEQ ID NO: 38, and the second polypeptide comprises an amino acid sequence of SEQ ID NO: 38;

the first polypeptide comprises an amino acid sequence of SEQ ID NO: 39, and the second polypeptide comprises an amino acid sequence of SEQ ID NO: 39;

the first polypeptide comprises an amino acid sequence of SEQ ID NO: 40, and the second polypeptide comprises an amino acid sequence of SEQ ID NO: 40;

the first polypeptide comprises an amino acid sequence of SEQ ID NO: 41, and the second polypeptide comprises an amino acid sequence of SEQ ID NO: 41;

the first polypeptide comprises an amino acid sequence of SEQ ID NO: 42, and the second polypeptide comprises an amino acid sequence of SEQ ID NO: 42;

the first polypeptide comprises an amino acid sequence of SEQ ID NO: 43, and the second polypeptide comprises an amino acid sequence of SEQ ID NO: 43;

the first polypeptide comprises an amino acid sequence of SEQ ID NO: 44, and the second polypeptide comprises an amino acid sequence of SEQ ID NO: 44;

the first polypeptide comprises an amino acid sequence of SEQ ID NO: 45, and the second polypeptide comprises an amino acid sequence of SEQ ID NO: 45;

the first polypeptide comprises an amino acid sequence of SEQ ID NO: 46, and the second polypeptide comprises an amino acid sequence of SEQ ID NO: 46;

the first polypeptide comprises an amino acid sequence of SEQ ID NO: 47, and the second polypeptide comprises an amino acid sequence of SEQ ID NO: 47;

the first polypeptide comprises an amino acid sequence of SEQ ID NO: 48, and the second polypeptide comprises an amino acid sequence of SEQ ID NO: 48;

the first polypeptide comprises an amino acid sequence of SEQ ID NO: 49, and the second polypeptide comprises an amino acid sequence of SEQ ID NO: 49;

the first polypeptide comprises an amino acid sequence of SEQ ID NO: 50, and the second polypeptide comprises an amino acid sequence of SEQ ID NO: 50;

the first polypeptide comprises an amino acid sequence of SEQ ID NO: 51, and the second polypeptide comprises an amino acid sequence of SEQ ID NO: 51;

the first polypeptide comprises an amino acid sequence of SEQ ID NO: 52, and the second polypeptide comprises an amino acid sequence of SEQ ID NO: 52;

the first polypeptide comprises an amino acid sequence of SEQ ID NO: 53, and the second polypeptide comprises an amino acid sequence of SEQ ID NO: 53;

the first polypeptide comprises an amino acid sequence of SEQ ID NO: 54, and the second polypeptide comprises an amino acid sequence of SEQ ID NO: 54;

the first polypeptide comprises an amino acid sequence of SEQ ID NO: 55, and the second polypeptide comprises an amino acid sequence of SEQ ID NO: 55;

the first polypeptide comprises an amino acid sequence of SEQ ID NO: 56, and the second polypeptide comprises an amino acid sequence of SEQ ID NO: 56;

the first polypeptide comprises an amino acid sequence of SEQ ID NO: 57, and the second polypeptide comprises an amino acid sequence of SEQ ID NO: 57;

the first polypeptide comprises an amino acid sequence of SEQ ID NO: 58, and the second polypeptide comprises an amino acid sequence of SEQ ID NO: 58;

the first polypeptide comprises an amino acid sequence of SEQ ID NO: 59, and the second polypeptide comprises an amino acid sequence of SEQ ID NO: 59;

the first polypeptide comprises an amino acid sequence of SEQ ID NO: 60, and the second polypeptide comprises an amino acid sequence of SEQ ID NO: 60;

the first polypeptide comprises an amino acid sequence of SEQ ID NO: 61, and the second polypeptide comprises an amino acid sequence of SEQ ID NO: 61;

the first polypeptide comprises an amino acid sequence of SEQ ID NO: 62, and the second polypeptide comprises an amino acid sequence of SEQ ID NO: 62;

the first polypeptide comprises an amino acid sequence of SEQ ID NO: 63, and the second polypeptide comprises an amino acid sequence of SEQ ID NO: 63;

the first polypeptide comprises an amino acid sequence of SEQ ID NO: 64, and the second polypeptide comprises an amino acid sequence of SEQ ID NO: 64;

the first polypeptide comprises an amino acid sequence of SEQ ID NO: 65, and the second polypeptide comprises an amino acid sequence of SEQ ID NO: 65;

the first polypeptide comprises an amino acid sequence of SEQ ID NO: 66, and the second polypeptide comprises an amino acid sequence of SEQ ID NO: 66;

the first polypeptide comprises an amino acid sequence of SEQ ID NO: 67, and the second polypeptide comprises an amino acid sequence of SEQ ID NO: 67;

the first polypeptide comprises an amino acid sequence of SEQ ID NO: 68, and the second polypeptide comprises an amino acid sequence of SEQ ID NO: 68;

the first polypeptide comprises an amino acid sequence of SEQ ID NO: 69, and the second polypeptide comprises an amino acid sequence of SEQ ID NO: 69;

the first polypeptide comprises an amino acid sequence of SEQ ID NO: 70, and the second polypeptide comprises an amino acid sequence of SEQ ID NO: 70;

the first polypeptide comprises an amino acid sequence of SEQ ID NO: 71, and the second polypeptide comprises an amino acid sequence of SEQ ID NO: 71;

the first polypeptide comprises an amino acid sequence of SEQ ID NO: 72, and the second polypeptide comprises an amino acid sequence of SEQ ID NO: 72;

the first polypeptide comprises an amino acid sequence of SEQ ID NO: 73, and the second polypeptide comprises an amino acid sequence of SEQ ID NO: 73;

the first polypeptide comprises an amino acid sequence of SEQ ID NO: 74, and the second polypeptide comprises an amino acid sequence of SEQ ID NO: 74;

the first polypeptide comprises an amino acid sequence of SEQ ID NO: 75, and the second polypeptide comprises an amino acid sequence of SEQ ID NO: 75;

the first polypeptide comprises an amino acid sequence of SEQ ID NO: 76, and the second polypeptide comprises an amino acid sequence of SEQ ID NO: 76;

the first polypeptide comprises an amino acid sequence of SEQ ID NO: 77, and the second polypeptide comprises an amino acid sequence of SEQ ID NO: 77;

the first polypeptide comprises an amino acid sequence of SEQ ID NO: 78, and the second polypeptide comprises an amino acid sequence of SEQ ID NO: 78;

the first polypeptide comprises an amino acid sequence of SEQ ID NO: 79, and the second polypeptide comprises an amino acid sequence of SEQ ID NO: 79;

the first polypeptide comprises an amino acid sequence of SEQ ID NO: 80, and the second polypeptide comprises an amino acid sequence of SEQ ID NO: 80;

the first polypeptide comprises an amino acid sequence of SEQ ID NO: 81, and the second polypeptide comprises an amino acid sequence of SEQ ID NO: 81;

the first polypeptide comprises an amino acid sequence of SEQ ID NO: 82, and the second polypeptide comprises an amino acid sequence of SEQ ID NO: 82;

the first polypeptide comprises an amino acid sequence of SEQ ID NO: 83, and the second polypeptide comprises an amino acid sequence of SEQ ID NO: 83;

the first polypeptide comprises an amino acid sequence of SEQ ID NO: 84, and the second polypeptide comprises an amino acid sequence of SEQ ID NO: 84;

the first polypeptide comprises an amino acid sequence of SEQ ID NO: 85, and the second polypeptide comprises an amino acid sequence of SEQ ID NO: 85;

the first polypeptide comprises an amino acid sequence of SEQ ID NO: 86, and the second polypeptide comprises an amino acid sequence of SEQ ID NO: 86;

the first polypeptide comprises an amino acid sequence of SEQ ID NO: 87, and the second polypeptide comprises an amino acid sequence of SEQ ID NO: 87;

the first polypeptide comprises an amino acid sequence of SEQ ID NO: 102, and the second polypeptide comprises an amino acid sequence of SEQ ID NO: 102;

the first polypeptide comprises an amino acid sequence of SEQ ID NO: 103, and the second polypeptide comprises an amino acid sequence of SEQ ID NO: 103; or the first polypeptide comprises an amino acid sequence of SEQ ID NO: 104, and the second polypeptide comprises an amino acid sequence of SEQ ID NO: 104.

123. The polypeptide of embodiment 93, wherein the polypeptide comprises at least one inhibitory receptor effector domains.

124. The polypeptide of embodiment 123, wherein the polypeptide comprises 2 inhibitory receptor effector domains.

125. The polypeptide of embodiment 124, wherein the 2 inhibitory receptor effector domains bind to the same inhibitory receptor.

126. The polypeptide of embodiment 124, wherein the 2 inhibitory receptor effector domains bind to different inhibitory receptors.

127. The polypeptide of any one of embodiments 93-126, wherein the inhibitory receptor effector domain is an antibody.

128. The polypeptide of any one of embodiments 93-127, wherein the inhibitory receptor effector domain is present in an antibody, in the format of an scFv, Fab, Fab', or F(ab')2.

129. The polypeptide of any one of embodiments 93-128, wherein the inhibitory receptor effector domain binds to a receptor encoded by LAG3, RSV, BTLA/CD272, CD200R1, CD200R1, CD22/Siglec2, CD300A, CD300LF/CD300F, CD33/Siglec3, CD5, CD72, CEACAM 1, CLEC12A, CLEC4A, CTLA4/CD152, FCGR2B/CD32B, KIRs, KLRB1/CD161, KLRC1, KLRG1, LAIR1, LILRB1, LILRB2, LILRB4, LILRB5, NCR2/NKp44, PDCD1, PECAM1/CD31, PILRA, PVR/CD155, SIGLEC11, SIGLEC5, SIGLEC7, SIGLEC8, SIGLEC9, SIRPA, TIGIT, VSTM1/SIRL1, MAFA, NKG2A, CMRF35H, CD66a, CD66d, CD33, SIGLEC6, ILT2,3,4,5, LIR8, KIR2DL, KIR3DL, SIRPa, KIR2DL2/3, KIR2DL5, KIRDL1, KIRDL2, KIRDL3, TIM3, Tactile, IRp60, NKRP1, IAP, PIR-B, CD5, 2B4, GP49B, Ly49Q, or MICL.

130. The polypeptide of any one of embodiments 93-129, wherein the inhibitory receptor effector domain binds to PD-1, LAG-3, RSV, or CTLA4.

131. The polypeptide of any one of embodiments 93-130, wherein the inhibitory receptor effector domain is an agonist of the receptor to which it binds.

132. The polypeptide of any one embodiments 93-131, wherein the inhibitory receptor effector domain is an antagonist of the receptor to which it binds.

133. The polypeptide of embodiment 93, wherein the FcγRII binding effector domain binds to FcγRIIβ.

134. The polypeptide of embodiment 133, wherein the FcγRII binding effector domains is an antibody.

135. The polypeptide of embodiment 134, wherein the antibody is an scFv, Fab, Fab', and F(ab')2.

136. A pharmaceutical composition comprising a polypeptide or composition of any of the preceding embodiments, and at least one pharmaceutically acceptable excipient.

137. A method of treating an autoimmune disorder in a subject, the method comprising administering a polypeptide or composition of any one of embodiments 1-135, or a pharmaceutical composition comprising the same, to the subject.

138. The method of embodiment 137, wherein the autoimmune disorder is selected from myocarditis, postmyocardial infarction syndrome, postpericardiotomy syndrome, subacute bacterial endocarditis, anti-glomerular basement membrane nephritis, interstitial cystitis, lupus nephritis, membranous glomerulonephropathy, chronic kidney disease (CKD), autoimmune hepatitis, primary biliary cirrhosis, primary sclerosing cholangitis, antisynthetase syndrome, alopecia areata, autoimmune angioedema, autoimmune progesterone dermatitis, overlap connective tissues disease syndromes, polymyalgia rheumatic, autoimmune urticaria, bullous pemphigoid, cicatricial pemphigoid, dermatitis herpetiformis, discoid lupus erythematosus, epidermolysis bullosa acquisita, erythema nodosum, anti-neutrophil cytoplasmic antibody associated vasculitis, Henoch-Schonlein purpura, Cogan's syndrome, Buerger's disease, Susan's disease, immune complex vasculitis, primary angiitis of the CNS, gestational pemphigoid, hidradenitis suppurativa, lichen planus, lichen sclerosus, linear iga disease (lad), morphea, pemphigus vulgaris, *Pityriasis lichenoides* et varioliformis acuta, mucha-habermann disease, psoriasis, systemic scleroderma, vitiligo, Addison's disease, autoimmune polyendocrine syndrome (APS) type 1, autoimmune polyendocrine syndrome (APS) type 2, juvenile idiopathic arthritis, juvenile dermatomyositis, autoimmune brain disease, autoimmune polyendocrine syndrome (APS) type 3, autoimmune pancreatitis (AIP), diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, Coeliac disease, Crohn's disease, microscopic colitis, ulcerative colitis, thrombocytopenia, adiposis, dolorosa, adult-onset Still's disease, ankylosing spondylitis, CREST syndrome, drug-induced lupus, enthesitis-related arthritis, cosinophilic fasciitis, Felty syndrome, IgG4-related disease, juvenile arthritis, lyme disease (chronic), mixed connective tissue disease (MCTD), palindromic rheumatism, Parry Romberg syndrome, Parsonage-Turner syndrome, psoriatic arthritis, IBD-associated arthritis, reactive arthritis, relapsing polychondritis, retroperitoneal fibrosis, rheumatic fever, rheumatoid arthritis, autoimmune complications of immune checkpoint inhibitors (IRAEs), sarcoidosis, neurosarcoidosis, Schnitzler syndrome, systemic lupus erythematosus (SLE), undifferentiated connective tissue disease (UCTD), dermatomyositis, IgG4 related disease, fibromyalgia, antiphospholipid syndrome, inclusion body myositis, myositis, myasthenia gravis, neuromyotonia, parancoplastic cerebellar degeneration, polymyositis, acute disseminated encephalomyelitis (ADEM), adult onset Still's disease, acute motor axonal neuropathy, anti-N-Methyl-D-Aspartate (anti-NMDA) receptor encephalitis, warm antibody hemolytic anemia (wAIHA), immune thrombocytopenia, immune thrombotic thrombocytopenia, thrombotic thrombocytopenia, pernicious anemia, aplastic anemia, Evan's syndrome, autoimmune neutropenia, acquired von Willibrand syndrome, recurring fetal loss, Rh mismatch, Balo concentric sclerosis, Bickerstaff's encephalitis, chronic inflammatory demyelinating polyneuropathy, Guillain-Barre syndrome, Hashimoto's encephalopathy, idiopathic inflammatory demyelinating diseases, Lambert-Eaton myasthenic syndrome, primary biliary sclerosis, glomerulonephritis, glomerular basement membrane disease, multiple sclerosis, Oshtoran syndrome, pediatric autoimmune neuropsychiatric disorder associated with *Streptococcus* (PANDAS), progressive inflammatory neuropathy, cutaneous lupus crythematosus, restless leg syndrome, pemphigus foliaceus including fogo selvage, transplantation, antibody-mediated rejection, alloantibody hypersensitization, xenoantibody mediated rejection, solid organ rejection, graft vs host disease acute and chronic, stiff person syndrome, Sydenham chorea, transverse myelitis, autoimmune retinopathy, autoimmune uveitis, uveitis, Cogan syndrome, Graves ophthalmopathy, amyotrophic lateral sclerosis (ALS), Parkinson's disease, autoimmune encephalitis, CNS vasculitis, chronic idiopathic demyelinating polyneuropathy (CIDP), keratitis, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, rheumatic heart disease, chronic rhinosinusitis with nasal polyps, allergic bronchoplmonary mycosis, hypersensitivity pneumonitis, rheumatoid arthritis-associated interstitial lung disease (RA-ILD), nonspecific interstitial pneumonia, allergic asthma, infectious disease/vaccination, antibody dependent enhancement (as with dengue virus infection), chronic meningitis, anti-myelin oligodendrocyte glycoprotein (MOG) disease, activated-DLBCL, anti-drug antibody, anti-gene therapy vector antibody (anti-AAV antibody), antibody to therapeutic biologic agents (cytokines, monoclonal antibodies, enzymes, coagulation factors), autoimmune inner ear disease (AIED), Ménière's disease, Behcet's disease, eosinophilic granulomatosis with polyangiitis (EGPA), giant cell arteritis, polyglandular autoimmune endocrine syndromes, granulmatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumaticia, vasculitis, primary immune deficiency, pyoderma gangrenosum, agammaglobulinemia, anyloidosis, anyotrophic lateral sclerosis, anti-tubular basement membrane nephritis, atopic allergy, atopic dermatitis, autoimmune peripheral neuropathy, Blau syndrome, Castleman's disease, Chagas disease, chronic obstructive pulmonary disease, chronic recurrent multifocal osteomyelitis, complement component 2 deficiency, contact dermatitis, Cushing's syndrome, cutaneous leukocytoclastic angiitis, Dego' deiase, eczema, cosinophilic gastroenteritis, cosinophilic pneumonia, erythroblastosis fetalsis, fibrodysplasia ossificans progressive, gastrointestinal pemphigoid, hypogammaglobulinemia, idiopathic giant-cell myocarditis, idiopathic pulmonary fibrosis, IgA nephropathy, immunoregulatory lipoproteins, IPEX syndrome, ligenous conjunctivitis, Majeed syndrome, narcolepsy, Rasmussen's encephalitis, schizophrenia, serum sickness, spondyloathropathy, Sweet's syndrome, Takayasu's arteritis, or any combination thereof.

139. A method of treating cancer in a subject, a polypeptide or composition of any one of embodiments 1-135, or a pharmaceutical composition comprising the same, to the subject.

140. The method of embodiment 139, wherein the cancer a solid or liquid tumor, including but not limited to, hematopoietic cancer, lymphoid cancer, skin cancer, head and neck cancer, genitourinary cancer, blood cancer, lung cancer, breast cancer, brain cancer, esophageal cancer, colorectal cancer, or pancreatic cancer.

141. A method of modulating the interaction of cells of at least two distinct types using a polypeptide, the method comprising contacting (introducing) a polypeptide or composition of any one of embodiments 1-135, or a pharmaceutical composition comprising the same, to the cells or to a subject comprising the cells.

142. The method of embodiment 141, wherein at least one cell is a T-cell, NK Cell, or Dendritic cell, and at least one cell is a B-Cell, an antigen presenting cell (APC), or a myeloid cell.

143. The method of embodiments 141 or 142, wherein the cells are present within the body of a subject.

144. A method of inhibiting an activated immune cell that is in contact with a B cell, an antigen presenting cell (APC), or a myeloid cell, the method comprising contacting (introducing) a polypeptide or composition of any one of embodiments 1-135, or a pharmaceutical composition comprising the same, to the cells or to a subject comprising the cells.

145. A method of activating or enhancing the behavior of an activated immune cell that is in contact with a B cell, an antigen presenting cell (APC), or a myeloid cell, the method comprising contacting (introducing) a polypeptide or composition of any one of embodiments 1-135, or a pharmaceutical composition comprising the same, to the cells or to a subject comprising the cells.

The following examples are illustrative, but not limiting, of the compounds, compositions and methods described herein. Other suitable modifications and adaptations known to those skilled in the art are within the scope of the following embodiments.

EXAMPLES

Example 1: Variant IgG Fc Polypeptide Expression in Expi293F Cells and Purification Thereof The variant IgG Fc polypeptides described herein were transiently expressed in Expi293F cells. The variant IgG Fc polypeptides were purified by passing through PrismA resins. Target antibodies were eluted with buffer 0.1M Glycine, pH 2.7. The flow through and prismA eluted samples were loaded to CE-SDS to check purification result. All variants were purified with majority population as monomers on analytical SEC.

Example 2: High-Throughput Screening of Antibodies Against Analytes PD-1 and FcγRII Receptors Antibodies comprising variant IgG Fc polypeptides described herein were captured on aprotein A/G chip at 10 ug/mL, 1 ug/mL, and 0.1 ug/mL concentrations (in duplicates). Each analyte binder was injected at seven concentrations with 5-fold serial dilutions, and kinetics data was collected. Binding kinetics (KD affinity, Kon association rate, Koff dissociation rate) were collected. Affinity KD of each Fc variant against human FcγRIIα_R167, FcγRIIα_H167, FcγRIIβ, and cyno FcγRIIα and FcγRIIβ was described in Table 6 below. Due to the limitation of affinity measurement, KD values were categorized as "no binding" when no response was observed, ">5 uM" when KD is weaker than 5 uM, and KD was measured if the KD was stronger than 5 uM. For IgG1 WT, KD of 5.1 μM is shown. This value was consistent with previous reports.

Example 3: Binding Profiles of the Variant IgG F Polypeptides Provided Herein Are Comparable to the P238D Molecule CHOK1 lines overexpressing either FcγRIIβ or IIα (R131) were detached, resuspended in PBS 3% FBS and incubated for 30 minutes at +4C with 40 μg/Ml of test articles. Cells were washed and incubated for additional 30 minutes at +4C with a detection antibody (BV421 conjugated) recognizing the human kappa chain of our test articles (Cat #316518). Cells were further washed, resuspend in fixation buffer (cat number) for 1 hour, then washed and resuspended in PBS before their acquisition at the flow cytometer. Binding curves (EC50) for each antibody against human FcγRIIβ and FcγRIIα (R131) were obtained, and are shown below in Table 7.

| | IIb | IIa | IIa/IIb |
|---|---|---|---|
| IgG1 P238D | 0.4 | −32.0 | −77.8 |
| IgG1 WT | 0.8 | −0.6 | −0.7 |
| IgG1 V12 | −0.1 | −0.4 | 5.5 |
| AB-155 | −0.2 | −0.5 | 3.3 |
| AB-161 | 0.0 | −1.0 | −52.4 |
| AB-166 | 0.3 | −57.5 | −209.6 |
| AB-167 | 0.0 | −1.3 | 27.6 |

The data illustrated in Table 7 shows that the variant IgG Fc polypeptides have comparable EC50 values to the IgG1 P238D molecule.

TABLE 6

| | Hu FcgRIIA_R167 | | | Hu FcgRIIA_H167 | | | Hu FcgRIIB | | | Ratio iia/iib (KD human iia R/KD | Ratio iib/iia (KD human iib/KD |
|---|---|---|---|---|---|---|---|---|---|---|---|
| ID | KD(M) | SD (M) | Fold | KD(M) | SD (M) | Fold | KD(M) | SD (M) | Fold | human iib) | human iia R) |
| IgG1 WT | 1.55E−06 | 2.12E−07 | 1.00 | 1.00E−06 | 7.56E−08 | 1.00 | 5.10E−06 | 9.52E−08 | 1.00 | 0.30 | 3.29 |
| IgG1 P238D | >5 μM | N/A | <0.3 | No binding | N/A | N/A | 1.60E−06 | 7.55E−08 | 3.18 | 3.12 | 0.32 |
| IgG1 V12 | 1.80E−06 | 7.07E−07 | 0.86 | 3.35E−06 | 1.56E−06 | 0.30 | 3.10E−08 | 1.38E−10 | 164.35 | 57.97 | 0.02 |
| AB-146 | >5 μM | N/A | <0.3 | 2.58E−06 | 1.84E−07 | 0.39 | 3.38E−06 | 6.86E−07 | 1.51 | 1.48 | 0.68 |
| AB-147 | No binding | N/A | N/A | No binding | N/A | N/A | 3.72E−06 | 8.66E−07 | 1.37 | >10 | <0.1 |
| AB-153 | No binding | N/A | N/A | No binding | N/A | N/A | 6.12E−06 | 3.08E−07 | 0.83 | >10 | <0.1 |
| AB-154 | >5 μM | N/A | <0.3 | >5 μM | N/A | <0.2 | 1.74E−06 | 2.60E−07 | 2.93 | 2.87 | 0.35 |
| AB-155 | >5 μM | N/A | <0.3 | 2.32E−06 | 7.31E−10 | 0.43 | 2.74E−07 | 5.24E−09 | 18.64 | 18.26 | 0.05 |
| AB-161 | >5 μM | N/A | N/A | >5 μM | N/A | <0.2 | 3.89E−06 | 1.05E−07 | 1.31 | 1.29 | 0.78 |
| AB-162 | 2.20E−06 | 5.66E−07 | 0.70 | 2.23E−06 | 3.82E−07 | 0.45 | 1.55E−06 | 3.54E−07 | 3.29 | 1.42 | 0.70 |
| AB-166 | >5 μM | N/A | <0.3 | No binding | N/A | N/A | 2.03E−06 | 5.72E−08 | 2.51 | 2.46 | 0.41 |
| AB-167 | >5 μM | N/A | <0.3 | >5 μM | N/A | <0.2 | 4.18E−07 | 1.74E−08 | 12.20 | 11.95 | 0.08 |

Ratio (iia/iib) = KD(iiA)/KD(iiB) (higher means stronger iib selectivity).

Fold = KD(IgG_WT)/KD(variants) (higher number means stronger Fcg receptor affinity).

Ratio (iib/iia) = KD(iiB)/KD(iiA) (lower means stronger iib selectivity).

Compared to IgG1 wild type, the FcγRIIβ selective clones may have stronger human FcγRIIβ binding, weaker human FcγRIIα binding, or both IIα & IIβ at the same time.

Example 4: Functional Assessment of the Variant IgG F Polypeptides Provided Herein Highlights Several Molecules with Stronger Agonism than "PD-1 IgG1 WT"

Raji B cells were removed from cell culture, resuspended in cell plating reagent with 3% FBS and incubated for 1 hour at 37C with (100 nM to 0.006 nM) of test articles. Jurkat PD-1 (SHP2) reporter cells were removed from cell culture, resuspended in cell plating reagent with 3% FBS, and incubated with the Raji cells with test articles for an additional 2 hours at room temperature. Detection reagents were added to each well and luminescence was read using a plate reader. Agonism produced in reporter cell lines was enhanced by antibodies with greater affinities to FcγRIIβ over the wild-type antibody control.

Example 5: Machine-Learning Designs with ddG Calculations, Public Data and Evolutionary Model to Target FcgRiib with Kinked Hinge at Interface 1

In-silico docking was performed to build Fc-FcgRiia with kinked hinge with PDB 3WJJ and PDB 1H9V. In-silico free energy calculations were performed for all publicly available Fc mutants with reported affinities to build a machine learning model for predicting mutation effects on the affinities. In-silico free energy calculations were performed for all possible point mutations near the interfaces between Fc and receptors and predict the affinities and selectivity. Evolutionary sequence modeling to predict mutation effects on Fc stability was performed. Mutation libraries were constructed, selectivity and evolutionary scores were co-optimized separately and top mutations and interfaces were combined. A number of mutations were introduced around residues P238 as alternatives to P238D at interface 1: P238E, P238F, P238N, P238Q, P238M. The model favored D/E mutations for the near contact residues to Y205: A327D and A330E. Additional close G237 was also identified with candidates: G237H, G237M and G237D, and G237E were also included due to proximity to Y205 and preferred D/E mutations to enhance selectivity.

Example 6: Machine-Learning Designs with ddG Calculations, Public Data and Evolutionary Model to Target FcgRiib with Kinked Hinge at Interface 2

In-silico docking was performed to build Fc-FegRiia with kinked hinge with PDB 3WJJ and PDB 1H9V. In-silico free energy calculations were performed for all publicly available Fc mutants with reported affinities to build a machine learning model for predicting mutation effects on the affinities. In-silico free energy calculations were performed for all possible point mutations near the interfaces between Fc and receptors and predict the affinities and selectivity. Evolutionary sequence modeling was performed to predict mutation effects on Fc stability. Mutation libraries were constructed, selectivity and evolutionary scores for interface 2 were co-optimized separately and top mutations and interfaces were combined. A number of mutations of interest were found near S177 of FcgRiib within 10 A: E269Y, D270E, T299F, D265F, forming hydrogen bonds. Y269N mutation targeted K172 of FcgRiib within 7 A to enhanced binding affinity. H268Q mutation had superior stability predicted from evolutionary model.

Example 7: Machine-Learning Designs with ddG Calculations, Public Data and Evolutionary Model to Target FcgRiib with Normal Hinge at Interface 1&2

In-silico docking was performed to build Fc-FcgRiia and Fc-FcgRiib with normal hinge with PDB 1E4K. In-silico free energy calculations were performed for all publicly available Fc mutants with reported affinities to build a machine learning model for predicting mutation effects on the affinities. In-silico free energy calculations were performed for all possible point mutations near the interfaces between Fc and receptors and predict the affinities and selectivity. Evolutionary sequence modeling was performed to predict mutation effects on Fc stability. Mutation libraries were constructed, selectivity and evolutionary scores for interface 1 were co-optimized separately and top mutations and interfaces were combined. L235G mutation showed upstream flexibility and G236Q mutation showed polar engagement to Y205 at interface 1 within 5A. P329R mutation showed backbone change with long polar residue, selectivity/affinity boosted by G237R with same reason at interface 1. A327D mutation targeted-OH of S177 within 5A at interface 2. S298Q mutation targeted K172 within 4A for enhanced affinity. Upstream mutations of L234M, G236P, G237L created nonpolar local environment to boost A327D affinity to S177.

Figure 1B:
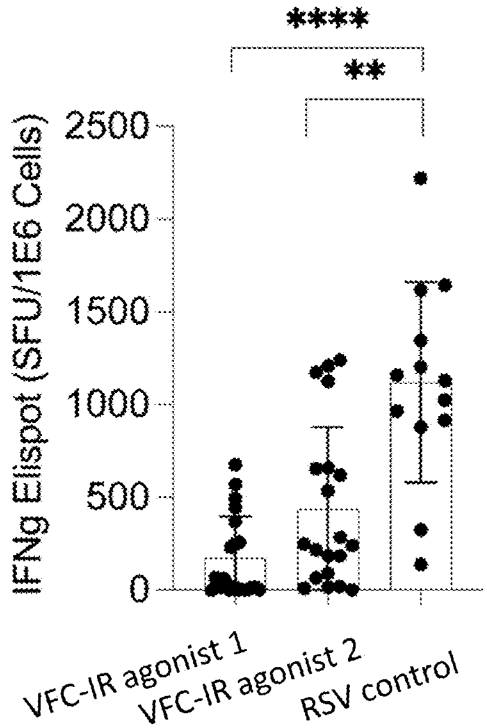
Figure 1C:
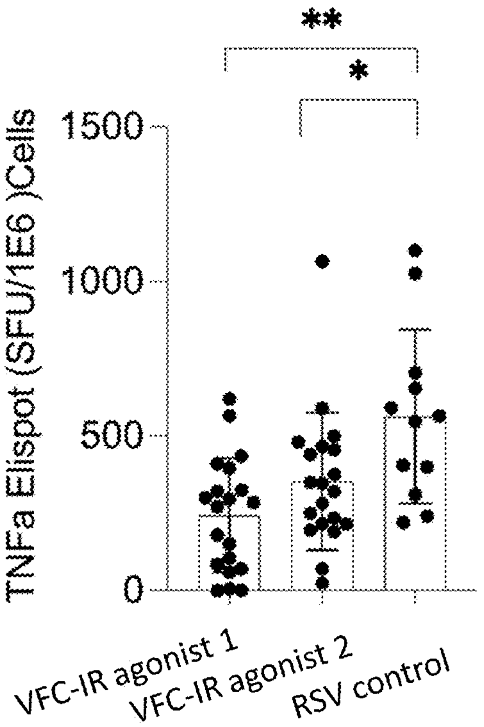

Example 8: Test Articles Reduce IL-2, IFNg, and TNFa Production in a GVHD Mouse Model A model of acute GVHD was developed through the co-transferring of donor humanized IR T cells and humanized FcgR+ cells (H-2b) in the BDF-1 models (H-2b,d). In brief, BDF1 H-2b,d mice were treated with cyclophosphamide on day-1. On day 0, donor cells were transferred (collected from KI huFcgR H-2b mice for T-cell depletion, and KI huIR H-2b mice for T-cell enrichment) in recipient BDF-1 H-2b,d, mice (n=10/treatment group) and the mice were dosed with test articles (VFC-IR agonist 1; VFC-IR agonist 2; or RSV control). The mice received subsequent doses of 1 mpk per test article twice a week for 2 weeks. Treatment with FcgRIIb selective IR agonist antibodies reduced IL-2, IFNg, and TNFa production, as shown in FIGS. 1A-1C.

Example 9

Figure 2A:
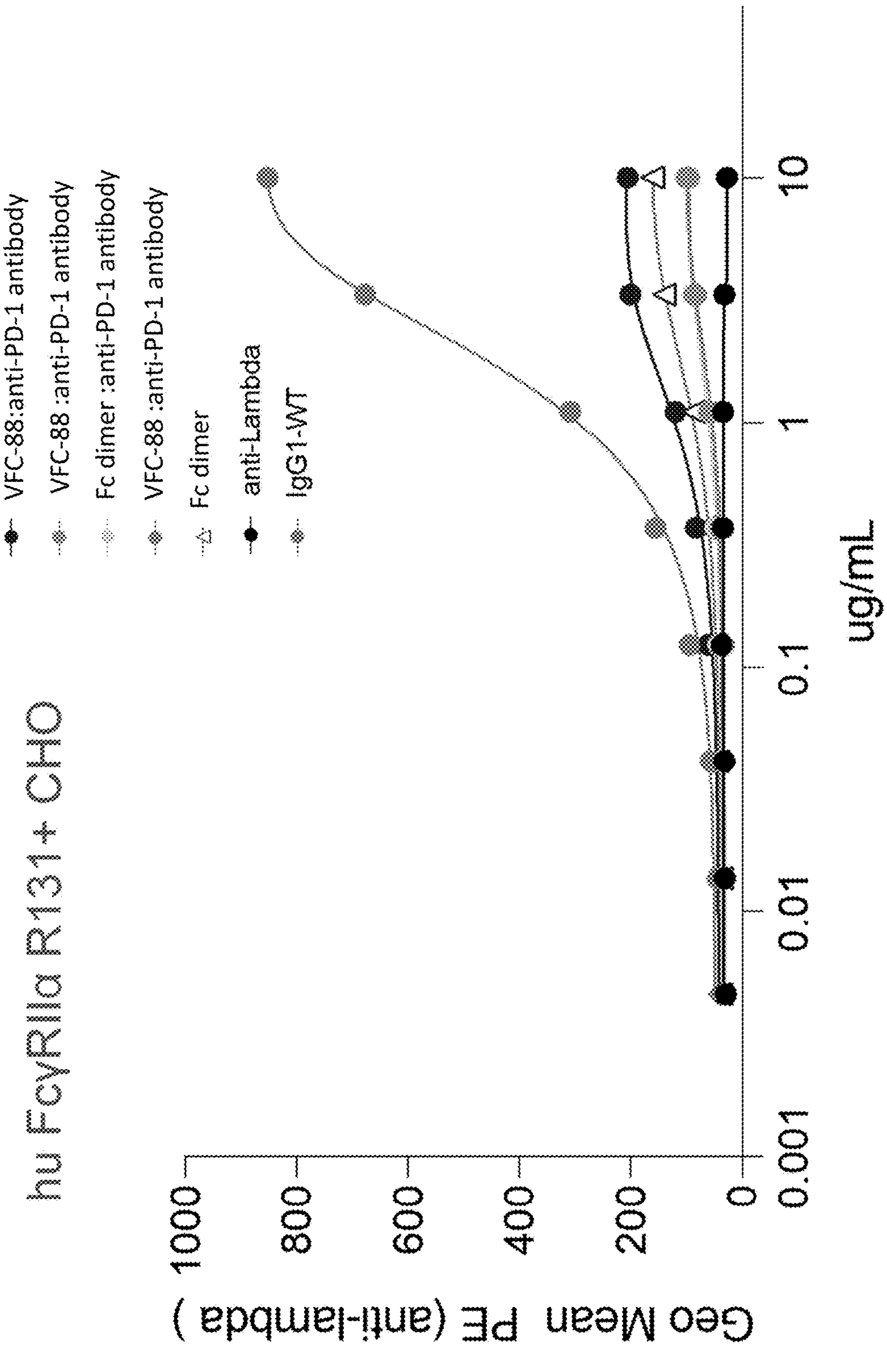
FIG. 2A-2C illustrate binding affinities of various articles.
Figure 2B:
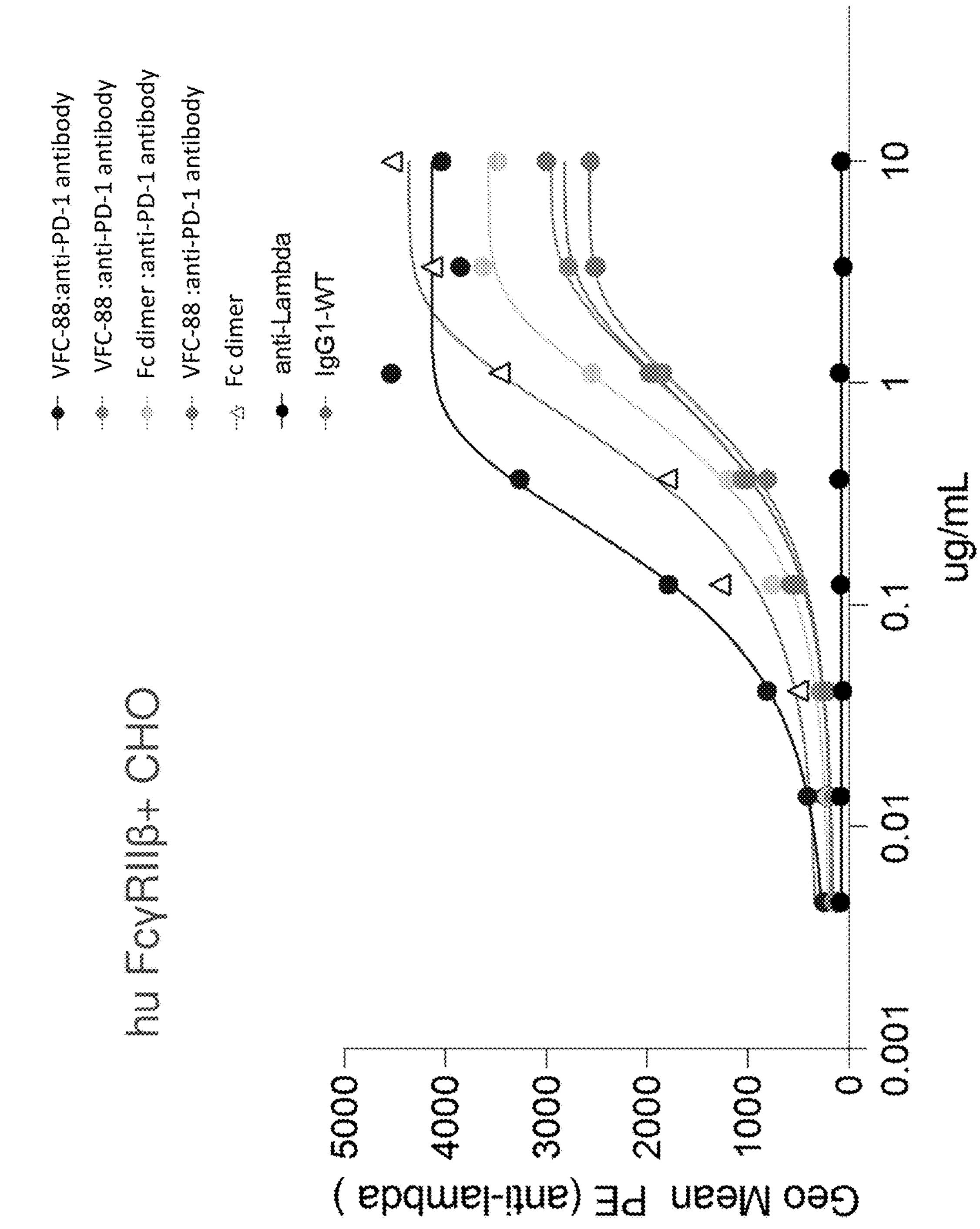
Figure 2C:
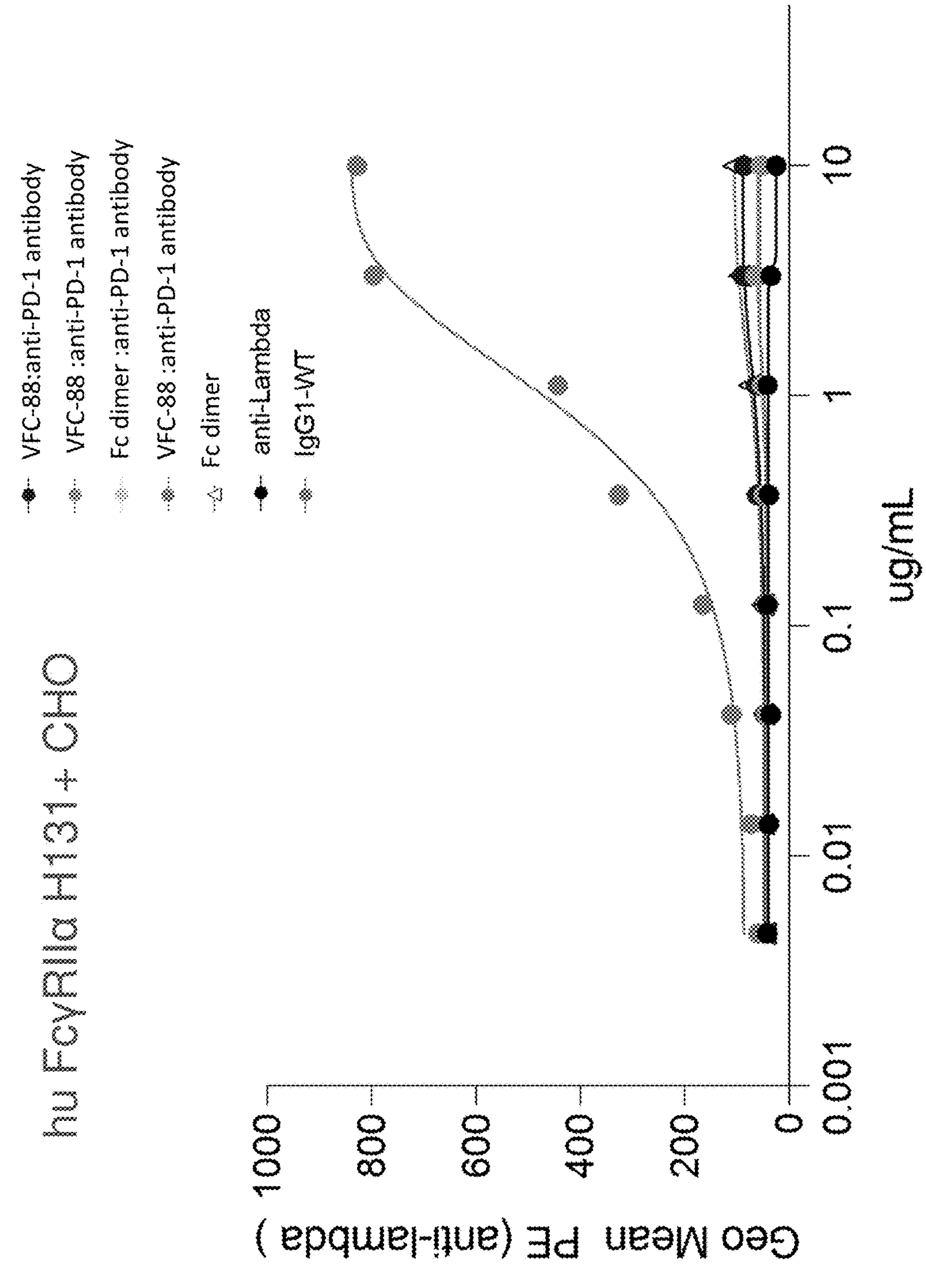

Binding of test articles (VFC-88 fused to various anti-PD-1 antibodies), or controls, to human FcγRIIβ, FcγRIIβ R131 or FcγRIIa H131 was assessed. In brief, human FcγRIIβ, FcγRIIβ R131, or FcγRIIβ H131 were expressed in Chinese hamster ovary (CHO) cells, and binding was assessed following administration of test articles or controls. As shown in FIGS. 2A-2C, test articles showed selectivity for FcγRIIβ as compared to controls.

Example 10

Figure 3:
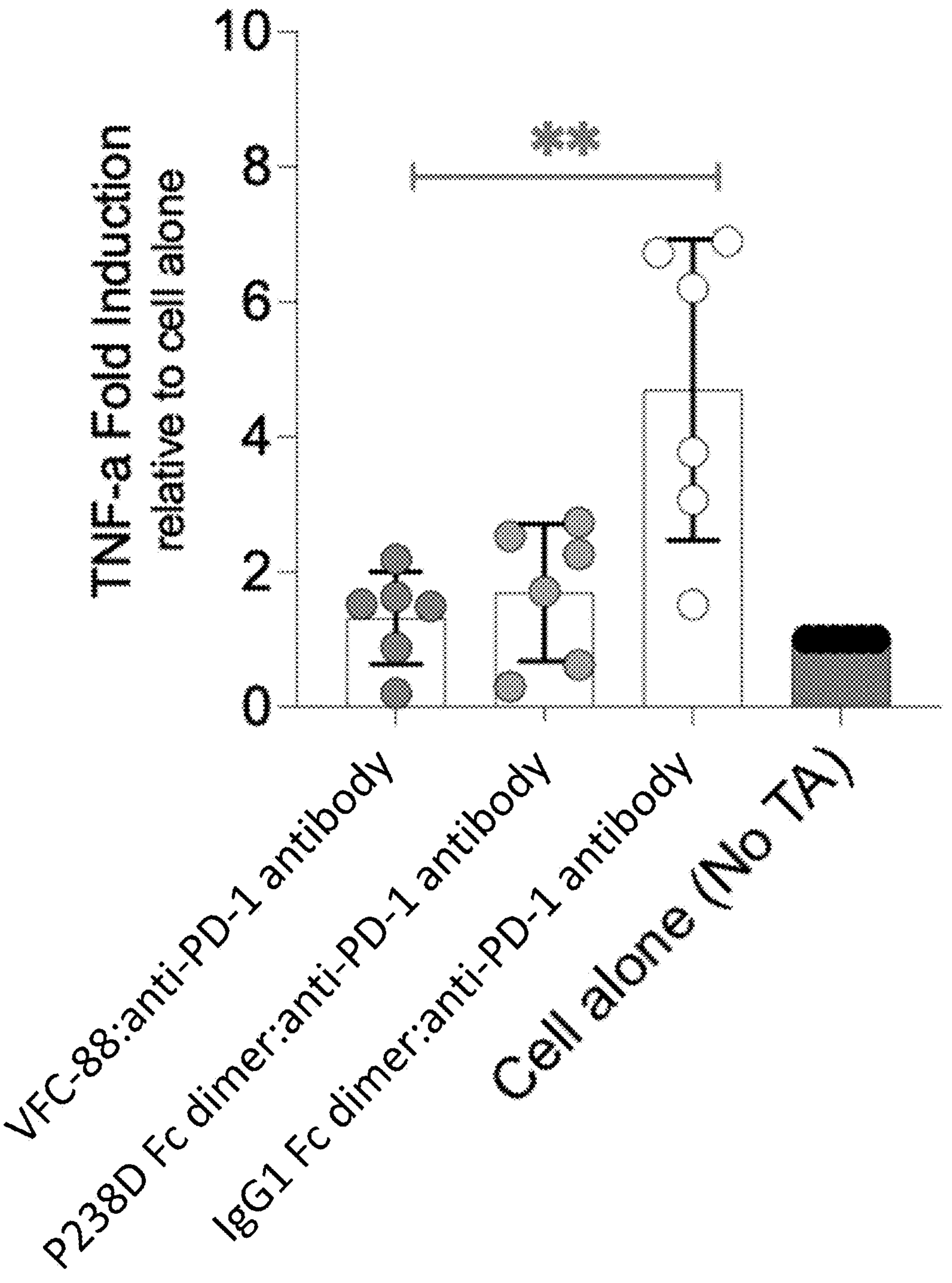
FIG. 3 illustrates TNF-alpha production in response to various articles.

Monocyte derived dendritic cells (DCs) form multiple human donors were exposed to 2 μg of test articles, a benchmark antibody, or untreated. As shown in FIG. 3, treatment with the test articles showed reduced TNF-α induction. Accordingly, reduced TNF-α induction was dependent upon FcγRII clustering on monocyte derived DCs.

Figure 4:
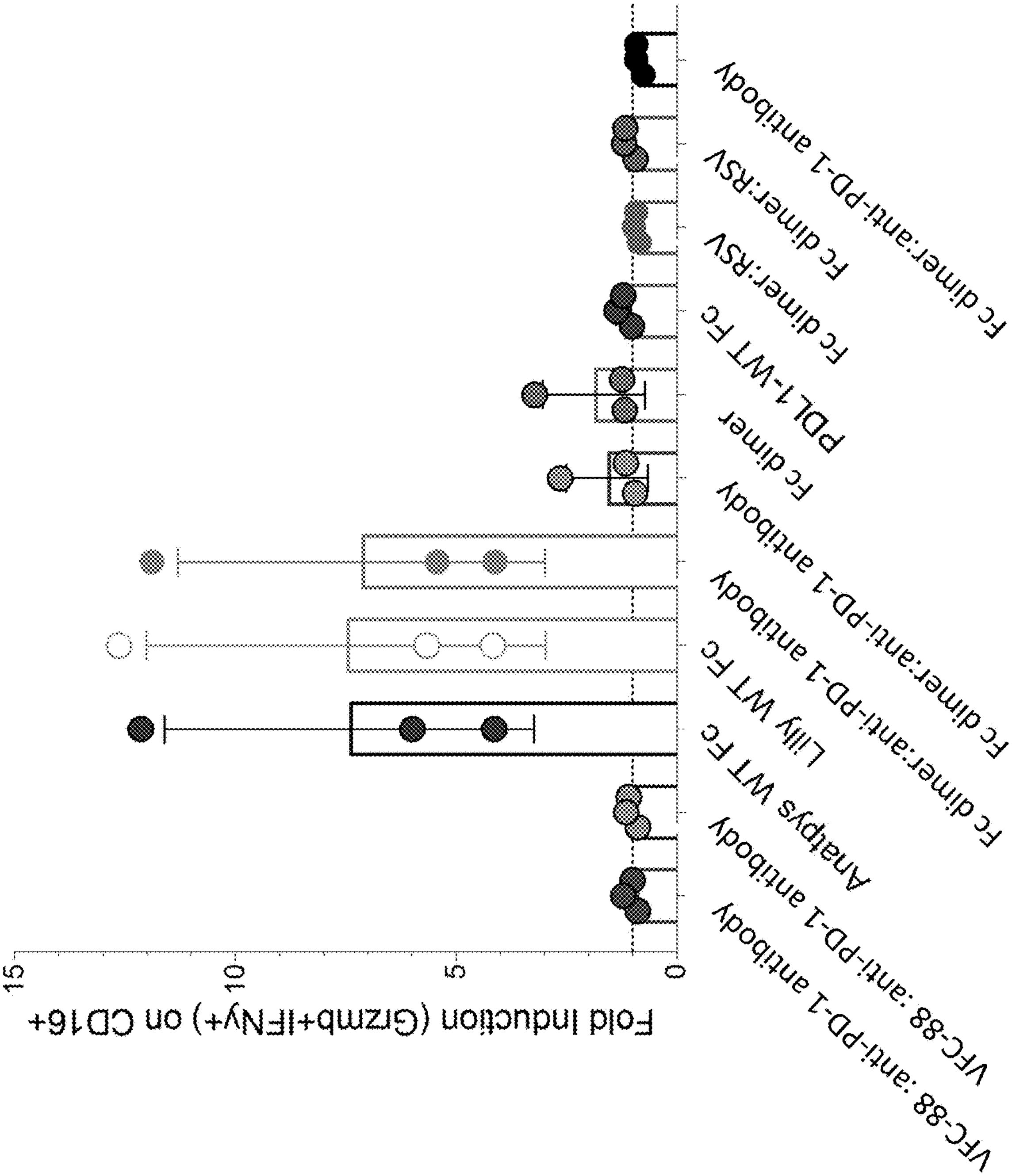
FIG. 4 illustrates granzyme B and IFN-gamma production in response to various articles.

In another experiment, CD16+ PMBCs from multiple human donors were treated with 100 nM of test articles (VFC-88 fused to various anti-PD-1 antibodies), higher affinity anti-PD-1 antibodies, lower affinity anti-PD-1 antibodies, or control molecules. As shown in FIG. 4, analysis of granzyme b and IFNγ showed a reduction following treatment with test articles, as compared to higher affinity anti-PD-1 antibodies In another set of experiments, PBMCs from three donors were treated with test articles (VFC-88 fused to various anti-PD-1 antibodies) or control molecules (benchmark antibody, or benchmark antibody fused to P238D mutant Fc). Data showed reduced induction of following treatment with test articles or the benchmark antibody fused to P238D mutant Fc, as compared to the benchmark antibody which exhibited at least 5-fold TNF-α induction.

Example 11

Figure 5A:
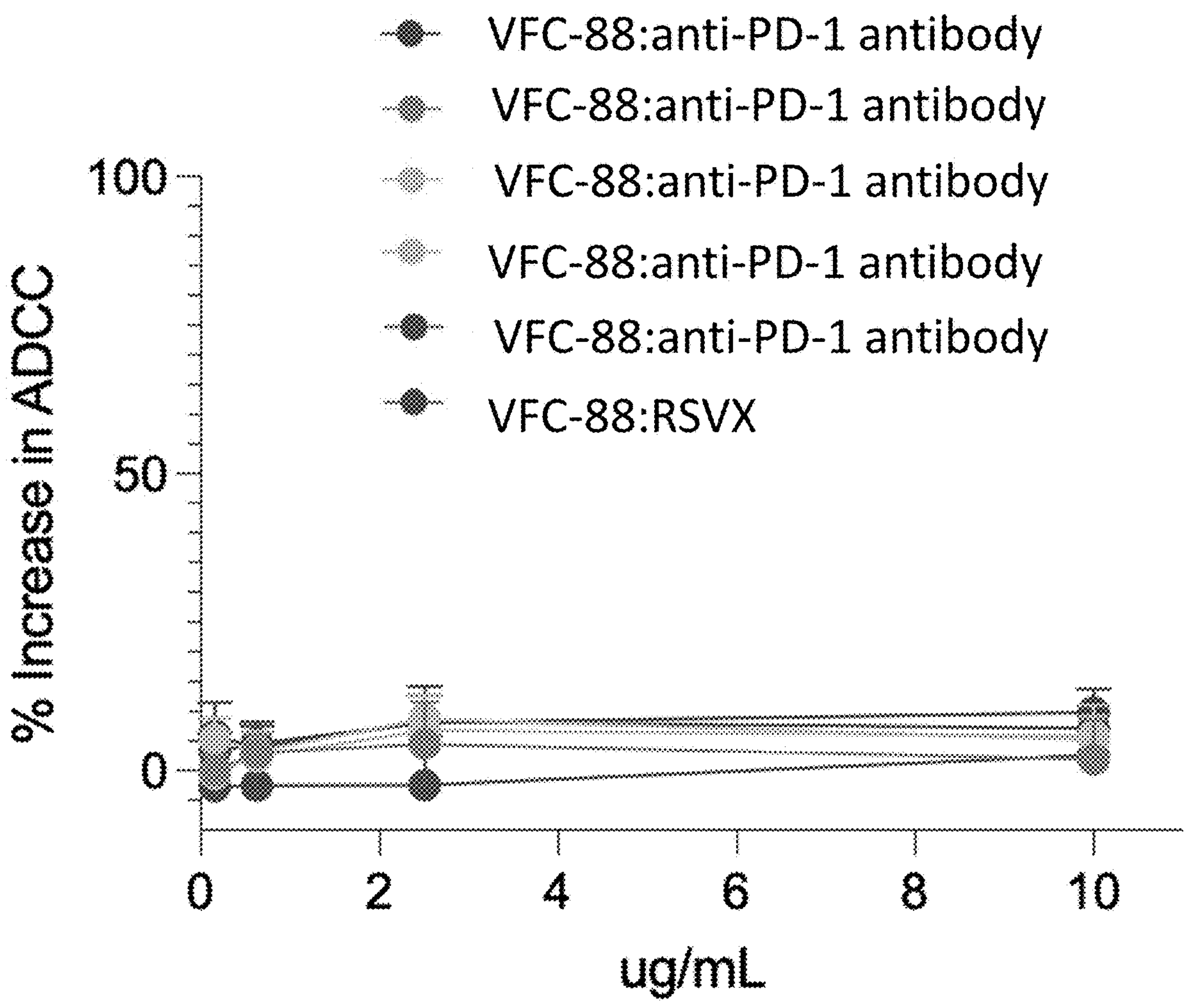
FIG. 5A-5B illustrate ADCC induction in response to various articles.
Figure 5B:
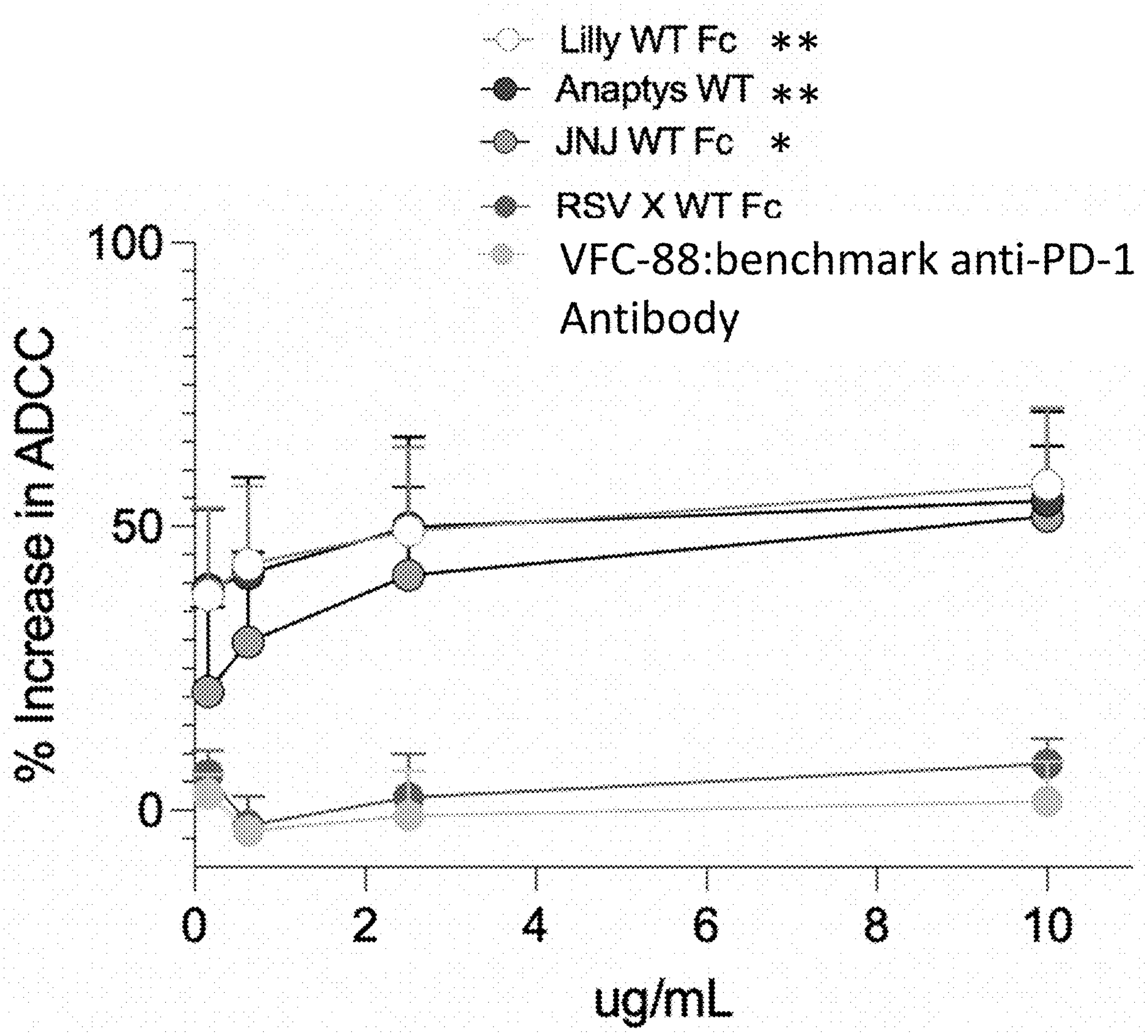

Antibody dependent cellular cytotoxicity (ADCC) was evaluated in NK cells from 4 donors. The NK cells were incubated with target Jurkat cells expressing PD-1. ADCC was evaluated following treatment with test articles (TA359, TA319, TA335, or TA333), control molecules, or benchmark molecules As shown in FIG. 5A and FIG. 5B, test articles did not trigger ADCC.

Example 12

Analysis of FcγRIIβ selectivity and binding to activating receptors FcγRIII and FcγRI of engineered Fc mutants showed FcγRIIβ selectivity and do not bind activating receptors FcγRIII and have reduced FcγRI binding when compared to WT, as shown in Table 8 below.

TABLE 8

Engineered Fc mutants

| PD-1: FcyRIIβ | KD R2b (μM) | KD R2a R131 (μM) | KD R2a H131 (μM) | R131/2b (fold) | H131/2b (fold) | KD RIII | Affinity to RI |
|---|---|---|---|---|---|---|---|
| VFC-88 fused to anti-PD-1 antibody | 3.5 | 33 | No binding | 9.7 | Highly selective | No binding | >10 fold lower than WT |
| VFC-88 fused to anti-PD-1 antibody | 3.1 | No binding | No binding | Highly selective | Highly selective | No binding | >10 fold lower than WT |
| VFC-88 fused to anti-PD-1 antibody | 2.1 | 7.9 | No binding | 3.2 | Highly selective | No binding | >10 fold lower than WT |
| VFC-88 fused to anti-PD-1 antibody | 2.4 | 6.8 | No binding | 2.8 | Highly selective | No binding | >10 fold lower than WT |
| VFC-88 fused to anti-PD-1 antibody | 2.3 | 8 | No binding | 3.5 | Highly selective | No binding | >10 fold lower than WT |

Example 13

Figure 6:
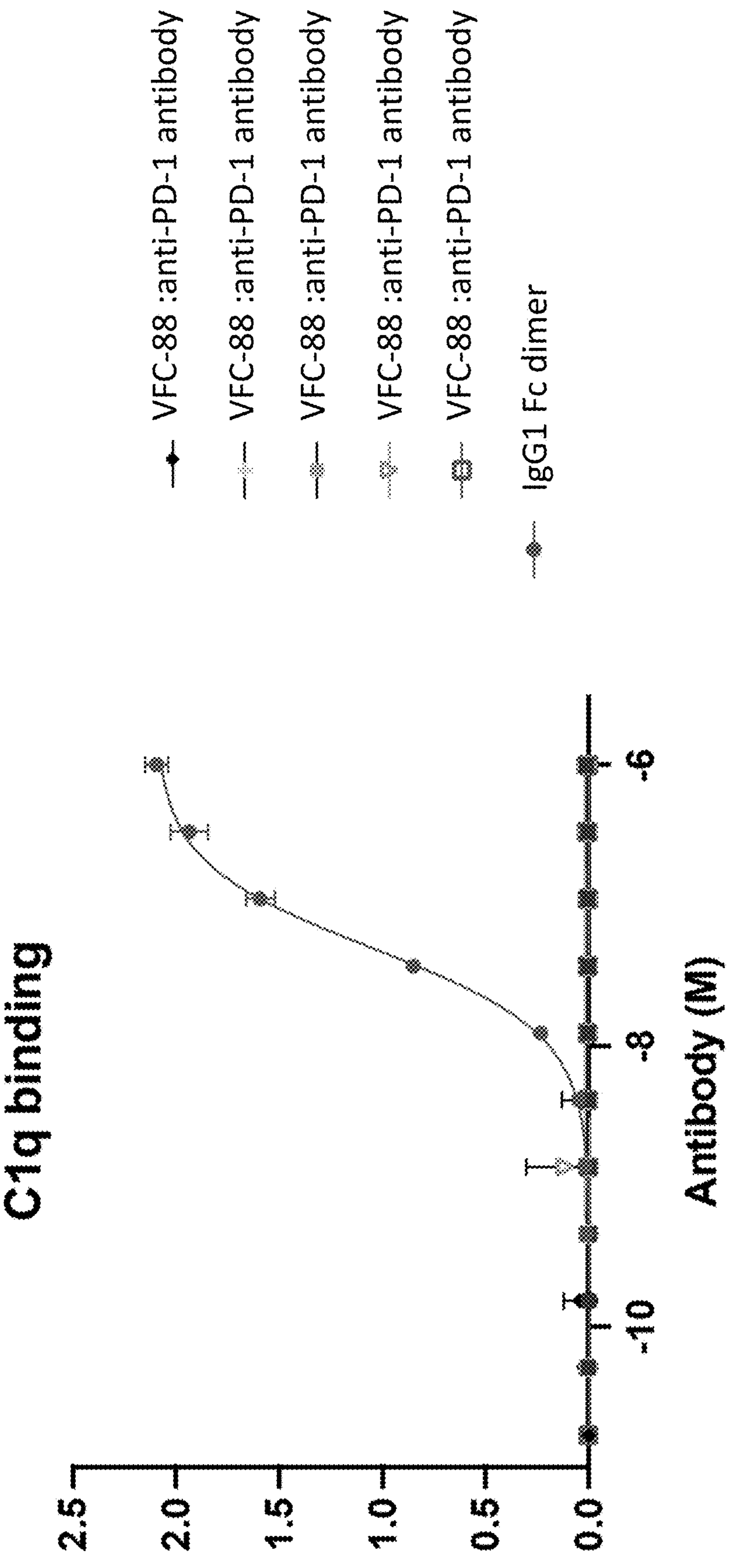
FIG. 6 illustrates C1q binding to various articles.

Binding ability of test articles comprising variant Fc molecules with increased affinity for FcγRIIβ to C1q was evaluated via enzyme-linked immunoassay. As shown in FIG. 6, test articles displayed no binding to C1q.

Example 14

Analysis of binding to FcRn of engineered Fc mutants displayed preserved FcRn binding, as shown in Table 9 below.

TABLE 9

Engineered Fc mutants

| Construct | Fc Type | Acidic Dissociation KD (M) | Neutral Dissociation KD (M) |
|---|---|---|---|
| WT Fc fused to anti-PD-1 antibody | WT | 9.6E−7 | 6.4E−4 |
| VFC-88 fused to anti-PD-1 antibody | VFC-88 | 9.9E−7 | 6.4E−7 |

The embodiments provided for herein demonstrate the surprising and unexpected results of generating Fc molecules that have increased affinity for FcγRIIβ, which can also be utilized in conjunction with other effector molecules, such as immune checkpoint modulators. The combination of the mutations in the Fc polypeptides, as provided for herein, to produce these variants with these properties could not have been predicted or expected to have such properties.

The disclosures of each and every patent, patent application, and publication cited herein are hereby incorporated herein by reference in their entirety. While various embodiments have been disclosed with reference to specific aspects, it is apparent that other aspects and variations of these embodiments may be devised by others skilled in the art without departing from the true spirit and scope of the embodiments. The appended claims are intended to be construed to include all such aspects and equivalent variations.

What is claimed:

1. A fusion protein comprising an Fc polypeptide linked to a heterologous protein, wherein the Fc polypeptide comprises an amino acid sequence having at least 95% identity to an amino acid sequence of SEQ ID NO: 88, provided that the Fc polypeptide comprises:

a glutamic acid residue at position 237 and a glutamic acid residue at position 238, wherein the positions are according to EU numbering;

an aspartic acid residue at position 237, a glycine residue at position 238, an alanine residue at position 240, an aspartic acid residue at position 269, a glutamic acid residue at position 270, and an arginine residue at position 330, wherein the positions are according to EU numbering; or a phenylalanine residue at position 234, a glutamic acid residue at position 235, an aspartic acid residue at position 268, a glycine residue at position 271, and an alanine residue at position 329, wherein the positions are according to EU numbering.

2. The fusion protein of claim 1, wherein the Fc polypeptide comprises the glutamic acid residue at position 237 and the glutamic acid residue at position 238, wherein the positions are according to EU numbering.

3. The fusion protein of claim 1, wherein the Fc polypeptide comprises the aspartic acid residue at position 237, the glycine residue at position 238, the alanine residue at position 240, the aspartic acid residue at position 269, the glutamic acid residue at position 270, and the arginine residue at position 330, wherein the positions are according to EU numbering.

4. The fusion protein of claim 1, wherein the Fc polypeptide comprises the phenylalanine residue at position 234, the glutamic acid residue at position 235, the aspartic acid residue at position 268, the glycine residue at position 271, and the alanine residue at position 329, wherein the positions are according to EU numbering.

5. The fusion protein of claim 1, wherein the Fc polypeptide comprises the amino acid sequence having at least 95% identity to an amino acid sequence of SEQ ID NO: 40.

6. The fusion protein of claim 5, wherein the Fc polypeptide comprises the amino acid sequence of SEQ ID NO: 40.

7. The fusion protein of claim 1, wherein the Fc polypeptide comprises the amino acid sequence having at least 95% identity to an amino acid sequence of SEQ ID NO: 102.

8. The fusion protein of claim 7, wherein the Fc polypeptide comprises the amino acid sequence of SEQ ID NO: 102.

9. The fusion protein of claim 1, wherein the Fc polypeptide comprises the amino acid sequence having at least 95% identity to an amino acid sequence of SEQ ID NO: 86.

10. The fusion protein of claim 9, wherein the Fc polypeptide comprises the amino acid sequence of SEQ ID NO: 86.

11. The fusion protein of claim 1, wherein the Fc polypeptide comprises the amino acid sequence having at least 95% identity to an amino acid sequence of SEQ ID NO: 103.

12. The fusion protein of claim 11, wherein the Fc polypeptide comprises the amino acid sequence of SEQ ID NO: 103.

13. The fusion protein of claim 1, wherein the Fc polypeptide comprises the amino acid sequence having at least 95% identity to an amino acid sequence of SEQ ID NO: 77.

14. The fusion protein of claim 13, wherein the Fc polypeptide comprises the amino acid sequence of SEQ ID NO: 77.

15. The fusion protein of claim 1, wherein the Fc polypeptide comprises the amino acid sequence having at least 95% identity to an amino acid sequence of SEQ ID NO: 104.

16. The fusion protein of claim 15, wherein the Fc polypeptide comprises the amino acid sequence of SEQ ID NO: 104.

17. The fusion protein of claim 1, wherein the heterologous protein is an antibody, or an antigen binding fragment thereof.

18. The fusion protein of claim 2, wherein the heterologous protein is an antibody, or an antigen binding fragment thereof.

19. The fusion protein of claim 3, wherein the heterologous protein is an antibody, or an antigen binding fragment thereof.

20. The fusion protein of claim 4, wherein the heterologous protein is an antibody, or an antigen binding fragment thereof.

21. The fusion protein of claim 5, wherein the heterologous protein is an antibody, or an antigen binding fragment thereof.

22. The fusion protein of claim 6, wherein the heterologous protein is an antibody, or an antigen binding fragment thereof.

23. The fusion protein of claim 8, wherein the heterologous protein is an antibody, or an antigen binding fragment thereof.

24. The fusion protein of claim 10, wherein the heterologous protein is an antibody, or an antigen binding fragment thereof.

25. The fusion protein of claim 12, wherein the heterologous protein is an antibody, or an antigen binding fragment thereof.

26. The fusion protein of claim 14, wherein the heterologous protein is an antibody, or an antigen binding fragment thereof.

27. The fusion protein of claim 16, wherein the heterologous protein is an antibody, or an antigen binding fragment thereof.

28. A pharmaceutical composition comprising the fusion protein of claim 1 and a pharmaceutically acceptable excipient.

29. The fusion protein of claim 1, wherein the Fc polypeptide is directly linked to the heterologous protein.

30. The fusion protein of claim 1, wherein the Fc polypeptide is linked to the heterologous protein with a peptide linker.

* * * * *